(12) United States Patent  
Wepplo et al.

(10) Patent No.: US 6,706,663 B2
(45) Date of Patent: Mar. 16, 2004

(54) HERBICIDAL 3-HETEROCYCLIC SUBSTITUTED BENZISOTHIAZOLE AND BENZISOXAZOLE COMPOUNDS

(75) Inventors: Peter John Wepplo, Princeton, NJ (US); Richard Anthony Rampulla, Whitehouse Station, NJ (US); Gavin David Heffernan, Florence, NJ (US); Michael Vernie Cossette, Plainsboro, NJ (US); Charles Malcolm Langevine, Brooklyn, NY (US); Venkataraman Kameswaran, Pennington, NJ (US); Robert Eugene Diehl, Yardley, PA (US); James Joseph Fiordeliso, Morrisville, PA (US); Gregory Jay Haley, Yardley, PA (US); Michael Anthony Guaciaro, Hightstown, NJ (US)

(73) Assignee: Wyeth, Madison, NJ (US)

( * ) Notice: Subject to any disclaimer, the term of this patent is extended or adjusted under 35 U.S.C. 154(b) by 131 days.

(21) Appl. No.: 09/836,082

(22) Filed: Apr. 17, 2001

(65) Prior Publication Data

US 2002/0028748 A1 Mar. 7, 2002

Related U.S. Application Data

(60) Provisional application No. 60/197,488, filed on Apr. 17, 2000.

(51) Int. Cl.[7] .................. C07D 417/14; C07D 419/14; C07D 417/04; A01N 43/54
(52) U.S. Cl. .................... 504/243; 544/310; 548/207
(58) Field of Search .................. 544/310; 504/243; 548/207

(56) References Cited

U.S. PATENT DOCUMENTS

| 4,277,477 A | | 7/1981 | Hagen et al. ............... 424/251 |
| 5,484,763 A | | 1/1996 | Wepplo ..................... 548/207 |
| 5,523,278 A | | 6/1996 | Wepplo ..................... 504/271 |
| 6,140,270 A | * | 10/2000 | Rampulla et al. ........... 504/239 |
| 6,191,275 B1 | * | 2/2001 | Kameswaran et al. ...... 544/310 |

FOREIGN PATENT DOCUMENTS

| EP | 0 908 457 A | 4/1999 |
| WO | WO 97 12886 A | 4/1997 |
| WO | WO 00 49003 A | 8/2000 |

* cited by examiner

Primary Examiner—Mukund J. Shah
Assistant Examiner—Venkataraman Balasubramanian
(74) Attorney, Agent, or Firm—Joseph M. Mazzarese

(57) ABSTRACT

There are provided 3-heterocyclic substituted benzisothiazole and benzisoxazole compounds having the structural formula I

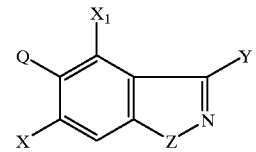

where Q, X, $X_1$ and Z are defined as in claim 1. Further provided are compositions and methods comprising those compounds for the control of undesirable plant species.

22 Claims, No Drawings

HERBICIDAL 3-HETEROCYCLIC SUBSTITUTED BENZISOTHIAZOLE AND BENZISOXAZOLE COMPOUNDS

This application claims priority from provisional application No. 60/197,488 filed on Apr. 17, 2000.

BACKGROUND OF THE INVENTION

Weeds cause tremendous global economic losses by reducing crop yields and lowering crop quality. World-wide, agronomic crops must compete with hundreds of weed species.

In spite of the commercial herbicides available today, damage to crops caused by weeds still occurs. Accordingly, there is ongoing research to create more effective and/or more selective herbicidal agents.

Certain benzisoxazole and benzisothiazole herbicidal agents are described in U.S. Pat. Nos. 5,484,763 and 5,523,278. Those patents generically disclose benzisoxazole and benzisothiazole compounds that are substituted in the 3-position with a variety of substituents, none of which are heterocycles. In addition, those patents do not disclose that their compounds are useful for the selective control of weeds in the presence of crops such as corn, soybeans, wheat and transplanted rice.

Surprisingly, it has now been found that bensizoxazole and bensizothazole compounds in which the 3-position is substituted by an optionally substituted heterocycle are more effective and more selective herbicidal agents than expected.

Therefore it is an object of this invention to provide 3-heterocyclic substituted benzisoxazole and benzisothiazole compounds which are highly effective for the control of undesirable plant species.

It is also an object of this invention to provide intermediate compounds useful in the manufacture of said compounds.

It is a further object of the invention to provide a method for the selective control of undesirable plant species in the presence of crops.

These and other objects and features of the invention will become more apparent from the detailed description thereof set forth below.

SUMMARY OF THE INVENTION

The present invention provides compounds of formula I

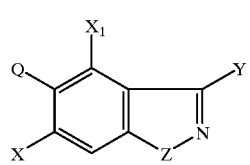

I wherein
Q is selected from

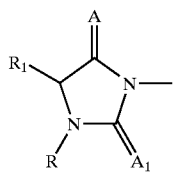

Q$_1$

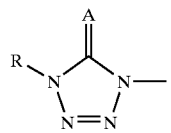

Q$_2$

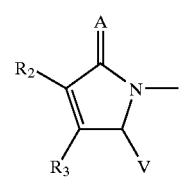

Q$_3$

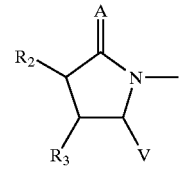

Q$_4$

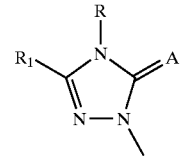

Q$_5$

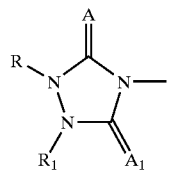

Q$_6$

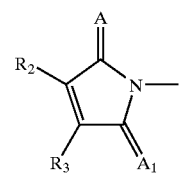

Q$_7$

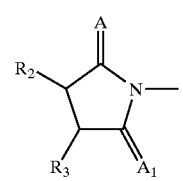

Q$_8$

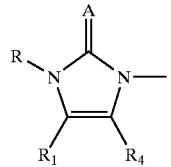

Q$_9$

Q10 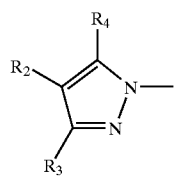
Q11 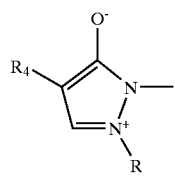
Q12 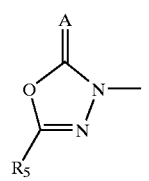
Q13 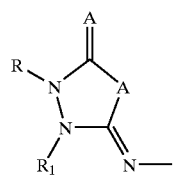
Q14 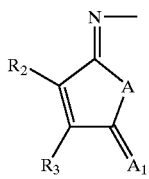
Q15 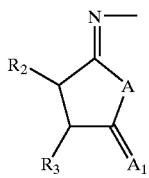
Q16 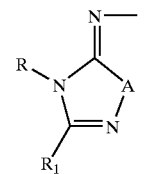
Q17 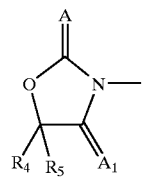
Q18 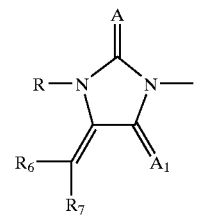
Q19 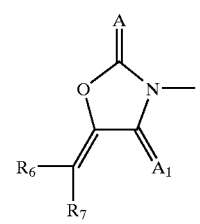
Q20 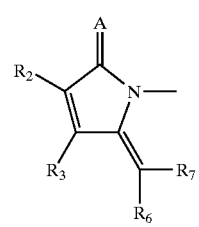
Q21 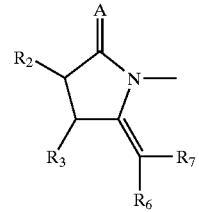
Q22 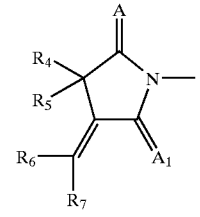
Q23 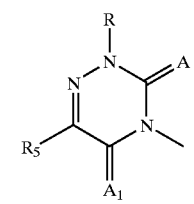
Q24 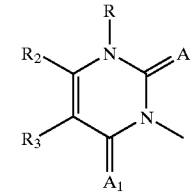

Q25 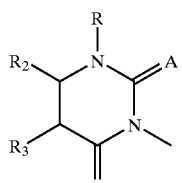
Q26 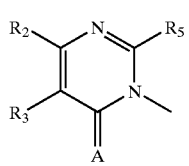
Q27 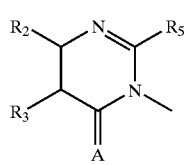
Q28 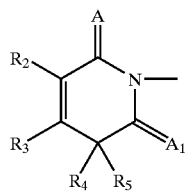
Q29 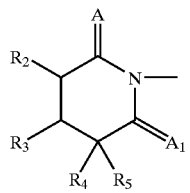
Q30 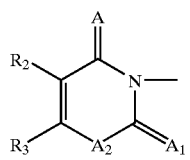
Q31 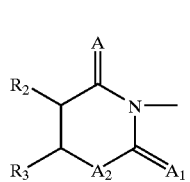
Q32 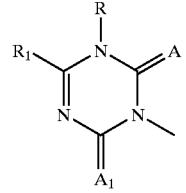
Q33 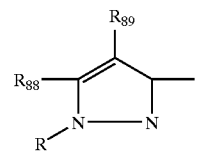
Q34 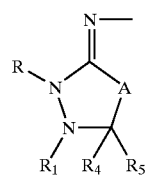
Q35 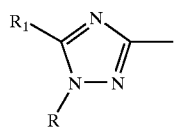
Q36 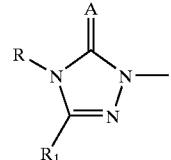
Q37 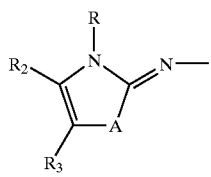
Q38 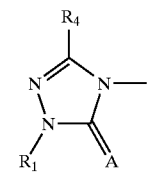
Q39 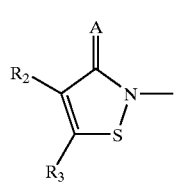
Q40 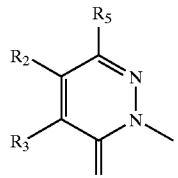
R is halogen, $C_1$–$C_6$ alkyl, $C_1$–$C_6$ haloalkyl, $C_3$–$C_7$ cycloalkyl, $C_2$–$C_6$ alkenyl, $C_2$–$C_6$ haloalkenyl, $C_3$–$C_6$ alkynyl, cyano, benzyl, OH, $NH_2$, $C_2$–$C_6$ cyanoalkyl and when R and $R_1$ are taken together with the other atoms to which they are attached, they represent a four to seven-membered ring optionally interrupted by oxygen, sulfur or nitrogen and optionally substituted with one to three methyl groups or one or more halogen atoms;

$R_1$ is hydrogen, halogen, $C_1-C_6$ alkyl, $C_1-C_6$ haloalkyl, $C_3-C_7$ cycloalkyl, $C_2-C_6$ alkenyl, $C_2-C_6$ haloalkenyl, $C_3-C_6$ alkynyl, cyano, benzyl, OH, $NH_2$, $C_2-C_6$ cyanoalkyl and when R and $R_1$ are taken together with the other atoms to which they are attached, they represent a four to seven-membered ring optionally interrupted by oxygen, sulfur or nitrogen and optionally substituted with one to three methyl groups or one or more halogen atoms;

$R_2$ and $R_3$ are each independently hydrogen, halogen, $C_1-C_6$ alkyl, $C_1-C_6$ haloalkyl, $C_3-C_7$ cycloalkyl, $C_2-C_6$ alkenyl, $C_2-C_6$ haloalkenyl, $C_3-C_6$ alkynyl, $OR_8$, $S(O)_mR_9$ or $NR_{10}R_{11}$ and when $R_2$ and $R_3$ are taken together with the atoms to which they are attached, they represent a four to seven-membered saturated or unsaturated ring optionally interrupted by oxygen, sulfur or nitrogen and optionally substituted with one to three methyl groups or one or more halogen atoms;

$R_4$, $R_6$ and $R_7$ are each independently hydrogen, halogen or $C_1-C_6$ alkyl;

$R_5$ is hydrogen, halogen, $C_1-C_6$ alkyl, $C_1-C_6$ haloalkyl, $C_3-C_7$ cycloalkyl, $C_3-C_6$ alkenyl, $C_2-C_6$ haloalkenyl, $C_3-C_6$ alkynyl, $OR_{12}$ or $SR_{13}$;

$R_8$, $R_9$, $R_{12}$, $R_{13}$, and $R_{14}$ are each independently hydrogen, $C_1-C_4$ alkyl, $C_1-C_4$ haloalkyl, $C_2-C_6$ alkenyl, $C_2-C_6$ haloalkenyl, $C_3-C_6$ alkynyl, $C_3-C_7$ cycloalkyl, $C_2-C_6$ cyanoalkyl, benzyl or (subst)phenyl;

$R_{10}$ is hydrogen, $C_1-C_6$ alkyl, (subst.)benzyl or (subst.)phenyl, $C_1-C_6$ haloalkyl;

$R_{11}$ is $C_1-C_6$ alkyl, $C_1-C_6$ alkenyl, $C_3-C_6$ alkynyl, $C_3-C_7$ cycloalkyl, $C_1-C_6$ haloalkyl, benzyl, (subst.)phenyl or $S(O)_nR_{14}$;

$R_{88}$ is cyano, $C_1-C_4$ alkyl, $C_1-C_4$haloalkyl, $C_1-C_4$alkoxy, $C_1-C_4$haloalkoxy, $C_1-C_4$alkylthio, $C_1-C_4$alkylsulfinyl, $C_1-C_4$alkylsulfonyl or $C_1-C_4$haloalkylsulfonyl;

$R_{89}$ is hydrogen, cyano, halogen, $C_1-C_4$alkyl or $C_1-C_4$halolakyl;

n is an integer of 0, 1 or 2;

A, $A_1$ and $A_2$ are each independently oxygen or sulfur;

X is hydrogen, halogen or $C_1-C_4$alkyl;

$X_1$ is hydrogen, halogen, $C_1-C_4$ alkyl, $C_1-C_4$ haloalkyl, $C_1-C_4$ alkoxy or, $C_1-C_4$haloalkoxy;

V is OH, halogen, $C_1-C_4$ alkoxy or $C_1-C_4$ alkylthio;

Y is an optionally substituted heterocyclic three to seven-membered ring containing one to four heteroatoms selected from oxygen, sulfur or nitrogen;

Z is O or $S(O)_m$;

m is an integer of 0, 1 or 2; and the optical isomers and diastereomers thereof.

Also provided are intermediate compounds useful in the preparation of the herbicidal formula I compounds.

The present invention further provides herbicidal compositions, and methods.

DETAILED DESCRIPTION OF THE INVENTION

Surprisingly, it has now been found that the Formula I compounds of the invention demonstrate increased weed control and enhanced crop selectivity. The formula I compounds of the present invention are particularly useful for the selective control of undesirable plant species in the presence of cereal crops such as corn, wheat and rice and in the presence of leguminous crops such as soybeans.

Preferred compounds of the invention are those compounds of formula I wherein

Q is $Q_7$ or $Q_{24}$;

R is $C_1-C_6$ alkyl, $C_2-C_6$ alkenyl, $C_3-C_6$ alkynyl or $NH_2$;

$R_2$ is $C_1-C_6$ alkyl or $C_1-C_6$ haloalkyl;

$R_3$ is hydrogen;

Y is selected from

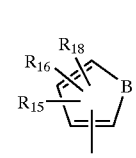

$Y_1$

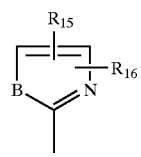

$Y_2$

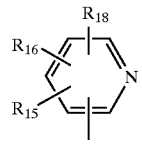

$Y_3$

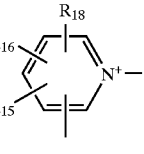

$Y_4$

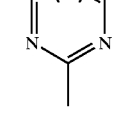

$Y_5$

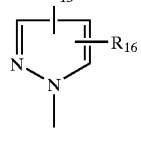

$Y_6$

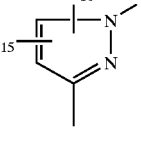

$Y_7$

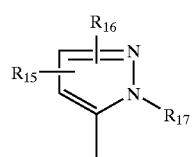 Y8
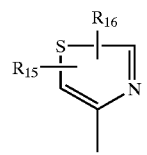 Y9
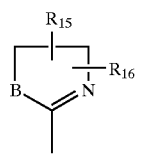 Y10
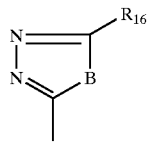 Y11
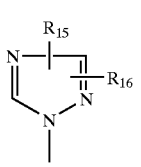 Y12
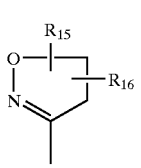 Y13
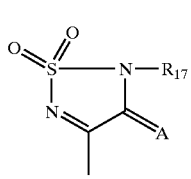 Y14
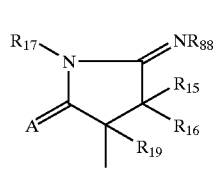 Y15
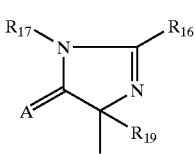 Y16
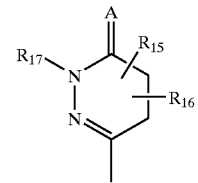 Y17
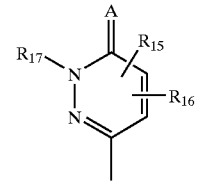 Y18
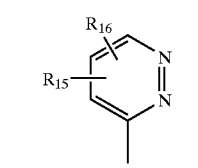 Y19
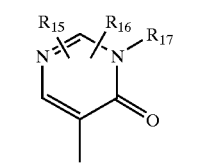 Y20
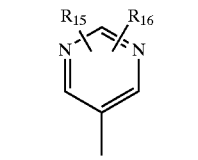 Y21
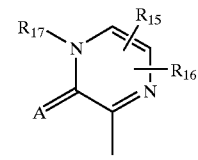 Y22
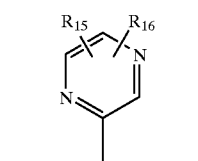 Y23
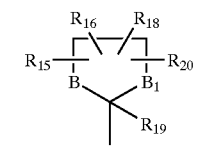 Y24
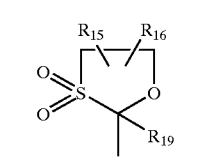 Y25

-continued

Y26 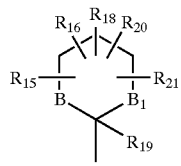

Y27 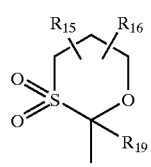

Y28 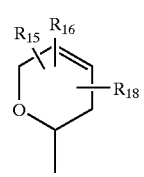

Y29 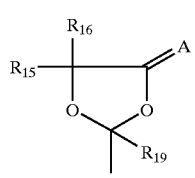

Y30 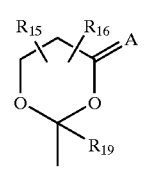

Y31 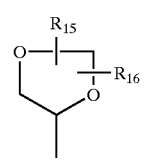

Y32 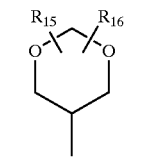

Y33 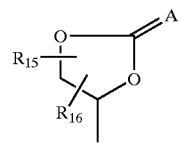

Y34 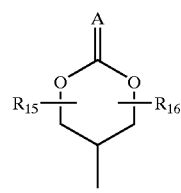

-continued

Y35 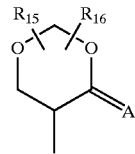

Y36 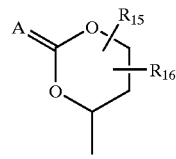

Y37 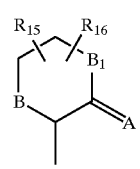

Y38 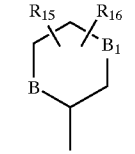

Y39 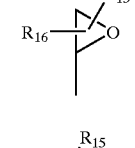

Y40 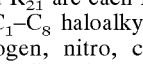

wherein $R_{15}$, $R_{18}$, $R_{20}$ and $R_{21}$ are each independently hydrogen, $C_1$–$C_8$ alkyl, $C_1$–$C_8$ haloalkyl, $C_1$–$C_8$ alkoxy, $C_1$–$C_8$ thioalkyl, halogen, nitro, cyano, hydroxy, $C_2$–$C_6$ alkenyl, $C_3$–$C_6$ alkynyl, $C_2$–$C_6$ haloalkenyl, $C_3$–$C_8$ cycloalkyl or $R_{20}$ and the carbon on Y to which $R_{20}$ is attached may form an exocyclic double bond or when $R_{20}$ and $R_{21}$ are attached to the same carbon of $Y_{25}$, $R_{20}$, $R_{21}$ and the carbon to which they are bonded may form a three- to six-membered heterocyclic ring;

$R_{16}$ is hydrogen, halogen, $C_1$–$C_8$ alkyl optionally substituted with $C(O)R_{22}$, $CO_2R_{23}$, $X_2R_{24}$, $S(O)_m$alkyl, $NR_{86}R_{87}$, $C_1$–$C_8$ haloalkyl, $C(O)R_{25}$, $CO_2R_{26}$, $X_3R_{27}$, $CH=CHR_{28}$, $C_3$–$C_8$ cycloalkyl, $N(R_{29})SO_2R_{30}$, (subst.) phenyl, or when $R_{15}$ and $R_{16}$ are attached to adjacent carbon atoms, they may be taken together with the atoms to which they are attached to form a six-membered ring;

$R_{17}$ is hydrogen, $C_1$–$C_8$ alkyl, $C_2$–$C_8$ alkenyl, $C_3$–$C_6$ alkynyl, $C(O)R_{25}$, or(subst.)benzyl;

$R_{19}$, $R_{29}$, $R_{33}$, $R_{34}$, $R_{35}$, $R_{37}$, $R_{38}$, $R_{39}$, $R_{42}$, $R_{43}$, $R_{44}$, $R_{46}$, $R_{47}$, $R_{48}$, $R_{50}$ $R_{51}$ $R_{52}$ $R_{53}$, $R_{55}$, $R_{56}$, $R_{57}$, $R_{60}$, $R_{61}$, $R_{62}$, $R_{64}$, $R_{65}$, $R_{66}$, $R_{69}$, $R_{70}$, $R_{71}$, $R_{73}$, $R_{74}$, $R_{75}$, $R_{76}$, $R_{80}$, $R_{85}$ and $R_{86}$ are each independently hydrogen, OH, $C_1$–$C_8$ alkyl, $C_1$–$C_4$ alkoxy, $C_3$–$C_8$ cycloalkyl, $C_2$–$C_8$ alkenyl, $C_3$–$C_6$ alkynyl, (subst.) benzyl or (subst.) phenyl;

$R_{23}$, $R_{26}$, $R_{31}$, $R_{40}$, $R_{49}$, $R_{58}$, $R_{67}$, and $R_{79}$ are each independently hydrogen, $C_1$–$C_8$ alkyl, $C_1$–$C_8$ haloalkyl, $C_3$–$C_8$ cycloalkyl, $C_3$–$C_8$ halocycloalkyl, $C_2$–$C_8$ alkenyl, $C_2$–$C_8$ haloalkenyl, $C_5$–$C_8$ cycloalkenyl, $C_5$–$C_8$ halocycloalkenyl, $C_3$–$C_8$ alkynyl, $C_3$–$C_8$ haloalkynyl, (subst.)benzyl, (subst.) phenyl, furfuryl, pyridyl, thienyl, an alkali metal, alkaline earth metal, manganese, copper, zinc, cobalt, silver, nickel ammonium or organic ammonium cation;

$R_{22}$, $R_{25}$, $R_{32}$, $R_{36}$, $R_{41}$, $R_{45}$, $R_{54}$, $R_{59}$, $R_{63}$, $R_{68}$, $R_{72}$, $R_{77}$, $R_{78}$, $R_{81}$, and $R_{87}$ are each independently hydrogen, $C_1$–$C_4$ alkyl, $C_1$–$C_4$ haloalkyl, $C_2$–$C_6$ alkenyl, $C_2$–$C_6$ haloalkenyl, $C_2$–$C_6$ alkynyl, $C_3$–$C_7$ cycloalkyl, $C_1$–$C_4$ cyanoalkyl, benzyl or (subsz.)phenyl;

$R_{24}$, $R_{27}$, and $R_{28}$ are each independently hydrogen,
  $C_1$–$C_{10}$ alkyl optionally substituted with one to six halogens, one $C_1$–$C_6$ alkoxy group, $CO_2R_{31}$, $C(O)R_{32}$, $C(OR_{33})_2$, $C(SR_{34})_2$, $C(O)NR_{35}R_{36}$, $C(O)ON=CR_{37}R_{38}$, cyano, (subst.)phenyl or $C(O)NHOR_{39}$;
  $C_2$–$C_{10}$ alkenyl optionally substituted with one $C_1$–$C_6$ alkyl group, one to three halogens, one $C_1$–$C_6$ alkoxy group, $CO_2R_{40}$, $C(O)R_{41}$, $C(OR_{42})_2$, $C(SR_{43})_2$, $C(O)NR_{44}R_{45}$, $C(O)ON=CR_{46}R_{47}$, cyano, (subst.) phenyl or $C(O)NHOR_{48}$;
  $C_3$–$C_8$ cycloalkyl optionally substituted with one $C_1$–$C_6$ alkyl group, one to three halogens, one $C_1$–$C_6$ alkoxy group, $CO_2R_{49}$, $C(O)R_{50}$, $C(OR_{51})_2$, $C(SR_{52})_2$, $C(O)NR_{53}R_{54}$, $C(O)ON=CR_{55}R_{56}$, cyano, (subst.)phenyl or $C(O)NHOR_{57}$;
  $C_5$–$C_8$ cycloalkenyl optionally substituted with one $C_1$–$C_6$ alkyl group, one to three halogens, $C_1$–$C_4$ alkoxy group, $CO_2R_{58}$, $C(O)R_{59}$, $C(OR_{60})_2$, $C(SR_{61})_2$, $C(O)NR_{62}R_{63}$, $C(O)ON=CR_{64}R_{65}$, cyano, (subst.)phenyl or $C(O)NHOR_{66}$;
  $C_3$–$C_8$ alkynyl optionally substituted with one $C_1$–$C_6$ alkoxy group, $CO_2R_{67}$, $C(O)R_{68}$, $C(OR_{69})_2$, $C(SR_{70})_2$, $C(O)NR_{71}R_{72}$, $C(O)ON=CR_{73}R_{74}$, cyano, (subst.)phenyl or $CO\, NHOR_{75}$;
  phenyl optionally substituted with one to three halogens, one to three $C_1$–$C_6$ alkyl groups, one to three $C_1$–$C_6$ alkoxy groups, one to three $C_1$–$C_6$ haloalkyl groups, one to three $C_1$–$C_6$ haloalkoxy groups, one cyano, one nitro, one $NR_{76}R_{77}$, one $C(O)R_{78}$ or one $CO_2R_{79}$;

$R_{30}$ is OH, $C_1$–$C_8$ alkyl, $C_3$–$C_8$ cycloalkyl, $C_1$–$C_8$ haloalkyl, $C_2$–$C_8$ alkenyl, $C_2$–$C_8$ haloalkenyl, $C_3$–$C_8$ alkynyl, (subst.)benzyl, (subst.) phenyl, or $NR_{80}R_{81}$;

B and $B_1$ are each independently oxygen, sulfur or $NR_{17}$;

$X_2$ and $X_3$ are each independently O or S; and the optical isomers and diastereomers thereof.

More preferred, are those compounds of Formula I wherein

Q is $Q_{24}$;

R is $C_1$–$C_3$ alkyl;

$R_2$ is $C_1$–$C_3$ haloalkyl;

X is hydrogen or halogen;

$X_1$ is hydrogen;

z is sulfur;

Y is selected from $Y_1$, $Y_2$, $Y_3$, $Y_4$, $Y_5$, $Y_6$, $Y_{10}$, $Y_{11}$, $Y_{14}$, $Y_{15}$, $Y_{16}$, $Y_{22}$, $Y_{24}$, $Y_{25}$, $Y_{26}$, $Y_{27}$, $Y_{28}$, $Y_{38}$, and $Y_{39}$. $R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy, halogen, hydroxy or when $R_{20}$ and $R_{21}$ are attached to the same carbon of $Y_{25}$ an epoxide ring is formed;

$R_{16}$ is hydrogen, halogen, $C_1$–$C_3$ alkyl optionally substituted with $C(O)R_{22}$, $CO_2R_{23}$, $X_2R_{24}$, or $S(O)_m$alkyl; phenyl; $C_1$–$C_3$ haloalkyl, $C(O)R_{25}$, $CO_2R_{26}$, $X_3R_{27}$, $C_3$–$C_8$ cycloalkyl, $N(R_{29})SO_2R_{30}$ or $C_2$–$C_4$ alkenyl;

$R_{17}$ is hydrogen, $C_1$–$C_3$ alkyl, $C_2$–$C_4$ alkenyl or $C(O)R_{25}$;

$R_{19}$, $R_{29}$ and $R_{80}$ are each independently hydrogen or $C_1$–$C_3$ alkyl;

$R_{22}$, $R_{25}$ and $R_{81}$ are each independently hydrogen, $C_1$–$C_3$ alkyl, benzyl or (subst)phenyl;

$R_{23}$, $R_{26}$ and $R_{31}$ are each independently hydrogen, $C_1$–$C_3$ alkyl, $C_2$–$C_4$ alkenyl, or $C_3$–$C_6$ alkynyl;

$R_{24}$ and $R_{27}$ are each independently hydrogen or $C_1$–$C_3$ alkyl optionally substituted with one $CO_2R_{31}$ group or one $C_1$–$C_3$ alkoxy group;

$R_{30}$ $C_1$–$C_3$ alkyl, $C_3$–$C_5$ cycloalkyl, $C_1$–$C_3$ haloalkyl, $C_2$–$C_4$ alkenyl (subst.)benzyl, (subst.)phenyl, or $NR_{80}R_{81}$;

$X_2$ and $X_3$ are O.

Most preferred compounds of the invention are those compounds of formula I wherein Q is

[structure: pyrimidinedione with $CF_3$, $CH_3$ on N, and N–CH$_3$]

Y is selected from $Y_1$

[structures of furan ($R_{15}$, $R_{16}$), furan ($R_{16}$, $R_{15}$), thiophene ($R_{18}$, $R_{15}$, $R_{16}$), thiophene ($R_{18}$, $R_{15}$, $R_{16}$), pyrrole ($R_{18}$, $R_{15}$, $R_{16}$, $R_{17}$)]

$Y_2$

[structures of thiazole ($R_{15}$, $R_{16}$) and imidazole ($R_{16}$, $R_{15}$, $R_{17}$)]

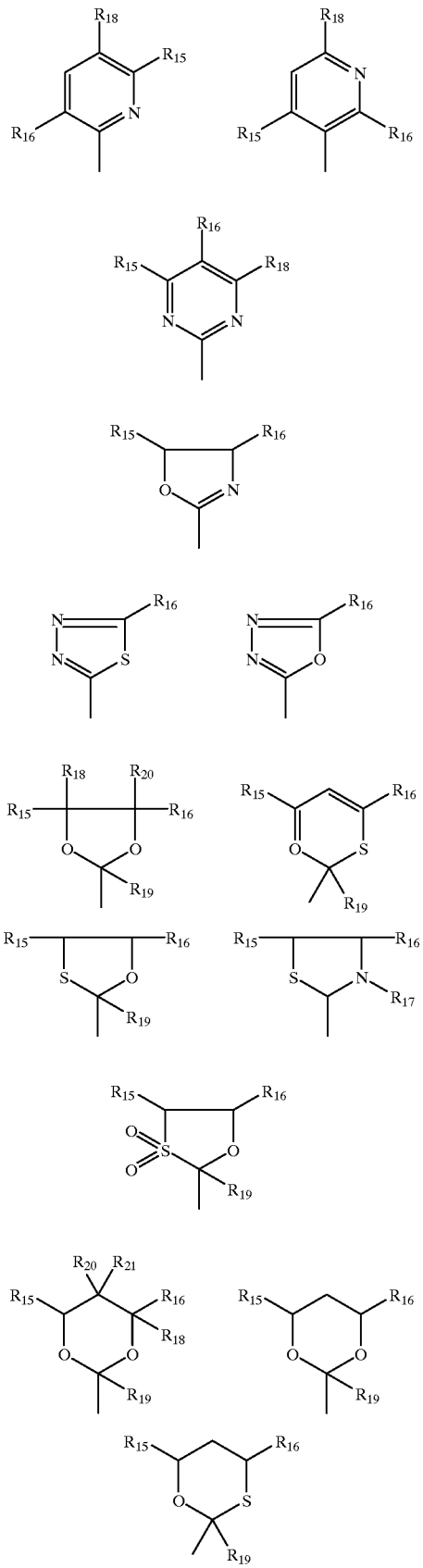
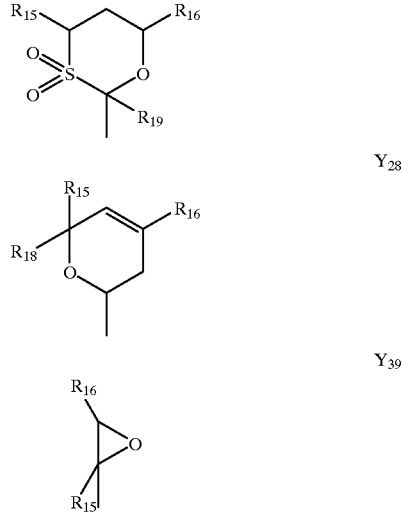

$R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy;

$R_{16}$ is hydrogen, halogen, $C_1$–$C_8$ alkyl optionally substituted with $X_2R_{24}$; $C_1$–$C_3$ haloalkyl, phenyl or $C_2$–$C_4$ alkenyl;

$R_{17}$ is hydrogen, methyl or $C(O)R_{25}$;

$R_{19}$ is hydrogen or $C_1$–$C_3$ alkyl;

$R_{24}$ is hydrogen or $C_1$–$C_3$ alkyl;

$R_{25}$ is $C_1$–$C_3$ alkyl or phenyl;

$X_2$ is oxygen.

$R_{88}$ is preferably $C_1$–$C_4$haloalkyl, $C_1$–$C_4$haloalkoxy or $C_1$–$C_4$alkylsulfonyl, in particular trifluoromethyl or difluoromethoxy, $R_{89}$ is preferably hydrogen or halogen, in particular chlorine or bromine.

Formula I compounds of the present invention which are particularly effective herbicidal agents include 1-methyl-3-[3-(3-thienyl)-1,2-benzisothiazol-5-yl]-6-(trifluoromethyl)uracil;

ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate;

1-methyl-3-[3-(2-thienyl)-1,2-benzisothiazol-5-yl]-6-(trifluoromethyl)uracil;

1-methyl-3-[3-(3-methyl-2-thienyl)-1,2-benzisothiazol-5-yl]-6-(trifluoromethyl)uracil;

1-methyl-3-[3-(1-methylimidazol-2-yl)-1,2-benzisothiazol-5-yl]-6-(trifluoromethyl)uracil;

1-methyl-3-[3-(1-methylpyrrol-2-yl)-1,2-benzisothiazol-5-yl]-6-(trifluoromethyl)uracil;

1-methyl-3-[3-(4-methyl-2-thiazolyl)-1,2-benzisothiazol-5-yl]-6-(trifluoromethyl)uracil;

3-[3-(2,5-diethyl-3-thienyl)-1,2-benzisothiazol-5-yl]-1-methyl-6-(trifluoromethyl)uracil;

1-methyl-3-[3-(2-pyrodyl)-1,2-benzisothiazol-5-yl]-6-(trifluoromethyl)uracil;

3-[3-(3-methoxy-2-thienyl)-1,2-benzisothiazol-5-yl]-1-methyl-6-(trifluoromethyl)uracil;

1-methyl-3-[3-(3-pyridyl)-1,2-benzisothiazol-5-yl]-6-(trifluoromethyl)uracil;

1-methyl-3-[3-(2-pyrimidinyl)-1,2-benzisothiazol-5-yl]-6-(trifluoromethyl)uracil;

3-[3-[(1R,2S)-1,2-epoxypropyl]-1,2-benzisothiazol-5-yl]-1-methyl-6-(trifluoromethyl)uracil;

3-[3-[(1R,2R)-1,2-epoxypropyl]-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil N",S,S-trioxide;

1-methyl-3-[3-(5-methyl-1,3,4-oxadiazol-2-yl)-1,2-benzisothiazol-5-yl]-6-(trifluoromethyl)uracil;

1-methyl-3-[3-(5-methyl-1,3,4-thiadiazol-2-yl)-1,2-benzisothiazol-5-yl]-6-(trifluoromethyl)uracil;

1,2-benzisothiazole-3-carboxanilide, 4'-chloro-5-[3,6-dihydro-3-methyl-2,6-dioxo-4-(trifluoromethyl)-1(2H)-pyrimidinyl]-N-methyl-;

1-methyl-3-[3-(3-methyl-2-pyridyl)-1,2-benzisothiazol-5-yl]-6-(trifluoromethyl)uracil;

N-[3-(5-methyl-2-thienyl)-1,2-benzisothiazol-5-yl]-1-cyclohexene-1,2-dicarboximide;

1-methyl-3-[3-(5-methyl-2-thienyl)-1,2-benzisothiazol-5-yl]-6-(trifluoromethyl)uracil;

methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate;

methyl 2-[(2-[5-[3,6-dihydro-3-methyl-2,6-dioxo-4-(trifluoromethyl)-1(2H)-pyrimidinyl]-1,2-benzisothiazol-3-yl]-3-thienyl]oxy]propionate;

3-[3-(1,3-dithiolan-2-yl)-1,2-benzisothiazol-5-yl]-1-methyl-6-(trifluoromethyl)uracil;

3-[6-fluoro-3-(2-pyridyl)-1,2-benzisothiazol-5-yl]-1-methyl-6-(trifluoromethyl)uracil;

1-methyl-3-[3-(4-methyl-3-thienyl)-1,2-benzisothiazol-5-yl]-6-(trifluoromethyl)uracil;

3-[3-(3,5-dimethyl-2-thienyl)-1,2-benzisothiazol-5-yl]-1-methyl-6-(trifluoromethyl)uracil;

3-(3-m-dioxan-2-yl-1,2-benzisothiazol-5-yl)-1-methyl-6-(trifluoromethyl)uracil;

3-acetyl-2-[5-[3,6-dihydro-3-methyl-2,6-dioxo-4-(trifluoromethyl)-1(2H)-pyrimidinyl]-1,2-benzisothiazol-3-yl]thiazolidine;

3-benzoyl-2-[5-[3,6-dihydro-3-methyl-2,6-dioxo-4-(trifluoromethyl)-1(2H)-pyrimidinyl]-1,2-benzisothiazol-3-yl]thiazolidine;

1-methyl-3-[3-(1,3-oxathiolan-2-yl)-1,2-benzisothiazol-5-yl]-6-(trifluoromethyl)uracil;

1-methyl-3-[3-(1,3-oxathioln-2-yl)-1,2-benzisothiazol-5-yl]-6-(trifluoromethyl)uracil S',S'-dioxide;

1,2-benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl) dithioacetal];

1-methyl-3-[3-(1,3-oxathian-2-yl)-1,2-benzisothiazol-5-yl]-6-(trifluoromethyl)uracil;

1-methyl-3-[3-(1,3-oxathian-2-yl)-1,2-benzisothiazol-5-yl]-6-(trifluoromethyl)uracil S',S'-dioxide;

3-[3(5,5-dimethyl-m-dioxan-2-yl)-1,2-benzisothiazol-5-yl]-1-methyl-6-(trifluoromethyl)uracil;

1-methyl-3-[3-(4-methyl-m-dioxan-2-yl)-1,2-benzisothiazol-5-yl]-6-(trifluoromethyl)uracil;

1-methyl-3-[3-(3-methylpyrazol-1-yl)-1,2-benzisothiazol-5-yl]-6-(trifluoromethl)uracil;

2-propynyl [[2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate;

3-[3-(4,6-dimethyl-2-pyrimidinyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[3-(4,6-diethoxy-2-pyrimidinyl)-1,2-benzisothiazol-5-yl]-1-methyl-6-(trifluoromethyl)uracil;

3-[6-fluoro-3-(3-methyl-2-pyridyl)-1,2-benzisothiazol-5-yl]-1-methyl-6-(trifluoromethyl)uracil;

3-[3-(1,3-dioxolan-2-yl)-1,2-benzisothiazol-5-yl]-1-methyl-6-(trifluoromethyl)uracil;

N-[6-fluoro-3-(3-methyl-2-pyridyl)-1,2-benzisothiazol-5-yl]-1-cyclohexene-1,2-dicarboximide;

3-[3-[(4R,5S)-4,5-dimethyl-1,3-dioxolan-2-yl]-1,2-benzisothiazol-5-yl]-1-methyl-6-(trifluoromethyl)uracil;

3-[3-[(4R,5R)-4,5-dimethyl-1,3-dioxolan-2-yl]-1,2-benzisothiazol-5-yl]-1-methyl-6-(trifluoromethyl)uracil;

1-methyl-6-(trifluoromethyl)-3-[3-(3,4,5-trimethyl-pyrazol-1-yl)-1,2-benzisothiazol-5-yl]uracil;

3-[3-[(4R,6S)-4,6-dimethyl-m-dioxan-2-yl]-1,2-benzisothiazol-5-yl]-1-methyl-6-(trifluoromethyl)uracil;

3-[3-[(4R,6S)-4,6-dimethyl-m-dioxan-2-yl]-1,2-benzisothiazol-5-yl]-1-methyl-6-(trifluoromethyl)uracil;

3-[3-(3-chloro-2-thienyl)-1,2-benzisothiazol-5-yl]-1-methyl-6-(trifluoromethyl)uracil;

1-methyl-3-[3-(2-thiazolyl)-1,2-benzisothiazol-5-yl]-6-(trifluoromethyl)uracil;

1-methyl-3-[3-(2-methyl-1,3-dioxolan-2-yl)-1,2-benzisothiazol-5-yl]-6-(trifluoromethyl)uracil;

1-methyl-6-(trifluoromethyl)-3-[3-(4,4,6-trimethyl-m-dioxan-2-yl)-1,2-benzisothiazol-5-yl]uracil;

1-methyl-3-[3-(4,4,5,5-tetramethyl-1,3-dioxolan-2-yl)-1,2-benzisothiazol-5-yl]-6-(trifluoromethyl)uracil;

1-methyl-3-[3-(4-methyl-1,3-dioxolan-2-yl)-1,2-benzisothiazol-5-yl]-6-(trifluoromethyl)uracil;

2,4(1H,3H)-pyrimidinedione, 1-methyl-3-[3-(5-methylene-m-dioxan-2-yl)-1,2-benzisothiazol-5-yl]-6-(trifluoromethyl)-;

1-methyl-3-[3-(4-methylpyrazol-1-yl)-1,2-benzisothiazol-5-yl]-6-(trifluoromethyl)uracil;

3-[3-(2-furyl)-1,2-benzisothiazol-5-yl]-1-methyl-6-(trifluoromethyl)uracil;

3-[3-(1,3-dioxolan-2-yl)-6-fluoro-1,2-benzisothiazol-5-yl]-1-methyl-6-(trifluoromethyl)uracil;

3-(3-m-dioxan-2-yl-6-fluoro-1,2-benzisothiazol-5-yl)-1-methyl-6-(trifluoromethyl)uracil;

3-[3-[(4R,5S)-4,5-dimethyl-1,3-dioxolan-2-yl]-6-fluoro-1,2-benzisothiazol-5-yl]-1-methyl-6-(trifluoromethyl)uracil 3-[3-[4-(methoxymethyl)-1,3-dioxolan-2-yl]-1,2-benzisothiazol-5-yl]-1-methyl-6-(trifluoromethyl)uracil;

3-[3-(3,6-dihydro-4,6,6-trimethyl-2H-pyran-2-yl)-1,2-benzisothiazol-5-yl]-1-methyl-6-(trifluoromethyl)uracil;

3-[3-[(4R,5S-)-4,5-dimethyl-1,3-dioxolan-2-yl]-6-fluoro-1,2-benzisothiazol-5-yl]-1-methyl-6-(trifluoromethyl)uracil;

3-[3-[(4R,6S)-4,6-dimethyl-m-dioxan-2-yl]-6-fluoro-1,2-benzisothiazol-5-yl]-1-methyl-6-(trifluoromethyl)uracil;

2,4(1H,3H)-pyrimidinedione, 1-methyl-3-[3-(2-methyl-3-thienyl)-1,2-benzisothiazol-5-yl]-6-(trifluoromethyl)-;

3-[3-[5-(bromomethyl)-5-hydroxy-m-diaxan-2-yl]-1,2-benzisothiazol-5-yl]-1-methyl-6-(trifluoromethyl)uracil;

1-methyl-3-(3-spiro[m-dioxane-5,2'-oxiran]-2-yl-1,2-benzisothiazol-5-yl)-6-(trifluoromethyl)uracil;

3-[3-(4,4-dimethyl-5-oxo-1,3-dioxolan-2-yl)-1,2-benzisothiazol-5-yl]-1-methyl-6-(trifluoromethyl)uracil;

3-[3-[4-(chloromethyl)-1,3-dioxolan-2-yl]-1,2-benzisothiazol-5-yl]-1-methyl-6-(trifluoromethyl)uracil;

3-[3-[4-(hydroxymethyl)-1,3-dioxolan-2-yl]-1,2-benzisothiazol-5-yl]-1-methyl-6-(trifluoromethyl)uracil;

3-[3-(4-isopropyl-2-oxazolin-2-yl)-1,2-benzisothiazol-5-yl]-1-methyl-6-(trifluoromethyl)uracil;

1-methyl-3-[3(2-oxazolin-2-yl)-1,2-benzisothiazol-5-yl]-6-(trifluoromethyl)uracil;

1-methyl-6-(trifluoromethyl)-3-[3-(4-vinyl-1,3-dioxolan-2-yl)-1,2-benzisothiazol-5-yl]uracil;

1-methyl-3-[3-(4-propyl-1,3-dioxolan-2-yl)-1,2-benzisothiazol-5-yl]-6-(trifluoromethyl)uracil;
1-methyl-3-[3-(4-phenyl-1,3-dioxolan-2-yl)-1,2-benzisothiazol-5-yl]-6-(trifluoromethyl)uracil;
3-[3-[4-(bromethyl)-1,3-dioxolan-2-yl]-1,2-benzisothiazol-5-yl]-1-methyl-6-(trifluoromethyl)uracil;
3-[3-[3-(bromomethl)-2-thienyl]-1,2-benzisothiazol-5-yl]-1-methyl-6-(trifluoromethyl)uracil;
3-[3-[3-(methoxymethyl)-2-thienyl]-1,2-benzisothiazol-5-yl]-1-methyl-6-(trifluoromethyl)uracil;
3-[3-(3,4-dimethyl-2-thienyl)-1,2-benzisothiazol-5-yl]-i-methyl-6-(trifluoromethyl)uracil;
3-[3-(3-furyl)-1,2-benzisothiazol-5-yl]-1-methyl-6-(trifluoromethyl)uracil;
1-methyl-3-[3-[4-[(methylthio)methyl]-1,3-dioxolan-2-yl]-1,2-benzisothiazol-5-yl]-6-(trifluoromethyl)uracil;
3-[3-[3-(hydroxymethyl)-2-thienyl]-1,2-benzisothiazol-5-yl]-1-methyl-6-(trifluoromethyl)uracil;
1-methyl-3-[3-[4-[(methylsulfonyl)methyl]-1,3-dioxolan-2-yl]-1,2-benzisothiazol-5-yl]-6-(trifluoromethyl)uracil;
1-methyl-3-[3-[4-[(methylsulfonyl)methyl]-1,3-dioxolan-2-yl]-1,2-benzisothiazol-5-yl]-6-(trifluoro-methyl)uracil;
1-methyl-3-[3-[4-[(methylsulfinl)methyl]-1,3-dioxolan-2-yl]-1,2-benzisothiazol-5-yl]-6-(trifluoromethyl)uracil;
[2-[5-[3,6-dihydro-3-methyl-2,6-dioxo-4-(trifluoromethyl)-1(2H)-pyrimidinyl]-1,2-benzisothiazol-3-l]-1,3-dioxolan-4-yl]methyl thiocyanate;
3-[3-(3,4-dihydro-3-oxo-2-quinoxalinyl)-1,2-benzisothiazol-5-yl]-1-methyl-6-(trifluoromethyl)uracil;
5-[5-[3,6-dihydro-3-methyl-2,6-dioxo-4-(trifluoromethyl)-1(2H)-pyrimidinyl]-1,2-benzisothiazol-3-yl]-1,6-hydro-6-oxo-2,3-pyrazinedicarbonitrile;
1-methyl-3-[3-(4-oxo-delta-2-1,2,5-thiadiazolin-3-yl)-1,2-benzisothiazol-5-yl]-6-(trifluoromethyl)uracil S',S'-dioxide;
3-[3-[2-(dimethylamino)-4-methoxy-5-oxo-2-imidazolin-4-yl]-1,2-benzisothiazol-5-yl]-1-methyl-6-(trifluoromethyl)uracil;
3-[3-(4-hydroxy-5-oxo-2-phenyl-2-imidazolin-4-yl)-1,2-benzisothiazol-5-yl]-1-methyl-6-(trifluoromethyl)uracil;
3-[3-(2-tert-butyl-4-hydroxy-5-oxo-2-imidazolin-4-yl)-1,2-benzisothiazol-5-yl]-1-methyl-6-(trifluoromethyl)uracil;
3-[3-(-hydroxy-5-imino-4,4-dimethyl-2-oxo-3-pyrrolidinyl)-1,2-benzisothiazol-5-yl]-1-methyl-6-(trifluoromethyl)uracil;
3-[3[4-methoxy-2-(methylimino) 5-oxo-4-imidazolidinyl]-1,2-benzisothiazol-5-yl]-1-methyl-6-(trifluoromethyl)uracil; and
3-[3[4-methoxy-2-(ethylimino)-5-oxo-4-imidazolidinyl]-1,2-benzisothiazol-5-yl]-1-methyl-6-(trifluoromethyl)uracil.

The Formula I compounds of the present invention are effective herbicidal agents useful for the control of a wide variety of undesirable plant species and for controlling weeds native to both dry land and wet land areas. The inventive compounds are effective in controlling the abovesaid plants when applied to the foliage thereof or to the soil or water containing seeds or other propagating organs thereof such as stolons, tubers or rhizomes, at rates of from about 0.01 kg/ha to 4 kg/ha and preferably from about 0.01 kg/ha to 1 kg/ha.

Advantageously, it has been found that the compounds of the invention are selective in the presence of soybeans or cereal crops such as corn, wheat and rice when applied preemergence or postemergence.

Beneficially, the formula I compounds may be used for the selective control of undesirable plant species in transplanted rice culture by applying a herbicidally effective amount of a formula I compound to the soil or water containing seeds or other propagating organs of said undesirable plant species after the rice has been transplanted.

Formula I compounds of this invention which are especially useful for the selective control of undesirable plant species in the presence of corn include
1-methyl-3-[3-(3-thienyl)-1,2-benzisothiazol-5-yl]-6-(trifluoromethyl)uracil;
3-[3-(3-chloro-2-thienyl)-1,2-benzisothiazol-5-yl]-1-methyl-6-(trifluoromethyl)uracil;
3-[3-(3,4-dimethyl-2-thienyl)-1,2-benzisothiazol-5-yl]-1-methyl-6-(trifluoromethyl)uracil;
3-[3-[(4R,5S)-4,5-dimethyl-1,3-dioxolan-2-yl]-1,2-benzisothiazol-5-yl]-1-methyl-6-(trifluoromethyl)uracil;
3-[3-[(4R,5R)-4,5-dimethyl-1,3-dioxolan-2-yl]-1,2-benzisothiazol-5-yl]-1-methyl-6-(trifluoromethyl)uracil; and
ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

Formula I compounds of the present invention which are particularly useful for the selective control of undesirable plant species in the presence of wheat include
1-methyl-3-[3-(3-thienyl)-1,2-benzisothiazol-5-yl]-6-(trifluoromethyl)uracil;
1-methyl-3-[3-(2-thienyl)-1,2-benzisothiazol-5-yl]-6-(trifluoromethyl)uracil;
1-methyl-3-[3-(3-methyl-2-thienyl)-1,2-benzisothiazol-5-yl]-6-(trifluoromethyl)uracil
1-methyl-3-[3-(5-methyl-2-thienyl)-1,2-benzisothiazol-5-yl]-6-(trifluoromethyl)uracil;
3-[3-(3-chloro-2-thienyl)-1,2-benzisothiazol-5-yl]-1-methyl-6-(trifluoromethyl)uracil;
3-[3-(3,4-dimethyl-2-thienyl)-1,2-benzisothiazol-5-yl]-1-methyl-6-(trifluoromethyl)uracil;
3-[3-(2,5-diethyl-3-thienyl)-1,2-benzisothiazol-5-yl]-1-methyl-6-(trifluoromethyl)uracil;
3-[3-(3-methoxy-2-pyridyl)-1,2-benzisothiazol-5-yl]-1-methyl-6-(trifluoromethyl)uracil;
3-[3-[(4R,5S)-4,5-dimethyl-1,3-dioxolan-2-yl]-1,2-benzisothiazol-5-yl]-1-methyl-6-(trifluoromethyl)uracil;
3-[3-[(4R,5S)-4,5-dimethyl-1,3-dioxolan-2-yl]-6-fluoro-1,2-benzisothiazol-5-yl]-1-methyl-6-(trifluoromethyl)uracil;
3-[3-[4-(hydroxymethyl)-1,3-dioxolan-2-yl]-1,2-benzisothiazol-5-yl]-1-methyl-6-(trifluoromethyl)uracil;
1-methyl-6-(trifluoromethyl)-3-[3-(4-vinyl-1,3-dioxolan-2-yl)-1,2-benzisothiazol-5-yl]uracil;
1-methyl-3-[3-(4-propyl-1,3-dioxolan-2-yl)-1,2-benzisothiazol-5-yl]-6-(trifluoromethyl)uracil;
3-[3-[4-(bromethyl)-1,3-dioxolan-2-yl]-1,2-benzisothiazol-5-yl]-1-methyl-6-(trifluoromethyl)uracil;
3-[3-(4-isopropyl-2-oxazolin-2-yl)-1,2-benzisothiazol-5-yl]-1-methyl-6-(trifluoromethyl)uracil; and
ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

Formula I compounds of this invention which are particularly useful for the selective control of undesirable plant species in the presence of soybeans include
1-methyl-3-[3-(3-thienyl)-1,2-benzisothiazol-5-yl]-6-(trifluoromethyl)uracil;
3-[3-(3-Methoxy-2-thienyl)-1,2-benzisothiazol-5-yl]-1-methyl-6-(trifluoromethyl)uracil;
1-methyl-3-[3-(5-methyl-2-thienyl)-1,2-benzisothiazol-5-yl]-6-(trifluoromethyl)uracil;

3-[3-(3-chloro-2-thienyl)-1,2-benzisothiazol-5-yl]-1-methyl-6-(trifluoromethyl)uracil;
3-[3-(3,4-dimethyl-2-thienyl)-1,2-benzisothiazol-5-yl]-1-methyl-6-(trifluoromethyl)uracil;
3-[3-(3-methoxy-2-pyridyl)-1,2-benzisothiazol-5-yl]-1-methyl-6-(trifluoromethyl)uracil;
1-methyl-3-[3-(5-methyl-2-pyridyl)-1,2-benzisothiazol-5-yl]-6-(trifluoromethyl)uracil;
3-[3-[4-(hydroxymethyl)-1,3-dioxolan-2-yl]-1,2-benzisothiazol-5-yl]-1-methyl-6-(trifluoromethyl)uracil;
1-methyl-3-[3-(2-pyrimidinyl)-1,2-benzisothiazol-5-yl]-6-(trifluoromethyl)uracil;
3-[3-[(4R,6S)-4,6-dimethyl-m-dioxan-2-yl]-6-fluoro-1,2-benzisothiazol-5-yl]-1-methyl-6-(trifluoromethyl)uracil; and
3-[3-(4-isopropyl-2-oxazolin-2-yl)-1,2-benzisothiazol-5-yl]-1-methyl-6-(trifluoromethyl)uracil.

Formula I compounds of this invention which are particularly useful for the selective control of undesirable plant species in the presence of transplanted rice include 1-methyl-3-[3-(5-methyl-2-thienyl)-1,2-benzisothiazol-5-yl]-6-(trifluoromethyl)uracil;
3-[3-(3-chloro-2-thienyl)-1,2-benzisothiazol-5-yl]-1-methyl-6-(trifluoromethyl)uracil;
3-[3-[(methoxymethyl)-2-thienyl]-1,2-benzisothiazol-5-yl]-1-methyl-6-(trifluoromethyl)uracil;
3-[3-(3,4-dimethyl-2-thienyl)-1,2-benzisothiazol-5-yl]-1-methyl-6-(trifluoromethyl)uracil;
3-[3-(2,5-diethyl-3-thienyl)-1,2-benzisothiazol-5-yl]-1-methyl-6-(trifluoromethyl)uracil;
3-[6-fluoro-3-(2-pyridyl)-1,2-benzisothiazol-5-yl]-1-methyl-6-(trifluoromethyl)uracil;
3-[3-(3-methoxy-2-pyridyl)-1,2-benzisothiazol-5-yl]-1-methyl-6-(trifluoromethyl)uracil;
1-methyl-3-[3-(5-methyl-2-pyridyl)-1,2-benzisothiazol-5-yl]-6-(trifluoromethyl)uracil;
3-[6-fluoro-3-(3-methyl-2-pyridyl)-1,2-benzisothiazol-5-yl]-1-methyl-6-(trifluoromethyl)uracil;
3-[3-(1,3-dioxolan-2-yl)-1,2-benzisothiazol-5-yl]-1-methyl-6-(trifluoromethyl)uracil;
3-[3-[(4R,5S)-4,5-dimethyl-1,3-dioxolan-2-yl]-1,2-benzisothiazol-5-yl]-1-methyl-6-(trifluoromethyl)uracil;
1-methyl-3-[3-(2-methyl-1,3-dioxolan-2-yl)-1,2-benzisothiazol-5-yl]-6-(trifluoromethyl)uracil;
3-[3-[(4R,5S)-4,5-dimethyl-1,3-dioxolan-2-yl]-6-fluoro-1,2-benzisothiazol-5-yl]-1-methyl-6-(trifluoromethyl)uracil;
1-methyl-6-(trifluoromethyl)-3-[3-(4-vinyl-1,3-dioxolan-2-yl)-1,2-benzisothiazol-5-yl]uracil;
1-methyl-3-[3-(4-propyl-1,3-dioxolan-2-yl)-1,2-benzisothiazol-5-yl]-6-(trifluoromethyl)uracil;
3-[3-(4-isopropyl-2-oxazolin-2-yl)-1,2-benzisothiazol-5-yl]-1-methyl-6-(trifluoromethyl)uracil;
1-methyl-3-[3-(2-thiazolyl)-1,2-benzisothiazol-5-yl]-6-(trifluoromethyl)uracil; and
ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

Formula I compounds of this invention which are particularly useful for total vegetation control include 3-[3-(1,3-dioxolan-2-yl)-1,2-benzisothiazol-5-yl]-1-methyl-6-(trifluoromethyl)uracil;
1-methyl-3-[3-(4-methyl-1,3-dioxolan-2-yl)-1,2-benzisothiazol-5-yl]-6-(trifluoromethyl)uracil;
3-[3-(1,3-dioxolan-2-yl)-6-fluoro-1,2-benzisothiazol-5-yl]-1-methyl-6-(trifluoromethyl)uracil;
3-[3-[4-(methoxymethyl)-1,3-dioxolan-2-yl]-1,2-benzisothiazol-5-yl]-1-methyl-6-(trifluoromethyl)uracil;
3-[3-[(4R,5S-)-4,5-dimethyl-1,3-dioxolan-2-yl]-6-fluoro-1,2-benzisothiazol-5-yl]-1-methyl-6-(trifluoromethyl)uracil;
3-(3-m-dioxan-2-yl-1,2-benzisothiazol-5-yl)-1-methyl-6-(trifluoromethyl)uracil;
3-[3-[(4R,6S)-4,6-dimethyl-m-dioxan-2-yl]-1,2-benzisothiazol-5-yl]-1-methyl-6-(trifluoromethyl)uracil; and
3-(3-m-dioxan-2-yl-6-fluoro-1,2-benzisothiazol-5-yl)-1-methyl-6-(trifluoromethyl)uracil.

While the compounds of this invention are effective for controlling undesirable plant species when employed alone, they may also be used in combination with or in conjunction with one or more other biological chemicals, including herbicides.

The compounds of this invention may be applied to the foliage of undesirable plant species or to the soil or water containing seeds or other propagating organs thereof in the form of a solid or liquid herbicidal composition, comprising a herbicidally effective amount of the desired compound dispersed or dissolved in an agronomically acceptable, inert solid or liquid carrier. The compositions may be applied as preemergence or postemergence treatments.

The formula I compounds of the present invention may be formulated as emulsifiable concentrates, wettable powders, granular formulations, suspension concentrates, flowable concentrates and the like.

Formula I compounds wherein Q is $Q_1$, $Q_2$, $Q_3$, $Q_5$, $Q_6$, $Q_7$, $Q_9$, $Q_{10}$, $Q_{11}$, $Q_{12}$, $Q_{13}$, $Q_{14}$, $Q_{16}$, $Q_{17}$, $Q_{18}$, $Q_{19}$, $Q_{20}$, $Q_{22}$, $Q_{24}$, $Q_{25}$, $Q_{36}$ and $Q_{40}$ may be prepared from 5-aminobenzisothiazoles and 5-aminobenzisoxazoles of Formula II

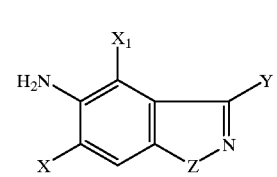

(II)

wherein X, $X_1$, Z and Y are as described hereinabove, using essentially the same procedures as described in U.S. Pat. Nos. 5,484,763 and 5,523,278.

Formula I compounds wherein Q is $Q_8$ may be prepared by reacting an amine of formula II with a substituted tetrahydrofuran of formula III as shown below in Flow Diagram I.

FLOW DIAGRAM I

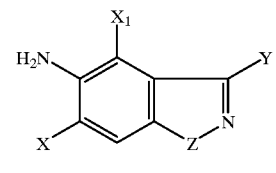

(II)

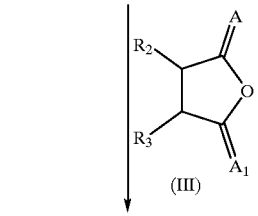

(III)

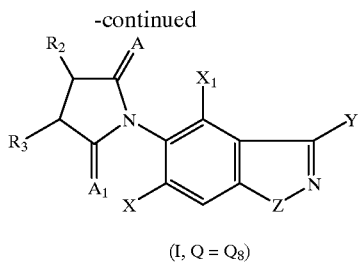

(I, Q = Q$_8$)

Formula I compounds wherein Q is Q$_4$ may be prepared from formula I compounds wherein Q is Q$_8$ using essentially the same procedures used to prepare formula I compounds wherein Q is Q$_3$ from formula I compounds wherein Q is Q$_7$.

Compounds of formula I wherein Q is Q$_{15}$ may be prepared by reacting an amine of formula II with a substituted tetrahydrofuran of formula III to form an acid-amide of formula IV, and dehydrating the acid-amide with a dehydrating agent such as 1,3-dicyclohexyl-carbodiimide. The reaction scheme is shown below in Flow Diagram II.

FLOW DIAGRAM II

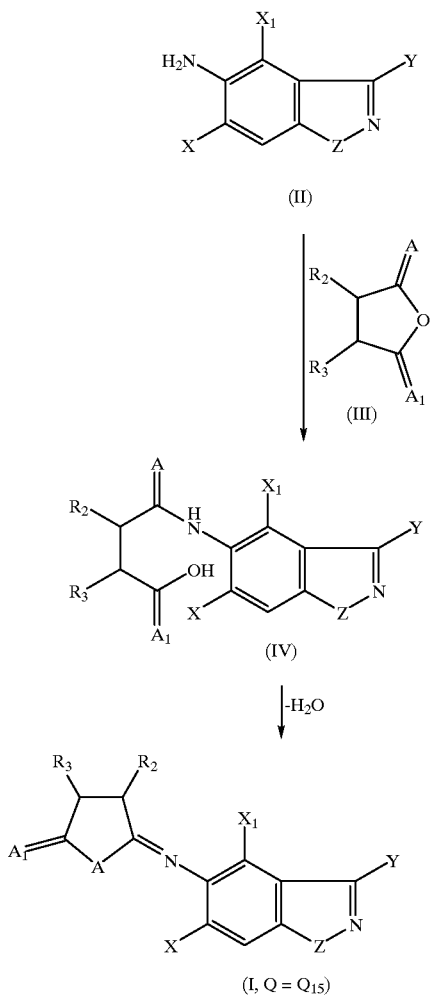

(I, Q = Q$_{15}$)

Formula I compounds wherein Q is Q$_{21}$ may be prepared from formula I compounds wherein Q is Q$_8$ using essentially the same procedure used to prepare formula I compounds wherein Q is Q$_{20}$ from formula I compounds wherein Q is Q$_7$.

Compounds of formula I wherein Q is Q$_{23}$ may be prepared by converting an amine of formula II to its corresponding isocyanate or isothiocyanate of formula V using standard methods such as phosgene or thiophosgene in an inert solvent or palladium chloride and carbon monoxide, reacting the formula V compound with a substituted hydrazine of formula VI to form an intermediate compound of formula VII, and reacting the formula VII compound with an ester of formula VIII. The reaction scheme is shown in Flow Diagram III.

FLOW DIAGRAM III

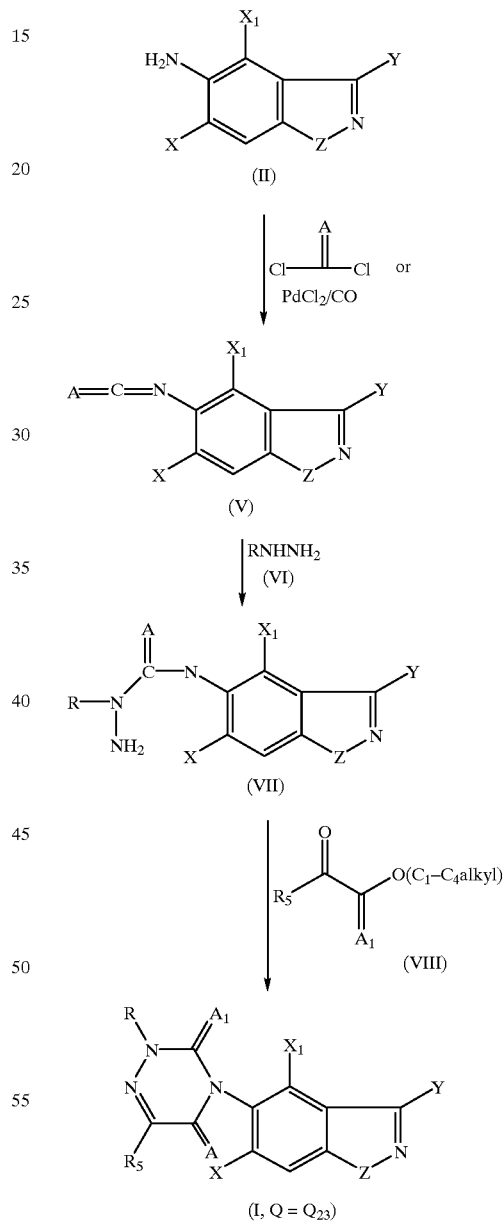

(I, Q = Q$_{23}$)

Formula I compounds wherein Q is Q$_{26}$ may be prepared by reacting an amine of formula II with a β-aminoacrylic acid chloride of formula IX to form an intermediate compound of formula X, and reacting the intermediate compound with an acid chloride of formula XI. The reaction scheme is shown in Flow Diagram IV.

FLOW DIAGRAM IV

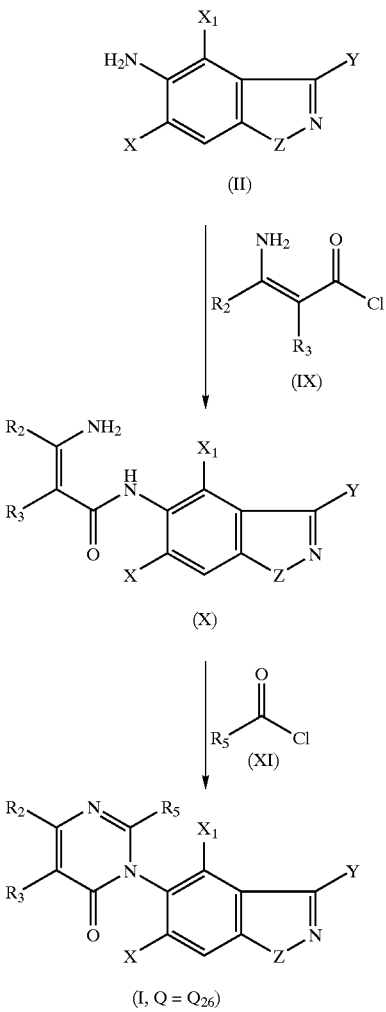

Compounds of formula I wherein Q is $Q_{27}$ may be prepared by reacting an amine of formula II with an acid chloride of Formula XII to form an intermediate compound of formula XIII, and reacting the intermediate compound (after deprotection) with an acid chloride of formula XI. The reaction sequence is shown below in Flow Diagram V.

FLOW DIAGRAM V

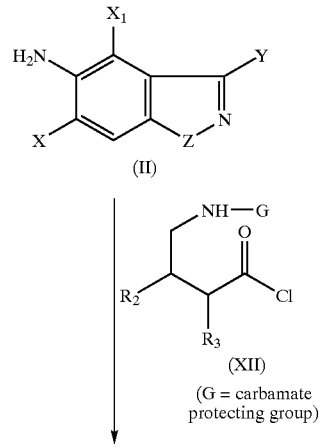

(G = carbamate protecting group)

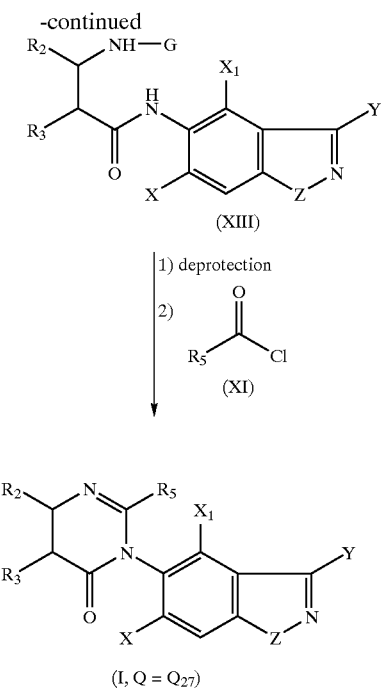

Formula I compounds wherein Q is $Q_{28}$ may be prepared by reacting an amine of formula II with an unsaturated lactone of formula XIV as shown below in Flow Diagram VI.

FLOW DIAGRAM VI

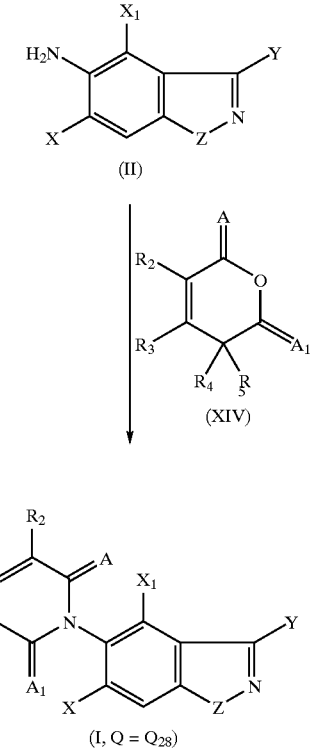

Similarly, formula I compounds wherein Q is $Q_{29}$ may be prepared by reacting an amine of formula II with a lactone of formula XV. The reaction scheme is shown in Flow Diagram VII.

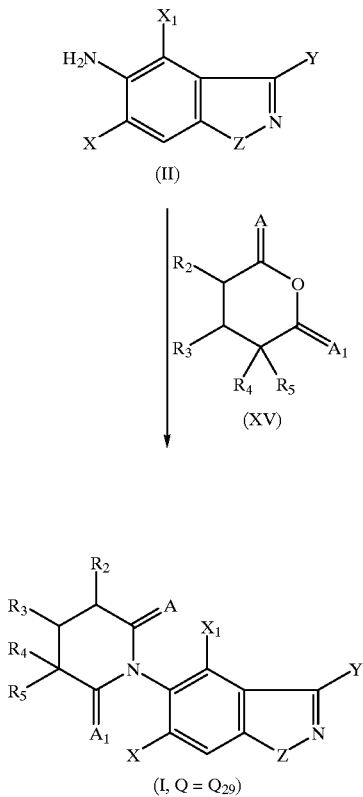

Compounds of formula I wherein Q is $Q_{30}$ may be prepared, as shown in Flow Diagram VIII, by reacting an isocyanate or isothiocyanate of formula V with an unsaturated lactone of formula XVI at an elevated temperature.

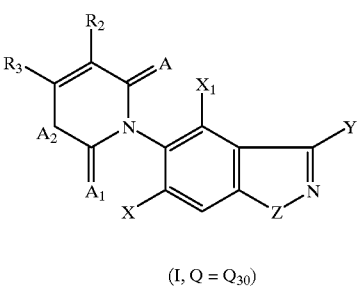

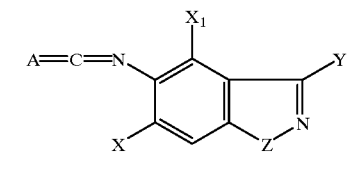

Similarly, formula I compounds wherein Q is $Q_{31}$ may be prepared by reacting an isocyanate or isothiocyanate of formula V with a lactone of formula XVII at an elevated temperature. The reaction scheme is shown in Flow Diagram IX.

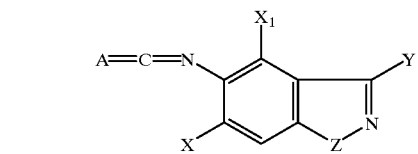

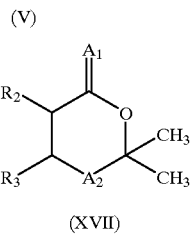

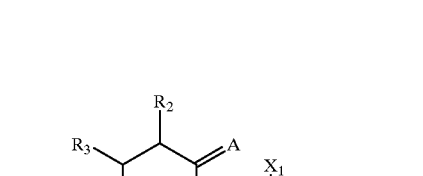

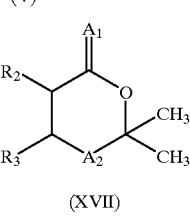

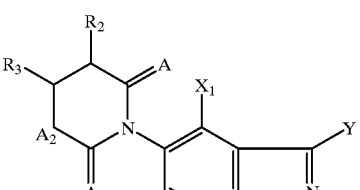

Formula I compounds wherein Q is $Q_{34}$ may be prepared, as shown in Flow Diagram X, by reacting an isocyanate or isothiocyanate of formula V with a substituted hydrazine of formula XVIII to form an intermediate compound of formula XIX, and reacting the formula XIX compound with an acetal of formula XX at an elevated temperature.

FLOW DIAGRAM X

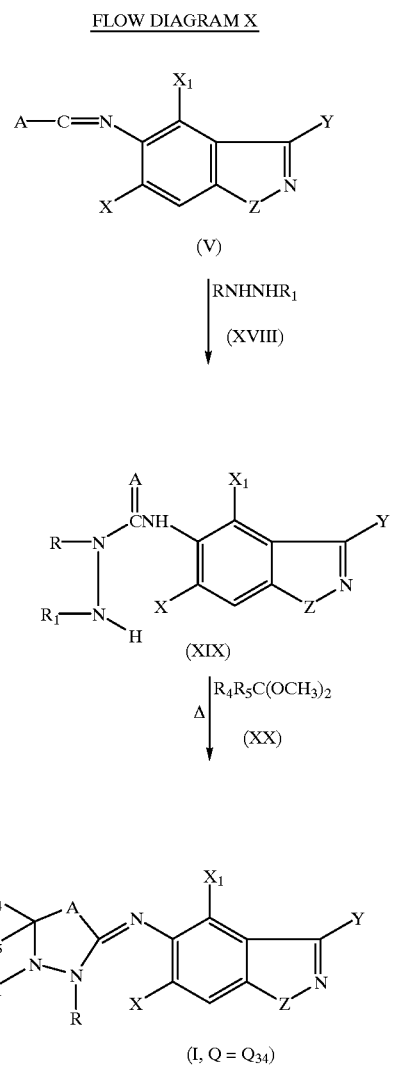

Formula I compounds wherein Q is $Q_{37}$ may be prepared, as shown in Flow Diagram XI, by reacting an isocyanate or isothiocyanate of formula V with an amine of formula XXI to form an intermediate of formula XXII, and reacting the intermediate with an α-haloketone of formula XXIII.

FLOW DIAGRAM XI

Compounds of formula II wherein Q is $Q_{38}$ may be prepared, as shown below in Flow Diagram XII, by reacting a urea or thiourea of formula VII with an acid chloride of formula XXIV.

FLOW DIAGRAM XII

Formula I compounds wherein Q is $Q_{39}$ may be prepared by reacting an amine of formula II with a chloride compound of formula XXV to form an intermediate compound of formula XXVI, and reacting the intermediate compound with hydrogen sulfide, hydrogen chloride and sodium periodate. The reaction scheme is shown in Flow Diagram XIII.

FLOW DIAGRAM XIII

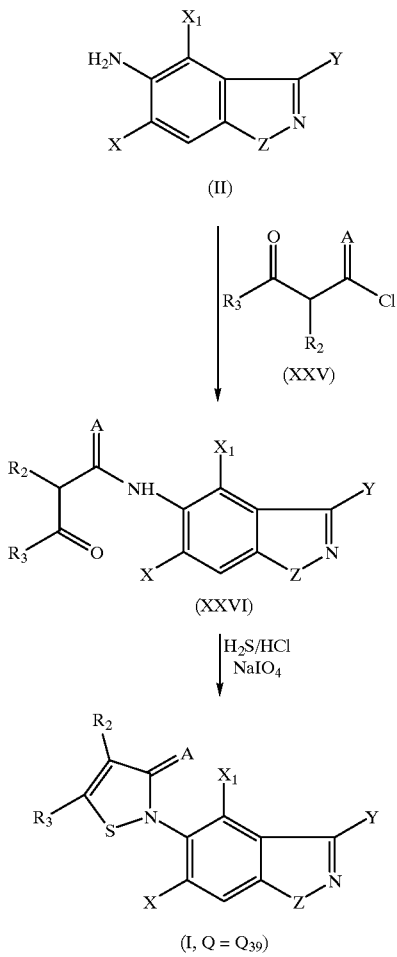

Compounds of formula I wherein Q is $Q_{35}$ may be prepared from amine compound II by treatment with nitrous acid to form an intermediate diazonium salt XXVII followed by treatment with cuprous cyanide and heating to afford intermediate cyano compound of formula XXVIII. Treatment of intermediate cyano compound XXVIII with a substituted hydrazine of formula VI to form an intermediate compound of formula XXIX, and reacting the intermediate compound with an acid chloride of formula XXX. The reaction scheme is show in Flow Diagram XIV.

FLOW DIAGRAM XIV

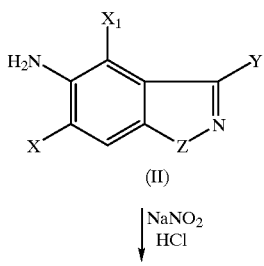

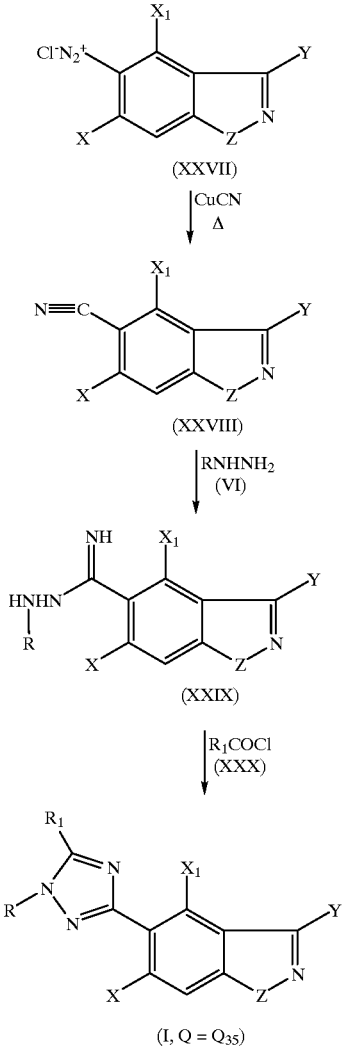

Compounds of formula I wherein Q is $Q_{33}$ may be prepared, as shown in Flow Diagram XV, by acylating a compound of formula XXXI with acetyl chloride and aluminum chloride to form an acetophenone of formula XXXII, reacting the acetophenone compound with an ester of formula XXXIII in the presence of a base to form a diketone compound of formula XXXIV, and reacting the formula XXXIV compound with a substituted hydrazine of formula VI.

FLOW DIAGRAM XV

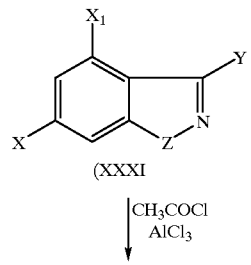

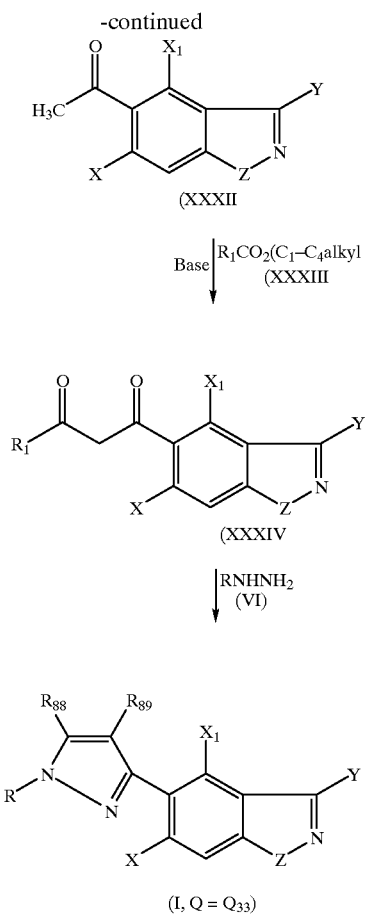

Further methods to prepare compound I with Q=$Q_{33}$ may be taken from EP-A361,164 and WO92/02503 Compounds of formula I wherein Q is $Q_{32}$ may be prepared as shown in Flow Diagram XVI by reacting an isocyanate or isothiocyanate of formula V with an amidine of formula XXXV to form an intermediate of formula XXXVI, reacting the formula XXXVI compound with phosgene or thiophosgene to form an intermediate of formula XXXVII, and alkylating the formula XXXVII compound with a halide of formula XXXVIII.

FLOW DIAGRAM XVI

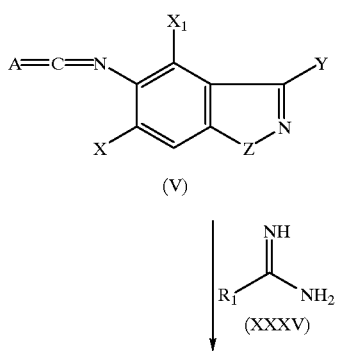

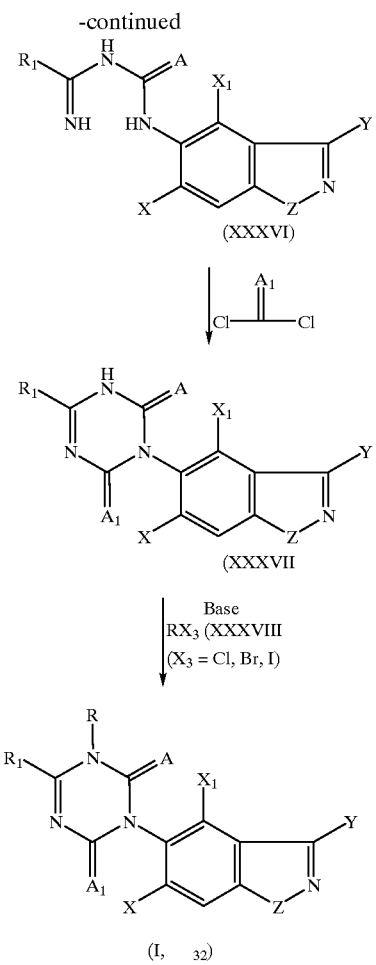

A preferred method for the preparation of formula I compounds wherein Q is $Q_{24}$ is shown in Flow Diagram XVII, wherein an amine of formula II is reacted with an oxazinone of formula XXXIX in the presence of an organic acid or base to form an intermediate compound of formula XL, which is alkylated with a halide of formula XXXVIII.

FLOW DIAGRAM XVII

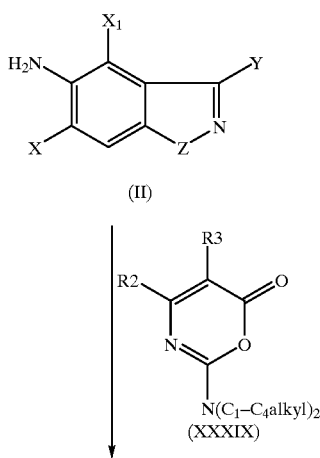

-continued

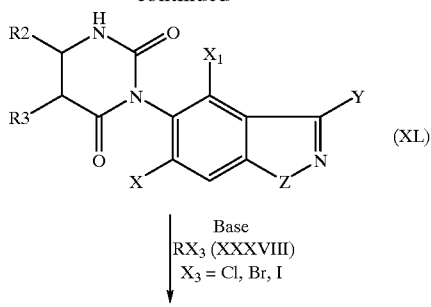

(XL)

Base
RX₃ (XXXVIII)
X₃ = Cl, Br, I

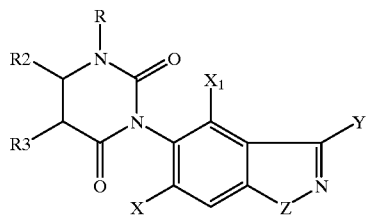

Formula I compounds wherein Q is $Q_{24}$ and the intermediates of formula XL may also be prepared from the amines II by using essentially the same procedures as described in W) 97/08171, WO 99/14216, WO 00/28822 amd DE-A 197,195.

Another preferred method for the preparation intermediates of formula XL is shown in Flow Diagram XVIII, by reaction of an amine of formula II with a urea of Formula XLI in the presence of an acid or base, wherein $R_{82}$ and $R_{83}$ are each independently $C_1$–$C_6$ alkyl or $R_{82}$ and $R_{83}$ may be taken together with the atom to which they are attached to form a 5-or 6-membered ring optionally containing one oxygen atom.

FLOW DIAGRAM XVIII

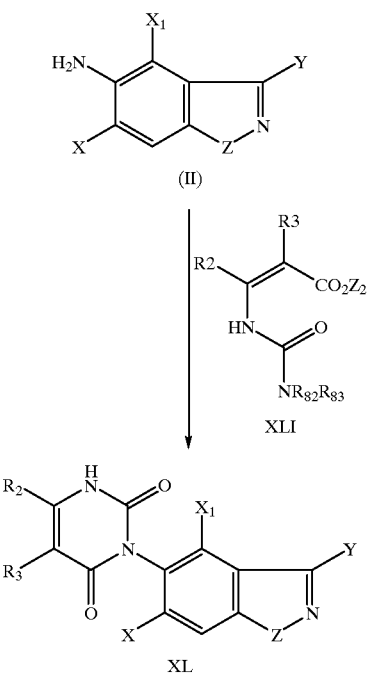

The compound of Formula XL is then reacted in the presence of Base with a compound of Formula XXXVIII (RX₃, where $X_3$ is Cl, Br, I) to obtain the compound of Formula I wherein Q is $Q_{24}$.

An alternate method for the preparation of formula I compounds wherein Q is $Q_{24}$ is shown in Flow Diagram XIX, wherein an amine of formula II is reacted with a carbamate of formula XLII wherein $R_{84}$ is $C_1$–$C_6$ alkyl, benzyl, $C_2$–$C_6$ alkenyl, $C_2$–$C_6$ alkynyl or $C_3$–$C_7$ cycloalkyl and $Z_2$ is $C_1$–$C_6$ alkyl.

FLOW DIAGRAM XIX

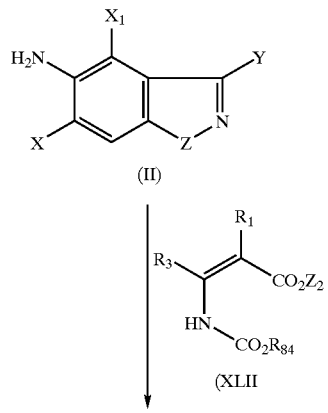

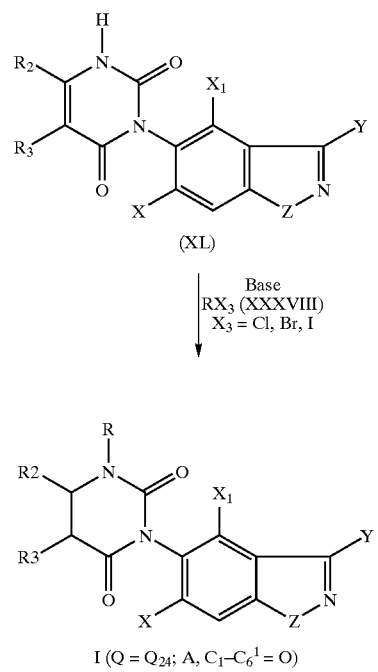

I (Q = $Q_{24}$; A, $C_1$–$C_6^1$ = O)

5-Aminobenzisothiazole and 5-aminobenzisoxazole compounds of formula II can be prepared by reduction of 5-nitro intermediates of formula XLIV as shown in Flow Diagram XX using standard conditions such as iron in acetic acid, stannous chloride and hydrochloric acid, or dithionite. The 5-nitro intermediates XLIV can be prepared from ketones of formula XLIII by methods described in U.S. Pat. No. 5,484,763, also shown in Flow Diagram XX.

FLOW DIAGRAM XX

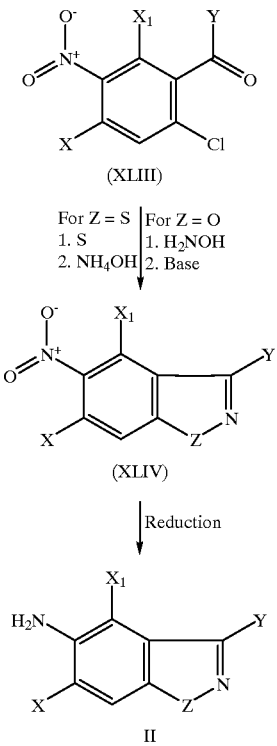

Alternatively, 5-aminobenzisothiazoles of formula II may be prepared as shown in Flow Diagram XXI. Nitration of ketones of formula XLV followed by reduction of the resulting intermediates XLVI affords amines of formula XLVII. Treatment of formula XLVII compounds with sodium isothiocyanate and bromine in the presence of acid affords intermediate isothiocyanate compounds of formula XLVIII, which on treatment with ammonium hydroxide in methanol afford 5-aminobenzisothiazole compounds of formula II (Z=S).

FLOW DIAGRAM XXI

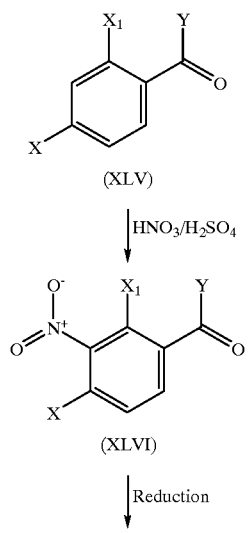

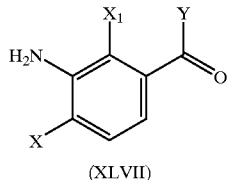

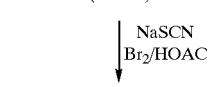

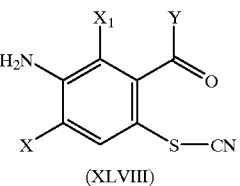

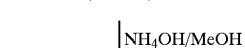

Ketones of formula XLIII where Y is Y1 may be prepared by reaction of organolithium reagents XLIX with zinc chloride followed by coupling with acid chloride LI in the presence of a palladium catalyst as shown in Flow Diagram XXII. Under essentially the same conditions, ketones of formula XLIII where Y is Y2 are prepared from organometallic reagents L. Organometallic reagents XLIX and L may be prepared by standard methods such as direct deprotonation of the heterocycle Y, or by halogen-metal exchange with a halogenated heterocycle Y.

FLOW DIAGRAM XXII

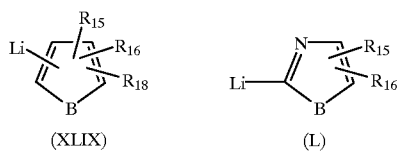

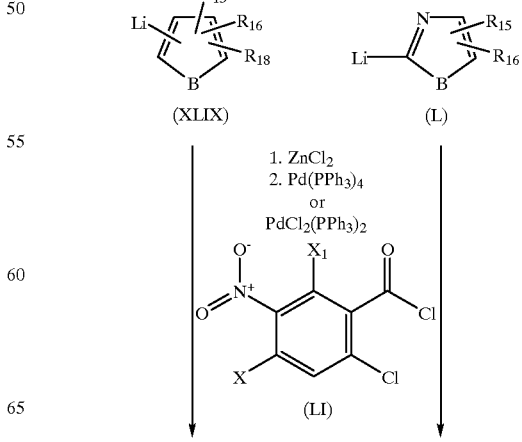

-continued

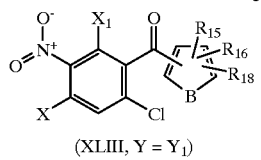
(XLIII, Y = Y$_1$)

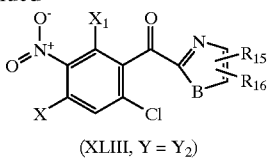
(XLIII, Y = Y$_2$)

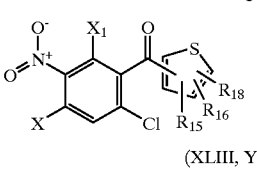
(XLIII, Y = Y$_1$, B = S)

Ketones of formula XLIII wherein Y$_1$ is a substituted 2-furanyl radical may additionaly be prepared by reaction of organotin reagent LII with acid chloride LI as shown in Flow Diagram XXIII.

FLOW DIAGRAM XXIII

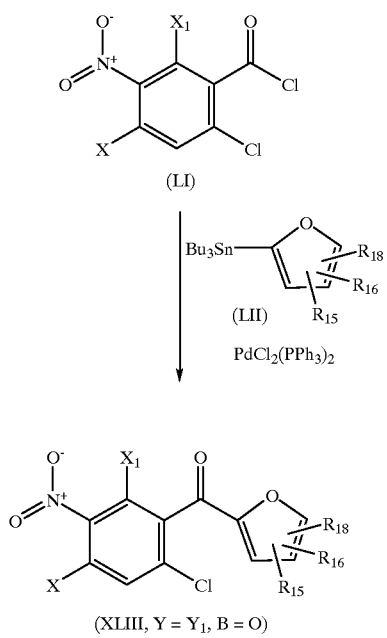

Ketones of formula XLIII wherein Y$_1$ is a substituted 2- or 3-thienyl radical may additionally be prepared by reaction of thiophene LIV with acid chloride LI, in the presence of a Lewis acid such as aluminum chloride as shown in Flow Diagram XLIII. Alternatively, ketones of formula XLIV wherein Y$_1$ is a substituted 2-thienyl radical may be prepared by treatment of acid LIII with thiophene LIV in the presence of phosphorous pentoxide.

FLOW DIAGRAM XXIV

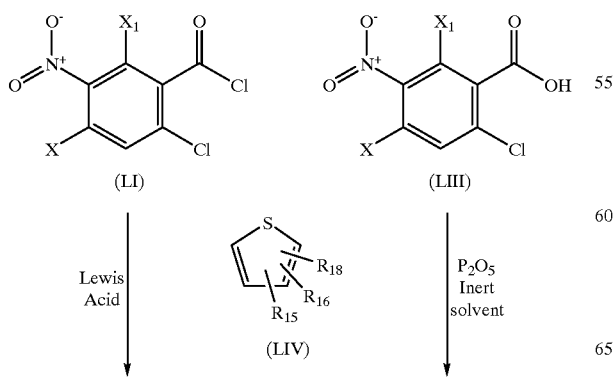

Ketones of formula XLIII wherein Y is Y$_3$ may be prepared by treatment of nitrile LV with lithiated pyridine LVI followed by acid hydrolysis to afford intermediate ketone compound LVII, which is nitrated under standard conditions as depicted in Flow Diagram XXV. Lithiated pyridine XLVI may be prepared from the corresponding bromopyridine by treatment with n-butyllithium.

FLOW DIAGRAM XXV

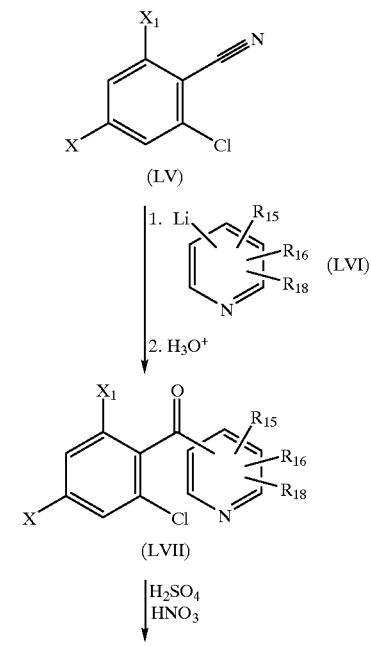

Ketones of formula XLIII wherein Y is Y$_5$ may be prepared by heating nitrile LVIII with bromopyrimidine LIX to afford intermediate LX, which on oxidation yields ketone LXI, which can be nitrated as depicted in Flow Diagram XXVI.

FLOW DIAGRAM XXVI

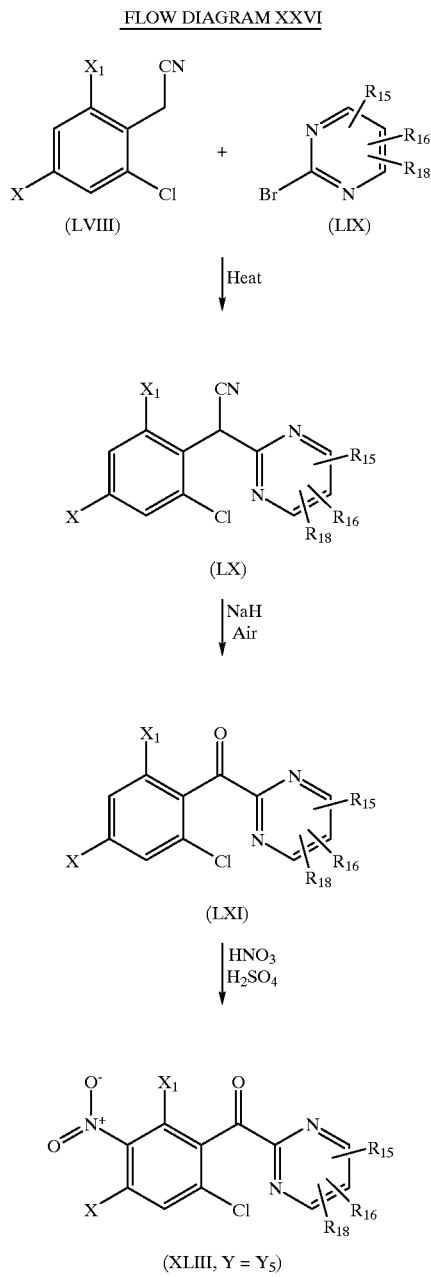

(XLIII, Y = Y5)

The aformentioned nitro ketones of formula XLIII where where Y is Y1, Y2, Y3 and Y5 may be converted into nitro intermediate XLIV and amino intermediate II by the methods shown in Flow Diagram XX.

Ketones of formula XLV wherein Y is Y3 may be prepared by reaction of nitrile LXII with organolithium reagent LXIV followed by hydrolysis under acidic conditions as shown in Flow Diagram XXVII. Alternatively, ketones XLV wherein Y is Y3 may be prepared by reaction of Grignard reagent LXIII with pyridylnitrile LXV followed by hydrolysis under acidic conditions as shown in Flow Diagram XXVII.

FLOW DIAGRAM XXVII

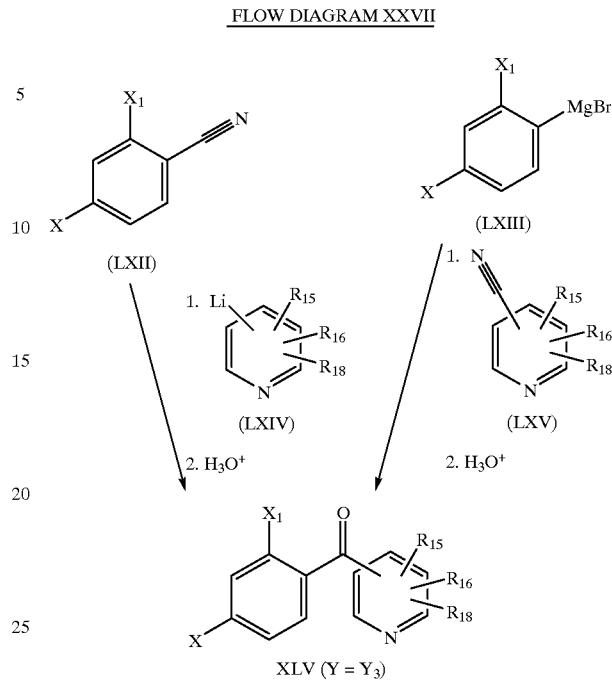

XLV (Y = Y3)

The aforementioned ketones XLV wherein Y is Y3 may be converted to 5-aminobenzisoxazoles and 5-aminobenzthiazoles wherein Y is Y3 by the method outlined in Flow Diagram XXI.

Compounds of formula I wherein Y is Y2 and B=S additionally may be prepared by treatment of thioamide LXVI with a bromoketone of formula LXVII in the presence of base as shown in Flow Diagram XXVIII.

FLOW DIAGRAM XXVIII

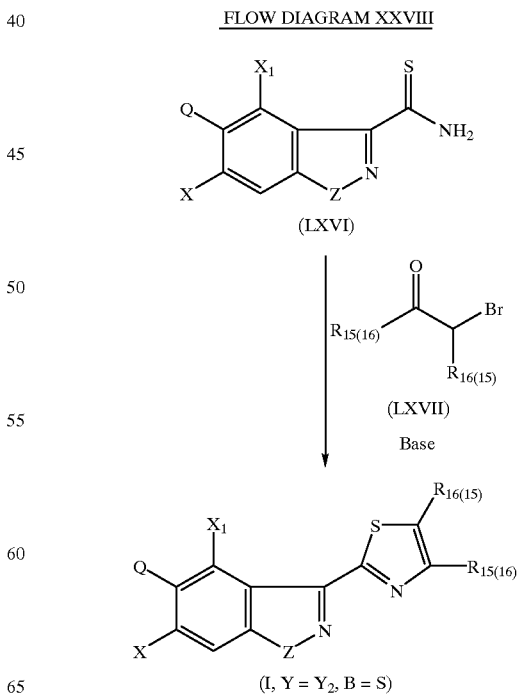

Intermediate thioamide compound of formula LXVI can be prepared by standard methods such as treatment amide compound of formula LXX with Lawesson's reagent or phosphorous pentasulfide. Formula LXX amides are prepared from acid LXVIII by treatment of its acid chloride derivative LXIX with ammonia as depicted in Flow Diagram XXIX.

afford a mixture of monobromo (LXXII) and dibromo (LXXIII) intermediate compounds, subsequent oxidation of this mixture with silver tetrafluoroborate to afford a mixture of alcohol LXXIV and aldehyde LXXV, and final oxidation of this mixture with potassium dichromate in the presence of acid as shown in Flow Diagram XXX.

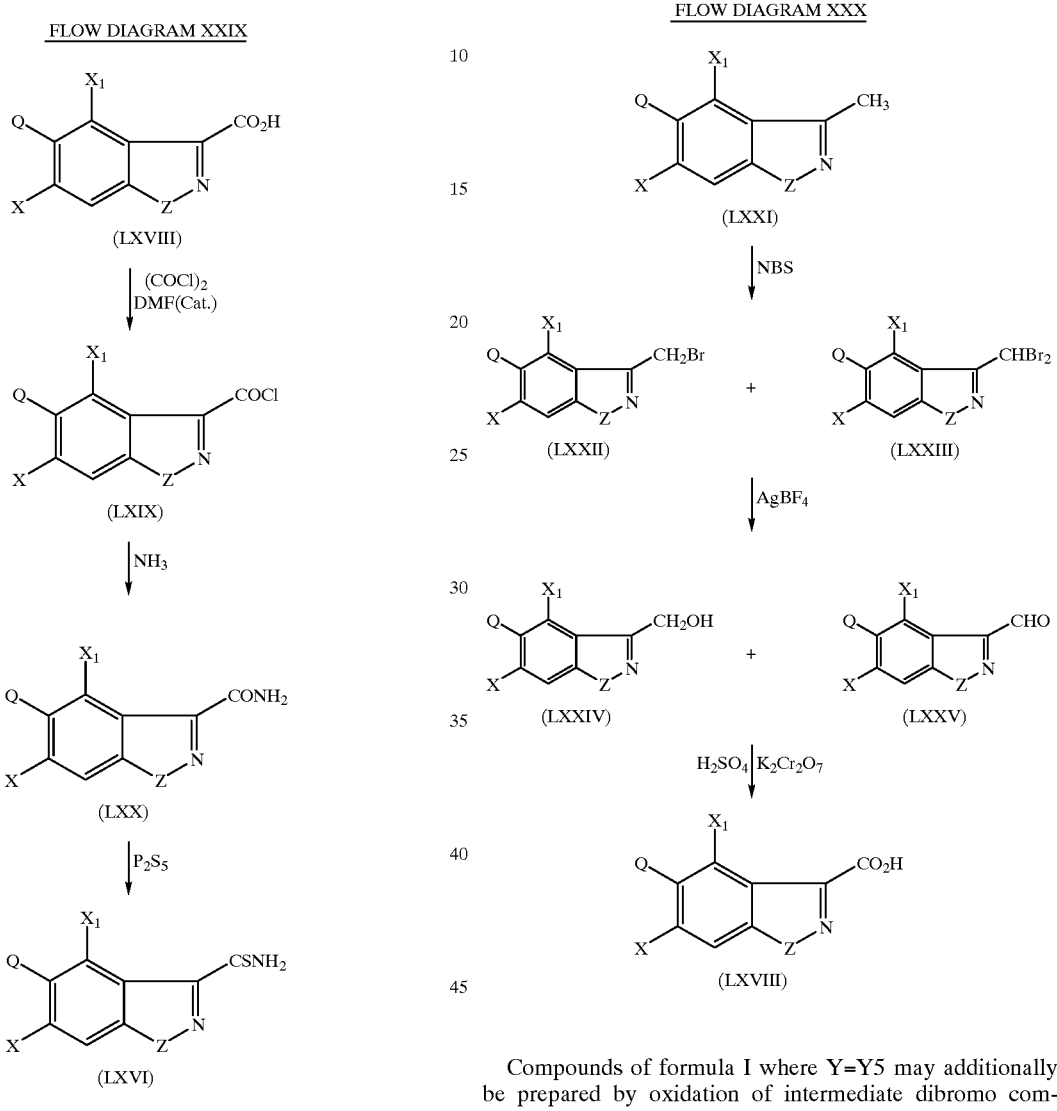

Intermediate acid compounds of formula LXVIII may be prepared by bromination of methyl intermediate LXXI to Compounds of formula I where Y=Y5 may additionally be prepared by oxidation of intermediate dibromo compound LXXIII to aldehyde LXXV followed by reaction with diketone LXXVI or imino ester LXXVII as depicted in Flow Diagram XXXI.

FLOW DIAGRAM XXXI

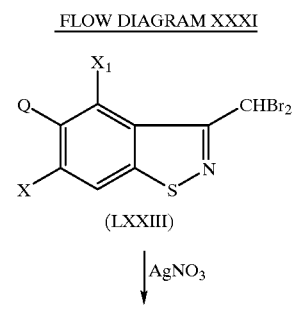

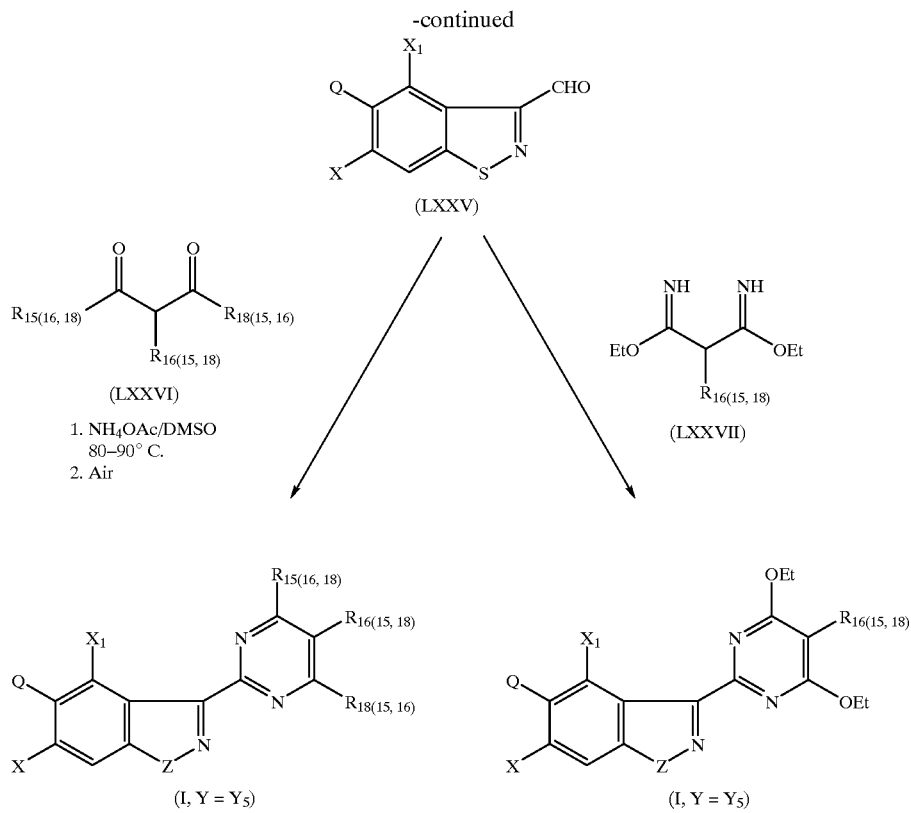

Compounds of formula I wherein Y is Y4 may be prepared by oxidation of pyridyl compounds of formula I (Y=Y3) with peracid under standard conditions as shown in Flow Diagram XXXII.

FLOW DIAGRAM XXXII

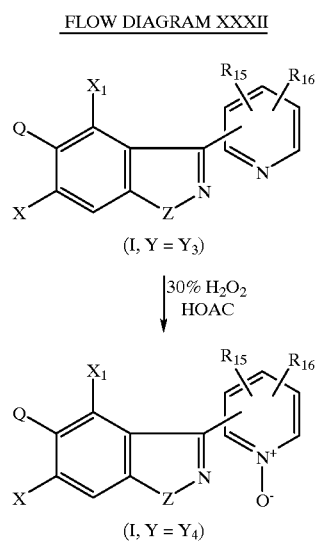

Nitro intermediates XLIV and benzisothiazoles and benzisozaxoles II wherein Y is $Y_6$ may be prepared from 3-chloro intermediate compounds LXXVIII and LXXIX respectively by treatment with pyrazole LXXX in the presence of an organic base as shown in Flow Diagram XXXIII.

FLOW DIAGRAM XXXIII

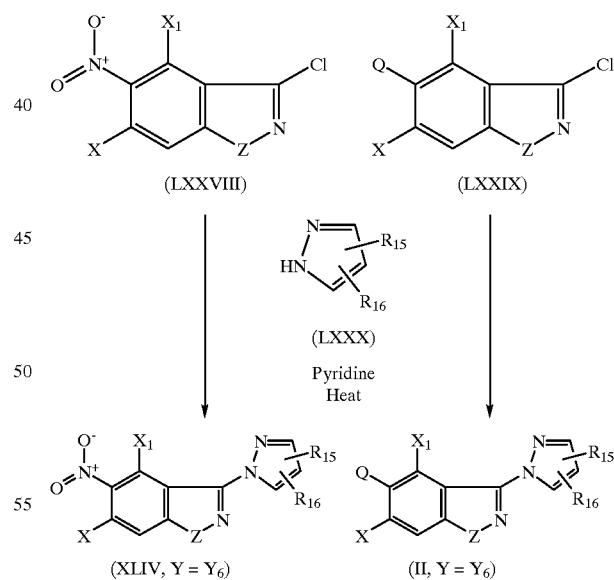

Nitro intermediate compounds LXXVIII are prepared from acid intermediate LIII by conversion to disulfide LXXXI by sequential treatment with base, sodium sulfide, and acid as depicted in Flow Diagram XXXIV. Intermediate disulfide compound LXXXI is converted to intermediate benxisothiazolone LXXXII by sequential treatment with thionyl chloride, bromine and ammonia, and this product then treated with phosphorous oxychloride in the presence of base.

FLOW DIAGRAM XXXIV

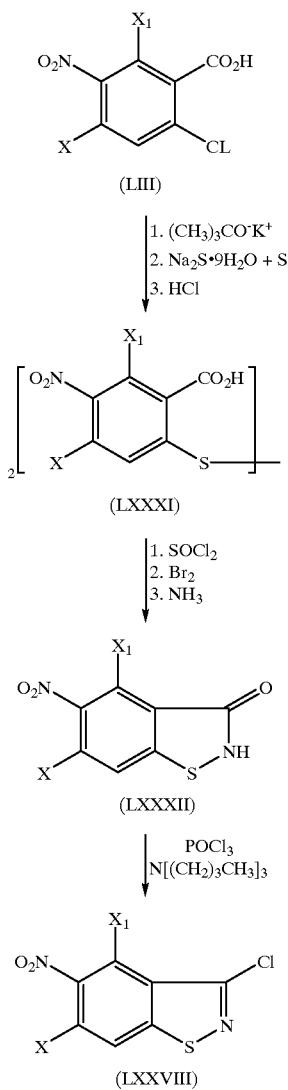

Benzisothiazole and benzisozaxole intermediate compound LXxix is prepared as shown in Flow Diagram XXXV from nitro intermediate LXXVIII by reduction to amino intermediate LXXXIII under standard conditions such as iron in the presence of acid, followed by elaboration of the amino functionality to Q groups as described in U.S. Pat. Nos. 5,484,763, 5,523,278 and Flow Diagrams I–XIX.

FLOW DIAGRAM XXXV

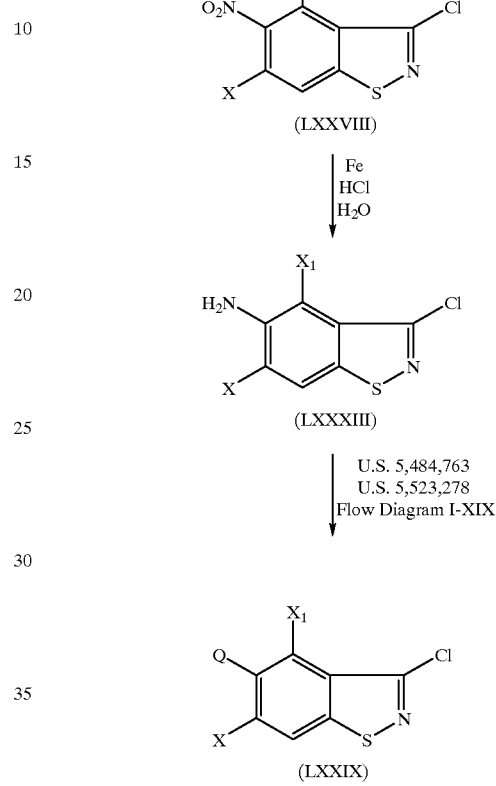

Compounds of formula I wherein Y is Y7 and Y8 may be prepared as shown in Flow Diagram XXXVI by treatment of acid chloride intermediate compound LXIX with organozinc reagent of formula LXXXIV to afford intermediate ketone compound LXXXV, which is acylated with acid chloride LXXXVI in the presence of base to afford intermediate diketone of formula LXXXVII. Diketone LXXXVII is treated with hydrazine to afford a mixture of pyrazole regioisomers LXXXVIII and LXXXIX, which is alkylated with an alkyl halide of formula XC to yield a mixture of regioisomeric pyrazoles which can be separated by column chromatography or fractional crystallization.

FLOW DIAGRAM XXXVI

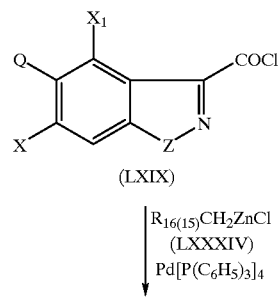

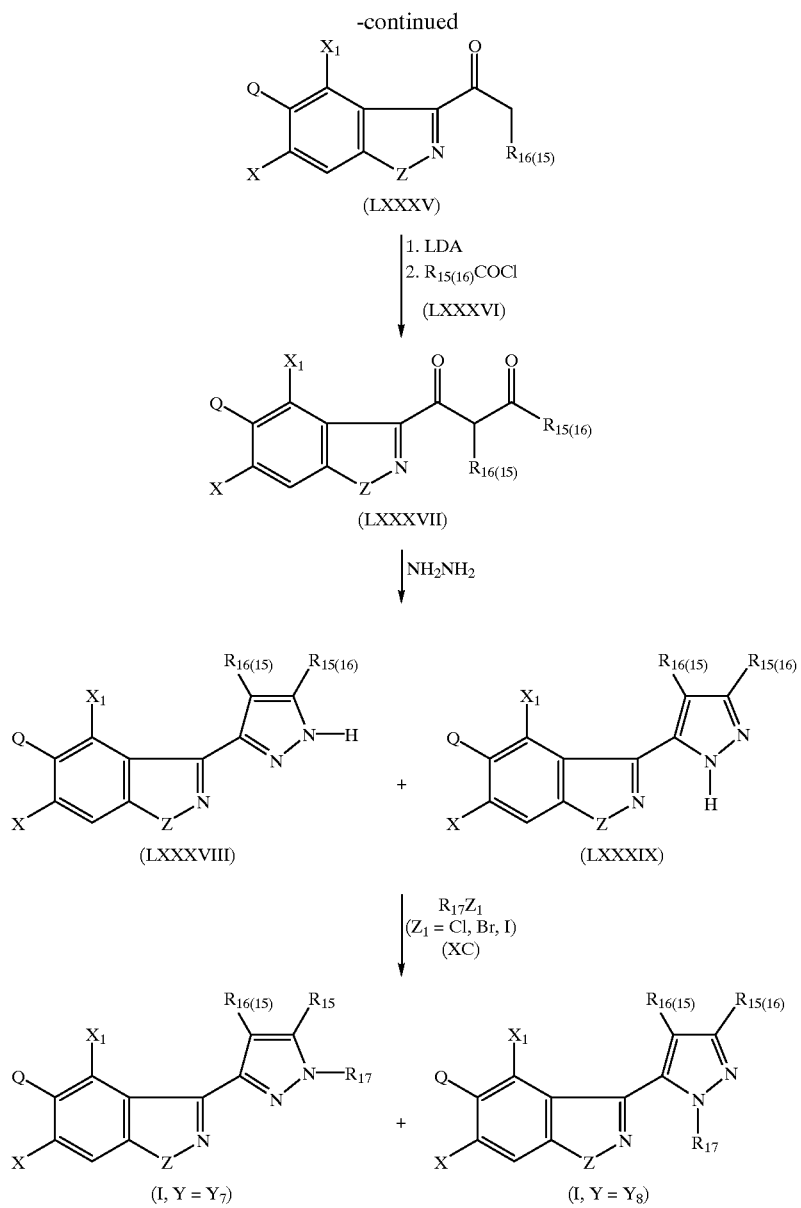
Compounds of formula I wherein Y is Y9 may be prepared as shown in Flow Diagram XXXVII by bromination of intermediate ketone of formula LXXXV and subsequent treatment of bromoketone intermediate XCI with thioamide XCII.
FLOW DIAGRAM XXXVII
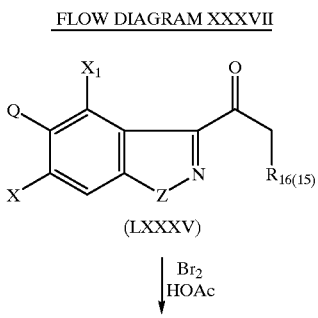

-continued

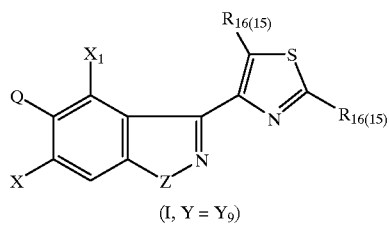

(I, Y = Y$_9$)

Compounds of formula I wherein Y is Y10 may be prepared as shown in Flow Diagram XXXVIII by reaction of acid chloride intermediate LXIX with amine compound XCIII to afford intermediate amide XCIV, which on sequential treatment with thionyl chloride followed by sodium hydride yields the compound of formula I wherein B=O. Alternatively, treatment of amide XCIV with phosphorous pentasulfide yields thioamide compound XCV, which on treatment with sodium hydride yields the compound wherein B=S. Treatment of amide XCIV with amine XCVI under dehydrating conditions affords compound I wherein B=NR17.

FLOW DIAGRAM XXXVIII

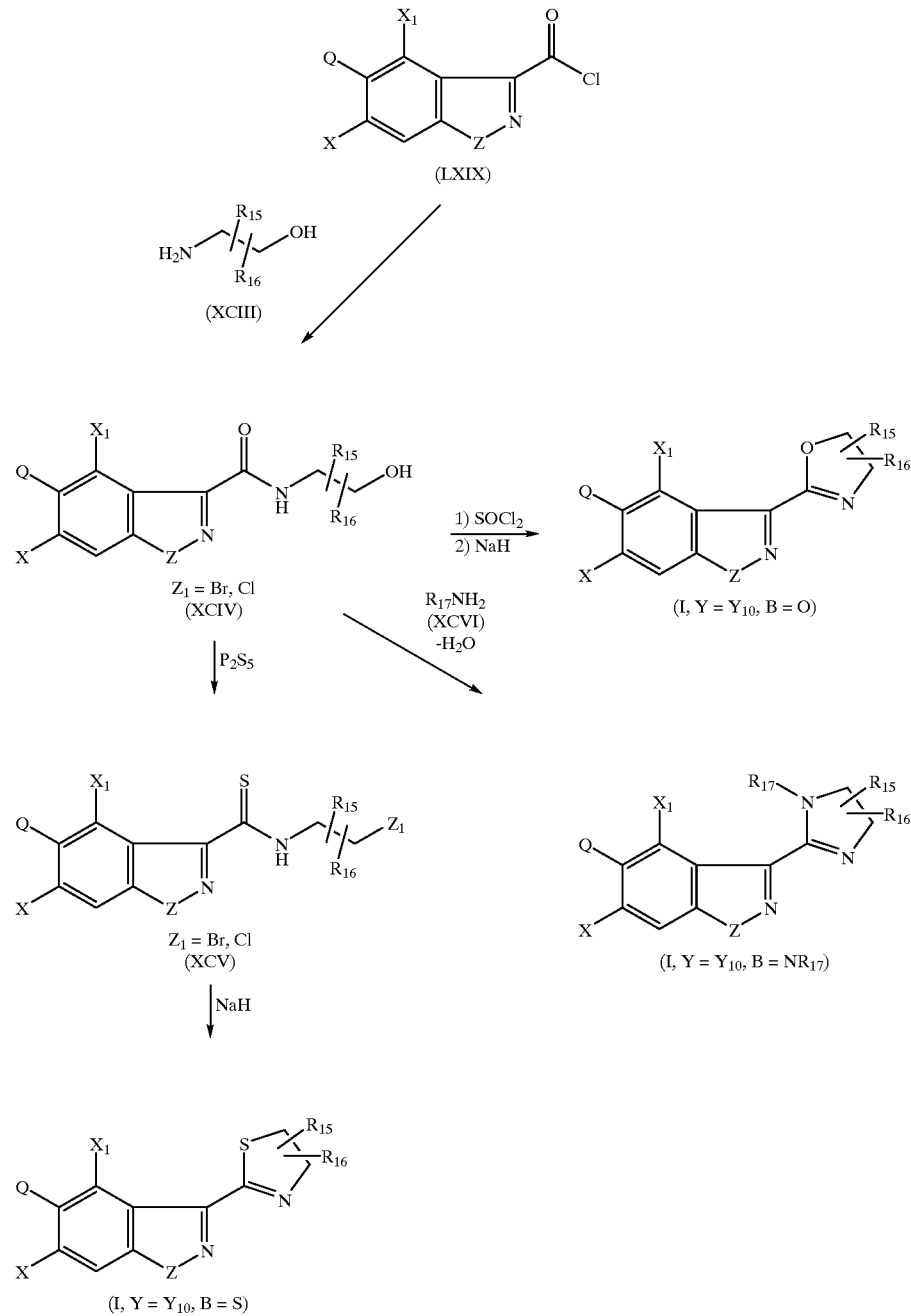

Compounds of formula I wherein Y is Y11 may be prepared as shown in Flow Diagram XXXIX by reaction of acid chloride LXIX with hydrazide XCVII to afford Intermediate hydrazide of formula XCVIII, which on treatment with phosphorous oxychloride and phosphorous pentasulfide yields compounds of formula I wherein B=O and B=S respectively.

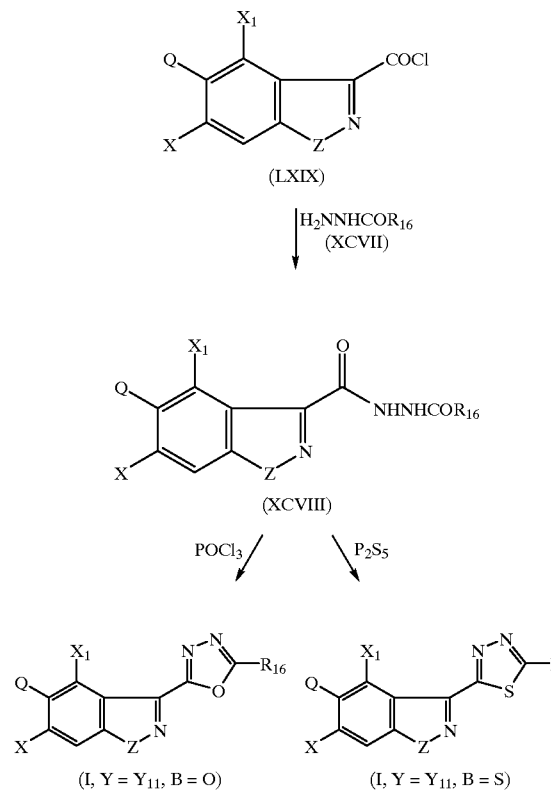

Treatment of acid chloride LXIX with amide XCIX affords amide intermediate C, which on treatment with hydrazine in the presence of acid yields triazole intermediate CI. Alkylation of triazole intermediate CI with alkyl halide XC affords compounds of formula I wherein Y=Y11 and B=NR17 as shown in Flow Diagram XL.

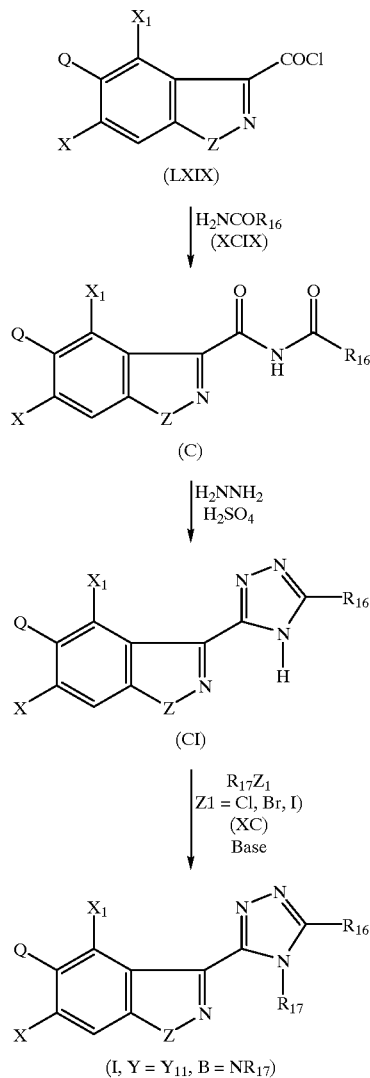

Alternatively nitro intermediates XLIV wherein Y=Y11 and B=O and B=S can be prepared as depicted in Flow Diagram XLI by conversion of acid chloride CII to hydrazide intermediate CIII with hydrazide reagent XCVII and subsequent treatment with phosphorous oxychloride and phosphorous pentasulfide, respectively.

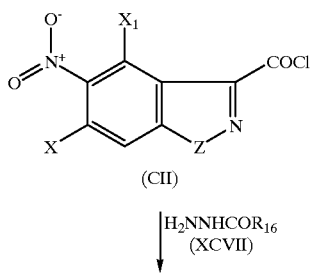

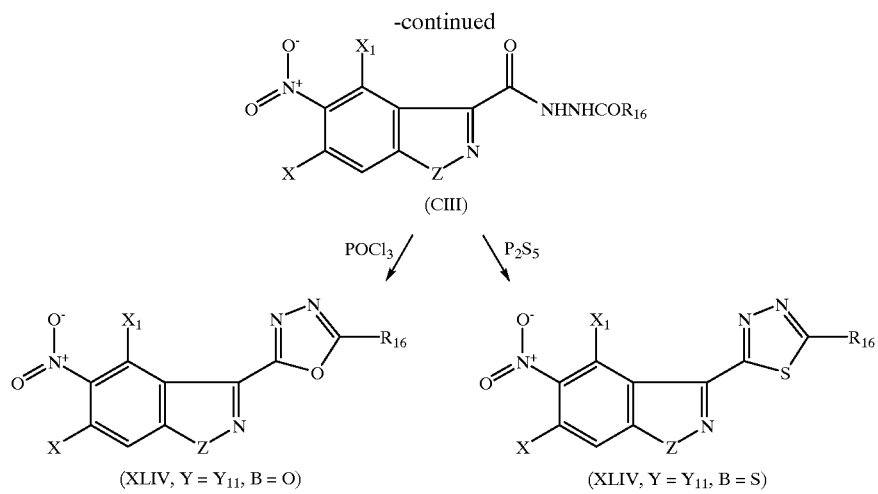

(CIII)

(XLIV, Y = Y₁₁, B = O)    (XLIV, Y = Y₁₁, B = S)

Acid chloride CIV may be prepared as outlined in Flow Diagram XLII. Treatment of thiophenol CIV with oxalyl chloride followed by aluminum chloride affords thiodione CV, which on treatment with ammonium hydroxide and hydrogen peroxide yields amide CVI. Basic hydrolysis of amide CVI affords acid CVII, which is nitrated under standard conditions to afford acid CVIII. Treatment of acid CVIII with thionyl chloride affords acid chloride CII.

FLOW DIAGRAM XLII

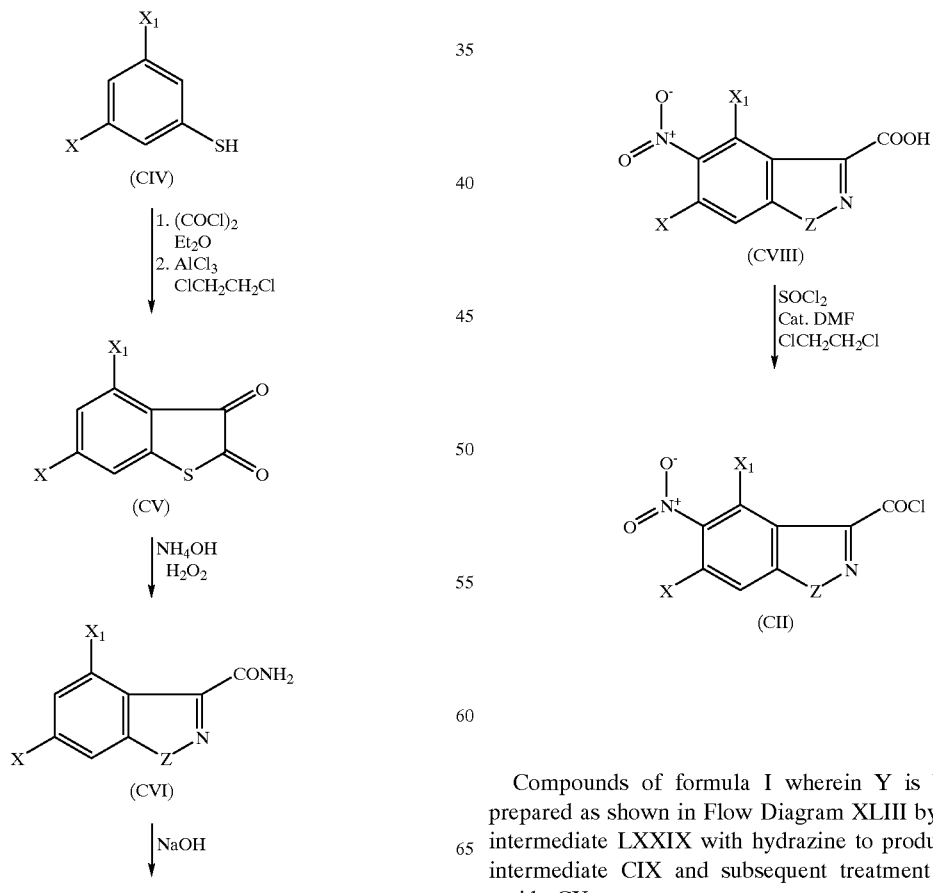

Compounds of formula I wherein Y is Y12 may be prepared as shown in Flow Diagram XLIII by treatment of intermediate LXXIX with hydrazine to produce hydrazino intermediate CIX and subsequent treatment of this with amide CX.

FLOW DIAGRAM XLIII

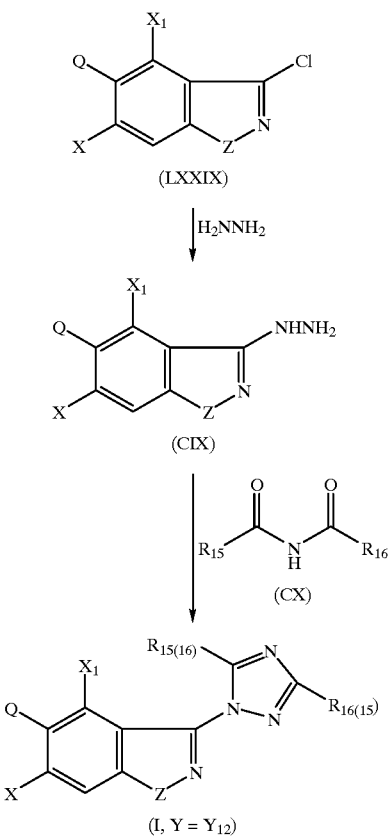

Compounds of formula I wherein Y is Y13 may be prepared as shown in Flow Diagram XLIV by conversion of aldehyde LXXV to chloro intermediate CXI, and subsequent treatment of this intermediate with an olefin CXII in the presence of a base such as triethylamine.

FLOW DIAGRAM XLIV

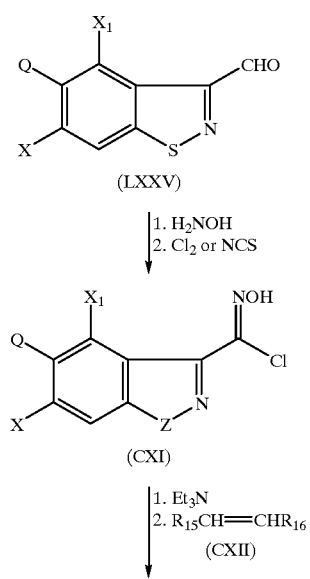

Compounds of formula I wherein Y is Y14 may be prepared by treatment of ketoester CXIII with sulfamide to afford intermediate of structural formula CXIV, and subsequent alkylation with alkyl halide XL as shown in Flow Diagram XLV.

FLOW DIAGRAM XLV

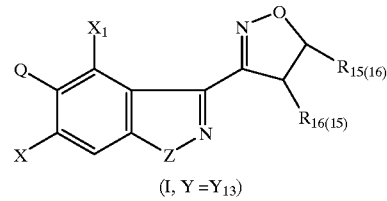

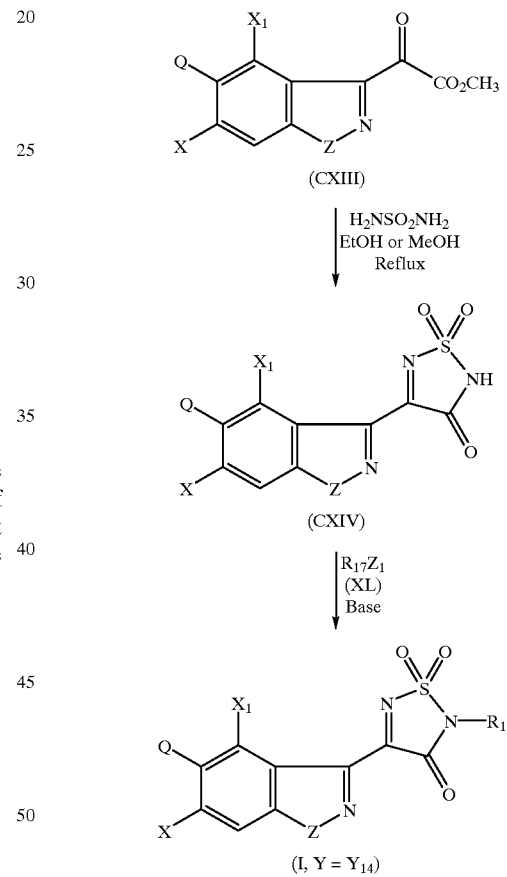

Intermediate ketoester CXIII is prepared from chloro intermediate LXXVIII by treatment with cyanoacetic ester in the presence of base to afford intermediate cyanoester CXV which on treatment with acetyl chloride affords nitro ester CXVI. Reduction of nitro ester CXVI with iron in acetic acid affords amino ester CXVII which can be elaborated into an intermediate ester of formula CXVIII by the methods described in Flow Diagrams I–XIX. Oxidation of ester CXVIII with selenium dioxide affords ketoester CXIII as shown in Flow Diagram XLV wherein R85 is C1–C6 alkyl, benzyl, C2–C6 alkenyl, C2–C6 alkynyl, or C3–C7 cycloalkyl.

FLOW DIAGRAM XLVI

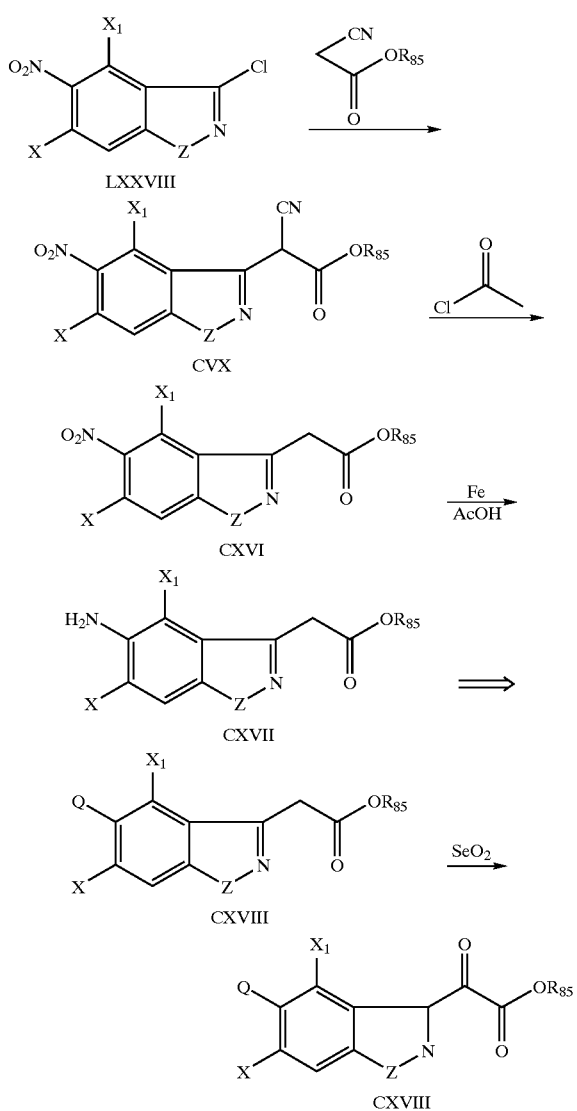

Compounds of formula I wherein Y is Y15 or Y16 may be prepared as outlined in Flow Diagram XLVII by treatment of keto ester CXIII with amidine CXIX and amidine or quanidine CXX, respectively

FLOW DIAGRAM XLVII

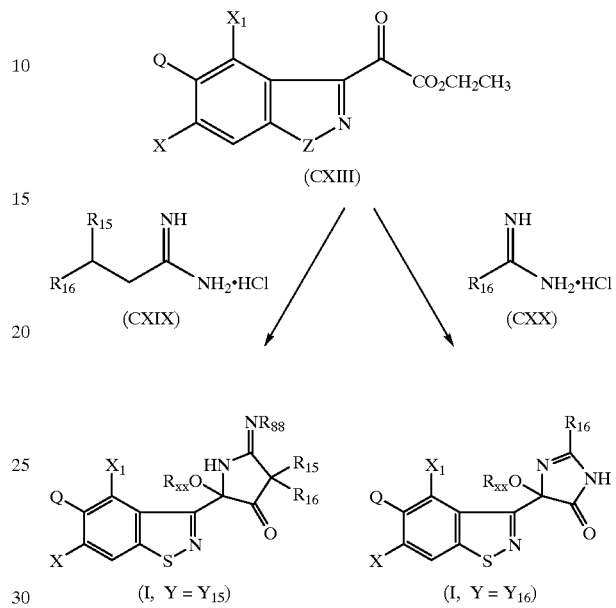

Compounds of formula XLIV wherein Y is Y17 or Y18 may be prepared as shown in Flow Diagram XLVIII. Acylation of ketone CXXI with ester CXXII in the presence of base affords intermediate keto ester CXXIII, which on treatment with hydrazine yields intermediate CXXIV, which can be alkylated with alkyl halide XL to afford compound XLIV wherein Y is Y17. Oxidation of intermediate CXXIV with bromine yields intermediate CXXV which can be alkylated with alkyl halide XL to afford compound XLIV wherein Y is Y18. Ketone CXXI can be prepared from acid chloride CII using the method described in Flow Diagram XXXVI for the synthesis of ketone LXXXV.

FLOW DIAGRAM XLVIII

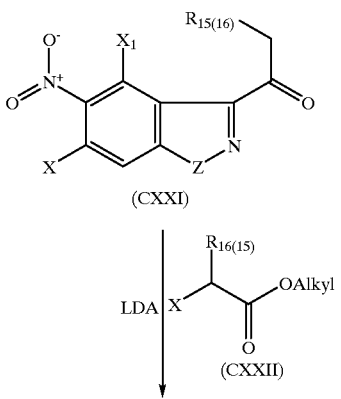

-continued
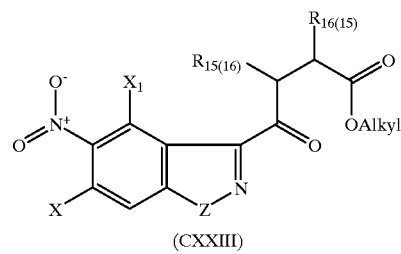
(CXXIII)
NH$_2$NH$_2$
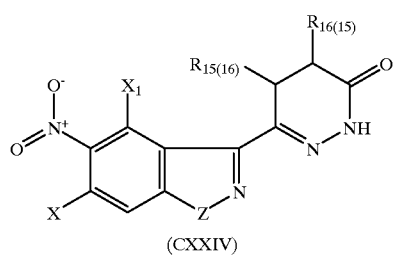
(CXXIV)
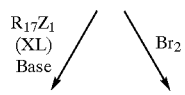R$_{17}$Z$_1$ (XL) Base  Br$_2$
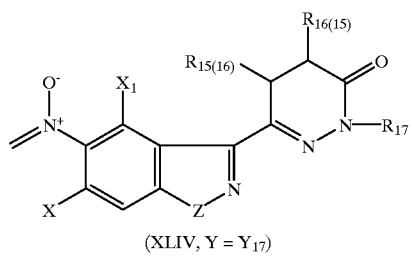
(XLIV, Y = Y$_{17}$)
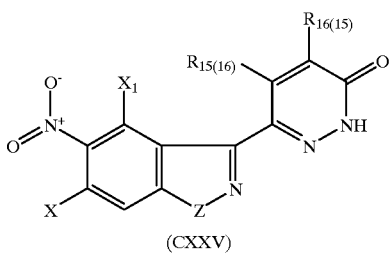
(CXXV)
R$_{17}$Z$_1$ (XL) Base
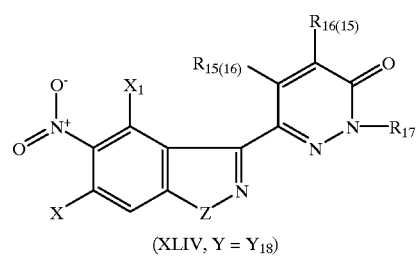
(XLIV, Y = Y$_{18}$)

Compounds XLIV wherein Y is Y19 can be prepared as depicted in Flow Diagram XLIX by alkylation of ketone CXXI with alkyl halide CXXVI in the presence of base and subsequent hydrolysis to afford intermediate keto aldehyde CXXVII, which is treated with hydrazine and oxidized as shown.

FLOW DIAGRAM XLIX

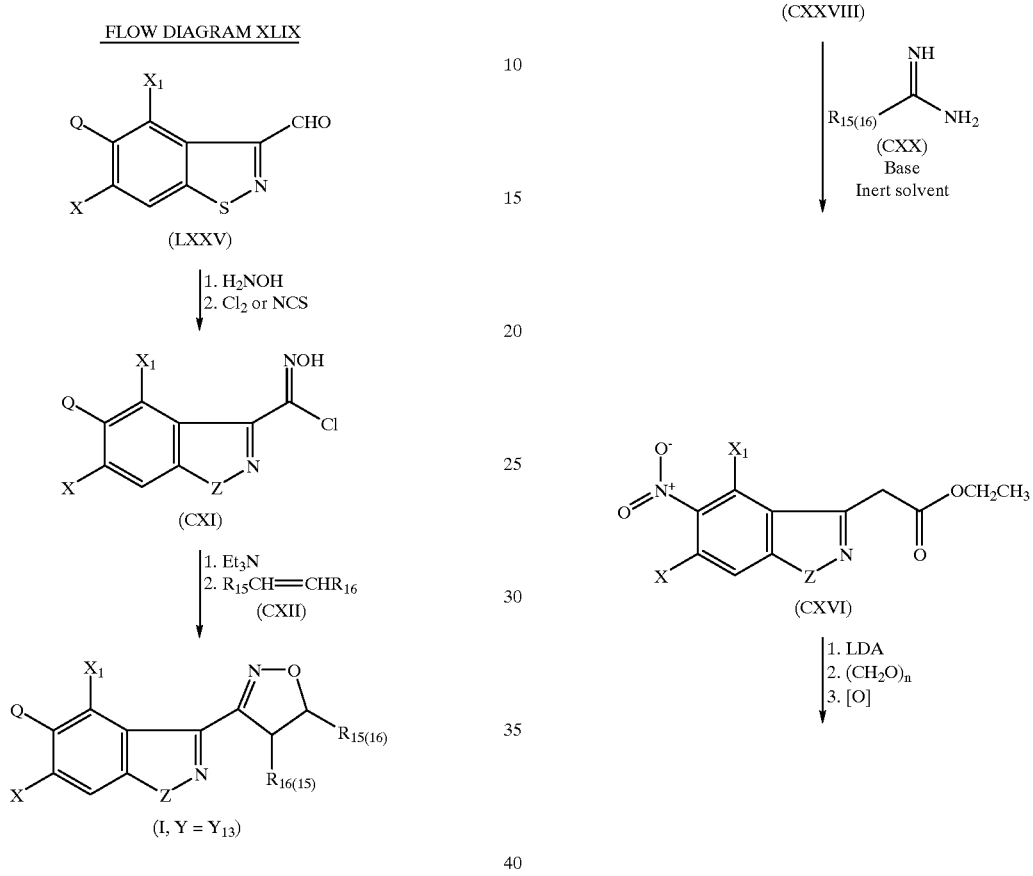

Compounds XLIV wherein Y is Y20 may be prepared by treatment of the anion of ester CXVI with paraformaldehyde followed by oxidation of the hydroxy ester product to ester aldehyde CXXVIII as shown in Flow Diagram L. Treatment of ester aldehyde intermediate CXXVIII with amidine CXX with a reducing agent such as di-isobutyl aluminum hydride (DIBAL) in an inert solvent in the presence of base affords intermediate CXXIX, which can be alkylated with alkyl halide XL as shown.

FLOW DIAGRAM L

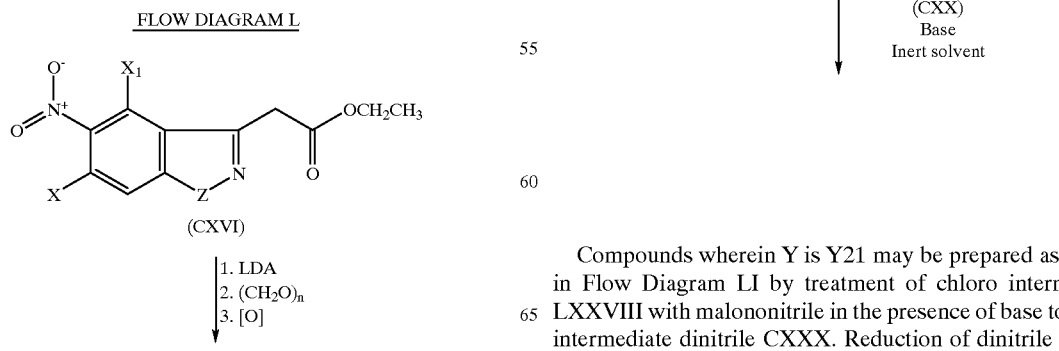

Compounds wherein Y is Y21 may be prepared as shown in Flow Diagram LI by treatment of chloro intermediate LXXVIII with malononitrile in the presence of base to afford intermediate dinitrile CXXX. Reduction of dinitrile CXXX with a reducing agent such as di-isobutyl aluminum hydride (DIBAL) affords dialdehyde CXXXI, which is treated with amidine CXX as shown.
FLOW DIAGRAM LI
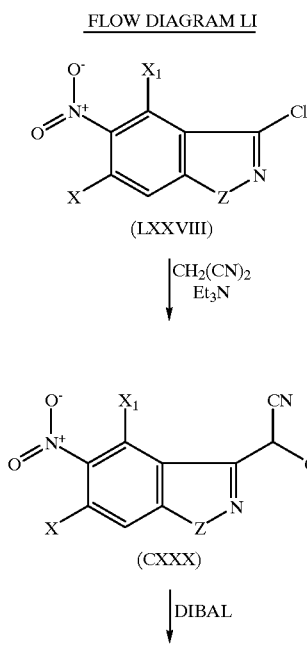
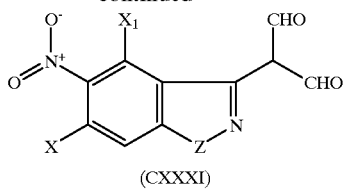
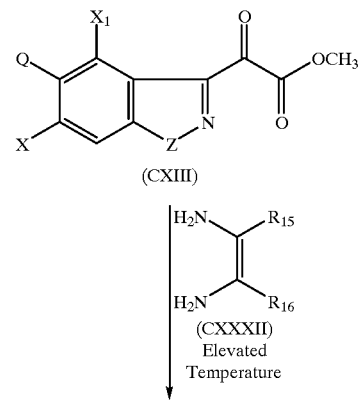
Compounds I wherein Y is Y22 and Y23 are prepared by treatment of keto ester CXIII with olefin CXXXII to afford intermediate CXXXIII, which is treated with phosphorous oxychloride or alkylated with alkyl halide LX as depicted in Flow diagram LII.
FLOW DIAGRAM LII
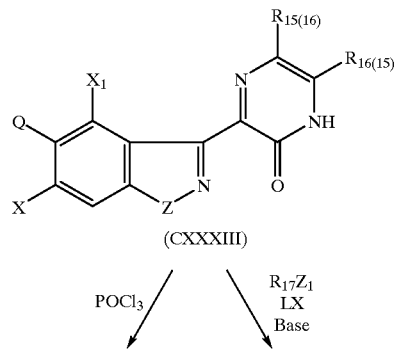

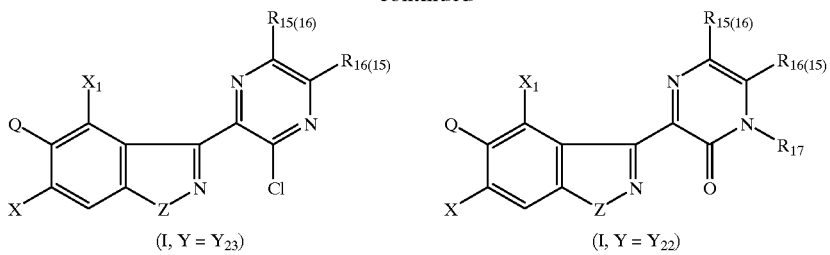

(I, Y = Y₂₃)    (I, Y = Y₂₂)

The syntheses of compounds I wherein Y is Y24 through Y27 are depicted in Flow Diagram LIII. Coupling of acid chloride LXIX with organozinc reagent CXXXIV in the presence of a palladium catalyst affords ketone CXXXV, which on treatment with CXXXVI under dehydration conditions yields compounds I wherein Y is Y24. Compounds I wherein Y is Y24, B is O, and B1 is sulfur can be oxidixed to compound I wherein Y is Y25. In similar fashion, intermediate ketone CXXXV can be reacted with intermediate CXXXVII to afford compound I wherein Y is Y26, and this compound wherein B is O, and B1 is S can be oxidized to compound I wherein Y is Y27.

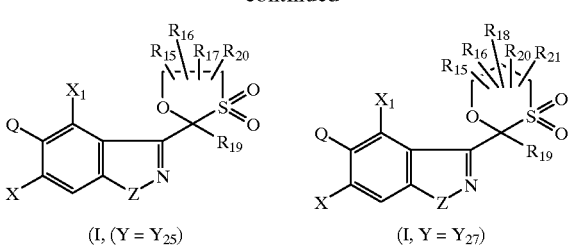

(I, (Y = Y₂₅))    (I, Y = Y₂₇)

Alternatively, compounds I wherein Y is Y24 and both B and B1 are oxygen can be prepared by treatment of dibromo intermediate LXXIII with dial CXXXVI in the presence of a silver salt such as silver trifluoromethanesulfonate as shown in Flow Diagram LIV.

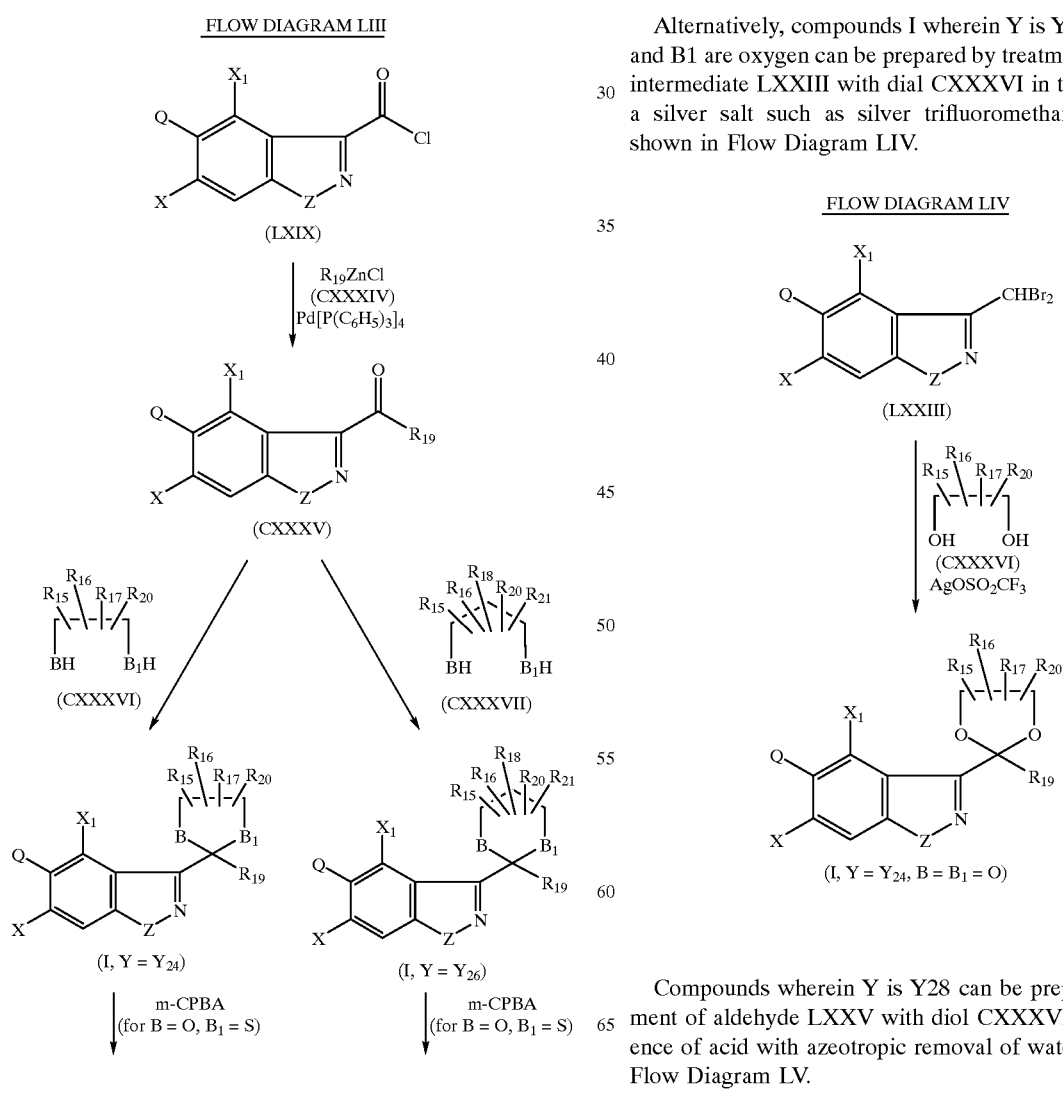

Compounds wherein Y is Y28 can be prepared by treatment of aldehyde LXXV with diol CXXXVIII in the presence of acid with azeotropic removal of water as shown in Flow Diagram LV.

FLOW DIAGRAM LV

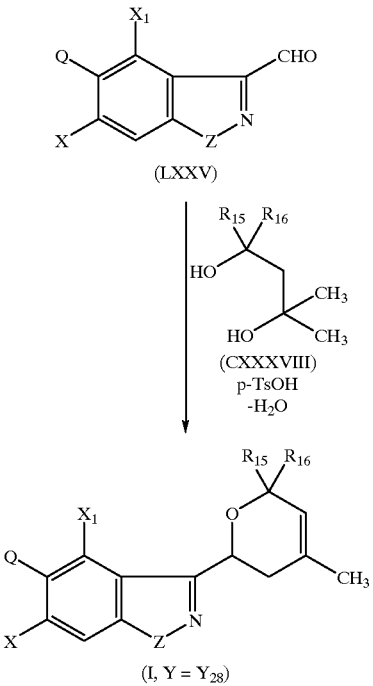

(I, Y = Y$_{28}$)

Compounds I wherein Y is Y29 and Y30 can be prepared by treatment of ketone CXXXV with hydroxy acids CXXXIX and CXL, respectively, under acidic conditions with azeotropic removal of water as shown in Flow Diagram LVI.

FLOW DIAGRAM LVI

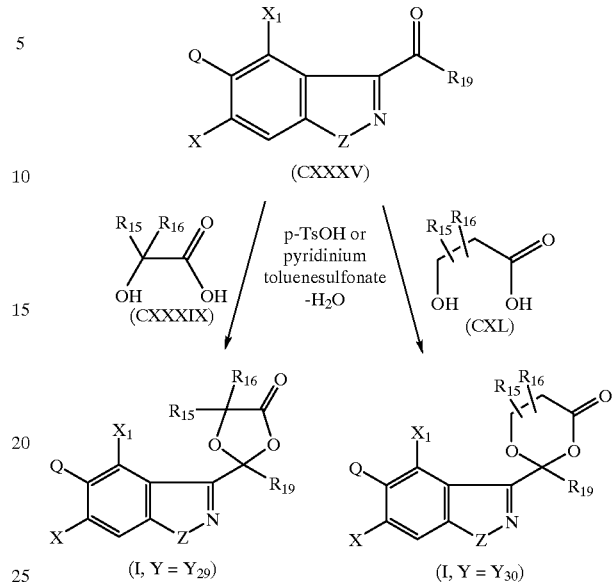

Compounds wherein Y is Y31 and Y33 can be prepared from keto ester CXLI by conversion to diol CXLIII by reduction for the case wherein R15(16) is hydrogen, or by reaction with organolithium reagent CXLII followed by reduction for the case wherein R15(16) is not hydrogen, and subsequent reaction of diol intermediate CXLIII with aldehyde CXLIV in the presence of acid, with azeotropic removal of water or by reaction with phosgene or thiophosgene as shown in Flow Diagram LVII.

FLOW DIAGRAM LVII

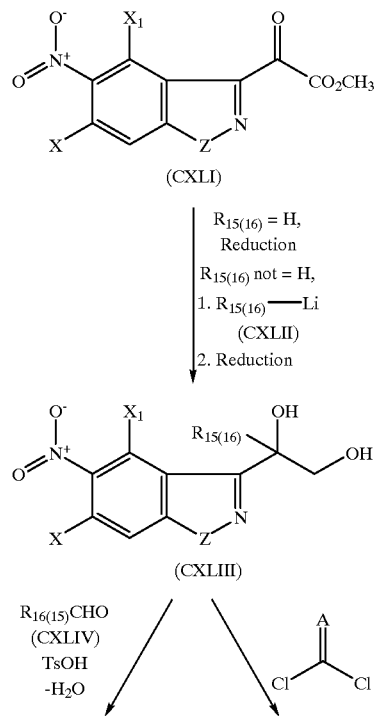

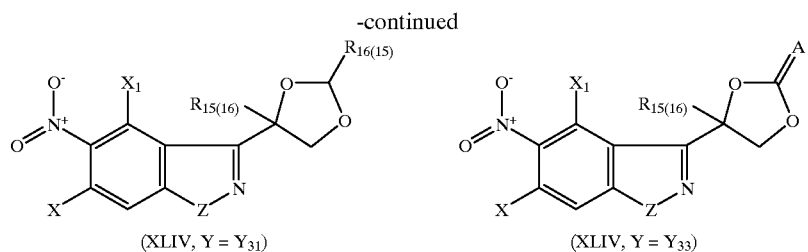

(XLIV, Y = Y₃₁)        (XLIV, Y = Y₃₃)

Keto ester CXXXII can be prepared from chloro intermediate LXXVIII using the procedure described in Flow Diagram XLV.

Compound XLIV wherein Y is Y32 and Y34 can be prepared from chloro intermediate LXXVIII by treatment with a dialkyl malonate in the presence of base to form diester CXLV, which can be alkylated with alkylating agent CXLVI to produce diester CXLVII. Diester CXLVII can be reduced to diol CXLVIII, which is treaed with aldehyde CXLIV in the presence of acid with azeotropic removal of water, or with phosgene or thiophosgene as depicted in Flow Diagram LVIII.

FLOW DIAGRAM LVIII

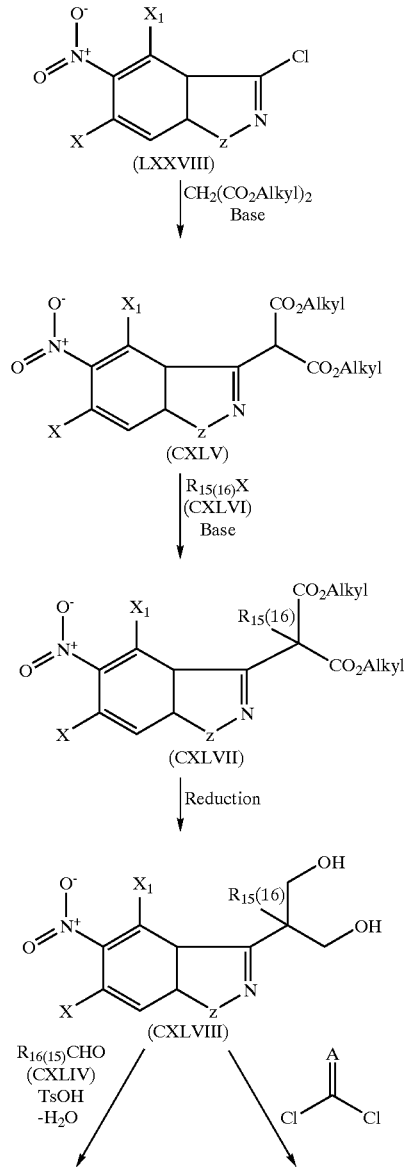

-continued

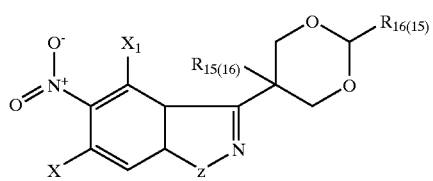

(I, Y=Y₃₂)

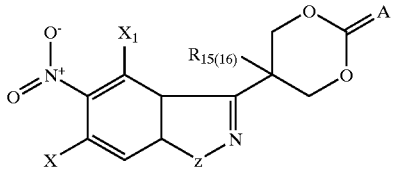

(I, Y=Y₃₄)

Compounds I wherein Y is Y35 may be prepared reaction of the anion of ester CXVIII with aldehyde CXLIV to generate diol intermediate CXLIX, which is treated with aldehyde CL in the presence of acid with azeotropic removal of water as depicted in Flow Diagram LIX.

FLOW DIAGRAM LIX

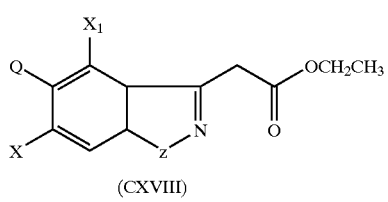

(CXVIII)

1. LDA
2. R₁₅₍₁₆₎CHO (CXLIV)
3. H₃O⁺

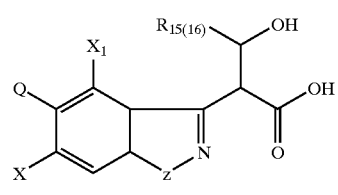

(CXLIX)

R₁₆₍₁₅₎CHO
(CL)
TsOH or
P₂O₅

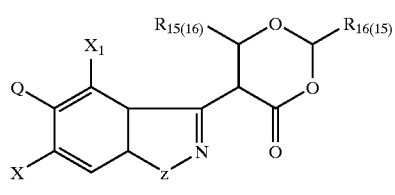

(I, (Y = Y₃₅))

FLOW DIAGRAM LX

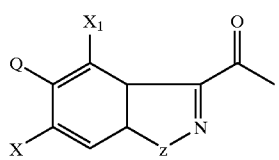

(CXXXV, R₁₉ = CH₃)

1. LDA
2. R₁₆₍₁₅₎CHO (CXLIV)
3. Reduction or R₁₅₍₁₆₎—Li (CXLII)

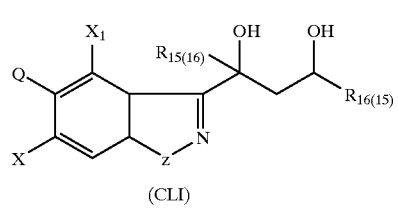

(CLI)

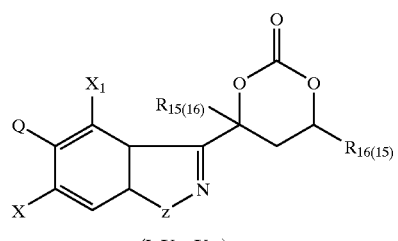

(I, Y = Y₃₆)

Compounds I wherein Y is Y36 may be prepared reaction of the anion of methyl ketone CXXXV (R19=CH3) with aldehyde CXLIV, followed by reduction with agents such as sodium borohydride for the case wherein R15(16) is hydrogen, or reaction with organolithium reagent CXLII for the case wherein R15(16) is not hydrogen, which affords diol intemediate CLI which is reacted with phosgene in the presence of a base as depicted in Flow Diagram LX.

Compounds I wherein Y is Y37 may be prepared by conversion of ester CXVIII to acid chloride CLII by sequential treatment with aqueous sodium hydroxide, N-chlorosuccinimide or N-bromosuccinimide, and oxalyl chloride. Treatment of acid chloride CLII with reagent CLIII in the presence of base affords compound I wherein Y is Y37.

FLOW DIAGRAM LXI

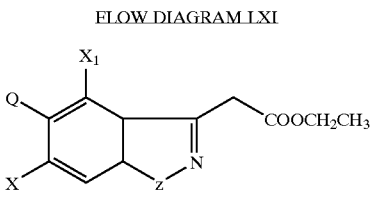

(CXVIII)

1. Aq. NaOH
2. NCS or NBS
3. (COCl)$_2$ $Z_1$ = Cl, Br (CLII)

(CLIII)
Base (I, Y = Y$_{37}$)

Compounds I wherein Y is Y38 may be prepared by conversion of diol CXLIII to halo intermediate CLIV and subsequent treatment with reagent CLV in the presence of a silver salt as depicted in Flow Diagram LXII.

FLOW DIAGRAM LXII

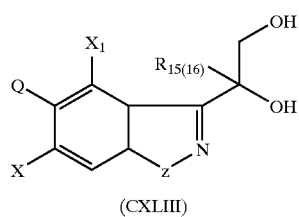

(CXLIII)

(CLIV)

(CLV)
AgOSO$_2$CF$_3$
B = O, S (I, Y = Y$_{38}$)

Compounds I wherein Y is Y39 and Y40 may be prepared by epoxidation of olefin CLVI and conversion of epoxide I (Y=Y39) to aziridine as depicted in Flow Diagram LXIII.

FLOW DIAGRAM LXIII

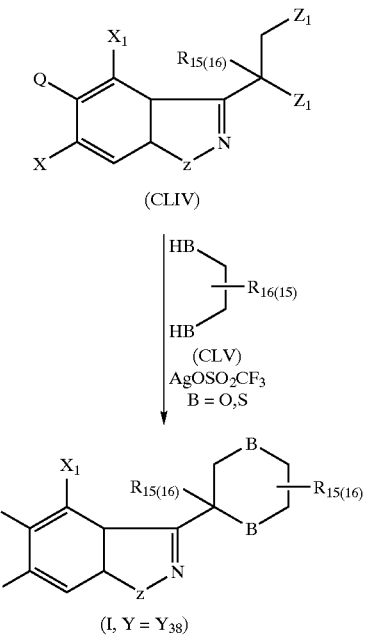

(CLVI)

1. NBS
   H$_2$O/dioxane
2. NaH
   or
   m-CPBA (I, Y=Y$_{39}$)

1. NaN$_3$
2. PPh$_3$ (I, Y=Y$_{40}$)

The present invention also relates to intermediate compounds of formula XL, formula XLIV or formula II (XL)
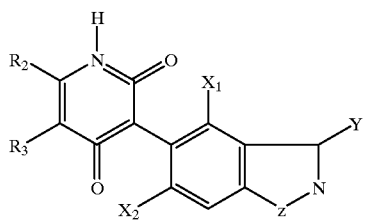
(XLIV)
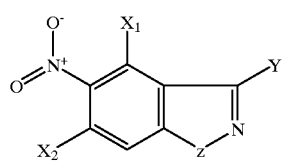
(II)
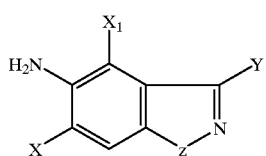
wherein $R_2$, $R_3$ $X$ $X_1$, Y and Z are as defined above for formula I.
Preferred intermediate compounds of formula XL, XLIV and II are those compounds wherein Y is
$Y_1$
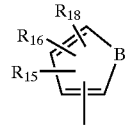
$Y_2$
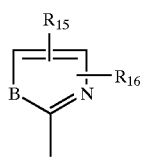
$Y_3$
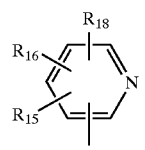
$Y_4$
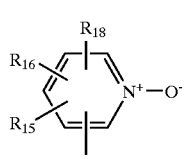
$Y_5$
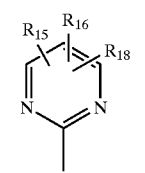
$Y_6$
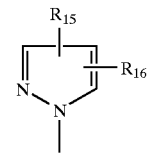
$Y_7$
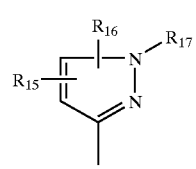
$Y_8$
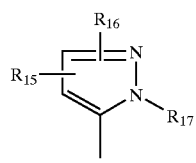
$Y_9$
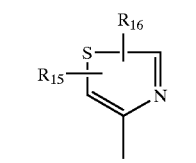
$Y_{10}$
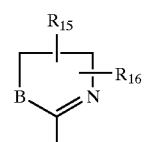
$Y_{11}$
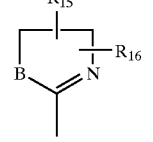
$Y_{12}$
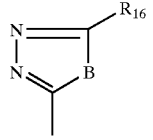
$Y_{13}$
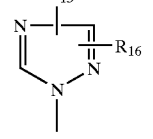
$Y_{14}$
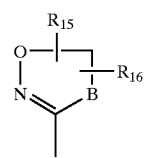

-continued

Y15

Y16

Y17

Y18

Y19

Y20

Y21

Y22

Y23

-continued

Y24

Y25

Y26

Y27

Y28

Y29

Y30

Y31

Y32

-continued

Y33 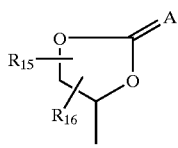

Y34 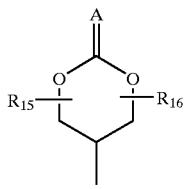

Y35 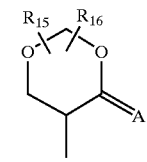

Y36 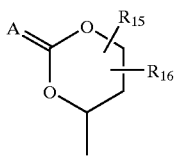

Y37 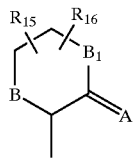

Y38 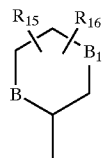

Y39 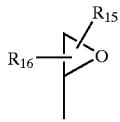

Y40 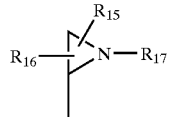

wherein $R_{15}$, $R_{18}$, $R_{20}$ and $R_{21}$ are each independently hydrogen, $C_1$–$C_8$ alkyl, $C_1$–$C_8$ haloalkyl, $C_1$–$C_8$ alkoxy, $C_1$–$C_8$ thioalkyl, halogen, nitro, cyano, hydroxy, $C_2$–$C_6$ alkenyl, $C_3$–$C_6$ alkynyl, $C_2$–$C_6$ haloalkenyl, $C_3$–$C_8$ cycloalkyl or $R_{20}$ and the carbon on Y to which $R_{20}$ is attached may form an exocyclic double bond or when $R_{20}$ and $R_{21}$ are attached to the same carbon of $Y_{25}$, $R_{20}$, $R_{21}$ and the carbon to which they are bonded may form a three- to six-membered heterocyclic ring;

$R_{16}$ is hydrogen, halogen, $C_1$–$C_8$ alkyl optionally substituted with $C(O)R_{22}$, $CO_2R_{23}$, $X_2R_{24}$, $S(O)_m$alkyl, $NR_{86}R_{87}$, $C_1$–$C_8$ haloalkyl, $C(O)R_{25}$, $CO_2R_{26}$, $X_3R_{27}$, $CH=CHR_{28}$, $C_3$–$C_8$ cycloalkyl, $N(R_{29})SO_2R_{30}$ or (subst.) phenyl;

When $R_{15}$ and $R_{16}$ are attached to separate adjacent carbons, as in Y24, they may form a six-membered heterocyclic or carbocyclic ring fused to the Y-ring;

$R_{17}$ is hydrogen, $C_1$–$C_8$ alkyl, $C_2$–$C_8$ alkenyl, $C_3$–$C_6$ alkynyl, $C(O)R_{25}$, or(subst.)benzyl;

$R_{19}$, $R_{29}$, $R_{33}$, $R_{34}$, $R_{35}$, $R_{37}$, $R_{38}$, $R_{39}$, $R_{42}$, $R_{43}$, $R_{44}$, $R_{46}$, $R_{47}$, $R_{48}$, $R_{50}$, $R_{51}$, $R_{52}$, $R_{53}$, $R_{55}$, $R_{57}$, $R_{60}$, $R_{61}$, $R_{62}$, $R_{64}$, $R_{65}$, $R_{66}$, $R_{69}$, $R_{70}$, $R_{71}$, $R_{73}$, $R_{74}$, $R_{75}$, $R_{76}$, $R_{80}$, and $R_{85}$ are each independently hydrogen, OH, $C_1$–$C_8$ alkyl, $C_1$–$C_4$ alkoxy, $C_3$–$C_8$ cycloalkyl, $C_2$–$C_8$ alkenyl, $C_3$–$C_6$ alkynyl, (subst.) benzyl or (subst.) phenyl;

$R_{22}$, $R_{25}$, $R_{32}$, $R_{36}$, $R_{41}$, $R_{45}$, $R_{54}$, $R_{59}$, $R_{63}$, $R_{68}$, $R_{72}R_{77}$, $R_{78}$, $R_{81}$, and $R_{87}$ are each independently hydrogen, $C_1$–$C_4$ alkyl, $C_1$–$C_4$ haloalkyl, $C_2$–$C_6$ alkenyl, $C_2$–$C_6$ haloalkenyl, $C_2$–$C_6$ alkynyl, $C_3$–$C_7$ cycloalkyl, $C_1$–$C_4$ cyanoalkyl, benzyl or (subst.)phenyl;

$R_{23}$, $R_{26}$, $R_{31}$, $R_{40}$, $R_{49}$, $R_{58}$, $R_{67}$, and $R_{79}$ are each independently hydrogen, $C_1$–$C_8$ alkyl, $C_1$–$C_8$ haloalkyl, $C_3$–$C_8$ cycloalkyl, $C_3$–$C_8$ halocycloalkyl, $C_2$–$C_8$ alkenyl, $C_2$–$C_8$ haloalkenyl, $C_5$–$C_8$ cycloalkenyl, $C_5$–$C_8$ halocycloalkenyl, $C_3$–$C_8$ alkynyl, $C_3$–$C_8$ haloalkynyl, (subst.)benzyl, (subst.) phenyl, furfuryl, pyridyl, thienyl, an alkali metal, alkaline earth metal, manganese, copper, zinc, cobalt, silver, nickel ammonium or organic ammonium cation;

$R_{24}$, $R_{27}$, and $R_{28}$ are each independently hydrogen,
$C_1$–$C_{10}$ alkyl optionally substituted with one to six halogens, one $C_1$–$C_6$ alkoxy group, $CO_2R_{31}$, $C(O)R_{32}$, $C(OR_{33})_2$, $C(SR_{34})_2$, $C(O)NR_{35}R_{36}$, $C(O)ON=CR_{37}R_{38}$, cyano, (subst.)phenyl or $C(O)NHOR_{39}$;

$C_2$–$C_{10}$ alkenyl optionally substituted with one $C_1$–$C_6$ alkyl group, one to three halogens, one $C_1$–$C_6$ alkoxy group, $CO_2R_{40}$, $C(O)R_{41}$, $C(OR_{42})_2$, $C(SR_{43})_2$, $C(O)NR_{44}R_{45}$, $C(O)ON=CR_{46}R_{47}$, cyano, (subst.) phenyl or $C(O)NHOR_{48}$;

$C_3$–$C_8$ cycloalkyl optionally substituted with one $C_1$–$C_6$ alkyl group, one to three halogens, one $C_1$–$C_6$ alkoxy group, $CO_2R_{49}$, $C(O)R_{50}$, $C(OR_{51})_2$, $C(SR_{52})_2$, $C(O)NR_{53}R_{54}$, $C(O)ON=CR_{55}R_{56}$, cyano, (subst.)phenyl or $C(O)NHOR_{57}$;

$C_5$–$C_8$ cycloalkenyl optionally substituted with one $C_1$–$C_6$ alkyl group, one to three halogens, $C_1$–$C_4$ alkoxy group, $CO_2R_{58}$, $C(O)R_{59}$, $C(OR_{60})_2$, $C(SR_{61})_2$, $C(O)NR_{62}R_{63}$, $C(O)ON=CR_{64}R_{65}$, cyano, (subst.)phenyl or $C(O)NHOR_{66}$;

$C_3$–$C_8$ alkynyl optionally substituted with one $C_1$–$C_6$ alkoxy group, $CO_2R_{67}$, $C(O)R_{68}$, $C(OR_{69})_2$, $C(SR_{70})_2$, $C(O)NR_{71}R_{72}$, $C(O)ON=CR_{73}R_{74}$, cyano, (subst.)phenyl or $C(O)NHOR_{75}$;

phenyl optionally substituted with one to three halogens, one to three $C_1$–$C_6$ alkyl groups, one to three $C_1$–$C_6$ alkoxy groups, one to three $C_1$–$C_6$ haloalkyl groups, one to three $C_1$–$C_6$ haloalkoxy groups, one cyano, one nitro, one $NR_{76}R_{77}$, one $C(O)R_{78}$ or one $CO_2R_{79}$;

$R_{30}$ is OH, $C_1$–$C_8$ alkyl, $C_3$–$C_8$ cycloalkyl, $C_1$–$C_8$ haloalkyl, $C_2$–$C_8$ alkenyl, $C_2$–$C_8$ haloalkenyl, $C_3$–$C_8$ alkynyl, (subst.)benzyl, (subst.) phenyl, or $NR_{80}R_{81}$;

B and $B_1$ are each independently oxygen, sulfur or $NR_{17}$; and $X_2$ and $X_3$ are each independently O or S; or the optical isomers or diastereomers thereof.

More preferred formula XL, XLIV and II intermediate compounds of this invention are those compounds wherein $R_2$ is $C_1$–$C_3$ haloalkyl;

X is hydrogen or halogen;

$X_1$ is hydrogen;

Z is sulfur;

Y is $Y_1$, $Y_2$, $Y_3$, $Y_4$, $Y_5$, $Y_6$, $Y_{10}$, $Y_{11}$, $Y_{14}$, $Y_{15}$, $Y_{16}$, $Y_{22}$, $Y_{24}$, $Y_{25}$, $Y_{26}$, $Y_{27}$, $Y_{28}$, $Y_{38}$, or $Y_{39}$;

$R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy, halogen, hydroxy or when $R_{20}$ and $R_{21}$ are attached to the same carbon of $Y_{25}$ an epoxide ring is formed;

$R_{16}$ is hydrogen, halogen, $C_1$–$C_3$ alkyl optionally substituted with $C(O)R_{22}$, $CO_2R_{23}$, $X_2R_{24}$, or $S(O)_m$alkyl; phenyl; $C_1$–$C_3$ haloalkyl, $C(O)R_{25}$, $CO_2R_{26}$, $X_3R_{27}$, $C_3$–$C_8$ cycloalkyl, $N(R_{29})SO_2R_{30}$ or $C_2$–$C_4$ alkenyl;

$R_{17}$ is hydrogen, $C_1$–$C_3$ alkyl, $C_2$–$C_4$ alkenyl or $C(O)R_{25}$;

$R_{19}$, $R_{29}$ and $R_{80}$ are each independently hydrogen or $C_1$–$C_3$ alkyl;

$R_{22}$, $R_{25}$ and $R_{81}$ are each independently hydrogen, $C_1$–$C_3$ alkyl, benzyl or (subst)phenyl;

$R_{23}$, $R_{26}$ and $R_{31}$ are each independently hydrogen, $C_1$–$C_3$ alkyl, $C_2$–$C_4$ alkenyl, or $C_3$–$C_6$ alkynyl;

$R_{24}$ and $R_{27}$ are each independently hydrogen or $C_1$–$C_3$ alkyl optionally substituted with one $CO_2R_{31}$ group or one $C_1$–$C_3$ alkoxy group;

$R_{30}$ $C_1$–$C_3$ alkyl, $C_3$–$C_5$ cycloalkyl, $C_1$–$C_3$ haloalkyl, $C_2$–$C_4$ alkenyl (subst.)benzyl, (subst.)phenyl, or $NR_{80}R_{81}$;

$X_2$ and $X_3$ are O.

Most preferred compounds of formula XL, XLIV and II are those compounds wherein $R_2$ is trifluoromethyl;

Z is S;

Y is $Y_1$

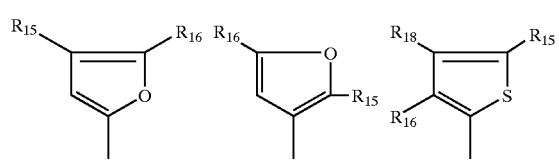

$Y_2$

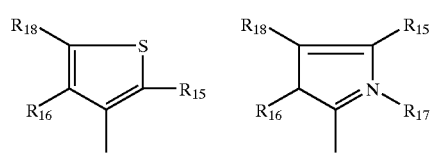

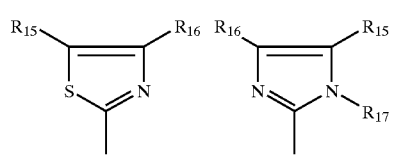

-continued $Y_3$

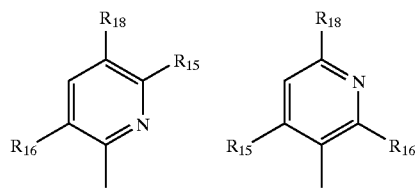

$Y_5$

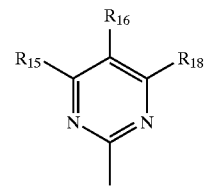

$Y_{10}$

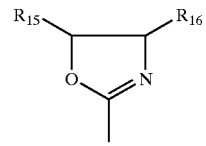

$Y_{11}$

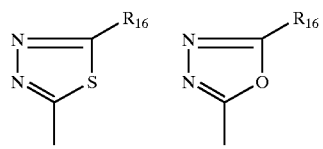

$Y_{24}$

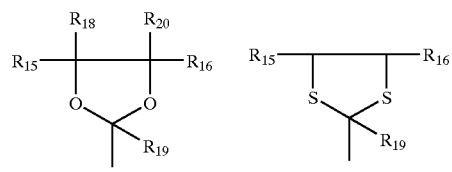

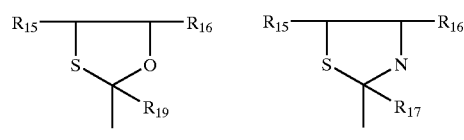

$Y_{25}$

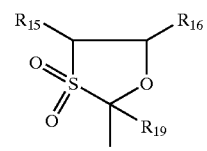

$Y_{26}$

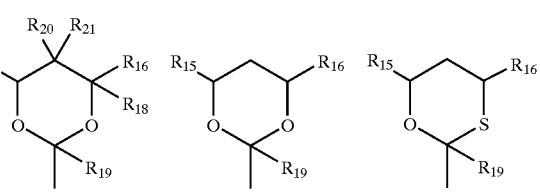

$Y_{27}$

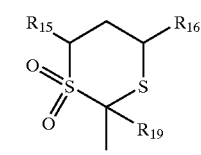

-continued $Y_{28}$

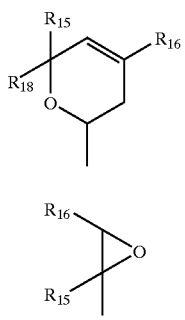

$Y_{38}$ $R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy;

$R_{16}$ is hydrogen, halogen, $C_1$–$C_8$ alkyl optionally substituted with $X_2R_{24}$; $C_1$–$C_3$ haloalkyl, phenyl or $C_2$–$C_4$ alkenyl;

$R_{17}$ is hydrogen, methyl or $C(O)R_{25}$;

$R_{19}$ is hydrogen or $C_1$–$C_3$ alkyl;

$R_{24}$ is hydrogen or $C_1$–$C_3$ alkyl;

$R_{25}$ is $C_1$–$C_3$ alkyl or phenyl; and $X_2$ is oxygen.

The present invention also provides intermediate compounds of formula CXIII

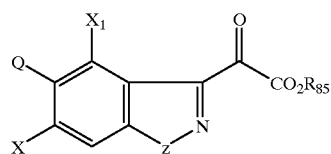

(CXIII)

wherein Q, X, $X_1$, and Z are defined as above for formula I and $R_{85}$ is $C_1$–$C_6$ alkyl, benzyl, $C_2$–$C_6$ alkenyl, $C_2$–$C_6$ alkynyl, or $C_3$–$C_7$ cycloalkyl.

Preferred compounds of formula CXIII are those wherein

Q is $Q_7$ or $Q_{24}$;

R is $C_1$–$C_6$ alkyl, $C_2$–$C_6$ alkenyl, $C_3$–$C_6$ alkynyl or $NH_2$;

$R_2$ is $C_1$–$C_6$ alkyl or $C_1$–$C_6$ haloalkyl;

$R_3$ is hydrogen; and $R_{85}$ is $C_1$–$C_6$ alkyl.

More preferred compounds of formula CXIII are those wherein

Q is $Q_{24}$;

R is $C_1$–$C_3$ alkyl;

$R_2$ is $C_1$–$C_3$ haloalkyl;

Z is sulfur;

X is hydrogen or halogen; and $X_1$ is hydrogen.

Most preferred compounds of formula CXIII are those wherein

Q is

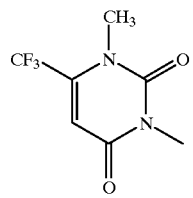

and

Z is sulfur.

In order to facilitate a further understanding of the invention, the following examples are presented to illustrate more specific details thereof. The invention is not to be limited thereby except as defined in the claims. The terms NMR and IR designate nuclear magnetic resonance and infrared, respectively.

EXAMPLE 1

Preparation of 2-Chloro-4-fluoro-5-nitrobenzoyl chloride

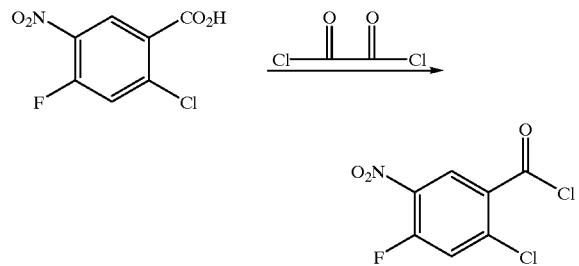

A mixture of 2-chloro-4-fluoro-5-nitrobenzoic acid (50.0 g, 0.228 mol) and N,N-dimethylformamide (5 drops) in 1,2-dichloroethane is treated dropwise with oxalyl chloride (30.8 mL, 0.353 mol), refluxed for 3 hours, cooled, and concentrated in vacuo to obtain the title product as an orange solid which is identified by NMR spectral analysis.

EXAMPLE 2

Preparation of 2-Chloro-5-nitrophenyl 1-methylpyrrol-2-yl ketone

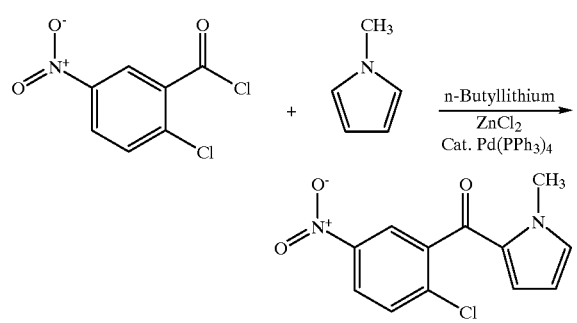

To a mixture of n-butyllithium (2.5 M in hexanes, 100 ml, 0.250 mol) and tetrahydrofuran at room temperature is added N-methylpyrrole (40.6 g, 0.500 mol) dropwise over 30 minutes. The resultant mixture is stirred 90 minutes at 35–40° C. and cooled to –70° C. Zinc chloride (0.5 M in tetrahydrofuran, 500 ml, 0.25 mol) is added dropwise such that the temperature does not exceed –60° C. The resultant mixture is allowed to warm to 0° C. and stirred one hour at 0° C. A solution of 2-chloro-5-nitrobenzoyl chloride (60.5 g, 0.275 mol) in tetrahydrofuran is added, followed by tetrakis triphenylphosphine palladium (5.00 g). The resultant mixture is allowed to warm to room temperature, stirred overnight, and quenched with 10% aqueous hydrochloric acid. The organic layer is saved and the aqueous layer is extracted with ethyl acetate. The organic layers are combined, washed with saturated sodium bicarbonate and brine and dried over anhydrous magnesium sulfate. Concentration in vacuo affords a maroon gum, which is chromatographed on silica gel with hexanes-ethyl acetate to afford the title compound as a yellow solid (12.7 g, 19.2%, mp 108.5–109.5° C.) which is identified by IR and NMR spectral analysis. Using an essentially identical procedure and the appropriate heterocycle the following ketones are prepared:

| Y | mp (° C.) |
|---|---|
| 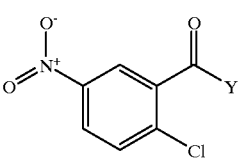 | |
| 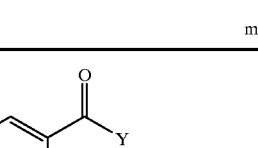 | 75–77 |
| 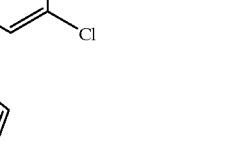 | 118–120 |
|  | 130–131 |
|  | — |
|  | 95–96 |
|  | 50–52 |

-continued

| Y | mp (° C.) |
|---|---|
| 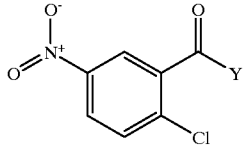 | |
| 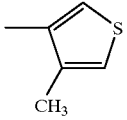 | 84–88 |
| 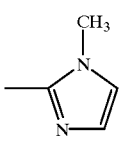 | 190–191.5 |
| 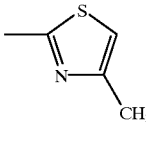 | 157–159 |
| 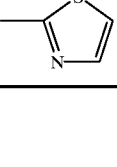 | 141–142 |

EXAMPLE 3

Preparation of 3-(1-Methylpyrrol-2-yl)-5-nitro-1,2-benzisothiazole

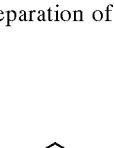

To a mixture of 2-chloro-5-nitrophenyl-1-methylpyrrol-2-yl ketone(7.00 g, 26.4 mmol) and dimethylformamide is added sulfur (0.850 g, 26.6 mmol) followed by ammonium hydroxide (25.0 ml). The resultant mixture is stirred two hours at 70–80° C. and overnight at ambient temperature. The mixture is poured into water and vacuum filtered. The resultant red solid is taken up in methylene chloride and chromatographed on silica gel with hexanes-methylene chloride to afford the title compound as an orange solid, identified by NMR spectral analysis.

Using essentially the same procedure on the appropriate ketones, the following products are obtained:

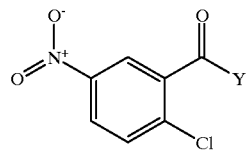

-continued

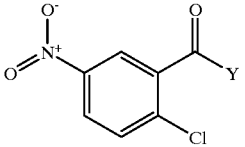

| Y | mp (° C.) |
|---|---|
| 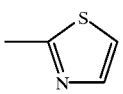 | 190–195 |
| 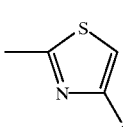 | 191–192 |

EXAMPLE 4

Preparation of 5-Amino-3-(1-methylpyrrol-2-yl)-1, 2-benzisothiazole

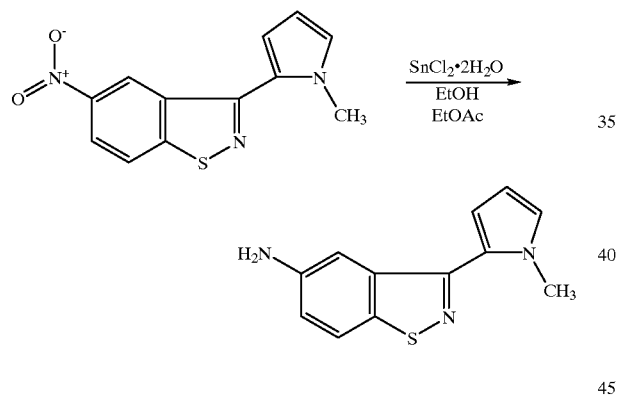

To a mixture of 3-(1-methylpyrrol-2-yl)-5-nitro-1,2-benzisothiazole(1.5 g, 5.79 mmol), ethyl acetate and ethanol is added tin(II) chloride dihydrate (6.5 g, 28.8 mmol). The resultant mixture is heated to reflux, stirred 30 min at reflux and cooled to room temperature. The mixture is diluted with ethyl acetate and slowly quenched with solid sodium bicarbonate and water. Brine is added and the resultant mixture stirred and allowed to stand until layer separation is complete. The organic layer is saved and the aqueous layer is extracted with ethyl acetate. The solids which form in the aqueous layer are triturated with ethyl acetate, filtered and the filtrate combined with the above organic layers. The combined organic layers are washed with brine, dried over anhydrous magnesium sulfate and concentrated in vacuo to afford the title compound as a brown oil (1.10 g, 84.6%) identified by NMR spectral analysis.

Using essentially the same procedure on the appropriate 5-nitro-3-heterocyclic benzisothiazole, the following compound is obtained:

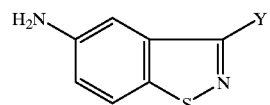

| Y | mp (° C.) |
|---|---|
| 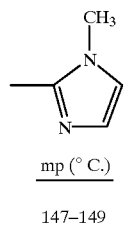 | 147–149 |

EXAMPLE 5

Preparation of 3-[3-(1-Methylpyrrol-2-yl)-1,2-benzisothiazol-5-yl]-6-(trifluoromethyl)uracil

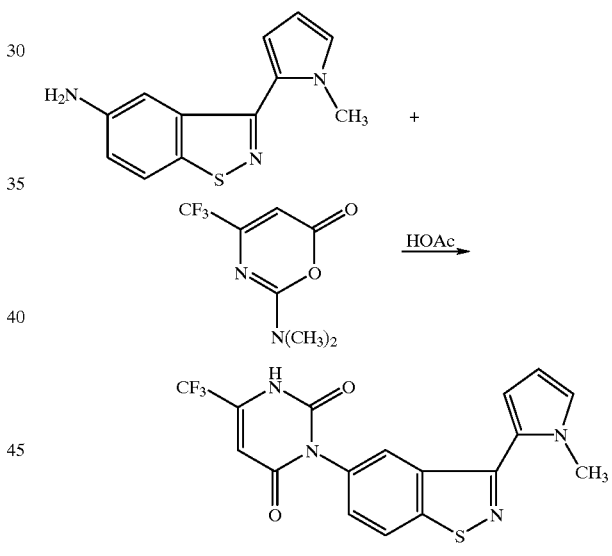

To a mixture of 5-amino-3-(1-methylpyrrol-2-yl)-1,2-benzisothiazole(1.05 g, 4.59 mmol) and acetic acid is added 2-(dimethylamino)-4-(trifluoromethyl)-5H-1,3-oxazin-6-one (0.960 g, 4.60 mmol). The resultant mixture is stirred at reflux for two hours, cooled to room temperature, diluted with ice water and stirred vigorously for approximately 15 minutes. Filtration and drying affords the title compound as a gray solid (1.50 g, 83.3%, mp 125–130° C.) which is identified by NMR spectral analysis.

Using essentially the same procedure with the appropriate aminobenzisothiazoles, the following products are obtained:

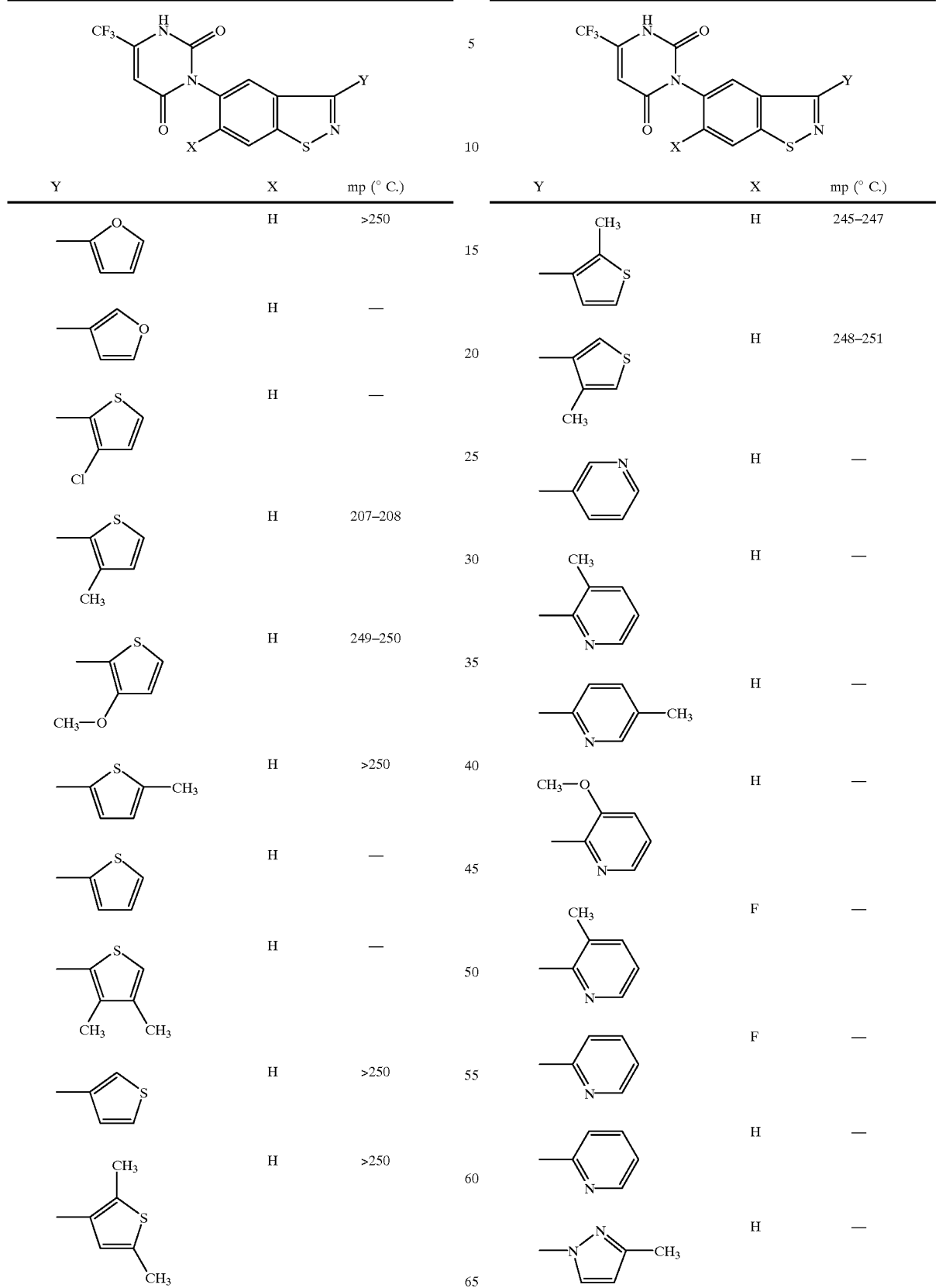

-continued

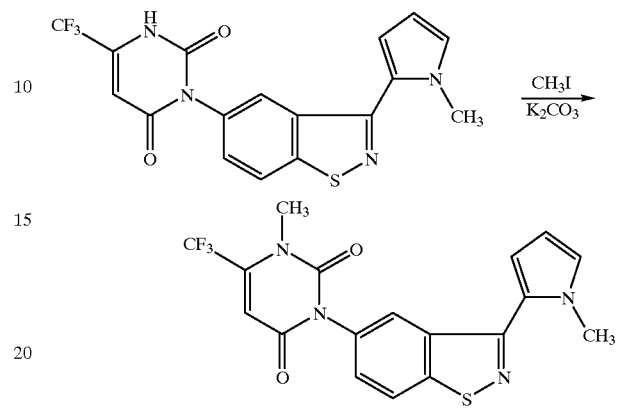

| Y | X | mp (° C.) |
|---|---|---|
| (1-methyl-pyrazol-4-yl, 4-CH3) | H | — |
| (1-methyl-3,5-dimethylpyrazol-4-yl) | H | — |
| (1-methylimidazol-2-yl) | H | >250 |
| (pyrimidin-2-yl) | H | — |
| (2,4-dimethylthiazol-5-yl) | H | >275 |
| (thiazol-2-yl) | H | >255 |
| (5-methyl-1,3,4-thiadiazol-2-yl) | H | — |
| (5-methyl-1,3,4-oxadiazol-2-yl) | H | — |

EXAMPLE 6

Preparation of 1-Methyl-3-[3-(1-methylpyrrol-2-yl)-1,2-benzisothiazol-5-yl]-6-(trifluoromethyl)uracil

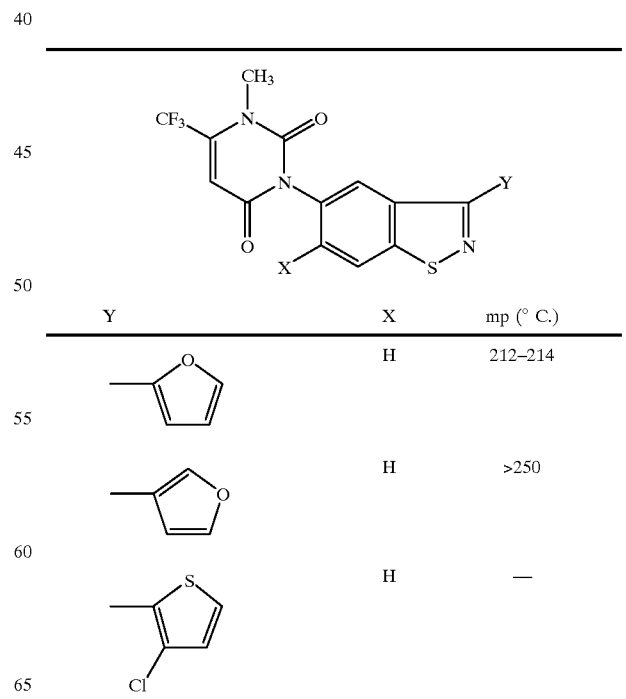

To a mixture of 3-[3-(1-methylpyrrol-2-yl)-1,2-benzisothiazol-5-yl]-6-(trifluoromethyl)uracil (1.35 g, 3.44 mmol), dry dimethylformamide and potassium carbonate (0.710 g, 5.14 mmol) is added iodomethane (0.730 g, 5.14 mmol). The resultant mixture is stirred overnight at room temperature and poured into ice water. Filtration and drying affords the title compound as a pink foam (0.300 g, 21.4%) which is identified by NMR spectral analysis.

Using essentially the same procedure on the appropriate uracil-substituted benzisothiazoles the following compounds are obtained:

| Y | X | mp (° C.) |
|---|---|---|
| (furan-2-yl) | H | 212–214 |
| (furan-3-yl) | H | >250 |
| (3-chlorothien-2-yl) | H | — |

-continued

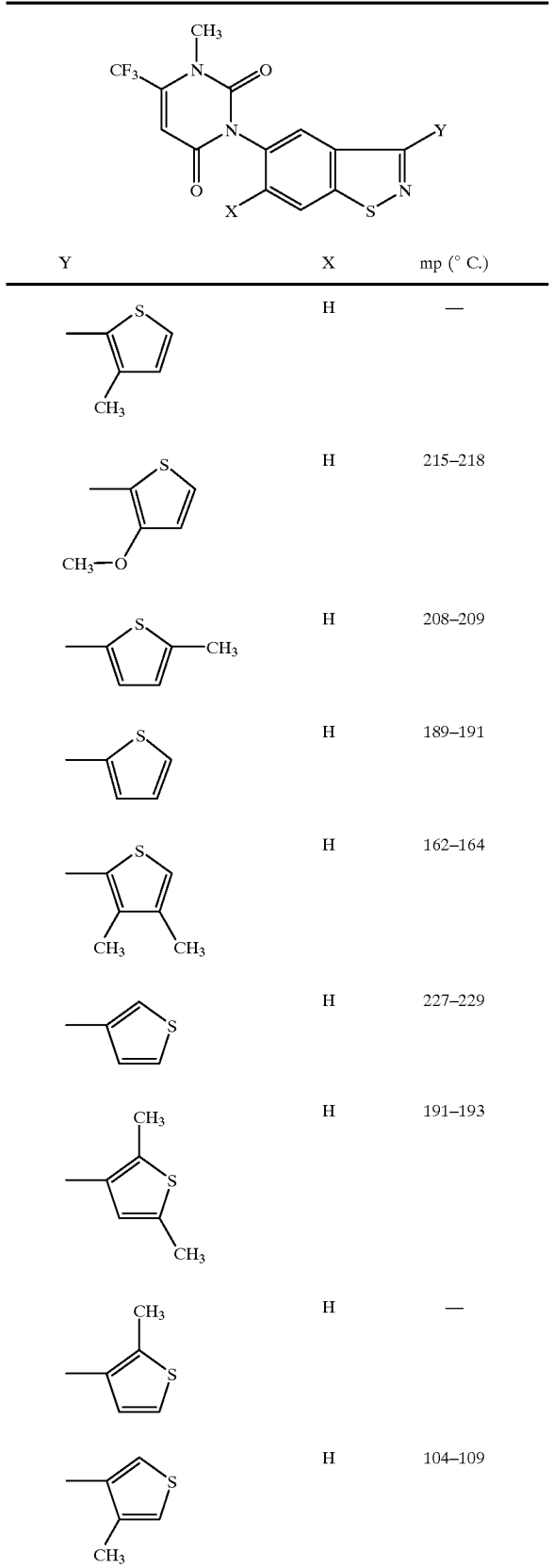

| Y | X | mp (° C.) |
|---|---|---|
| 2-methyl-3-thienyl (CH3 at 2) | H | — |
| 2-methyl-3-methoxy-thienyl | H | 215–218 |
| 2,5-dimethyl-thienyl | H | 208–209 |
| 2-thienyl | H | 189–191 |
| 2,3-dimethyl-thienyl | H | 162–164 |
| 3-thienyl | H | 227–229 |
| 2,4,5-trimethyl-thienyl | H | 191–193 |
| 2,3-dimethyl-thienyl (alt) | H | — |
| 3,4-dimethyl-thienyl | H | 104–109 |

-continued

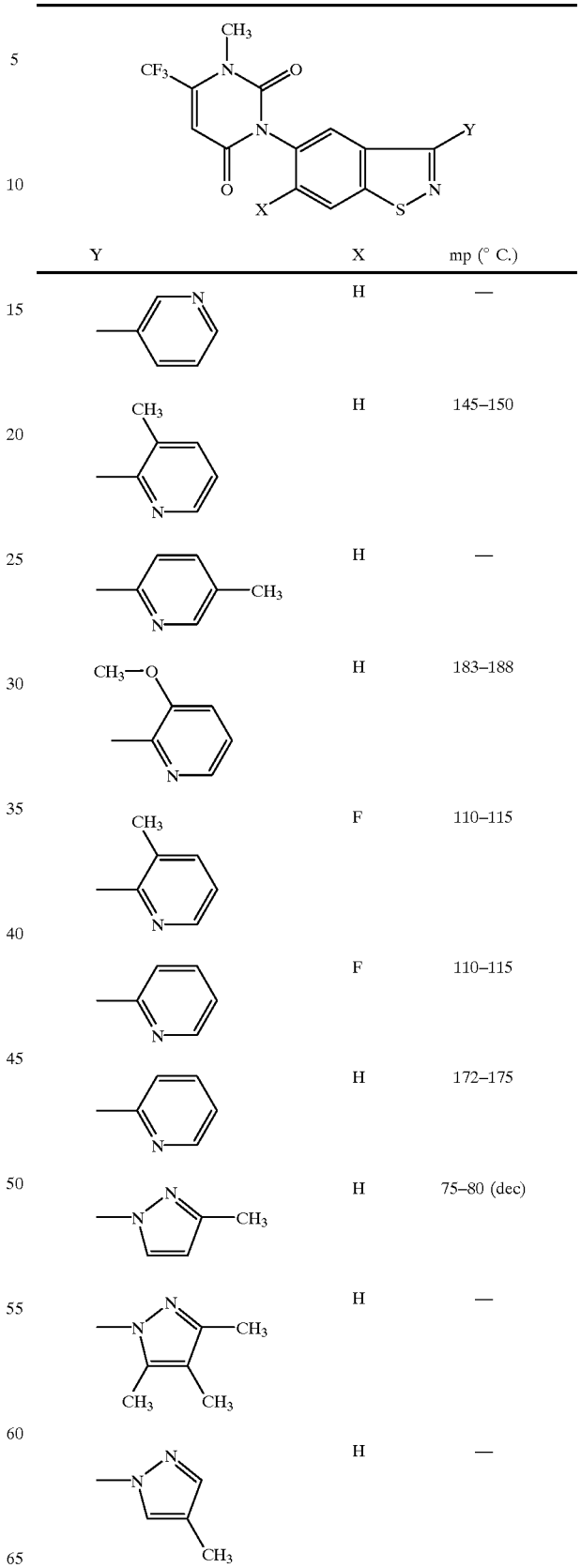

| Y | X | mp (° C.) |
|---|---|---|
| 3-pyridyl | H | — |
| 2,3-dimethylpyridyl | H | 145–150 |
| 2,5-dimethylpyridyl | H | — |
| 2-methyl-3-methoxy-pyridyl | H | 183–188 |
| 2,3-dimethylpyridyl | F | 110–115 |
| 2-pyridyl | F | 110–115 |
| 2-pyridyl | H | 172–175 |
| 1,3-dimethylpyrazolyl | H | 75–80 (dec) |
| 1,3,4,5-tetramethylpyrazolyl | H | — |
| 1-methyl-4-methylpyrazolyl | H | — |

-continued

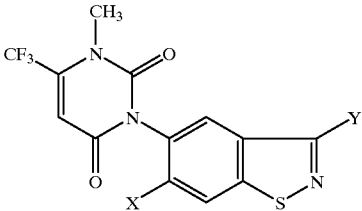

| Y | X | mp (° C.) |
|---|---|---|
| 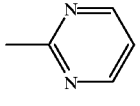 | H | 177–178 |
| 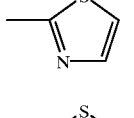 | H | — |
| 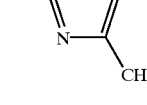 | H | 203–204 |
| 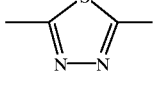 | H | 205–207 |
| 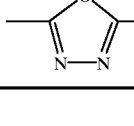 | H | — |
| 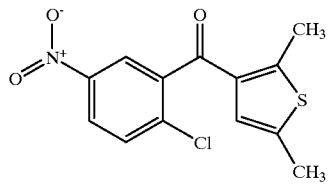 | H | — |

EXAMPLE 7

Preparation 2-Chloro-5-nitrophenyl 2-furyl ketone

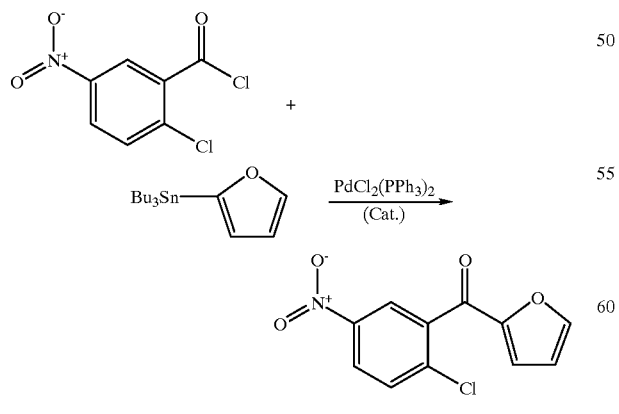

To a mixture of 2-chloro-5-nitrobenzoyl chloride(5.50 g, 0.0250 mol) and tetrahydrofuran is added 2-tributylstannylfuran (10.1 g, 0.0275 mol) followed by dichloro-bis-triphenylphosphine palladium (0.540 g, 0.00075 mol). The resultant mixture is stirred overnight at room temperature and concentrated in vacuo. The resultant oil is chromatographed on silica gel with methylene chloride-hexanes to afford the title compound as a bright yellow solid (4.95 g, 78.7%, mp 93–96° C.) which is identified by IR and NMR spectral analysis.

EXAMPLE 8

Preparation of 2-Chloro-5-nitrophenyl 3-chloro-2-thienyl ketone

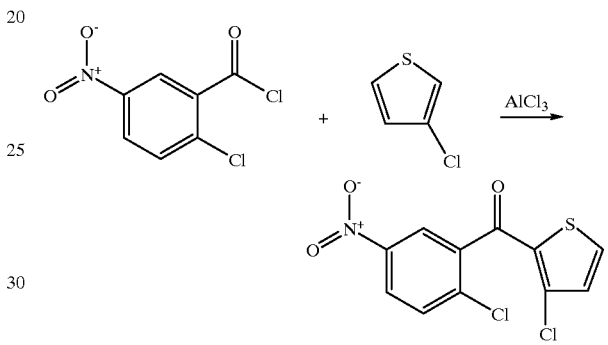

To a mixture of aluminum chloride (1.33 g, 0.0102 mol) and methylene chloride is added 3-chlorothiophene (1.21 g, 0.0102 mol) dropwise. The resultant mixture is stirred 30 minutes and treated with a solution of 2-chloro-5-nitrobenzoyl chloride (2.20 g, 0.0100 mol) in methylene chloride. The resultant mixture is stirred overnight at room temperature, poured into ice, acidified with concentrated hydrochloric acid and extracted twice with methylene chloride. The combined organic layers are washed with water and brine, dried over anhydrous magnesium sulfate and concentrated in vacuo to a brown oil. Trituration with ether affords the title compound as a brown solid (1.33 g, 44.0%, mp 114–116° C.) which is identified by NMR spectral analysis.

In essentially the same manner, treatment of 2-chloro-5-nitrobenzoyl chloride with 2,5-dimethylthiophene affords the following compound:

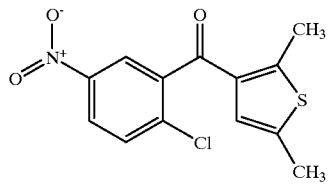

EXAMPLE 9

Preparation of 2-Chloro-5-nitrophenyl-5-methyl-2-thienyl-ketone

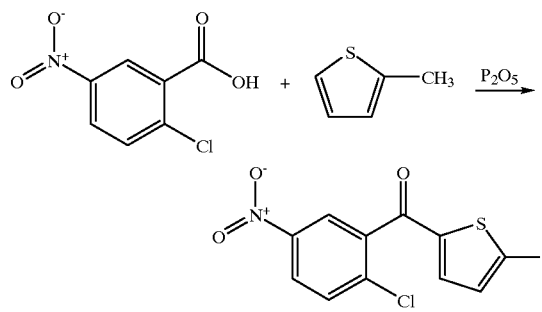

To a mixture of 2-chloro-5-nitrobenzoic acid (40.4 g, 0.200 mol), 2-methylthiophene (20.0 g, 0.200 mol) and methylene chlolride is added phosphorous pentoxide (142 g, 1.00 mol). The resultant mixture is stirred overnight at room temperature and quenched with dropwise addition of water. The organic layer is saved and the aqueous layer is extracted with methylene chloride. The combined organic layers are washed with water and brine, dried over anhydrous magnesium sulfate and concentrated in vacuo. The residue is chromatographed on silica gel with methylene chloride to afford the title compound as a solid (26.6 g. 47.6%, mp 68–69° C.) which is identified by IR and NMR spectral analyses.

Using essentially the same procedure with 2-chloro-5-nitrobenzoic acid and 3,4-dimethylthiophene, the following compound is obtained (mp 100–103° C.):

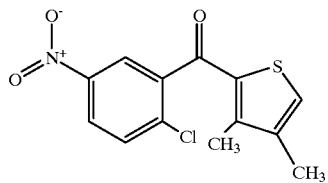

EXAMPLE 10

Preparation of 5-Amino-3-(3-chloro-2-thienyl)-1,2-benzisothiazole

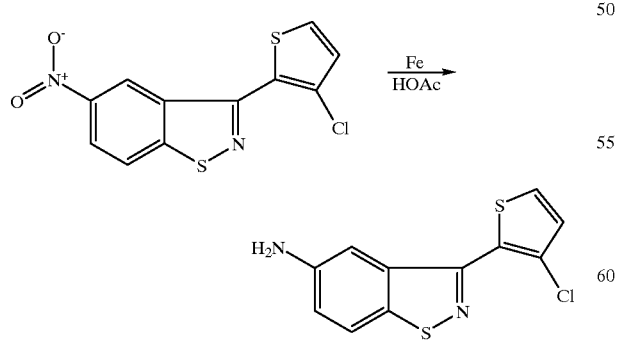

To a mixture of 3-(5-chloro-2-thienyl)-5-nitrobenzisothiazole (5.67 g, 0.0191 mol), ethyl acetate and glacial acetic acid at 70° C. is added iron powder (5.50 g, 0.0955 mol) portion-wise. The resultant mixture is stirred overnight at 70° C. and filtered after cooling with ethyl acetate wash. The organic layer is washed with three portions of water and one of brine, dried over anhydrous magnesium sulfate and concentrated in vacuo. Chromatography of the residue on silica gel with methylene chloride-diethyl ether affords a yellow foam, which is recrystallized from ether to afford the title compound as a yellow solid (3.13 g, 61.5%, mp 128–132° C.), which is identified by NMR and IR spectral analysis.

In essentially the same manner the appropriate nitrobenzothiazoles afford the following compounds:

| Y | mp (° C.) |
|---|---|
| furan (2-yl) | 114–115 |
| furan (3-yl) | 102–104 |
| 3-methyl-2-thienyl | 108–110 |
| 3-methoxy-2-thienyl | — |
| 5-methyl-2-thienyl | — |
| 3,4-dimethyl-2-thienyl | 146–148 |
| 3-thienyl | 100–101 |
| 2,4-dimethyl-5-thienyl | — |

-continued

[Structure: 5-amino-1,2-benzisothiazole with Y at 3-position]

| Y | mp (° C.) |
|---|---|
| 2-methyl-3-thienyl | 118–119 |
| 4-methyl-3-thienyl | 121–123 |
| 3-pyridyl | — |
| 2-methyl-3-pyridyl | — |
| 2-methyl-5-pyridyl | — |
| 3-methoxy-2-pyridyl | — |
| 2-pyridyl | — |
| 2-pyrimidinyl | — |
| 2-thiazolyl | 132–134 |
| 4-methyl-2-thiazolyl | 149–151 |
| 5-methyl-1,3,4-thiadiazol-2-yl | — |

-continued

[Structure: 5-amino-1,2-benzisothiazole with Y at 3-position]

| Y | mp (° C.) |
|---|---|
| 5-methyl-1,3,4-oxadiazol-2-yl | — |

EXAMPLE 11

Preparation of N-[3-(3-Methoxy-2-thienyl)-1,2-benzisothiazol-5-yl]-1-cyclohexene-1,2-dicarboximide A mixture of 3-(5-methoxy-3-thienyl)-5-aminobenzisothiazole (0.440 g, 1.68 mmol), tetrahydrophthalic anhydride (0.280 g, 1.84 mmol) and acetic acid is stirred three hours at reflux, cooled to room temperature and allowed to stand overnight. The resultant suspension is filtered to afford the title compound as yellow crystals (0.550 g, 82.6%, mp 146–149° C.) which is identified by IR and NMR spectral analyses.

Using essentially the same procedure and the appropriate amine the following compounds are obtained:

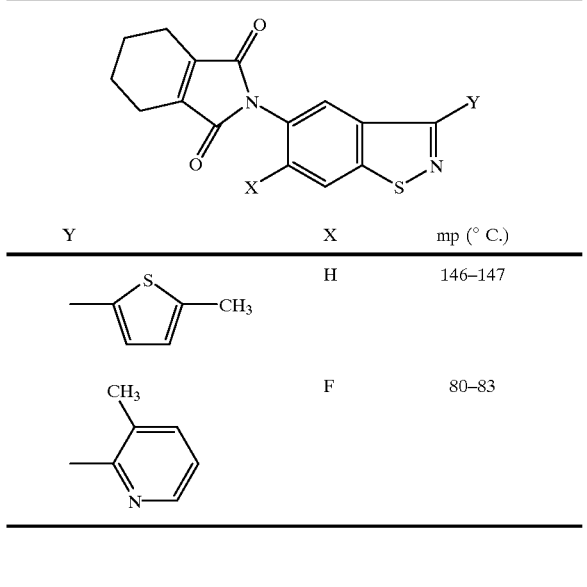

| Y | X | mp (° C.) |
|---|---|---|
| ![thiophene-CH3] | H | 146–147 |
| ![methylpyridine] | F | 80–83 |

EXAMPLE 12

Preparation of 3-[3-(3-Hydroxy-2-thienyl)-1,2-benzisothiazol-5-yl]-1-methyl-6-(trifluoromethyl) uracil

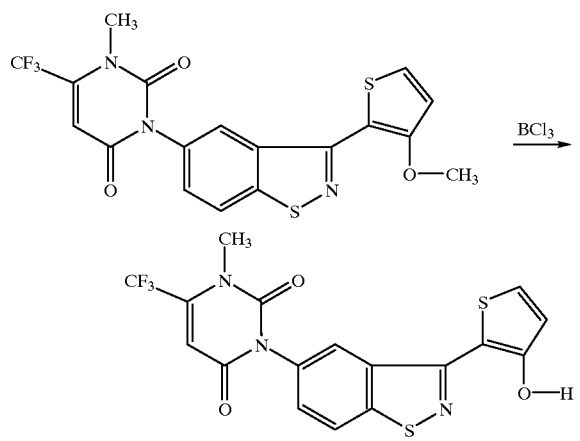

To a mixture of 3-[3-(3-methoxy-2-thienyl)-1,2-benzisothiazol-5-yl]-1-methyl-6-(trifluoromethyl)uracil (0.500 g, 1.14 mmol) and methylene chloride at −5° C. is added boron trichloride (1M in methylene chloride, 2.30 ml, 2.3 mmol) via syringe. The resultant mixture is stirred two hours at −5° C., warmed to room temperature, stirred overnight and poured into cold 10% hydrochloric acid. The mixture is extracted with methylene chloride. The organic layer is washed with water and brine, dried over anhydrous magnesium sulfate and concentrated in vacuo to an oil. The oil is crystallized in ether to afford the title compound as pale yellow-green crystals (0.350 g, 72.2%) which is characterized by NMR spectral analysis.

EXAMPLE 13

Preparation of Methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate

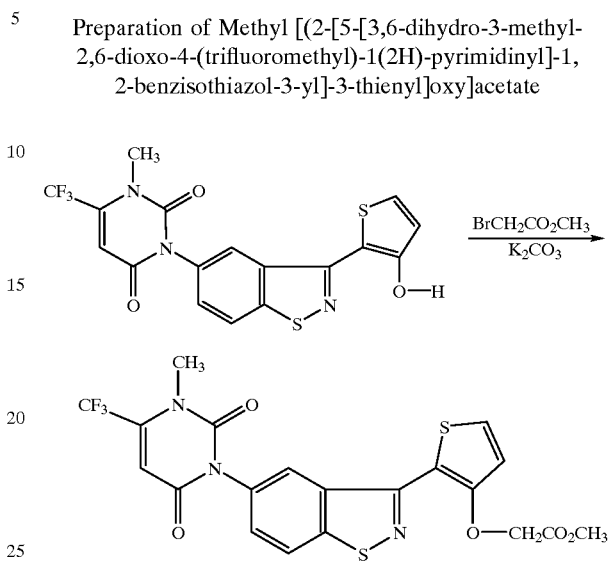

To a mixture of 3-[3-(3-hydroxy-2-thienyl)-1,2-benzisothiazol-5-yl]-1-methyl-6-(trifluoromethyl)uracil (0.580 g, 1.36 mmol) in dimethylformamide is added potassium carbonate (0.230 g, 1.66 mmol). The resultant mixture is stirred 30 minutes and treated with methyl bromoacetate (0.230 g, 1.50 mmol). The mixture is stirred over a weekend at room temperature and poured into water. Filtration and drying affords the title compound as an off-white solid (0.550 g, 81.4%, mp 73–79° C.) which is identified by NMR spectral analysis.

In essentially the same manner, treatment of 3-[3-(3-hydroxy-2-thieny 1)-1,2-benzisothiazol-5-yl]-1-methyl-6-(trifluoromethyl)uracil with the appropriate alkylating agent gives the following compounds:

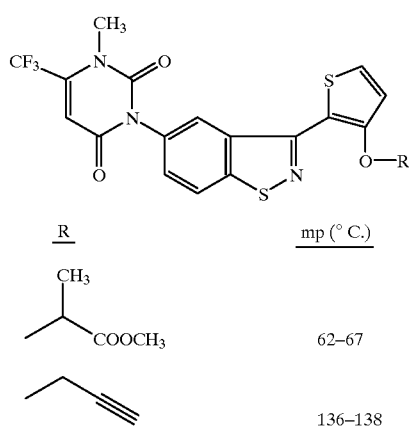

| R | mp (° C.) |
|---|---|
| ![isopropyl-COOCH3] | 62–67 |
| ![propargyl] | 136–138 |

EXAMPLE 14

Preparation of 3-[3-[3-(Bromomethyl)-2-thienyl]-1,2-benzisothiazol-5-yl]-1-methyl-6-(trifluoromethyl)uracil

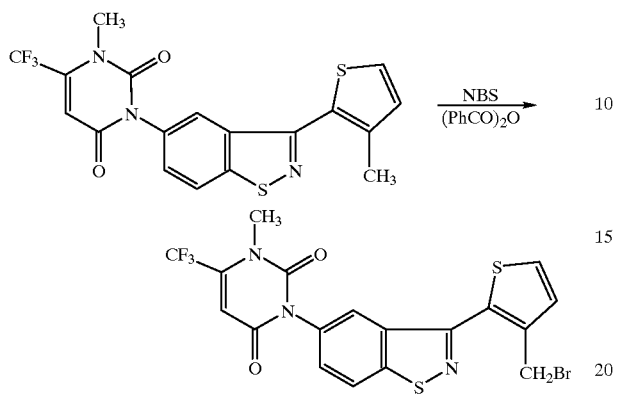

To a mixture of 3-[3-[3-(methyl)-2-thienyl]-1,2-benzisothiazol-5-yl]-1-methyl-6-(trifluoromethyl)uracil (0.420 g, 0.993 mmol) and carbon tetrachloride is added N-bromosuccinimide (0.200 g, 1.12 mmol) and benzoyl peroxide (10.0 mg). The resultant mixture is stirred overnight at reflux, cooled and filtered. The filtrate is concentrated in vacuo and the residue partitioned between water and methylene chloride. The organic layer is washed with brine, dried over anhydrous magnesium sulfate and concentrated in vacuo. The residue is chromatographed on silica gel with methylene chloride-diethyl ether to afford a pale yellow oil, which is crystallized in diethyl ether to afford the title compound as a cream-colored solid (0.340 g, 68.1%, mp 169° C.(dec)) which is identified by NMR spectral analysis.

EXAMPLE 15

Preparation of 3-[3-[3-(Methoxymethyl)-2-thienyl]-1,2-benzisothiazol-5-yl]-1-methyl-6-(trifluoromethyl)uracil

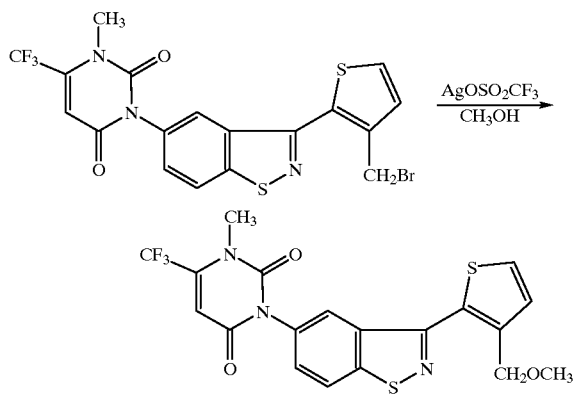

To a mixture of 3-[3-[3-(bromomethyl)-2-thienyl]-1,2-benzisothiazol-5-yl]-1-methyl-6-(trifluoromethyl)uracil (1.00 g, 1.99 mmol), methylene chloride and methanol is added silver trifluorormethanesulfonate. The resultant white suspension is stirred overnight at room temperature and filtered through a pad of diatomaceous earth with methylene chloride wash. The filtrate is washed with saturated sodium bicarbonate and brine, dried over anhydrous magnesium sulfate and concentrated in vacuo to a pale yellow solid, which is recrystallized from diethyl ether to afford the title compound (0.790 g, 87.7%, mp 131–133° C.) which is identified by NMR spectral analysis.

EXAMPLE 16

Preparation of 3-[3-[3-(Hydroxymethyl)-2-thienyl]-1,2-benzisothiazol-5-yl]-1-methyl-6-(trifluoromethyl)uracil

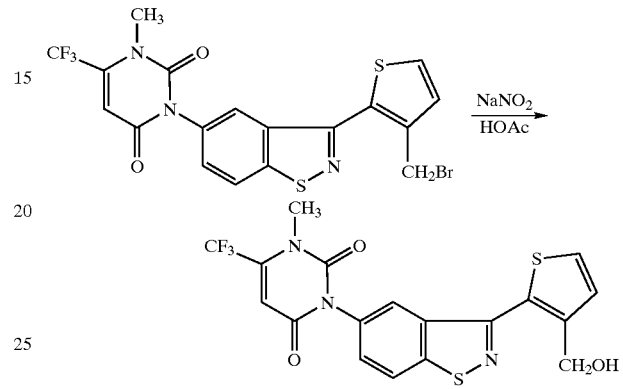

To a mixture of 3-[3-[3-(bromomethyl)-2-thienyl]-1,2-benzisothiazol-5-yl]-1-methyl-6-(trifluoromethyl)uracil (0.840 g, 1.67 mmol), dimethylsulfoxide and sodium nitrite is added glacial acetic acid. The resultant mixture is stirred overnight at 50° C., cooled and acidified with 10% aqueous hydrochloric acid. The mixture is diluted with water and extracted twice with ethyl acetate. The combined organic layers are washed with saturated sodium carbonate, water and brine, dried over anhydrous magnesium sulfate and concentrated in vacuo. The residue is chromatographed on silica gel with diethyl ether-methylene chloride to afford the title compound as an off-white solid (0.290 g, 38.3%, mp 168–169° C.) which is identified by IR and NMR spectral analysis.

EXAMPLE 17

Preparation of o-Chlorophenyl-3-pyridyl ketone

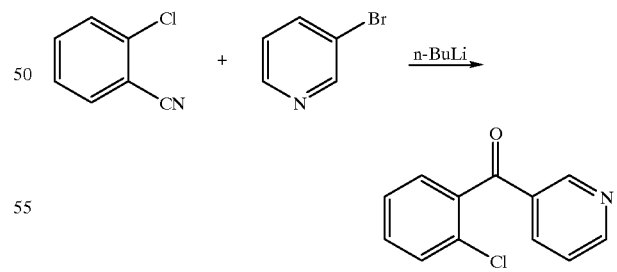

To a mixture of n-butyllithium (1.7 M in hexanes, 100 ml, 0.170 mol) and diethyl ether at −78° C. under an inert atmosphere is added a solution of 3-bromopyridine (24.0 g, 0.152 mol) in diethyl ether dropwise, followed by dropwise addition of a solution of 2-chlorobenzonitrile (20.7 g, 0.151 mol) in diethyl ether. The resultant mixture is stirred at −78° C. for one hour, warmed to room temperature and diluted with hydrochloric acid (1.9 N, 300 ml). The organic layer is extracted with 3N hydrochloric acid. The acidic aqueous layers are combined, stirred one hour at reflux and cooled to room temeperature. The mixture is basified with 5% aqueous sodium hydroxide and extracted with diethyl ether. The organic layer is concentrated in vacuo and the residue is chromatographed on silica gel to provide the title compound as a yellow oil (22.3 g, 68.0%) which is identified by NMR spectral analysis.

Using essentially the same procedure with 2-chlorobenzonitrile and the appropriate bromopyridine the following compounds are obtained:

| Y | mp (° C.) |
|---|---|
| 3-methyl-2-pyridyl | — |
| 5-methyl-2-pyridyl | — |
| 3-methoxy-2-pyridyl | — |
| 2-pyridyl | — |

EXAMPLE 18

Preparation of 3-(2-Chloro-5-nitrobenzoyl)pyridine

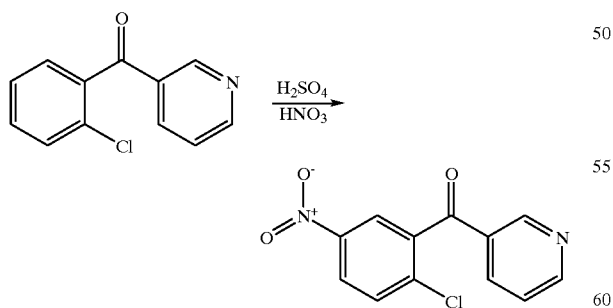

To a mixture of o-chlorophenyl 3-pyridyl ketone (10.0 g, 0.460 mol) and concentrated sulfuric acid at 0° C. is added dropwise a mixture of 90% nitric acid (2.40 ml) and concentrated sulfuric acid (6.0 ml). The resultant mixture is stirred one hour at 0° C., poured onto ice and neutralized with 30% ammonium hydroxide. Filtration and drying affords the title compound as a solid (11.4 g, 94.2%) which is identified by mass spectral analysis.

Using essentially the same procedure and the appropriate ketones the following compounds are obtained:

| Y | X | mp (° C.) |
|---|---|---|
| 3-methyl-2-pyridyl | H | — |
| 5-methyl-2-pyridyl | H | — |
| 3-methoxy-2-pyridyl | H | — |
| 3-methyl-2-pyridyl | F | — |
| 2-pyridyl | H | — |
| 2-pyridyl | F | — |
| 2-pyrimidinyl | H | — |

EXAMPLE 19

Preparation of 2-Chlorophenyl-(2-pyrimidinyl)acetonitrile

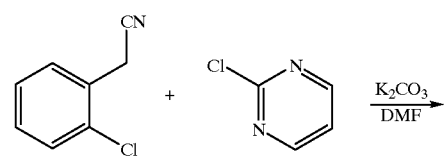

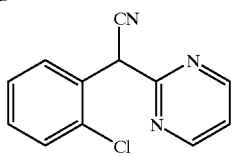

A mixture of 2-chlorobenzyl cyanide (4.50 g, 0.297 mol), potassium carbonate (6.84 g, 0.0495 mol) and dimethylformamide is stirred 30 minutes at 100° C. and treated dropwise with a solution of 2-chloropyrimidine (2.30 g, 0.0201 mol) in dimethylformamide. The resultant mixture is stirred overnight at 100° C. and treated with additional 2-chlorobenzyl cyanide (1.54 g, 0.0102 mol). The mixture is stirred several more hours at 100° C., cooled and diluted with water. The mixture is extracted three times with ethyl acetate. The combined organic layers are washed with water and brine, dried over sodium sulfate and concentrated in vacuo. The resultant brown oil is chromatographed on silica gel with ethyl acetate-hexanes to afford the title compound as a brown oil (3.25 g, 70.8%) which is identified by NMR spectral analysis.

EXAMPLE 20

Preparation of 2-(2-Chlorobenzoyl)pyrimidine

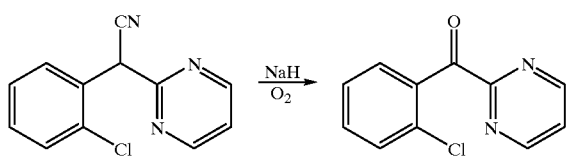

A mixture of 2-chlorophenyl(2-pyrimidinyl)acetonitile (3.25 g, 0.0142 mol), sodium hydride (60% in mineral oil, 1.07 g, 0.016 mol) and anhydrous tetrahydrofuran is stirred two hours at reflux and cooled to room temperature. Dry air is bubbled into the mixture while stirring three days. The mixture is quenched by dropwise addition of a 3:1 water:methanol mixture and then water. The tetrahydrofuran is removed in vacuo and the aqueous residue filtered to afford the title compound as a brown solid (2.00 g, 64.7%) which is identified by NMR spectral analysis.

EXAMPLE 21

Preparation of 2-(4-Fluorobenzoyl)-3-methylpyridine

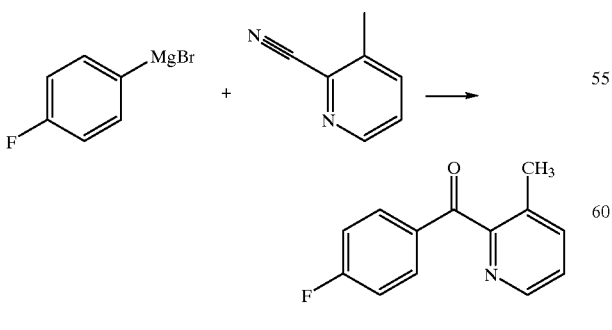

To a mixture of 4-fluorophenylmagnesium bromide (1.0 M in tetrahydrofuran, 100 ml, 0.100 mol) and tetrahydrofuran at 0° C. is added dropwise a solution of 2-cyano-3-methylpyrydine (11.8 g, 0.100 mol) in tetrahydrofuran. The resultant mixture is stirred one hour at 0° C. and overnight at room temperature. The mixture is slowly neutralized with 3N hydrochloric acid and extracted three times with ethyl acetate. The combined organic extracts are dried over anhydrous magnesium sulfate and concentrated in vacuo to afford the title compound as a brown liquid (2.32 g, 34.0%) which is identified by NMR spectral analysis.

Using essentially the same procedure on 2-cyanopyridine the following compound is obtained:

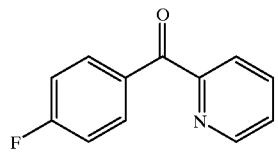

EXAMPLE 22

Preparation of 3-Amino-4-fluorophenyl 3-methyl-2-pyridyl ketone

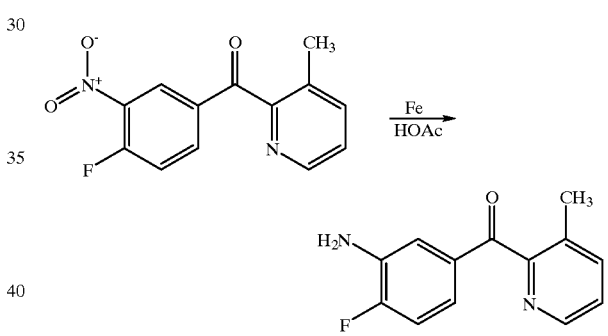

To a mixture of 2-(4-fluoro-5-nitrobenzoyl)-3-methylpyridine (7.13 g, 0.0258 mol) and glacial acetic acid at 70–80° C. is added iron powder (7.76 g, 0.130 mol) in three portions. The resultant mixture is stirred overnight at 70–80° C., cooled to room temperature and extracted three times with ethyl acetate. The combined organic layers are filtered through Celite, dried over anhydrous magnesium sulfate and concentrated in vacuo to afford the title compound as a tan solid (4.36 g, 69.8%) which is identified by NMR spectral analysis.

Using essentially the same procedure on 2-(4-fluoro-5-nitrobenzoyl)pyridine the following compound is obtained:

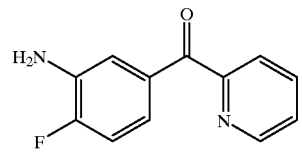

EXAMPLE 23

Preparation of 4-Amino-5-fluoro-2-(3-methylpicolinoyl)phenyl thiocyanate

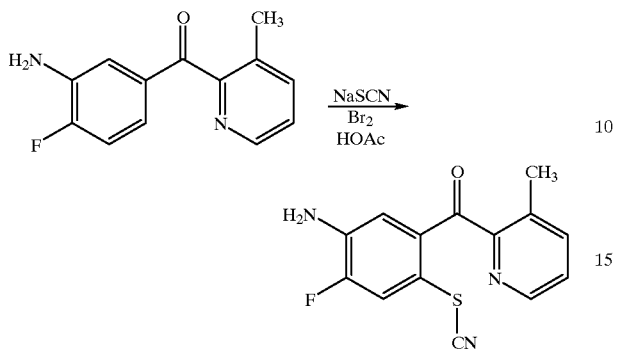

To a mixture of 3-amino-4-fluorophenyl 3-methyl-2-pyridyl ketone(4.20 g, 0.171 mol), sodium thiocyanate (4.19 g, 0.0517 mol) and glacial acetic acid is added a solution of bromine in acetic acid (2M, 12 ml, 0.0240 mol) over a one hour period. The resultant mixture is stirred one hour at room temperature and poured into cold water. The precipitate is filtered and dried to afford the title compound as a green solid (5.43 g, >100%) which is identified by NMR and mass spectral analysis.

Using essentially the same procedure on 2-(3-amino-4-fluorobenzoyl)pyridine the following compound is obtained:

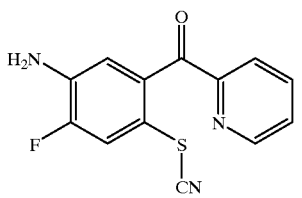

EXAMPLE 24

Preparation of 5-Amino-6-fluoro-3-(3-methyl-2-pyridyl)-1,2-benzisothiazole

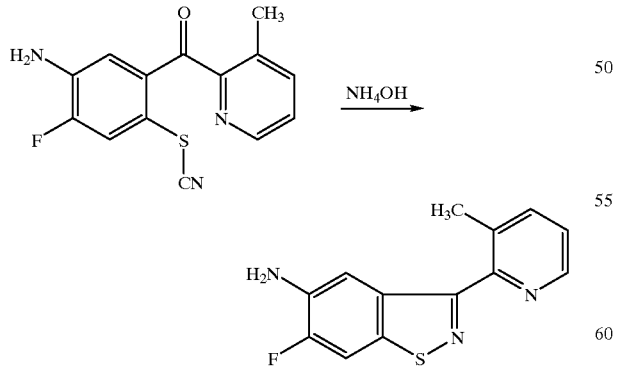

A mixture of 4-amino-5-fluoro-2-(3-methylpicolinoyl) phenyl thiocyanate(3.06 g, 0.0112 mole), concentrated ammonium hydroxide (300 ml) and methanol (300 ml) is stirred overnight at room temperature. The methanol is removed in vacuo and the resultant mixture is filtered to afford the title compound as a green solid (1.93 g, 66.6%) which is identified by NMR spectral analysis.

Using essentially the same procedure on 2-(3-methyl-2-pyridoyl)-4-amino-5-fluoro-phenylthiocyanate the following compound is obtained:

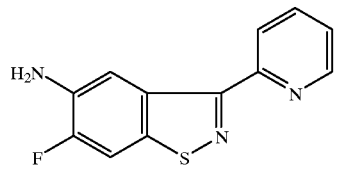

EXAMPLE 25

Preparation of 1-Methyl-3-[3-(2-pyridyl)-1,2-benzisothiazol-5-yl]-6-(trifluoromethyl)uracil N",S,S-trioxide

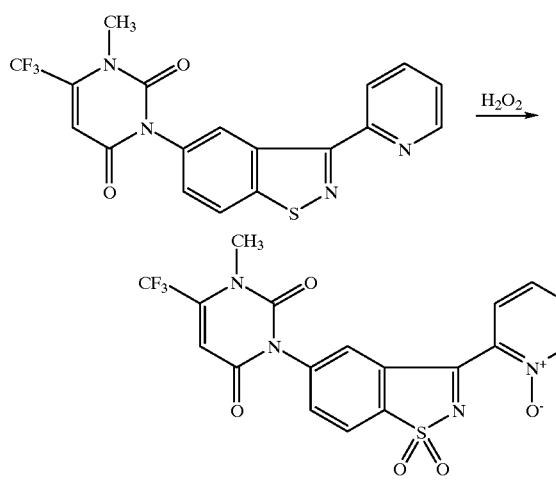

A mixture of 1-methyl-3-[3-(2-pyridyl)-1,2-benzisothiazol-5-yl]-6-(trifluoromethyl)uracil (0.450 g, 11.1 mmol), hydrogen peroxide (30% in water, 5 ml) and glacial acetic acid is stirred one hour at reflux, cooled to room temperature and stirred overnight. The excess peroxide is quenched by addition of saturated sodium sulfite and the mixture is extracted with hot ethyl acetate. The organic layers are dried over anhydrous magnesium sulfate and concentrated in vacuo to afford the title compound as a yellow semi-solid (0.0800 g, 17.2%) which is identified by NMR and mass spectral analyses.

EXAMPLE 26

Preparation of 2,2'-Dithiobis[5-nitrobenzoic acid]

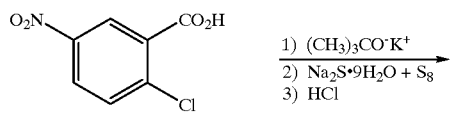

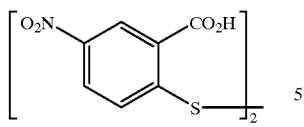

A mixture of 2-chloro-5-nitrobenzoic acid (100 g, 0.496 mol) in ethanol is treated portionwise with potassium tert-butoxide (55.5 g, 0.495 mol), diluted with additional ethanol, heated to reflux, treated portionwise with a solution prepared from sodium sulfide nonahydrate (60.0 g, 0.249 mol), sulfur (8.80 g, 0.274 mol) and water, refluxed for two hours, cooled to room temperature, and treated with concentrated hydrochloric acid. The resultant acidic mixture is stirred for one hour and filtered to obtain a solid. The solid is washed with water and air-dried to give the title product as a yellow powder which is identified by NMR spectral analysis.

EXAMPLE 27

Preparation of 5-Nitro-1,2-benzisothiazol-3(2H)-one

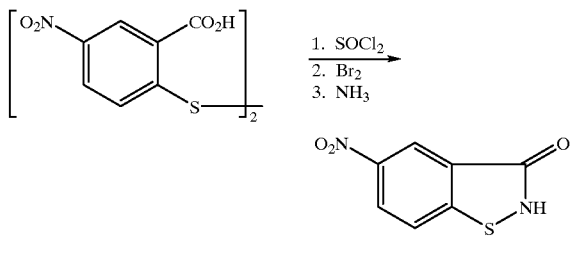

A mixture of 2,2'-dithiobis[5-nitrobenzoic acid] (44.6 g, 0.113 mol) and thionyl chloride (49.0 mL, 0.670 mol) in methylene chloride is treated with N,N-dimethylformamide (0.800 mL), refluxed overnight, concentrated in vacuo, and diluted with 1,2-dichloroethane. The resultant organic solution is treated with bromine (22.5 mL, 0.436 mol), stirred at room temperature for 20 minutes, refluxed for 3.5 hours, and concentrated in vacuo to obtain a residue. A solution of the residue in 1,2-dichloroethane is cooled with an ice-water bath, treated with concentrated ammonia (112 mL) over 15 minutes, stirred at room temperature for 16 hours, cooled with an ice-water bath, and treated with concentrated hydrochloric acid. The resultant aqueous mixture is stirred at room temperature for one hour and filtered to obtain a solid. The solid is washed with water and air-dried to give the title product as a yellow solid which is identified by NMR spectral analysis.

EXAMPLE 28

Preparation of 3-Chloro-5-nitro-1,2-benzisothiazole

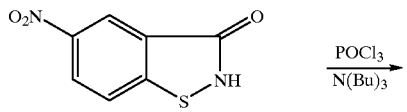

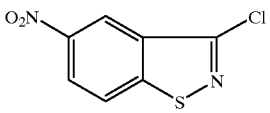

A mixture of 5-nitro-1,2-benzisothiazol-3(2H)-one (10.0 g, 0.0510 mol), phosphorus oxychloride (40.0 mL, 0.429 mol) and tributylamine (12.0 mL, 0.050 mol) is heated at 103–115° C. for six hours, stirred at room temperature overnight, and poured into an ice-water mixture. The resultant aqueous mixture is extracted with methylene chloride. The combined organic extracts are washed sequentially with water and saturated sodium hydrogen carbonate solution, dried over anhydrous sodium sulfate, and concentrated in vacuo to obtain a gum. Column chromatography of the gum using silica gel and methylene chloride gives the title product as an orange-yellow solid which is identified by NMR spectral analysis.

EXAMPLE 29

Preparation of 3-(3,5-Dimethylpyrazol-1-yl)-5-nitro-1,2-benzisothiazole

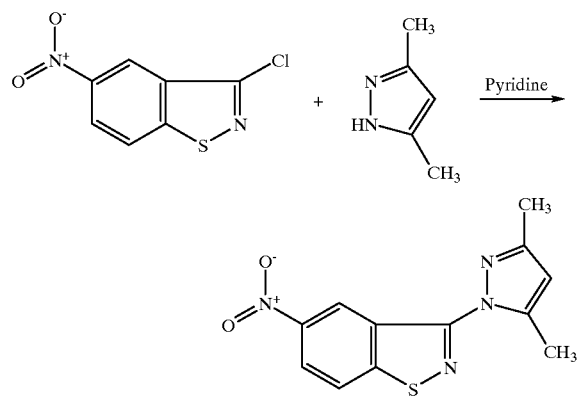

A mixture of 3-chloro-5-nitrobenzisothiazole (5.3 g, mmol), 3,5-dimethylpyrazole (2.40 g, 25.0 mmol) and pyridine is stirred overnight at reflux, cooled to room temperature and diluted with ethyl acetate. The resultant mixture is filtered and the filtrate is washed with three portions of 10% hydrochloric acid and one portion of water. The organic layer is dried over anhydrous magnesium sulfate and concentrated in vacuo to afford the title compound (2.85 g, 43.8%) which is identified by NMR spectral analysis.

In essentially the same manner, treatment of 3-chloro-5-nitrobenzisothiazole with the appropriate heterocycles affords the following compounds:

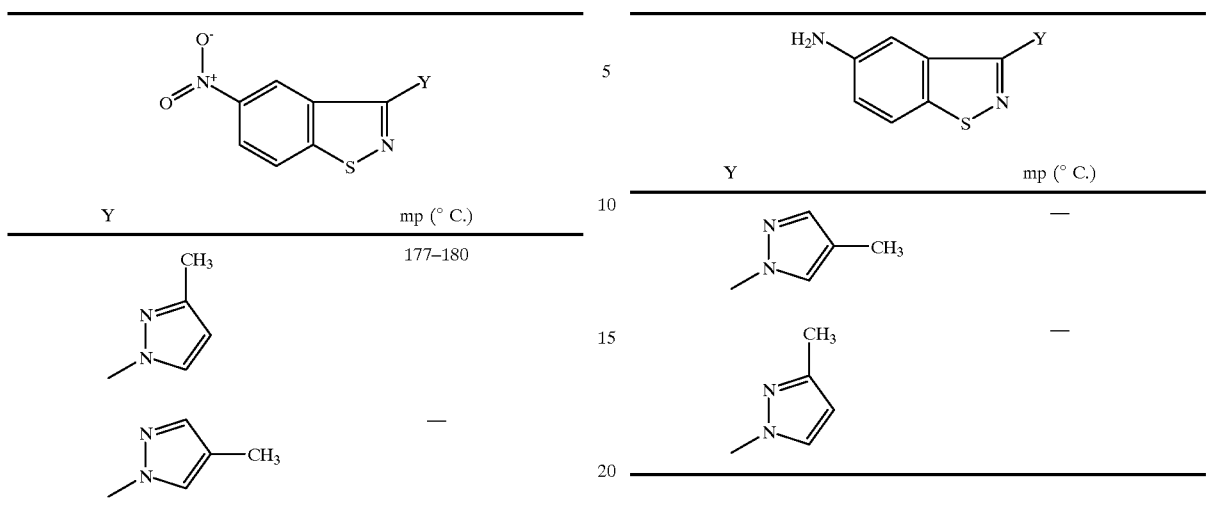

| Y | mp (° C.) |
|---|---|
| (3-methylpyrazol-1-yl, CH₃) | 177–180 |
| (4-methylpyrazol-1-yl, CH₃) | — |

| Y | mp (° C.) |
|---|---|
| (4-methylpyrazol-1-yl, CH₃) | — |
| (3-methylpyrazol-1-yl, CH₃) | — |

EXAMPLE 30

Preparation of 5-Amino-3-(3-methylpyrazol-1-yl)-1,2-benzisothiazole

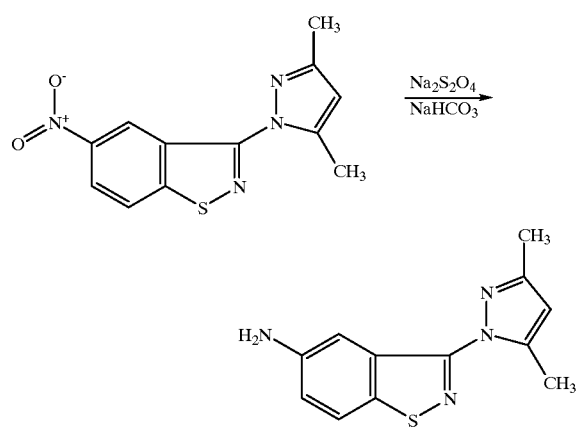

A mixture of 5-nitro-3-(3-methylpyrazol-1-yl)-1,2-benzisothiazole (3.12 g, 12.0 mmol), sodium bicarbonate (2.00 g, 23.8 mmol), acetonitrile and water is stirred one hour at 70° C. and treated with sodium hydrosulfite (8.70 g, 50.0 mmol) in portions. The resultant mixture is stirred overnight at reflux, cooled to room temperature and diluted with ethyl acetate. The organic layer is dried over anhydrous magnesium sulfate and concentrated in vacuo. The residue is washed with a mixture of methylene chloride and ethyl acetate. The organic layer is decanted to afford the title compound as a viscous brown oil which is identified by NMR spectral analysis.

Using essentially the same procedure on the appropriate 5-nitrobenzisothiazole the following compounds are obtained:

EXAMPLE 31

Preparation of 5-Amino-3-chloro-1,2-benzisothiazole

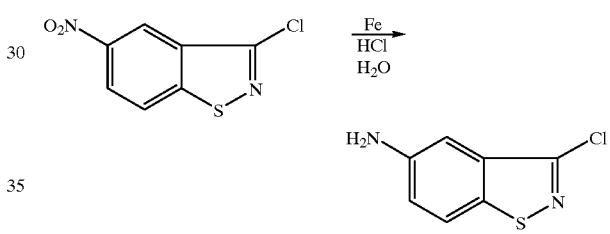

A solution of 3-chloro-5-nitro-1,2-benzisothiazole (2.00 g) in toluene is treated with iron powder (8.40 g, 325 mesh) and concentrated hydrochloric acid (8 drops), heated to reflux, treated dropwise with water (8.00 mL), refluxed for 35 minutes, cooled to room temperature, and filtered through diatomaceous earth. The resultant filtrate is concentrated in vacuo to obtain a residue. Flash column chromatography of the residue using silica gel and an ethyl acetate/hexanes solution (1:1) gives the title product.

EXAMPLE 32

Preparation of 3-(3-Chloro-1,2-benzisothiazol-5-yl)-6-(trifluoromethyl)-2,4(1H,3H)--pyrimidinedione

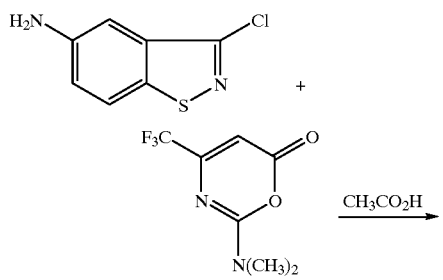

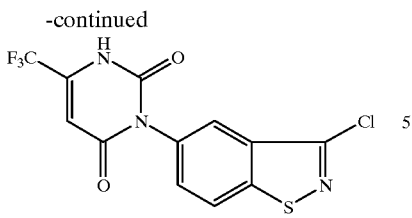

A mixture of 5-amino-3-chloro-1,2-benzisothiazole (1.10 g) and 2-dimethylamino-4-(trifluoromethyl)-6H-1,3-oxazin-6-one (1.38 g) in acetic acid (15.1 mL) is stirred at 90–105° C. for two hours, cooled to room temperature, and filtered to obtain 0.500 g of the title product as a solid. The resultant filtrate is diluted with water and filtered to obtain an additional 1.11 g of the title product.

EXAMPLE 33

Preparation of 3-(3-Chloro-1,2-benzisothiazol-5-yl)-1-methyl-6-(trifluoromethyl)-2,4(1H,3H)-pyrimidinedione

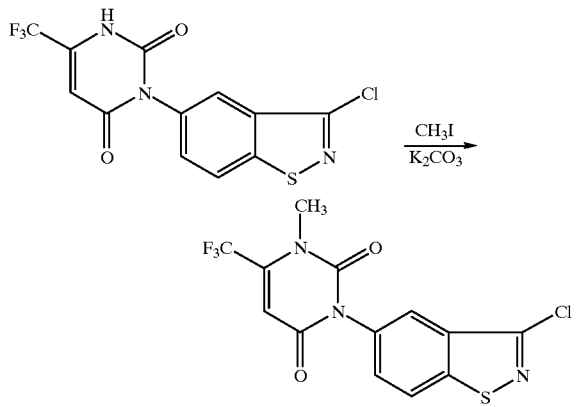

A mixture of 3-(3-chloro-1,2-benzisothiazol-5-yl)-6-(trifluoromethyl)-2,4(1H,3H)-pyrimidinedione (1.06 g), potassium carbonate (0.470 g) and iodomethane (0.500 mL) in N,N-dimethylformamide is stirred at room temperature for 90 minutes, treated with additional iodomethane (0.500 mL), stirred at room temperature for 15 minutes, and diluted with water. The resultant aqueous mixture is filtered to obtain a solid. The solid is washed with water and dried in a vacuum oven at room temperature to give the title product as a solid which is identified by NMR spectral analysis.

EXAMPLE 34

Preparation of 2'-Chloro-4'-fluoro-5'-nitroacetophenone

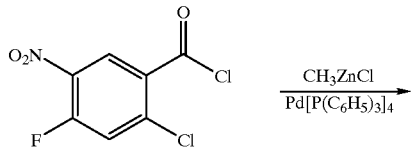

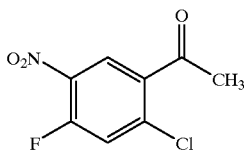

A 2 M solution of methylzinc chloride in tetra-hydrofuran (5.00 mL, 10.1 mmol) is treated dropwise with a solution of 2-chloro-4-fluoro-5-nitrobenzoyl chloride (2.00 g, 8.40 mmol) in tetrahydrofuran, treated with tetrakis(triphenylphosphine)palladium(0) (0.400 g, 0.350 mmol), stirred at room temperature for one hour, and poured into 3 N hydrochloric acid. The resultant aqueous mixture is extracted with ethyl acetate. The organic extracts are combined, washed sequentially with water and saturated sodium hydrogen carbonate solution, dried over anhydrous magnesium sulfate, and concentrated in vacuo to obtain a dark liquid. Flash column chromatography of the liquid using silica gel and a methylene chloride in hexanes solution (6:4) gives the title product as an off-white solid (mp 66–68° C.) which is identified by NMR spectral analyses.

EXAMPLE 35

Preparation of 3-Methyl-5-nitro-1,2-benzisothiazole

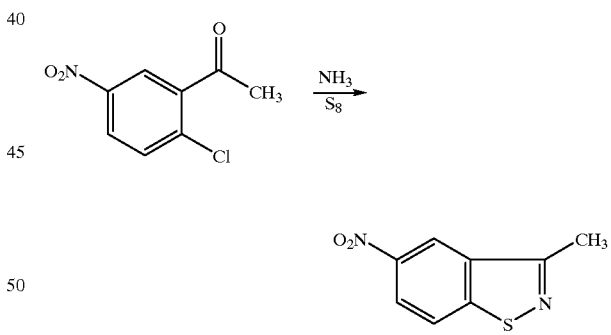

Ammonia (45 g, 2,642 mmol) is bubbled into methanol at −40° C. in a steel bomb. Sulfur (30.5 g, 95.0 mmol) and 2'-chloro-5'-nitroacetophenone (19 g, 95.0 mmol) are then added. The bomb is sealed and heated at about 90° C. overnight. After cooling, the reaction mixture is removed from the bomb and concentrated in vacuo to obtain a residue. The residue is diluted with methylene chloride, passed through a plug of silica gel and concentrated in vacuo to give the title product as an orange solid (12.0 g) which is identified by NMR spectral analyses.

EXAMPLE 36

Preparation of 3-[3-(Bromomethyl)-1,2-benzisothiazol-5-yl]-1-methyl-6-(trifluoromethyl)-2,4(1H,3H)-pyrimidinedione and 3-[3-(Dibromomethyl)-1,2-benzisothiazol-5-yl]-1-methyl-6-(trifluoromethyl)-2,4(1H,3H)-pyrimidinedione

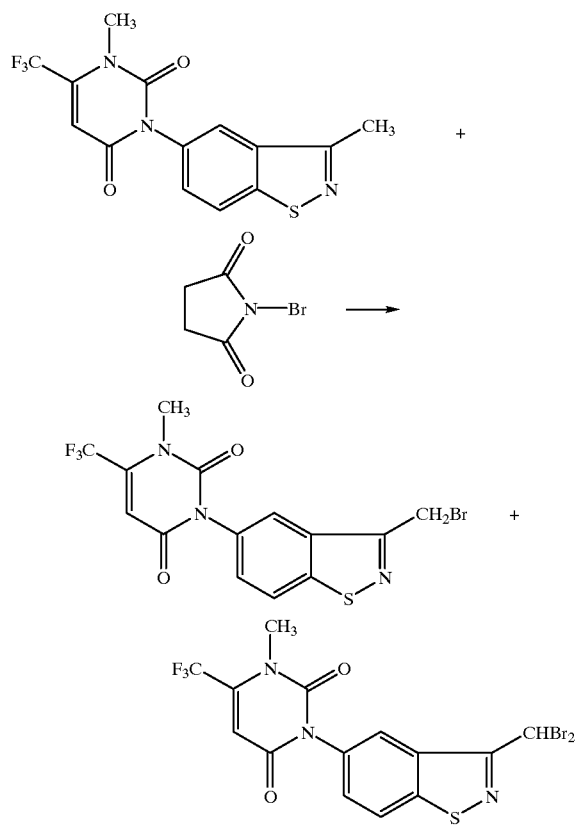

A mixture of 1-methyl-3-(3-methyl-1,2-benzisothiazol-5-yl)-6-(trifluoromethyl)-2,4(1H,3H)-pyrimidinedione (16.6 g, 48.8 mmol), N-bromosuccinimide (34.8 g, 195 mmol) and benzoyl peroxide (0.295 g, 1.22 mmol) in 1,2-dichloroethane is refluxed for one hour, treated with additional benzoyl peroxide (0.30 g), refluxed for 3.5 hours, and cooled to room temperature. Column chromatography of the cooled reaction mixture using silica gel and a methylene chloride/hexanes solution (1:1) gives a mixture of the title products which is dissolved in methylene chloride. The resultant organic solution is washed sequentially with 15% sodium hydrogen sulfite solution and water, dried over anhydrous magnesium sulfate, and concentrated in vacuo to obtain a yellow solid. Column chromatography of the yellow solid using silica gel and a 1% tert-butyl methyl ether in methylene chloride solution gives 3-[3-(bromomethyl)-1,2-benzisothiazol-5-yl]-1-methyl-6-(trifluoromethyl)-2,4(1H,3H)-pyrimidinedione as an off-white solid, mp 203–204° C., and 3-[3-(dibromomethyl)-1,2-benzisothiazol-5-yl]-1-methyl-6-(trifluoromethyl)-2,4(1H,3H)-pyrimidinedione as an off-white solid, mp 107–110° C.

Using essentially the same procedure on 1-methyl-3-(3-methyl-6-fluoro-1,2-benzisothiazol-5-yl)-6-(trifluoromethyl)-2,4(1H,3H)-pyrimidinedione, the following compounds are obtained:

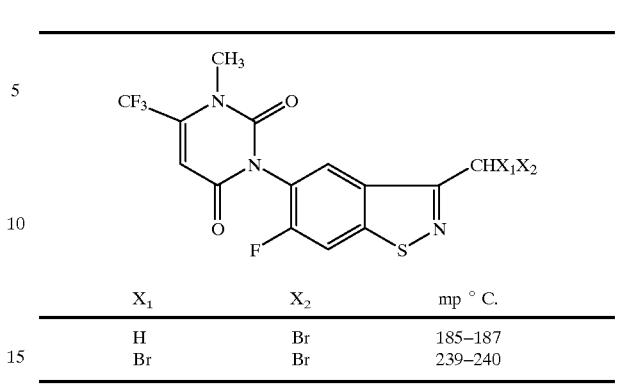

| $X_1$ | $X_2$ | mp ° C. |
|---|---|---|
| H | Br | 185–187 |
| Br | Br | 239–240 |

EXAMPLE 37

Preparation of a mixture of 3-[3-(Hydroxymethyl)-1,2-benzisothiazol-5-yl]-1-methyl-6-(trifluoromethyl)-2,4(1H,3H)-pyrimidinedione and 5-[3,6-Dihydro-3-methyl-2,6-dioxo-4-(trifluoromethyl)-1(2H)-pyrimidinyl]-1,2-benzisothiazole-3-carboxaldehyde, (2:3)

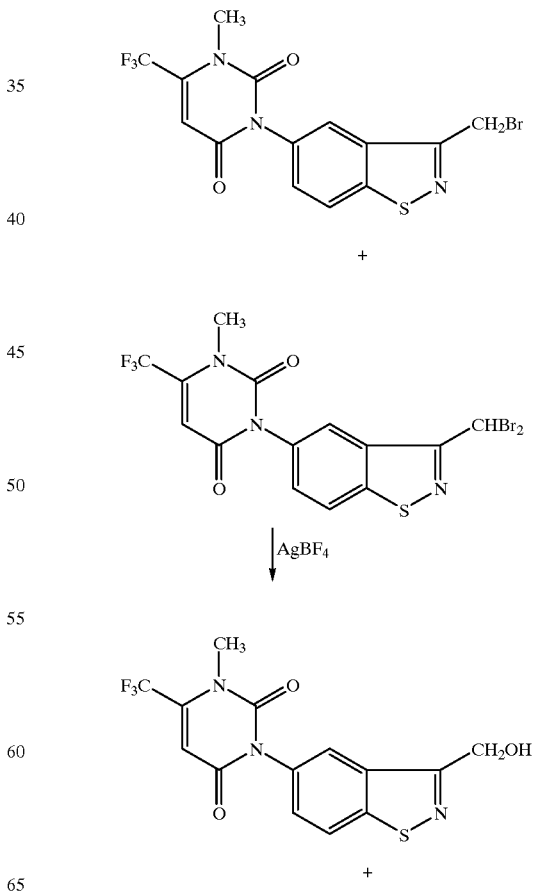

-continued

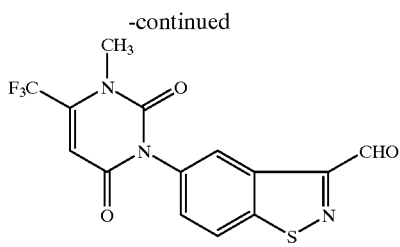

A solution of a 2:3 mixture of 3-[3-(bromomethyl)-1,2-benzisothiazol-5-yl]-1-methyl-6-(trifluoromethyl)-2,4(1H,3H)-pyrimidinedione and 3-[3-(dibromomethyl)-1,2-benzisothiazol-5-yl]-1-methyl-6-(trifluoromethyl)-2,4(1H,3H)-pyrimidinedione (5.00 g), silver tetrafluoroborate (3.50 g), 1,4-dioxane (30.0 mL) and water (10.0 mL) is refluxed for 2 hours, cooled, and filtered to remove solids. The resultant filtrate is poured into a methylene chloride and water mixture. The organic phase is separated, washed sequentially with water and brine, dried over anhydrous sodium sulfate, and concentrated in vacuo to give a 2:3 mixture of the title products.

EXAMPLE 38

Preparation of 5-[3,6-Dihydro-3-methyl-2,6-dioxo-4-(trifluoromethyl)-1(2H)-pyrimidinyl]-1,2-benzisothiazole-3-carboxylic acid

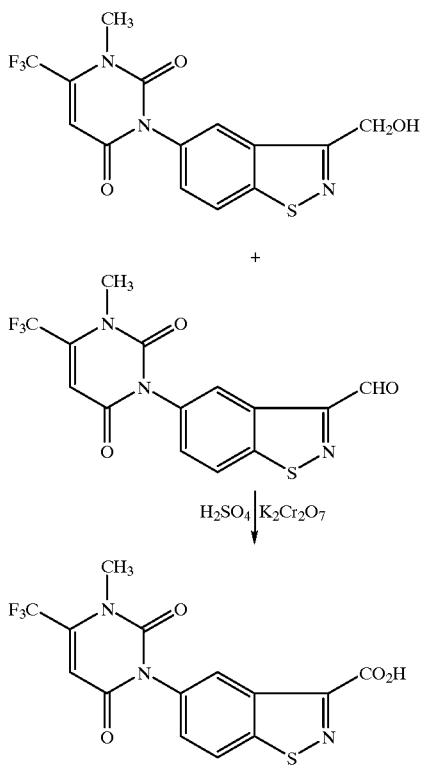

A solution of potassium dichromate (10.0 g) in 1.5 M sulfuric acid (200 mL) is cooled to 0° C., treated dropwise with a solution of a 2:3 mixture of 3-[3-(hydroxymethyl)-1,2-benzisothiazol-5-yl]-1-methyl-6-(trifluoromethyl)-2,4 (1H,3H)-pyrimidinedione and 5-[3,6-dihydro-3-methyl-2,6-dioxo-4-(trifluoromethyl)-1(2H)-pyrimidinyl]-1,2-benzisothiazole-3-carboxaldehyde (12.0 g) in acetic acid, stirred at room temperature for 2 hours, and diluted with water. The resultant aqueous mixture is extracted with methylene chloride. The organic extracts are combined, washed sequentially with water and brine, dried over anhydrous sodium sulfate, and concentrated in vacuo to give the title product as a white solid (8.50 g, mp 149–152° C.).

EXAMPLE 39

Preparation of 5-[3,6-Dihydro-3-methyl-2,6-dioxo-4-(trifluoromethyl)-1(2H)-pyrimidinyl]-1,2-benzisothiazole-3-carboxylic acid chloride

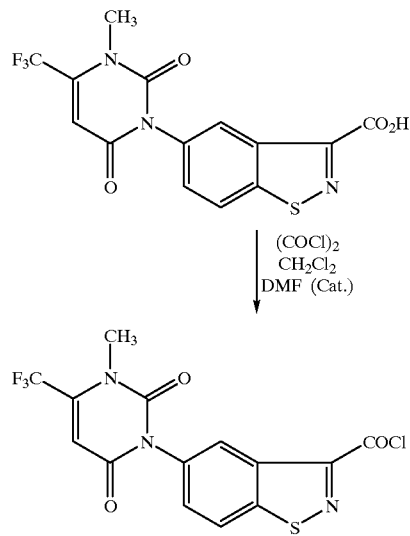

To a solution of 5-[3,6-dihydro-3-methyl-2,6-dioxo-4-(trifluoromethyl)-(2H)-pyrimidinyl]-1,2-benzisothiazole-3-carboxylic acid (0.200 g, 0.000540 mol) in methylene chloride is added N,N-dimethylformamide (one drop) followed by oxalyl chloride in methylene chloride (2.0 M, 0.540 ml, 0.00108 mol). The resultant mixture is stirred at room temperature for 90 minutes and concentrated in vacuo to a white solid, which is used without further purification.

EXAMPLE 40

Preparation of 5-[3,6-Dihydro-3-methyl-2,6-dioxo-4-(trifluoromethyl)-1(2H)-pyrimidinyl]-N-[1-(hydroxymethyl)-2-methylpropyl]-1,2-benzisothiazole-3-carboxamide

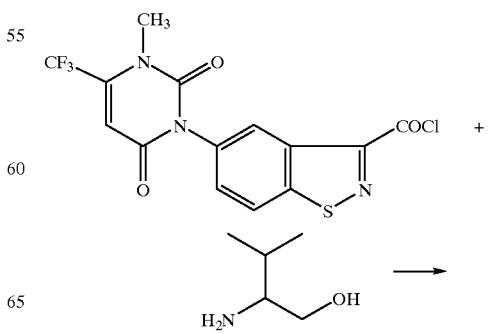

-continued

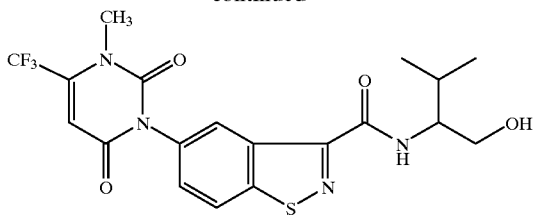

To a solution of 2-amino-3-methyl-1-butanol (1.39 g, 13.5 mmol) in anhydrous tetrahydrofuran at 0° C. is added dropwise a solution of 5-[3,6-Dihydro-3-methyl-2,6-dioxo-4-(trifluoromethyl)-1(2H)-pyrimidinyl]-1,2-benzisothiazole-3-carboxylic acid chloride (2.10 g, 5.39 mmol) in tetrahydrofuran. The resultant mixture is stirred 7.5 hours at ambient temperature, diluted with diethyl ether, washed with 1M aqueous hydrochloric acid, saturated sodium bicarbonate and brine, dried over anhydrous magnesium sulfate and concentrated in vacuo. The residue is chromatographed on silica gel with hexanes-ethyl acetate to afford the title compound as a solid (2.12 g, 86.2%, mp 120° C.) which is identified by NMR spectral analysis.

Using essentially the same procedure and employing ethanolamine, the following product is obtained, mp130° C.:

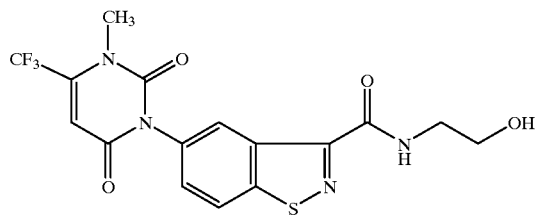

EXAMPLE 41

Preparation of N-[1-(Chloromethyl)-2-methylpropyl]-5-[3,6-dihydro-3-methyl-2,6-dioxo-4-(trifluoromethyl)-1(2H)-pyrimidinyl]-1,2-benzisothiazole-3-carboxamide

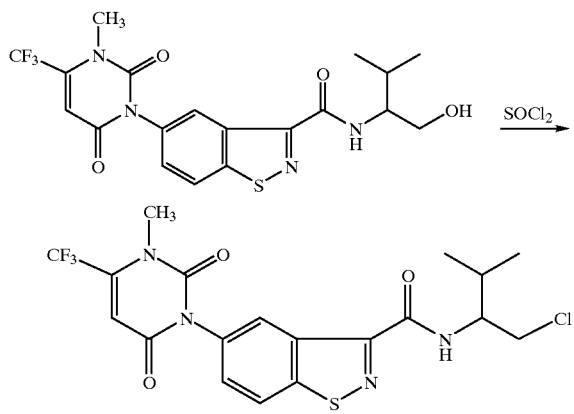

To 5-[3,6-dihydro-3-methyl-2,6-dioxo-4-(trifluoromethyl)-1(2H)-pyrimidinyl]-N-[1-(hydroxymethyl)-2-methylpropyl]-1,2-benzisothiazole-3-carboxamide(1.89 g, 4.14 mmol) at 0° C. is added thionyl chloride (5.00 ml). The resultant mixture is stirred one hour at 0° C. and two hours at room temperature. Anhydrous diethyl ether is added and the resultant suspension stirred vigorously for 1.75 hour. The suspension is filtered to afford the title compound as a cream-colored solid (1.77 g, 89.8%, mp>220° C.) which is identified by NMR spectral analysis.

Using essentially the same procedure, the following product is obtained, mp 196°–197° C.

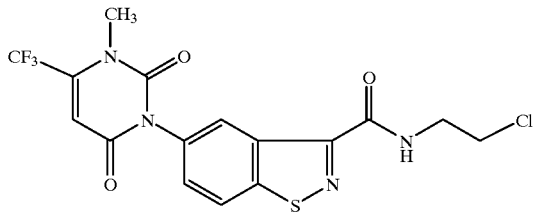

EXAMPLE 42

Preparation of 3-[3-(4-Isopropyl-2-oxazolin-2-yl)-1,2-benzisothiazol-5-yl]-1-methyl-6-(trifluoromethyl) uracil

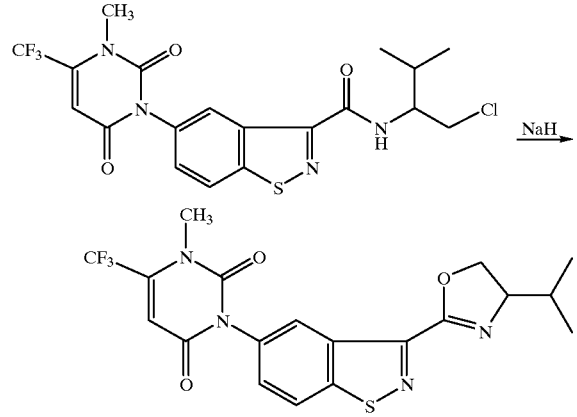

To a solution of N-[1-(chloromethyl)-2-methylpropyl]-5-[3,6-dihydro-3-methyl-2,6-dioxo-4-(trifluoromethyl)-1(2H)-pyrimidinyl]-1,2-benzisothiazole-3-carboxamide(1.25 g, 2.63 mmol) in anhydrous tetrahydrofuran is added sodium hydride (60% oil dispersion, 0.116 g, 2.90 mmol). The resultant mixture is stirred 1.5 hour at room temperature, quenched with saturated ammonium chloride, diluted with diethyl ether, washed with saturated ammonium chloride and brine, and dried over anhydrous magnesium sulfate. Concentration in vacuo affords a yellow syrup, which is combined with material from a previous run and chromatographed on silica gel to afford the title compound as a white crystalline solid (mp 100–105° C.) which is identified by NMR spectral analysis.

In essentially the same manner, the following product is obtained, mp 198°–199° C.

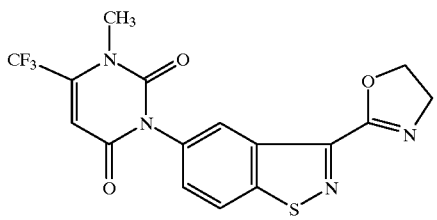

EXAMPLE 43

Preparation of 1-Acetyl-2-(1,2-benzisothiazol-3-ylcarbonyl)hydrazine

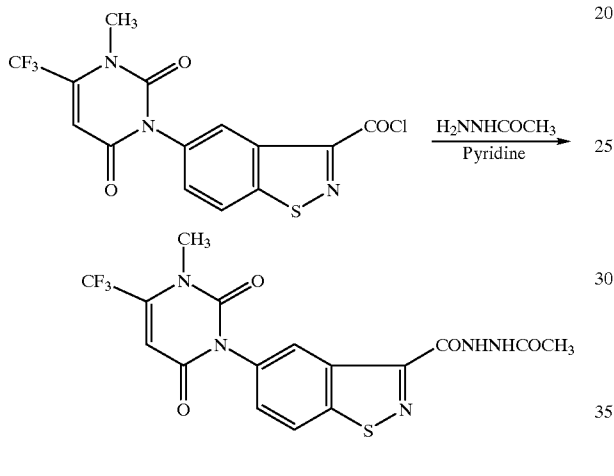

To a mixture of acetylhydrazide (6.93 g, 0.0935 mol) and pyridine at 0° C. is added a solution of 5-[3,6-dihydro-3-methyl-2,6-dioxo-4-(trifluoromethyl)-1(2H)-pyrimidinyl]-1,2-benzisothiazole-3-carboxylic acid chloride (20.3 g, 0.103 mol) in pyridine in four portions such that the temperature does not exceed 40° C. The resultant mixture is heated to reflux, stirred 30 minutes, cooled and concentrated in vacuo. The residue is mixed with ice water and filtered to afford the title compound as an off-white solid (17.5 g, 79.5%) which is identified by NMR analysis.

EXAMPLE 44

Preparation of 3-(5-Methyl-1,3,4-thiadiazol-2-yl)-1,2-benzisothiazole

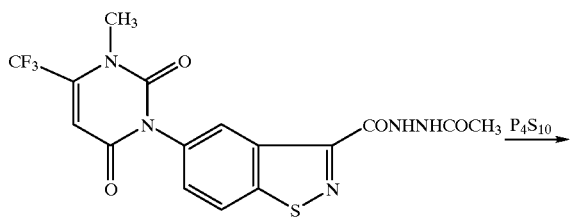

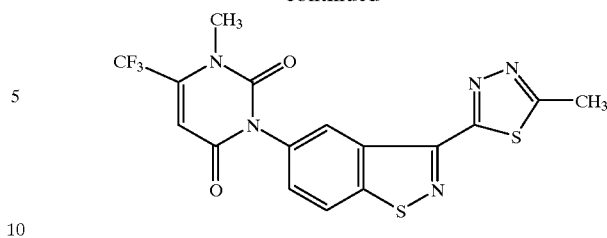

A mixture of 1-acetyl-2-(1,2-benzisothiazol-3-ylcarbonyl)hydrazine (17.5 g, 0.0744 mol) and phosphorous pentasulfide (53.0 g, 0.119 mol) is heated to 150–160° C. After two hours, the mixture is cooled and the residue carefully digested with warm 2N aqueous sodium hydroxide until gas evolution subsides. The resultant tan solid is filtered and dried to afford the title compound (21.8 g, >100%) which is identified by NMR spectral analysis.

EXAMPLE 45

Preparation of 3-(5-Methyl-1,3,4-thiadiazol-2-yl)-5-nitro-1,2-benzisothiazole

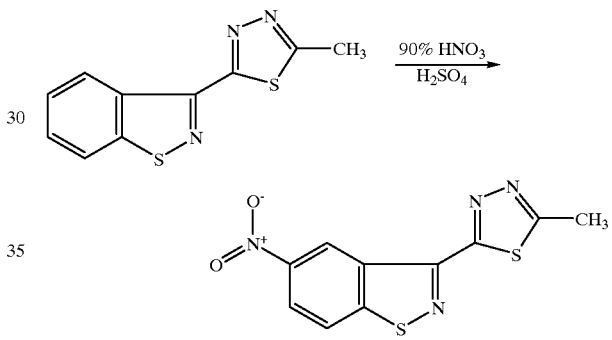

To a mixture of 3-(5-methyl-1,3,4-thiadiazol-2-yl)-1,2-benzisothiazole(6.8 g, 0.0291 mol) and conc. sulfuric acid at 10° C. is added 90% nitric acid (3.20 ml, 0.582 mol) dropwise. The resultant mixture is stirred 90 min at 0–10° C. and poured into ice water with stirring. Filtration affords a solid which is stirred in hot methylene chloride and filtered to afford the title compound as a tan solid (mp 239–240° C.) which is identified by NMR analysis.

EXAMPLE 46

Preparation of 1-Benzothiophen-2,3-dione

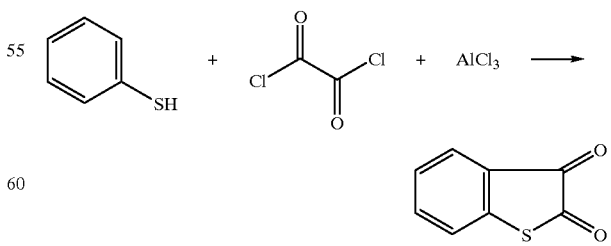

To a solution of thiophenol (100 g, 0.907 mol) in ether is added dropwise a solution of oxalyl chloride (175 g, 1.38 mol) in ether. The mixture is stirred two hours at reflux and concentrated in vacuo. The residue is taken up in methylene chloride and cooled to 0° C. Aluminum chloride (145 g, 1.09 mol) is added in portions such that the temperature does not exceed 25° C. The resultant mixture is stirred 30 minutes at reflux, cooled to room temperature and poured into ice water with stirring. The organic layer is washed with saturated sodium bicarbonate, water and brine, dried over anhydrous magnesium sulfate, filtered and concentrated in vacuo to an orange solid which is recrystallized from methylene chloride:hexanes to afford the title compound (102 g, 69.0%) which is identified by NMR spectral analysis.

EXAMPLE 47

Preparation of 1,2-Benzisothiazole-3-carboxamide

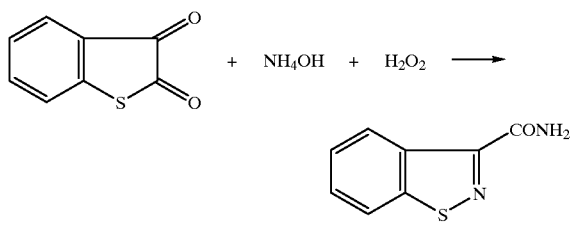

To ammonium hydroxide (1.78 l) is added 1-benzothiophen-2,3-dione (87.0 g, 0.530 mol) at 5–10° C., followed by hydrogen peroxide (30% aqueous, 178 ml). The resultant mixture is filtered to obtain a yellow solid which is dried (77.0 g, 81.7%) and identified as the title compound by NMR and IR spectral analysis.

EXAMPLE 48

Preparation of 1,2-Benzisothiazole-3-carboxylic acid

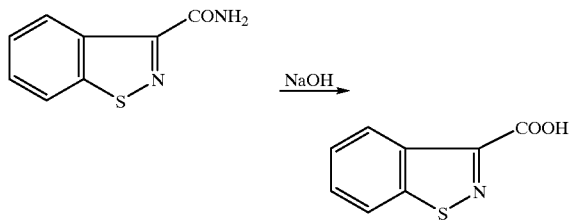

A mixture of 1,2-benzisothiazole-3-carboxamide (5.0 g, 0.028 mole) and 1N aqueous sodium hydroxide (55 ml) is heated on a steam bath until solution is achieved (approximately 30 minutes), cooled to room temperature, and acidified with 2N hydrochloric acid. The resulting precipitate is filtered and dried in vacuo to afford the title compound (1.85 g, 96%) as a white solid, which is identified by NMR and IR spectral analysis.

EXAMPLE 49

Preparation of 5-Nitro-1,2-benzisothiazole-3-carboxylic acid and of 7-Nitro-1,2-benzisothiazole-3-carboxylic acid

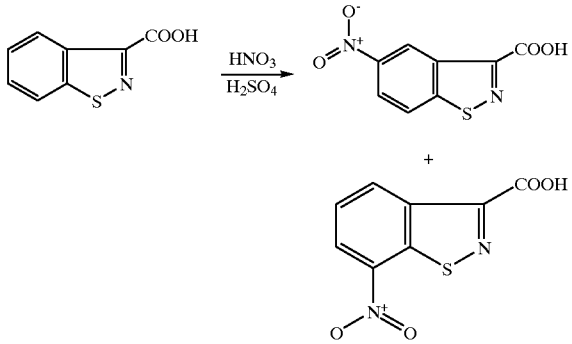

To a stirred solution of 1,2-benzisothiazole-3-carboxylic acid (20.0 g, 0.112 mol) in concentrated sulfuric acid (120 ml) at 0° C. is added dropwise 90% nitric acid (5.25 ml, 1.3 equivalents) such that the reaction temperature does not exceed 10° C. The solution is stirred for an additional two hours at 10° C., carefully poured into vigorously stirred ice water, and the resulting solid filtered and dried in vacuo to afford a solid (25 g), which by NMR analysis consists of a 2:1 mixture of 7- and 5-nitro isomers.

The above solid is suspended in ethyl acetate, the undissolved solid filtered and recrystallized from ethyl acetate to afford 7-nitro-1,2-benzisothiazole-3-carboxylic acid (3.3 g) identified by NMR spectral analysis.

The initial ethyl acetate filtrate from above is concentrated in vacuo, and the residue recrystallized from acetonitrile (200 ml) to afford 5-nitro-1,2-benzisothiazole-3-carboxylic acid (6.2 g) as a yellow solid which is identified by NMR spectral analysis.

EXAMPLE 50

Preparation of 5-Nitro-1,2-benzisothiazole-3-carboxylic acid chloride

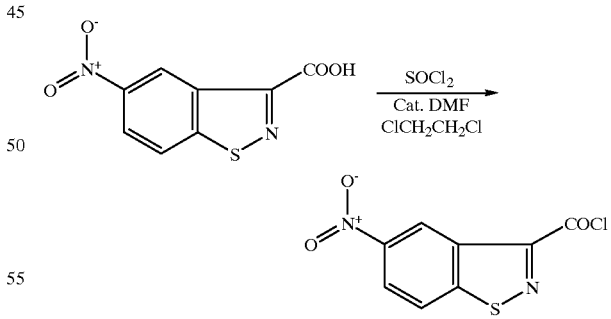

To a stirred mixture of 5-nitro-1,2-benzisothiazole-3-carboxylic acid (5.5 g, 0.0246 mole) and ethylene dichloride (55 ml) is added thionyl chloride (2.92 g, 1.63 ml, 1.0 eq.), and the reaction mixture heated to 70° C. An additional portion of thionyl chloride (1.46 g, 0.82 ml, 0.5 eq) is added and heating at 70° C. continued for 2.5 hours. The cooled solution is concentrated in vacuo to afford the title compound which is identified by NMR and IR analysis, and used without further purification.

EXAMPLE 51

Preparation of 1-Acetyl-2-[(5-nitro-1,2-benzisothiazol-3-yl)carbonyl]hydrazine

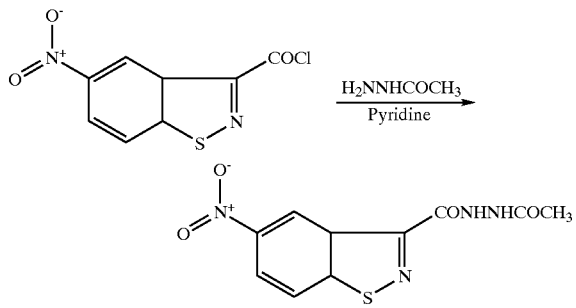

To a mixture of acetylhydrazide (90%, 1.84 g, 0.0224 mol) and pyridine at 0–5° C. is added dropwise a solution of 5-nitro-1,2-benzisothiazole-3-carboxylic acid chloride (5.96 g, 0.0246 mol) in pyridine. The resultant mixture is brought to reflux, stirred 30 minutes at reflux and cooled to 40° C. The excess pyridine is removed in vacuo and the residue added slowly to ice water with stirring. Filtration affords the title compound as a tan solid (5.22 g, 75.8%) which is characterized by NMR spectral analysis.

EXAMPLE 52

Preparation of 3-(5-Methyl-1,3,4-oxadiazol-2-yl)-5-nitro-1,2-benzisothiazole

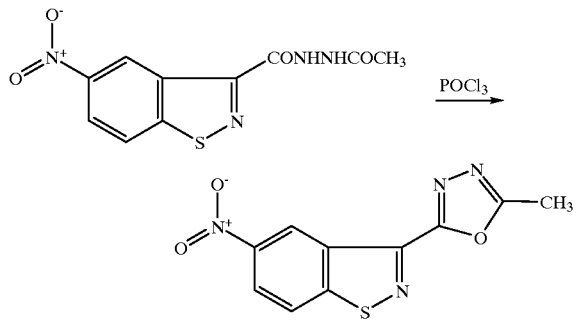

To a mixture of 1-acetyl-2-[(5-nitro-1,2-benzisothiazol-3-yl)carbonyl]hydrazine(4.55 g, 0.0163 mol) and acetonitrile at room temperature is added phosphorous oxychloride (14.9 g, 0.0972 mol). The resultant mixture is heated to reflux, stirred two hours, cooled to room temperature and filtered to afford the title compound as an off-white solid (mp>250° C.) which is identified by NMR spectral analysis.

EXAMPLE 53

Preparation of Ethyl α-cyano-5-nitro-1,2-benzisothiazole-3-acetate

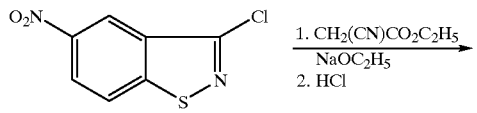

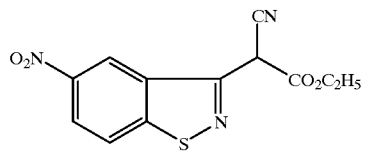

A sodium ethoxide solution (previously prepared from ethanol and sodium (1.00 g, 0.0430 mol)) is cooled with an ice-acetone bath, treated portionwise with ethyl cyanoacetate (4.51 g, 0.0398 mol), stirred at room temperature for 30 minutes, treated with 3-chloro-5-nitro-1,2-benzisothiazole (4.27 g, 0.0199 mol), stirred at room temperature overnight, cooled to 0° C., and treated dropwise with 10% hydrochloric acid (15.0 mL). The resultant mixture is stirred at room temperature for one hour and filtered to obtain a solid. The solid is washed with ethanol and air-dried to give the title product as a yellow solid which is identified by NMR spectral analysis.

EXAMPLE 54

Preparation of Ethyl 5-nitro-1,2-benzisothiazole-3-acetate

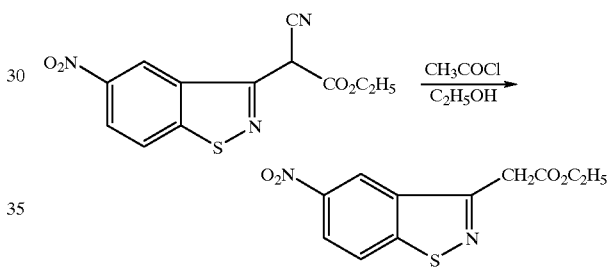

Ethyl α-cyano-5-nitro-1,2-benzisothiazole-3-acetate (6.67 g, 0.0229 mol) is added to a solution of acetyl chloride (67.0 mL) in ethanol. The reaction mixture is refluxed overnight, cooled, and filtered to remove solids. The resultant filtrate is concentrated in vacuo to obtain a brown semi-solid. A mixture of the semi-solid in diethyl ether is stirred for two hours and filtered to obtain a solid. The solid is washed with diethyl ether and air-dried to give the title product as yellow crystals (1.04 g, mp 91–92° C.).

EXAMPLE 55

Preparation of Ethyl 5-amino-1,2-benzisothiazole-3-acetate

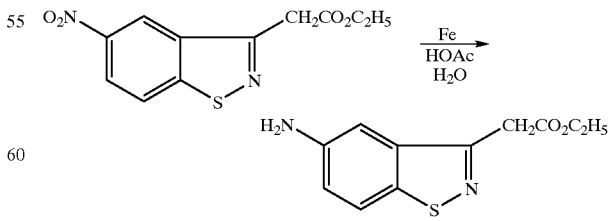

A 10% acetic acid solution (31.0 mL) is stirred at 50° C., treated with iron powder (0.656 g), treated dropwise with a solution of ethyl 5-nitro-1,2-benzisothiazole-3-acetate (1.03 g, 3.88 mmol) in ethyl acetate, stirred at 50° C. for two hours, treated with additional iron powder (0.305 g), stirred at 50° C. for 15 minutes, and poured into saturated sodium hydrogen carbonate solution. The resultant aqueous mixture is extracted with ethyl acetate. The combined organic extracts are washed sequentially with water and brine, dried over anhydrous sodium sulfate, and concentrated in vacuo to obtain an oil. Column chromatography of the oil using silica gel and methylene chloride gives the title product as a yellow oil.

EXAMPLE 56

Preparation of Ethyl 5-[3,6-dihydro-2,6-dioxo-4-(trifluoromethyl)-1(2H)-pyrimidinyl]-1,2-benzisothiazole-3-acetate

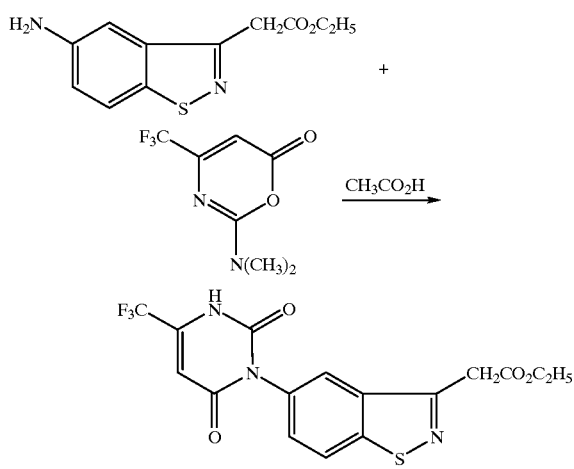

A mixture of ethyl 5-amino-1,2-benzisothiazole-3-acetate (0.748 g, 3.16 mmol) and 2-dimethylamino-4-(trifluoromethyl)-6H-1,3-oxazin-6-one (0.660 g, 3.17 mmol) in acetic acid is refluxed for three hours, concentrated in vacuo, and diluted with saturated sodium hydrogen carbonate solution. The resultant mixture is extracted with methylene chloride. The combined organic extracts are washed with water, dried over anhydrous sodium sulfate, and concentrated in vacuo to give the title product as a tan solid which is identified by NMR spectral analysis.

EXAMPLE 57

Preparation of Ethyl 5-[3,6-dihydro-3-methyl-2,6-dioxo-4-(trifluoromethyl)-1(2H)-pyrimidinyl]-1,2-benzisothiazole-3-acetate

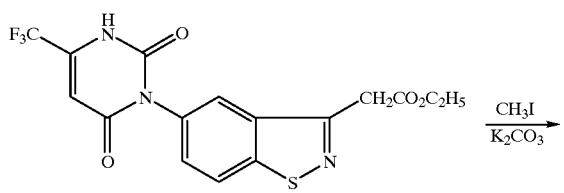

-continued

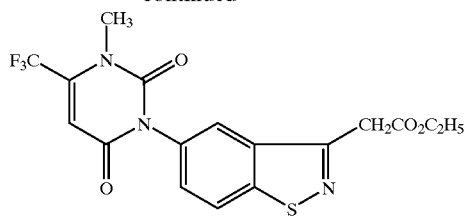

A mixture of ethyl 5-[3,6-dihydro-2,6-dioxo-4-(trifluoromethyl)-1(2H)-pyrimidinyl]-1,2-benzisothiazole-3-acetate (0.643 g, 0.00160 mol) and potassium carbonate (0.243 g, 0.00170 mol) in N,N-dimethylformamide is stirred at room temperature for 90 minutes, treated with iodomethane (0.320 mL, 0.00500 mol), stirred at room temperature overnight, and diluted with water. The resultant aqueous mixture is extracted with methylene chloride. The organic extract is washed with water, dried over anhydrous magnesium sulfate, and concentrated in vacuo to obtain a brown oil. Column chromatography of the oil using silica gel and a 10% ethyl acetate in hexanes solution gives the title product as a tan solid (0.362 g, mp 150–152° C.).

EXAMPLE 58

Preparation of Methyl 5-[3-,6-dihydro-3-methyl-2,6-dioxo-4-(trifluoromethyl)-1(2H)-pyrimidinyl]-1,2-benzisothiazole-3-glyoxylate

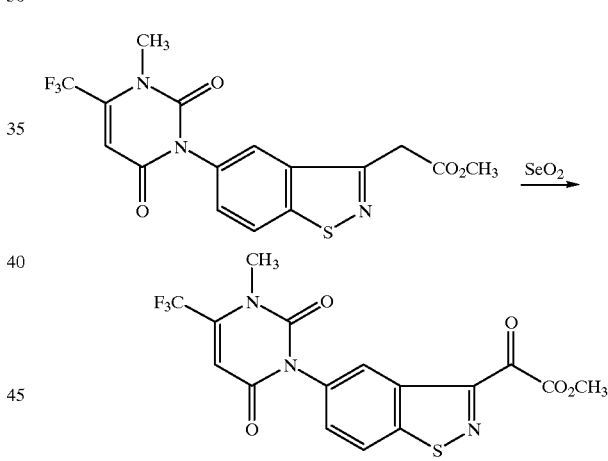

A mixture of ethyl 5-[3,6-dihydro-3-methyl-2,6-dioxo-4-(trifluoromethyl)-1(2H)-pyrimidinyl]-1,2-benzisothiazole-3-acetate(30.0 g, 0.0750 mol), selenium dioxide (15.0 g, 0.135 mol) and glacial acetic acid is stirred two hours at reflux, cooled and filtered through a pad of Celite. The filtrate is concentrated in vacuo and the residue is stirred in methylene chloride. The mixture is filtered and the filtrate filtered through a pad of Celite. The resultant filtrate is treated with saturated sodium bicarbonate and solid sodium bicarbonate with stirring until bubbling ceases. The organic layer is saved. The aqueous layer is extracted with methylene chloride. The combined organic layers are washed with saturated sodium bicarbonate, dried over anhydrous magnesium sulfate and concentrated in vacuo. The residue is stirred overnight in diethyl ether-methylene chloride to afford, after filtration, the title compound as a white solid (24.5 g, 79.0%, mp 101–103° C.) which is identified by NMR spectral analysis.

EXAMPLE 59

Preparation of Methyl-3-[3-(4-oxo-delta-2-1,2,5-thiadiazolin-3-yl)-1,2-benzisothiazol-5-yl]-6-(trifluoromethyl)uracil S',S'-dioxide

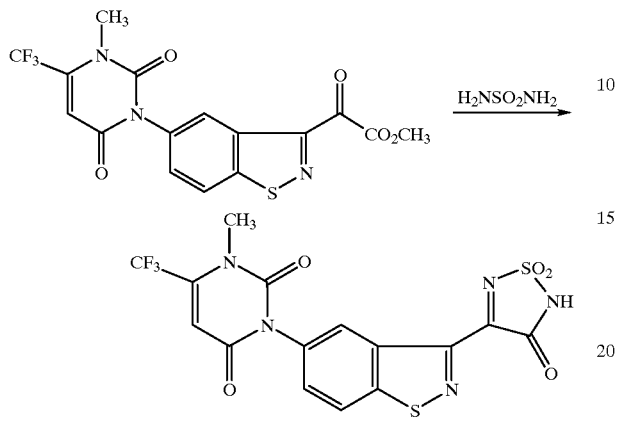

A mixture of methyl 5-[3-,6-dihydro-3-methyl-2,6-dioxo-4-(trifluoromethyl)-1(2H)-pyrimidinyl]-1,2-benzisothiazole-3-glyoxylate(0.750 g, 1.82 mmol), sulfamide (0.869 g, 9.05 mmol) and absolute ethanol is stirred five days at reflux. The resultant mixture is cooled and filtered to afford the title compound as a yellow solid (0.430 g, 51.4%) which is identified by NMR and mass spectral analysis.

EXAMPLE 60

Preparation of 3-[3[4-Methoxy-2-(ethylimino)-5-oxo-4-imidazolidinyl]-1,2-benzisothiazol-5-yl]-1-methyl-6-(trifluoromethyl)uracil

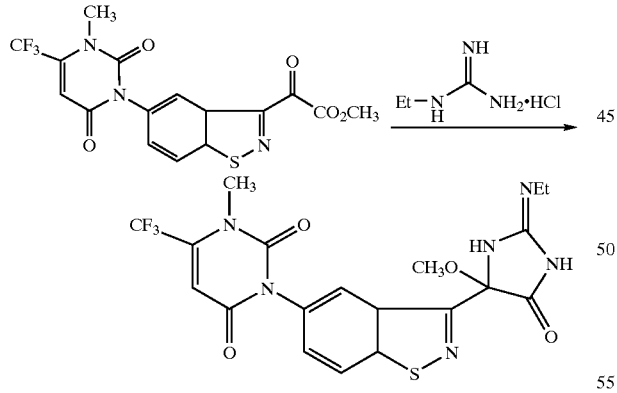

A mixture of methyl 5-[3-,6-dihydro-3-methyl-2,6-dioxo-4-(trifluoromethyl)-1(2H)-pyrimidinyl]-1,2-benzisothiazole-3-glyoxylate (0.0820 g, 1.98 mmol), ethyl guanidine hydrochloride (0.270 g, 2.18 mmol), sodium bicarbonate (0.180 g, 2.14 mmol) and methanol is stirred overnight at reflux, cooled to room temperature and poured into water. The resultant suspension is stirred 20 minutes and filtered with cold water wash to afford the title compound as a white solid (0.610 g, 63.9%, mp 257° C.) which is identified by NMR spectral analysis.

Using essentially the same procedure and methyl guanidine hydrochloride the following product is obtained (mp 205° C.):

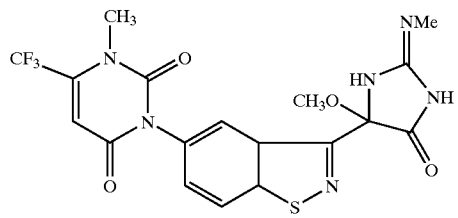

EXAMPLE 61

Preparation of 3-[3-[2-(Dimethylamino)-4-methoxy-5-oxo-2-inidazolin-4-yl]-1,2-benzisothiazol-5-yl]-1-methyl-6-(trifluoromethyl)uracil

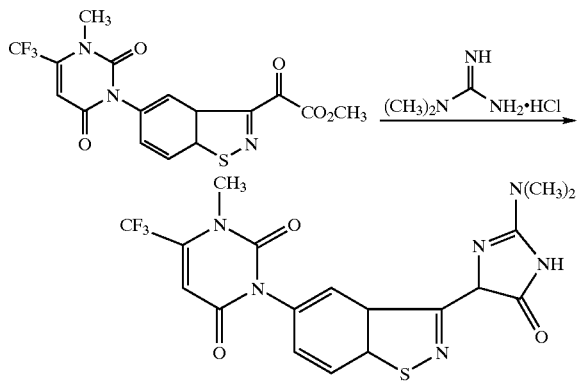

A mixture of methyl 5-[3-,6-dihydro-3-methyl-2,6-dioxo-4-(trifluoromethyl)-1(2H)-pyrimidinyl]-1,2-benzisothiazole-3-glyoxylate (0.620 g, 1.50 mmol), dimethyl guanidine hydrochloride (0.200 g, 1.62 mmol), sodium bicarbonate (0.140 g, 1.67 mmol) and methanol is stirred four hours at reflux, cooled to room temperature and partitioned between water and methylene chloride. The combined organic layers are concentrated in vacuo and the residue is chromatographed on silica gel with methylene chloride-methanol (98:2) to afford the title compound as a solid (0.340 g, 47%, mp 238–240° C.) which is identified by NMR spectral analysis.

EXAMPLE 62

Preparation of 3-[3-(4-Hydroxy-5-oxo-2-phenyl-2-imidazolin-4-yl)-1,2-benzisothiazol-5-yl]-1-methyl-6-(trifluoromethyl)uracil

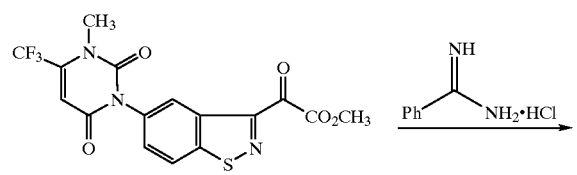

-continued

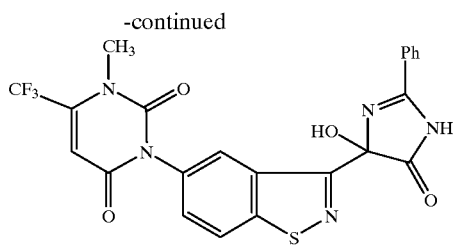

A mixture of 5-[3-,6-dihydro-3-methyl-2,6-dioxo-4-(trifluoromethyl)-1(2H)-pyrimidinyl]-1,2-benzisothiazole-3-glyoxylate (0.620 g, 1.50 mmol), phenyl amidine hydrochloride (0.258 g, 1.65 mmol) and 2-methoxyethanol is stirred 40 minutes at reflux, cooled to room temperature and poured into water. The resultant yellow precipitate is filtered and saved. The filtrate is extracted four times with methylene chloride; the combined organic layers are concentrated in vacuo and the residue is triturated with ether to afford a yellow solid. The yellow solids are combined and chromatographed on silica gel with methylene chloride-methanol to afford the title compound as a solid (0.110 g, 14.6%, mp 139–141° C.) which is identified by NMR spectral analysis.

Using essentially the same procedure and employing tert-butyl amidine hydrochloride, the following product is obtained (mp 192° C.):

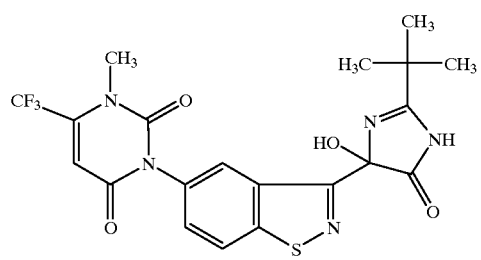

EXAMPLE 63

Preparation of 3-[3-(-Hydroxy-5-imino-4,4-dimethyl-2-oxo-3-pyrrolidinyl)-1,2-benzisothiazol-5-yl]-1-methyl-6-5(trifluoromethyl)uracil

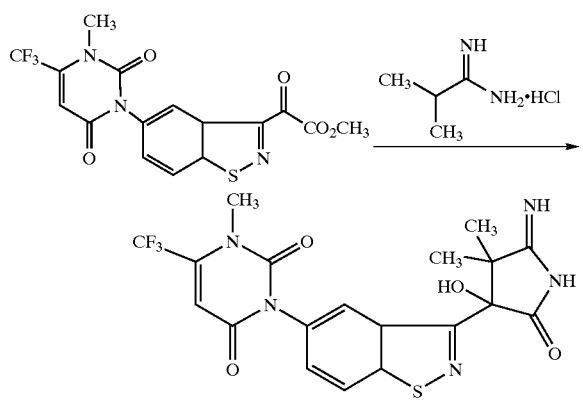

A mixture of 5-[3-,6-dihydro-3-methyl-2,6-dioxo-4-(trifluoromethyl)-1(2H)-pyrimidinyl]-1,2-benzisothiazole-3-glyoxylate (0.620 g, 1.50 mmol), isopropyl amidine hydrochloride (0.200 g, 1.65 mmol), sodium bicarbonate (0.140 g, 1.67 mmol) and 2-methoxyethanol is stirred one hour at reflux, cooled to room temperature and poured into ice water. The resultant suspension is filtered and the filtrate extracted four times with methylene chloride. The combined organic layers are concentrated in vacuo and the residue triturated with ether to afford a solid, which is chromatographed on silica gel with methylene chloride-methanol to afford the title compound as a solid (0.270 g, 38.5%, mp 125–127° C.) which is identified by NMR spectral analysis.

EXAMPLE 64

Preparation of 3-[3-(3,4-Dihydro-3-oxo-2-quinoxalinyl)-1,2-benzisothiazol-5-yl]-1-methyl-6-(trifluoromethyl)uracil

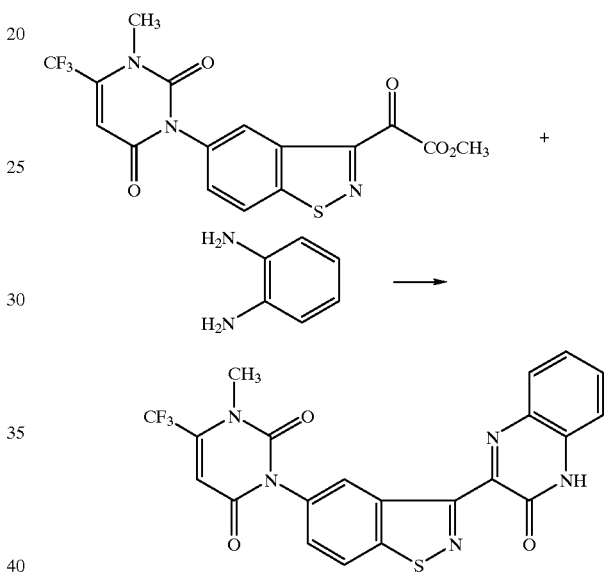

A mixture of methyl 5-[3-,6-dihydro-3-methyl-2,6-dioxo-4-(trifluoromethyl)-1(2H)-pyrimidinyl]-1,2-benzisothiazole-3-glyoxylate (0.7500 g, 1.81 mmol), 1,2-diaminobenzene (0.200 g, 1.84 mmol) and ethanol is stirred 16 hours at reflux and filtered hot. The filtrate is concentrated in vacuo to afford the title compound as a light yellow solid (0.480 g, 56.3%, mp >250° C.) which is identified by NMR analysis.

In essentially the same manner and employing diaminomaleonitrile, the following compound is obtained as a white solid, (mp>250° C.):

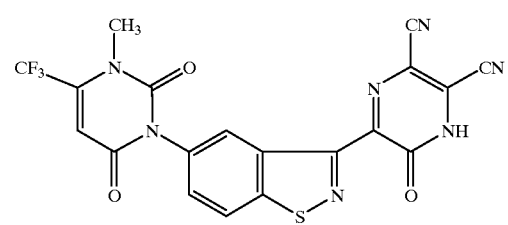

EXAMPLE 65

Preparation of 3-[3-(4,6-Diethoxy-2-pyrimidinyl)-1,2-benzisothiazol-5-yl]-1-methyl-6-(trifluoromethyl)uracil

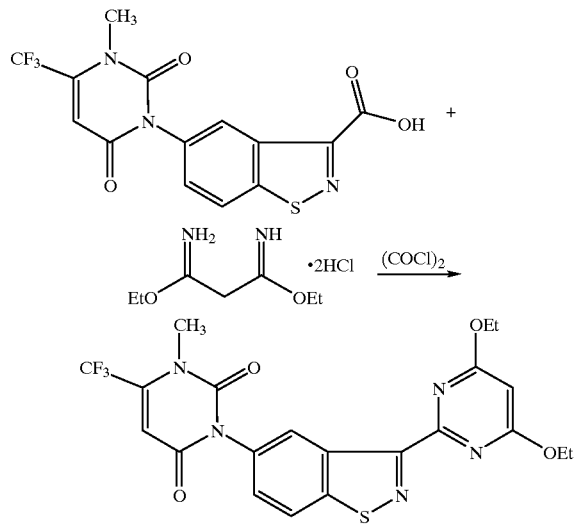

To a cooled mixture of 5-[3,6-dihydro-3-methyl-2,6-dioxo-4-(trifluoromethyl)-1(2H)-pyrimidinyl]-1,2-benzisothiazole-3-carboxylic acid (3.71 g, 10.0 mmol), diethyl ether and N,N-dimethylformamide (3.0 ml) is added oxalyl chloride (1.52 g, 12.0 mmol). The mixture is allowed to warm to room temperature and stirred overnight. The mixture is allowed to settle and the supernatant is decanted and concentrated in vacuo. The residue is taken up in methylene chloride and added dropwise to a stirred mixture of diethyl malonimidate dihydrochloride (2.31 g, 10.0 mmol), diisopropylethylamine (10 ml) and methylene chloride at −40° C. over one hour. The resultant mixture is allowed to warm to room temperature, diluted with methylene chloride, washed with water, 10% aqueous hydrochloric acid and water, dried over anhydrous magnesium sulfate and concentrated in vacuo to afford the title compound as a white solid (0.410 g, 8.31%, mp 197–200° C.) which is identified by NMR spectral analysis.

EXAMPLE 66

Preparation of 5-[3,6-Dihydro-3-methyl-2,6-dioxo-4-(trifluoromethyl)-1(2H)-pyrimidinyl]-1,2-benzisothiazole-3-carboxaldehyde

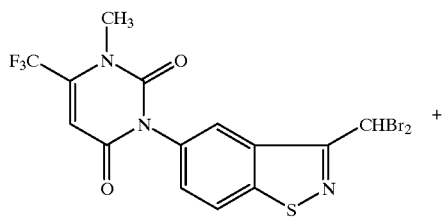

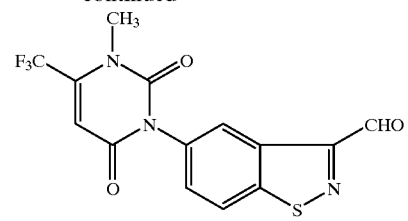

A solution of 3-[3-(dibromomethyl)-1,2-benzisothiazol-5-yl]-1-methyl-6-(trifluoromethyl)-2,4(1H,3H)-pyrimidinedione (0.500 g, 0.00100 mol) in a dioxane/water mixture (5:2) is treated with silver nitrate (0.340 g, 0.00200 mol), refluxed for 90 minutes, cooled to room temperature, stirred for 18 hrs, refluxed for three hrs, cooled, and filtered through a pad of diatomaceous earth. The resultant filtrate is concentrated in vacuo to obtain an aqueous mixture. The aqueous mixture is extracted with methylene chloride. The organic extract is washed sequentially with water and brine, dried over anhydrous magnesium sulfate, and concentrated in vacuo to obtain a solid. Column chromatography of the solid using silica gel and methylene chloride gives the title product as a solid (0.240 g, mp 193–194.5° C.).

Using essentially the same procedure on 3-[6-fluoro-3-(dibromomethyl)-1,2-benzisothiazol-5-yl]-1-methyl-6-(trifluoromethyl)-2,4(1H,3H)-pyrimidinedione, 5-[3,6-dihydro-3-methyl-2,6-dioxo-4-(trifluoromethyl)-1(2H)-pyrimidnyl-6-fluoro-1,2-benzisothiazole-3-carboxaldehyde is obtained.

EXAMPLE 67

Preparation of 1-Methyl-6-(trifluoromethyl)-3-(3-valeryl-1,2-benzisothiazol-5-yl)-2,4(1H,3H)-pyrimidinedione

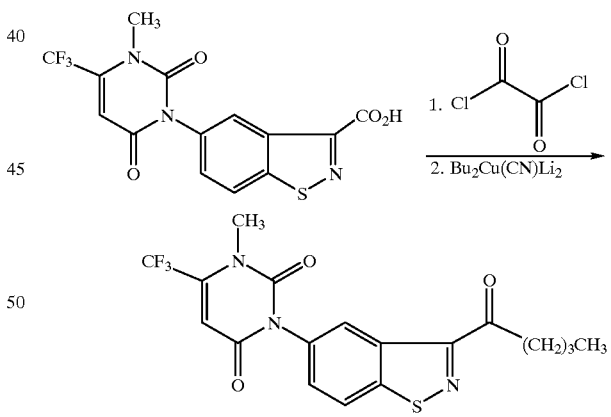

To a solution of 5-[3,6-dihydro-3-methyl-2,6-dioxo-4-(trifluoromethyl)-1(2H)-pyrimidinyl]-1,2-benzisothiazole-3-carboxylic acid (0.200 g, 0.000540 mol) in methylene chloride is added N,N-dimethylformamide (one drop) followed by oxalyl chloride in methylene chloride (2.0 M, 0.540 ml, 0.00108 mol). The resultant mixture is stirred at room temperature for 90 minutes and concentrated in vacuo to a white solid, which is saved. To a suspension of copper cyanide (0.061 g, 0.000675 mol) in tetrahydrofuran, is added dropwise n-butyllithium (2.5 M in hexanes, 0.540 ml, 0.00135 mol) at −78° C. The reaction mixture is allowed to warm for 5 minutes and then cooled back to −78° C. The mixture is then treated with a solution of the white solid from the first step in tetrahydrofuran, and the resultant mixture stirred one hour at −78° C. The reaction mixture is quenched with saturated ammonium chloride and diluted with ethyl acetate. The organic layer is washed sequentially with saturated ammonium chloride, water and brine, dried over anhydrous magnesium sulfate, filtered, and concentrated in vacuo to a yellow syrup. Chromatography of the syrup on silica gel using hexanes:ethyl acetate gives the title compound as a colorless syrup (0.142 g, 64.0%) which is identified by NMR spectral analysis.

Using essentially the same procedure, the following compounds are obtained:

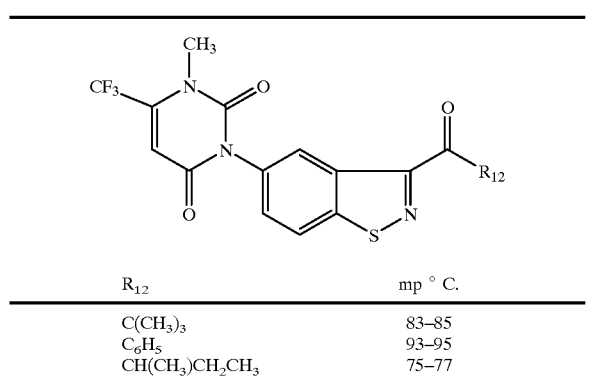

| $R_{12}$ | mp ° C. |
|---|---|
| $C(CH_3)_3$ | 83–85 |
| $C_6H_5$ | 93–95 |
| $CH(CH_3)CH_2CH_3$ | 75–77 |

EXAMPLE 68

Preparation of 3-[3-(4,6-Dimethyl-2-pyrimidinyl)-1,2-benzisothiazol-5-yl]-1-methyl-6-(trifluoromethyl)uracil

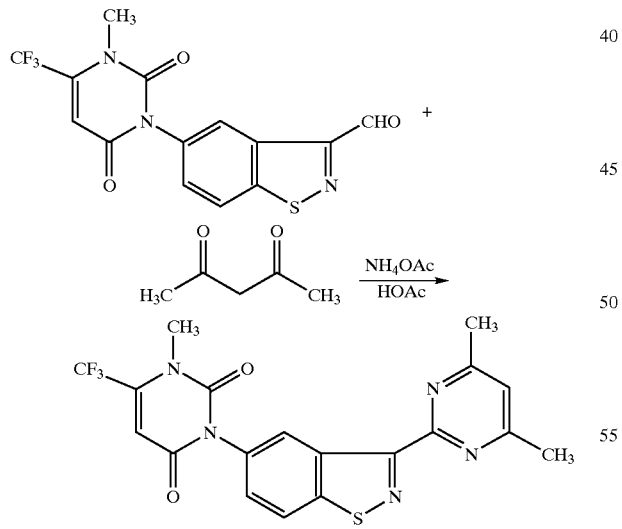

A stirred mixture of 5-[3,6-Dihydro-3-methyl-2,6-dioxo-4-(trifluoromethyl)-1(2H)-pyrimidinyl]-1,2-benzisothiazole-3-carboxaldehyde (3.35 g, 10.0 mmol), 2,4-pentanedione (1.00 g, 10.4 mmol), ammonium acetate (8.00 g, 10.4 mmol), glacial acetic acid and dimethylsulfoxide is heated to 80–90° C. and stirred overnight while air is bubbled through the mixture at 80–90° C. The mixture is cooled to room temperature and diluted with chloroform. The organic layer is washed five times with water, dried over anhydrous magnesium sulfate and concentrated in vacuo. The residue is chromatographed on silica gel to afford the title compound as a yellow solid (1.68 g, 40.1%) which is identified by NMR spectral analysis.

EXAMPLE 69

Preparation of 3-[3-(1,3-Dioxolan-2-yl)-1,2-benzisothiazol-5-yl]-1-methyl-6-(trifluoromethyl)uracil

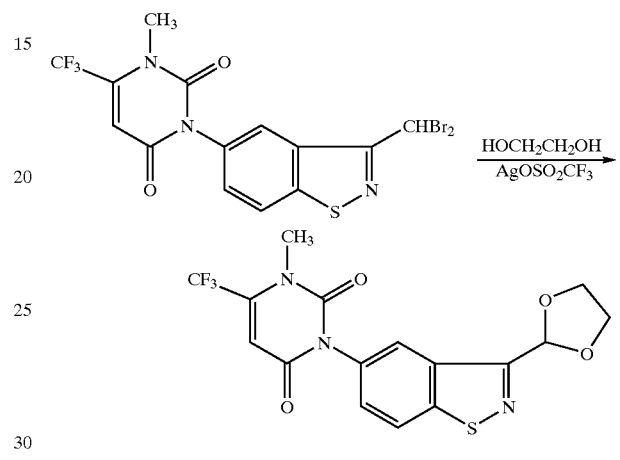

A mixture of 3-[3-(dibromomethyl)-1,2-benzisothiazol-5-yl]-1-methyl-6-(trifluoromethyl)-2,4(1H,3H)-pyrimidinedione (0.500 g, 10.0 mmol), silver trifluoromethanesulfonate (0.500 g, 19.5 mmol), ethylene glycol (5.00 ml), dichloromethane and dimethoxymethane is stirred three days at room temperature and treated with additional silver trifluoromethanesulfonate (0.300 g, 11.7 mmol). The resultant mixture is stirred one day at room temperature and treated with additional silver trifluoromethanesulfonate (0.400 g, 15.6 mmol) and ethylene glycol (1.00 ml), stirred another day at room temperature and treated again with silver trifluoromethanesulfonate (0.300 g, 11.7 mmol) and ethylene glycol (1.0 ml). After stirring an additional day the mixture is filtered. The filtrate is diluted with dichloromethane, washed with water, dried over anhydrous magnesium sulfate and concentrated in vacuo. The residue is triturated with hexanes-ethyl acetate to afford the title compound as a white solid (0.070 g, 17.5%, mp 213–216° C.) which is identified by NMR spectral analysis.

EXAMPLE 70

Preparation of 1-Methyl-3-[3-(4-methyl-1,3-dioxolan-2-yl)-1,2-benzisothiazol-5-yl]-6-(trifluoromethyl)uracil

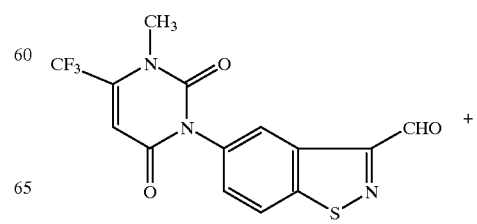

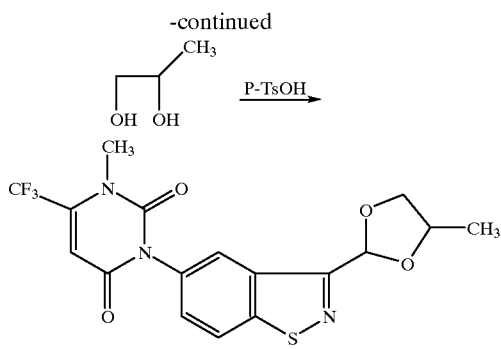

A mixture of 5-[3,6-dihydro-3-methyl-2,6-dioxo-4-(trifluoromethyl)-1(2H)-pyrimidinyl]-1,2-benzisothiazole-3-carboxaldehyde (0.500 g, 1.41 mmol), 1,2-propanediol (0.130 ml, 1.83 mmol), p-toluenesulfonic acid (0.0100 g, 0.0100 g, 0.071 mmol) and toluene is stirred at reflux with azeotropic removal of water overnight, cooled to room temperature, diluted with diethyl ether, washed twice with water and once with brine and dried over anhydrous magnesium sulfate. Concentration in vacuo affords a yellow oil, which is chromatographed on silica gel to afford the title compound as a yellow solid (0.510 g, 87.6%, mp 81–83° C.) which is identified by NMR spectral analysis.

Using essentially the same procedure, treatment of various aldehydes or ketones with the appropriate diols affords the following compounds:

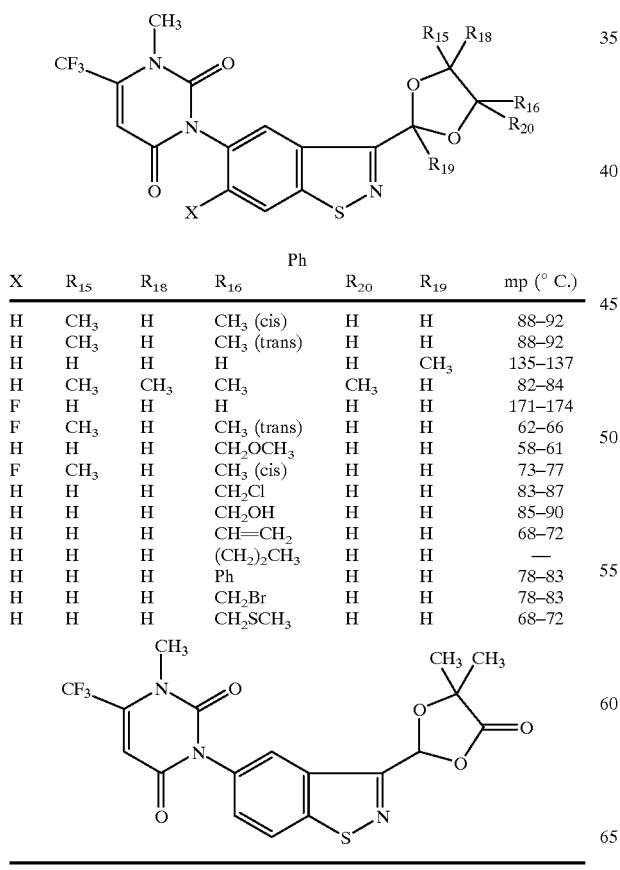

| X | $R_{15}$ | $R_{18}$ | $R_{16}$ | $R_{20}$ | $R_{19}$ | mp (° C.) |
|---|---|---|---|---|---|---|
| H | $CH_3$ | H | $CH_3$ (cis) | H | H | 88–92 |
| H | $CH_3$ | H | $CH_3$ (trans) | H | H | 88–92 |
| H | H | H | H | H | $CH_3$ | 135–137 |
| H | $CH_3$ | $CH_3$ | $CH_3$ | $CH_3$ | H | 82–84 |
| F | H | H | H | H | H | 171–174 |
| F | $CH_3$ | H | $CH_3$ (trans) | H | H | 62–66 |
| H | H | H | $CH_2OCH_3$ | H | H | 58–61 |
| F | $CH_3$ | H | $CH_3$ (cis) | H | H | 73–77 |
| H | H | H | $CH_2Cl$ | H | H | 83–87 |
| H | H | H | $CH_2OH$ | H | H | 85–90 |
| H | H | H | $CH=CH_2$ | H | H | 68–72 |
| H | H | H | $(CH_2)_2CH_3$ | H | H | — |
| H | H | H | Ph | H | H | 78–83 |
| H | H | H | $CH_2Br$ | H | H | 78–83 |
| H | H | H | $CH_2SCH_3$ | H | H | 68–72 |

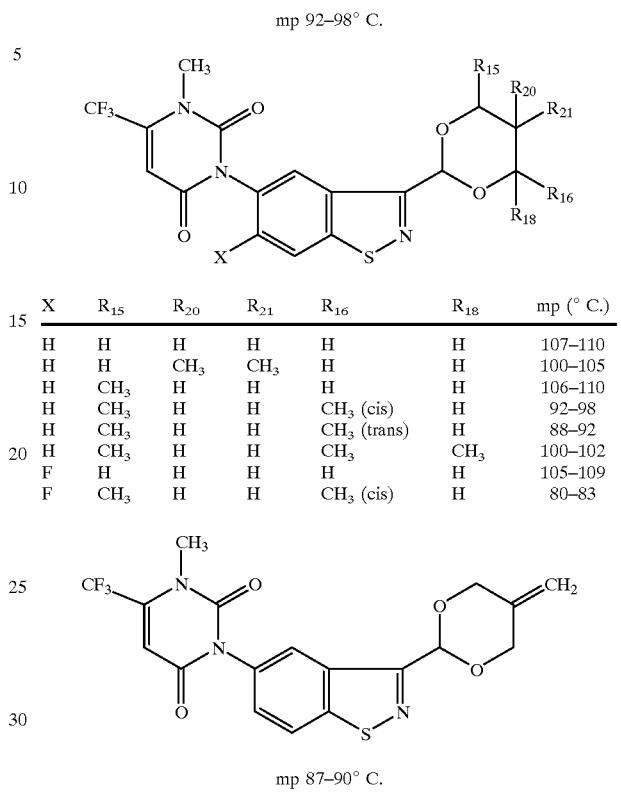

mp 92–98° C.

| X | $R_{15}$ | $R_{20}$ | $R_{21}$ | $R_{16}$ | $R_{18}$ | mp (° C.) |
|---|---|---|---|---|---|---|
| H | H | H | H | H | H | 107–110 |
| H | H | $CH_3$ | $CH_3$ | H | H | 100–105 |
| H | $CH_3$ | H | H | H | H | 106–110 |
| H | $CH_3$ | H | H | $CH_3$ (cis) | H | 92–98 |
| H | $CH_3$ | H | H | $CH_3$ (trans) | H | 88–92 |
| H | $CH_3$ | H | H | $CH_3$ | $CH_3$ | 100–102 |
| F | H | H | H | H | H | 105–109 |
| F | $CH_3$ | H | H | $CH_3$ (cis) | H | 80–83 | mp 87–90° C.

Using essentially the same procedure with 5-[3,6-dihydro-3-methyl-2,6-dioxo-4-(trifluoromethyl)-1(2H)-pyrimidinyl]-1,2-benzisothiazole-3-carboxaldehyde and 2-mercaptoethanol the following product is obtained

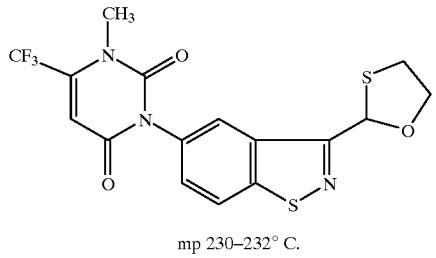

mp 230–232° C.

EXAMPLE 71

Preparation of 1-Methyl-3-[3-[4-[(methylsulfonyl)methyl]-1,3-dioxolan-2-yl]-1,2-benzisothiazol-5-yl]-6-(trifluoromethyl)uracil (two diastereoisomers)

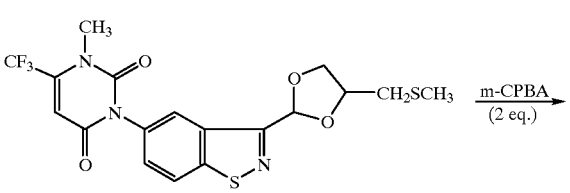

145
-continued

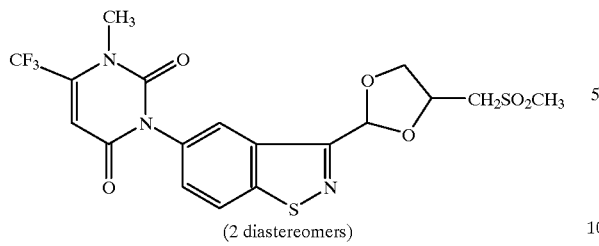

(2 diastereomers)

A mixture of 1-methyl-3-[3-[4-[(methylthio)methyl]-1,3-dioxolan-2-yl]-1,2-benzisothiazol-5-yl]-6-(trifluoromethyl) uracil(1.20 g, 26.1 mmol), m-chloroperbenzoic acid (75%, 0.620 g, 26.1 mmole) and methylene chloride is stirred two hours at room temperature, treated with additional m-chloroperbenzoic acid (0.620 g, 26.1 mmole) and stirred one hour at room temperature. The mixture is concentrated in vacuo. The residue is taken up in ethyl acetate and washed twice with 5% aqueous sodium carbonate and once with water. The organic layer is dried over anhydrous magnesium sulfate and concentrated in vacuo to a pale yellow oil, which is chromatographed on silica gel with ethyl acetate-hexanes, resulting in separation of the two diastereomers. The first diastereomer is isolated as a white solid (0.41 g, 31.5%, mp 184–188° C.) and the second is isolated as a white solid (0.35 g, 29.7%, mp 112–117° C.)

EXAMPLE 72

Preparation of 1-Methyl-3-[3-[4-[(methylsulfinyl) methyl]-1,3-dioxolan-2-yl]-1,2-benzisothiazol-5-yl]-6-(trifluoromethyl)uracil

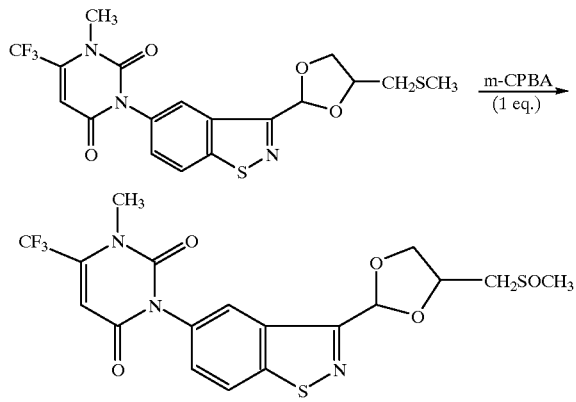

A mixture of 1-methyl-3-[3-[4-[(methylthio)methyl]-1,3-dioxolan-2-yl]-1,2-benzisothiazol-5-yl]-6-(trifluoromethyl) uracil (0.970 g, 21.1 mmol), m-chloroperbenzoic acid (72%, 0.500 g, 21.1 mmol) and methylene chloride is stirred one hour at room temperature and concentrated in vacuo. The residue is taken up in ethyl acetate and washed twice with 5% aqueous sodium carbonate and once with brine. The organic layer is dried over anhydrous magnesium sulfate and concentrated in vacuo to a white solid, which is chromatographed on silica gel with ethanol-ethyl acetate to afford the title compound as a white solid (0.700 g, 70.0%, mp 72–75° C.) which is identified by IR and NMR spectral analysis.

146

EXAMPLE 73

Preparation of [2-[5-[3,6-Dihydro-3-methyl-2,6-dioxo-4-(trifluoromethyl)-1(2H)-pyrimidinyl]-1,2-benzisothiazol-3-1[-1,3-dioxolan-4-yl]methyl thiocyanate

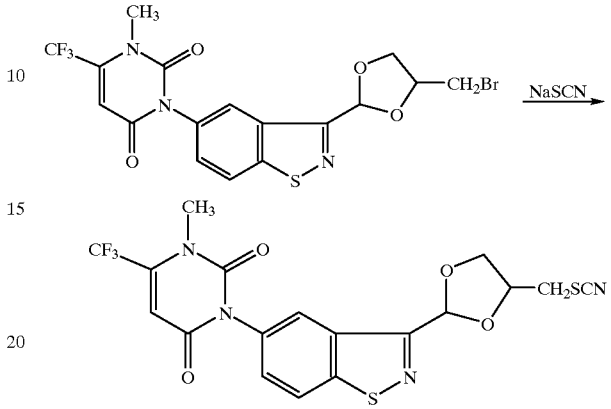

A mixture of 3-[3-[4-(bromomethyl)-1,3-dioxolan-2-yl]-1-methyl-6-(trifluoromethyl)uracil (0.500 g, 1.02 mmol), sodium thiocyanate (0.410 g, 5.06 mmol) and dimethyl sulfoxide is stirred at 70° C. for 24 hours, treated with additional sodium thiocyanate (0.290 g, 3.58 mmol) and stirred overnight at 70° C. The resultant mixture is treated again with sodium thiocyanate (0.220 g, 2.71 mmol), stirred several hours at 70° C., treated with more sodium thiocyanate (0.16 g, 1.97 mmol), stirred several more hours at 70° C. and cooled to room temperature. The mixture is poured into water and extracted three times with ethyl acetate. The combined organic layers are washed with brine, dried over anhydrous magnesium sulfate and concentrated in vacuo to a yellow oil, which is chromatographed on silica gel with ethyl acetate-hexanes to afford the title compound as a white solid (0.340 g, 70.8%, mp 75° C.) which is identified by IR and NMR analysis.

EXAMPLE 74

Preparation of 3-[3-[5-(Bromomethyl)-5-hydroxy-m-dioxan-2-yl]-1,2-benzisothiazol-5-yl]-1-methyl-6-(trifluoromethyl)uracil

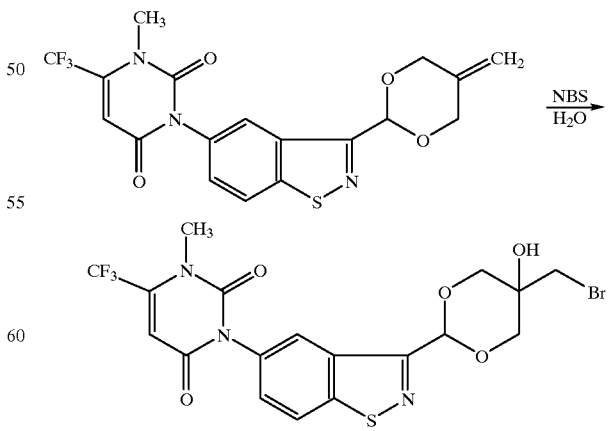

To a mixture of 1-methyl-3-[3-(5-methylene-m-dioxan-2-yl)-1,2-benzisothiazol-5-yl]-6-(trifluoromethyl)-2,4(1H, 3H)-pyrimidone (1.00 g, 2.35 mmol), water and dioxane is added N-bromosuccinimide (0.500 g, 2.81 mmol). The resultant mixture is stirred overnight at room temperature, poured into water and extracted twice with diethyl ether. The organic layers are washed with water and brine, dried over anhydrous magnesium sulfate and concentrated in vacuo. The residue is chromatographed on silica gel with diethyl ether-methylene chloride to afford the title compound as a white solid (1.00 g, 81.3%, mp 105–110° C.) which is identified by IR and NMR spectral analysis.

EXAMPLE 75

Preparation of 1-Methyl-3-(3-spiro[m-dioxane-5,2'-oxiran]-2-yl-1,2-benzisothiazol-5-yl)-6-(trifluoromethyl)uracil

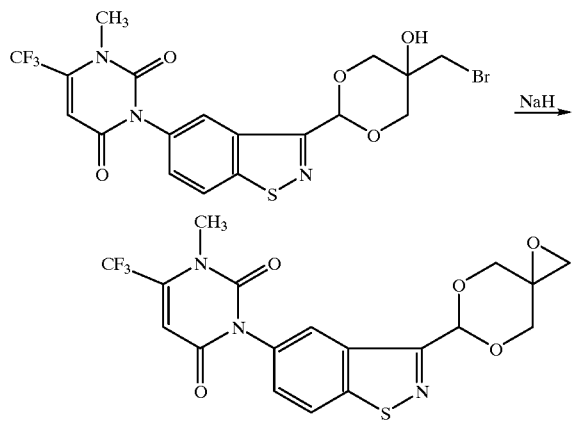

To a mixture of 3-[3-[5-(bromomethyl)-5-hydroxy-m-dioxan-2-yl]-1,2-benzisothiazol-5-yl]-1-methyl-6-(trifluoromethyl)uracil (0.580 g, 1.11 mmol) and tetrahydrofuran at 5° C. is added sodium hydride (60% dispersion in mineral oil, 0.0400 g, 1.11 mmol). The resultant mixture is stirred overnight at ambient temperature and treated with additional sodium hydride (0.0400 g, 1.11 mmol). The mixture is poured into saturated ammonium chloride and extracted twice with diethyl ether. The combined organic extracts are washed with water and brine, dried over anhydrous magnesium sulfate and concentrated in vacuo. The residue is chromatographed on silica gel with diethyl ether-methylene chloride to afford the title compound (0.0800 g, 16.3%, mp 203–206° C.) which is identified by NMR spectral analysis.

EXAMPLE 76

Preparation of 3-[3-(1,3-Dithiolan-2-yl)-1,2-benzisothiazol-5-yl]-1-methyl-6-(trifluoromethyl)uracil

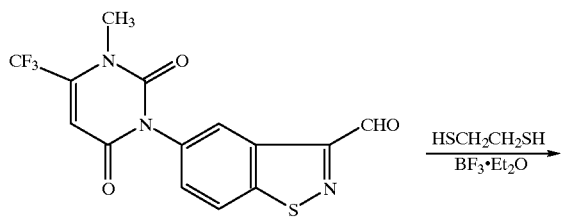

-continued

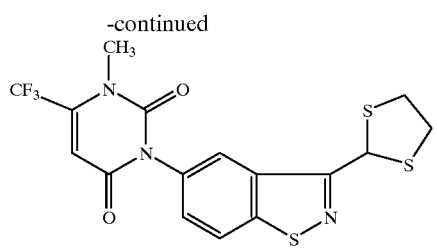

To a mixture of 5-[3,6-dihydro-3-methyl-2,6-dioxo-4-(trifluoromethyl)-1(2H)-pyrimidinyl]-1,2-benzisothiazole-3-carboxaldehyde (0.300 g, 0.850 mmol) and methylene chloride is added ethanedithiol (0.0940 g, 1.00 mmol) and boron trifluoride-etherate (0.200 ml). The resultant mixture is stirred overnight at room temperature and partitioned between methylene chloride and saturated sodium bicarbonate. The organic layer is dried over anhydrous magnesium sulfate and concentrated in vacuo to a yellow solid which is stirred in hot methylcyclohexane and filtered to afford the title compound as a light yellow solid (0.170 g, 46.3%, mp 227–232° C.) which is identified by NMR spectral analysis.

EXAMPLE 77

Preparation of 3-[3-(3,6-Dihydro-4,6,6-trimethyl-2H-pyran-2-yl)-1,2-benzisothiazol-5-yl]-1-methyl-6-(trifluoromethyl)uracil

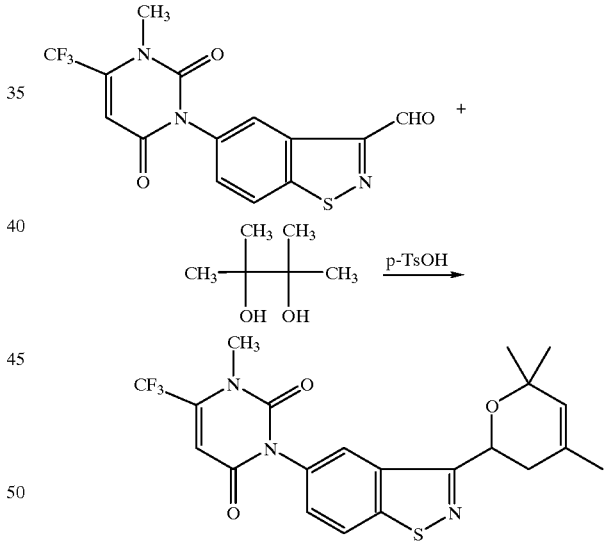

A mixture of 5-[3,6-dihydro-3-methyl-2,6-dioxo-4-(trifluoromethyl)-1(2H)-pyrimidinyl]-1, 2-benzisothiazole-3-carboxaldehyde(0.500 g, 0.00141 mol), 2,4-dimethyl-2,4-pentanediol (0.260 g, 0.00183 mol), p-toluenesulfonic acid (0.0100 g, 0.000071 mol) and toluene is stirred overnight at reflux with azeotropic removal of water. The mixture is cooled to room temperature, diluted with diethyl ether and ethyl acetate and washed with two prortions of water and brine. The organic layer is dried and concentrated in vacuo to a brown oil, which is chromatographed on silica gel with ethyl acetate-hexanes to afford the title compound as a white solid (0.200 g, 31.4%, mp 88–92° C.) which is characterized by NMR spectral analysis.

EXAMPLE 78

Preparation of Ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate

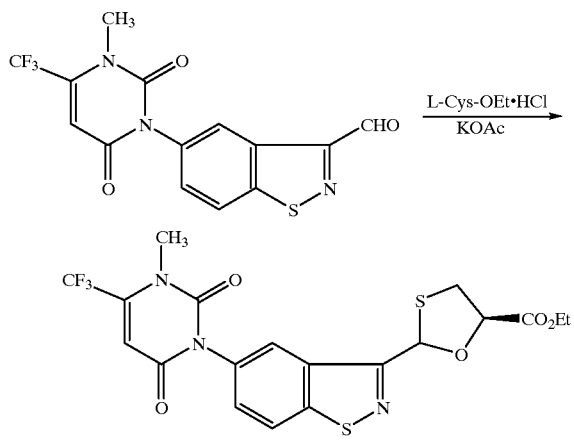

To a mixture of L-cysteine ethyl ester hydrochloride (0.580 g, 3.12 mmol), potassium acetate (0.300 g, 3.06 mmol) and 50% acetone-water is added dropwise a solution 5-[3,6-Dihydro-3-methyl-2,6-dioxo-4-(trifluoromethyl)-1 (2H)-pyrimidinyl]-1,2-benzisothiazole-3-carboxaldehyde (1.00 g, 2.81 mmol) in acetone. The resultant mixture is stirred four days at room temperature and treated with additional L-cysteine ethyl ester hydrochloride (0.580 g, 3.12 mmol) and, potassium acetate (0.300 g, 3.06 mmol). The resultant mixture is warmed to 35° C. and stirred overnight. The mixture is concentrated in vacuo and the residue is extracted with methylene chloride. The organic layer is washed with water, treated with charcoal, dried over anhydrous magnesium sulfate and concentrated in vacuo. The residue is chromatographed on silica gel with methylene chloride-ethyl acetate to afford the title compound as an off-white solid (0.600 g, 43.9%, mp 97–98° C.) which is identified by NMR spectral analysis.

EXAMPLE 79

Preparation of 3-[3-(3-Butyl-2-thiazolidinyl)-1,2-benzisothiazol-5-yl]-1-methyl-6-(trifluoromethyl) uracil

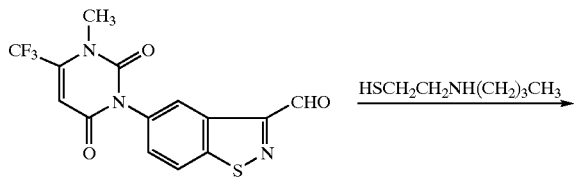

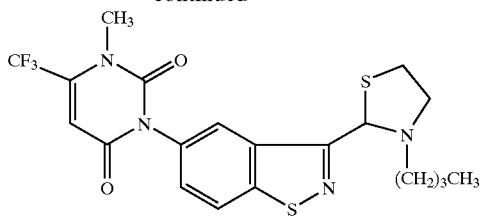

A mixture of 5-[3,6-dihydro-3-methyl-2,6-dioxo-4-(trifluoromethyl)-1(2H)-pyrimidinyl]-1,2-benzisothiazole-3-carboxaldehyde (0.500 g, 1.41 mmol), 2-(butylamino) ethanethiol (0.250 ml, 1.69 mmol), ethanol and tetrahydrofuran is stirred overnight at room temperature and concentrated in vacuo. The residue is chromatographed on silica gel with ethyl acetate-hexanes to afford the title compound as a light yellow solid (0.210 g, 31.7%, mp 78–82° C.) which is identified by NMR spectral analysis.

EXAMPLE 80

Preparation of 3-Acetyl-2-[5-[3,6-dihydro-3-methyl-2,6-dioxo-4-(trifluoromethyl)-1(2H)-pyrimidinyl]-1,2-benzisothiazol-3-yl]thiazolidine

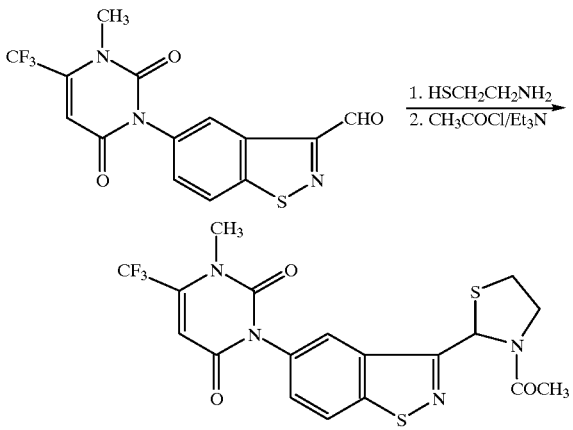

A mixture of 5-[3,6-dihydro-3-methyl-2,6-dioxo-4-(trifluoromethyl)-1(2H)-pyrimidinyl]-1,2-benzisothiazole-3-carboxaldehyde (0.500 g, 1.41 mmol), 2-aminoethanethiol (0.13 g, 1.69 mmol), ethanol and tetrahydrofuran is stirred overnight at room temperature. The mixture is concentrated in vacuo and the residue taken up in methylene chloride. The resultant mixture is treated with triethylamine (0.340 ml, 2.41 mmol), then acetyl chloride (0.120 ml, 1.69 mmol), stirred 90 minutes and poured into water. The resultant mixture is diluted with methylene chloide. The organic layer is washed with brine, dried over anhydrous magnesium sulfate and concentrated in vacuo to a white solid, which is chromatographed on silica gel with methanol-methylene chloride to afford the title compound as a white solid (0.600 g, 93.3%, mp 135–140° C.) which is identified by NMR spectral analysis.

Using essentially the same procedure and employing 2-aminoethanethiol and benzoyl chloride, the following compound is obtained, mp148–152° C.:

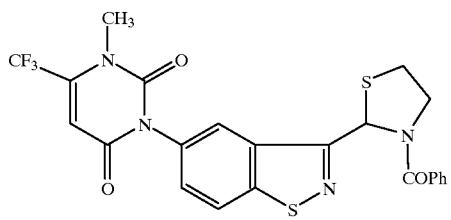

EXAMPLE 81

Preparation of 1-Methyl-3-[3-(1,3-oxathian-2-yl)-1,2-benzisothiazol-5-yl]-6-(trifluoromethyl)uracil

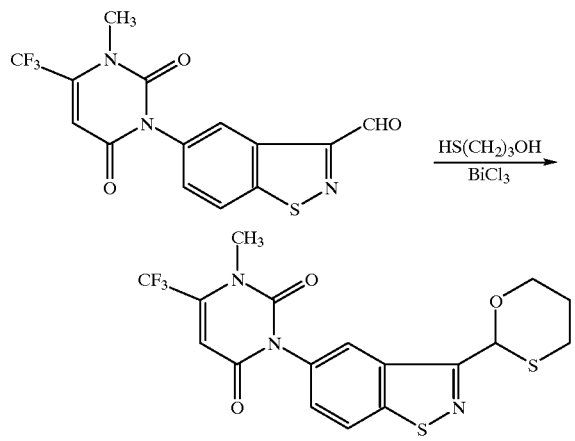

A mixture of 5-[3,6-dihydro-3-methyl-2,6-dioxo-4-(trifluoromethyl)-1(2H)-pyrimidinyl]-1,2-benzisothiazole-3-carboxaldehyde (2.86 g, 8.05 mmol), 3-mercapto-1-propanol (0.600 ml, 6.84 mmol), bismuth (III) chloride (0.090 g, 0.285 mol) and acetonitrile is stirred overnight at room temperature. Additional 3-mercapto-1-propanol (0.200 ml, 2.31 mmol) and bismuth (III) chloride are added and the resultant mixture is concentrated in vacuo. The residue is chromatographed with ethyl acetate-hexanes to afford a solid, which is taken up in diethyl ether, washed with water, once with brine and dried over anhydrous magnesium sulfate. Concentration in vacuo affords the title compound as a white solid (1.15 g, 33.2%, mp 125–130° C.) which is identified by NMR spectral analysis.

EXAMPLE 82

Preparation of 1-Methyl-3-[3-(1,3-oxathian-2-yl)-1,2-benzisothiazol-5-yl]-6-(trifluoromethyl)uracil S"-dioxide

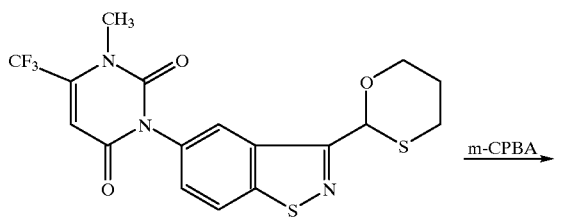

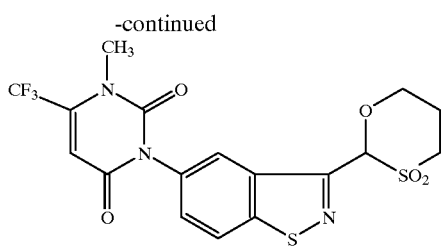

A mixture of 1-methyl-3-[3-(1,3-oxathian-2-yl)-1,2-benzisothiazol-5-yl]-6-(trifluoromethyl)uracil (0.960 g, 2.24 mmol), m-chloroperbenzoic acid (72%, 0.790 g, 3.30 mmol) and methylene chloride is stirred one hour at room temperature, poured into saturated sodium bicarbonate and extracted twice with ethyl acetate. The combined organic layers are washed with 5% aqueous sodium carbonate and brine, dried over anhydrous magnesium sulfate and concentrated in vacuo. The resultant white solid is chromatographed on silica gel with ethyl acetate-hexanes to afford the title compound as a white solid (0.75 g, 73.9%, mp>230° C.) which is identified by NMR spectral analysis.

Using essentially the same procedure and employing the appropriate substrate, the following compound is obtained, mp 219–222° C.:

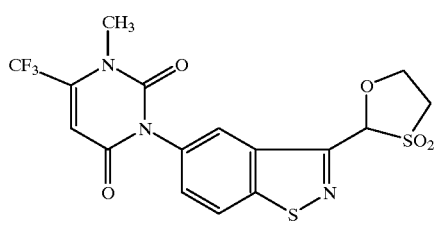

EXAMPLE 83

Preparation of 1-Methyl-3-(3-propenyl-1,2-benzisothiazol-5-yl)-6-(trifluoromethyl)-2,4(1H,3H)-pyrimidinedione, (Z)- and 1-Methyl-3-propenyl-1,2-benzisothiazol-5-yl)-6-(trifluoromethyl)-2,4(1H,3H)-pyrimidinedione, (E)- and (Z)-, (3:1)

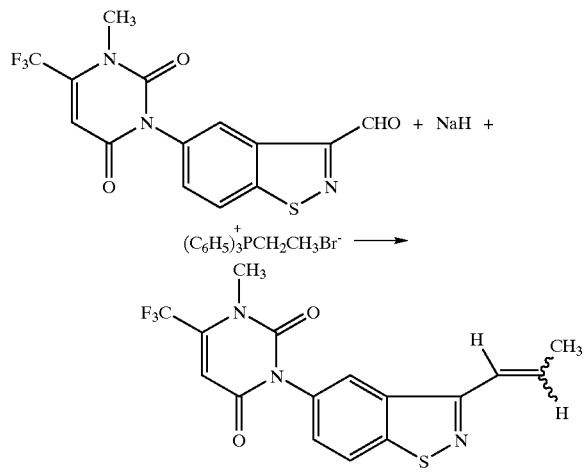

A mixture of (ethyl)triphenylphosphonium bromide (1.15 g, 0.00310 mol) in tetrahydrofuran is treated with sodium hydride (0.120 g, 0.00310 mol), stirred at room temperature for one hour, treated with a mixture of 5-[3,6-dihydro-3-methyl-2,6-dioxo-4-(trifluoromethyl)-1(2H)-pyrimidinyl]-1,2-benzisothiazole-3-carboxaldehyde (1.00 g, 0.00280 mol) in tetrahydrofuran, stirred at room temperature for one hour, and filtered. The resultant filtrate is partially concentrated in vacuo, diluted with methylene chloride, washed sequentially with water and brine, dried over anhydrous magnesium sulfate, and concentrated in vacuo to obtain an orange solid. Flash column chromatography of the solid using silica gel and a 1% diethyl ether in methylene chloride solution gives 1-methyl-3-(3-propenyl-1,2-benzisothiazol-5-yl)-6-(tri-fluoromethyl)-2,4(1H,3H)-pyrimidinedione, (Z)-as a white solid (0.350 g, mp 200–201° C.) and 1-methyl-3-(3-propenyl-1,2-benzisothiazol-5-yl)-6-(trifluoromethyl)-2,4(1H,3H)-pyrimidinedione, (E)- and (Z)-, (3:1) as a white solid (0.450 g, mp 228–230° C.)

Following essentially the same procedure and using the appropriately substituted phosphonium bromide, the following compounds are obtained:

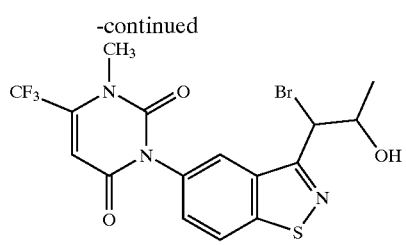

| $W_{10}$ | $W_{11}$ | mp ° C. |
|---|---|---|
| $CO_2CH_3$ | H | >230 |
| $C(O)CH_3$ | H | >230 |
| CHO | H | >230 |
| $CH_2Br$ | H | 235 (dec) |
| $C(O)C_6H_5$ | H | |
| $C(O)N(CH_3)OCH_3$ | H | |
| $CO_2CH_2=CH_2$ | H | |
| CHO | $CH_2CH_3$ | |

EXAMPLE 84

Preparation of 3-[3-(2(and 1)-Bromo-1(and 2)-hydroxypropyl)-1,2-benzisothiazol-5-yl]-1-methyl-6-5(trifluoromethyl)-2,4(1H,3H)-pyrimidinedione, (4:1) Mixture of Diastereomers

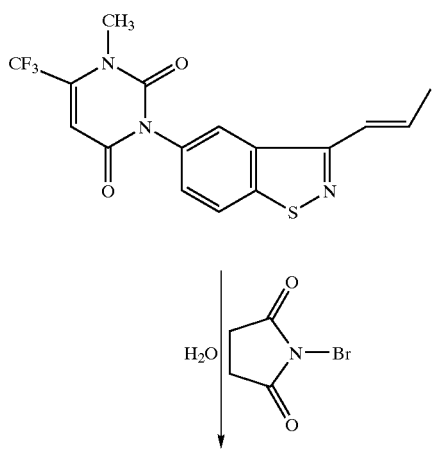

-continued

To a mixture of 1-methyl-(3-propenyl-1,2-benzisothiazol-5-yl)-6-(trifluoromethyl)-2,4(1H,3H)-pyrimidinedione (1.00 g, 0.00272 mol), dioxane and water is added N-bromosuccinimide (0.570 g, 0.00321 mol). The resultant mixture is stirred 23 hours at room temperature, poured into water and extracted with ether. The organic layers are washed with water, dried over anhydrous magnesium sulfate, filtered, and concentrated in vacuo to a yellow foam. The foam is chromatographed on silica gel with methylene chloride:ether to afford the title mixture of isomers as a white foam (1.03 g, 82.4%, mp 100–103° C.) which is identified by NMR spectral analysis.

EXAMPLE 85

Preparation of 3-[3-[(1R,2S)-1,2-Epoxypropyl]-1,2-benzisothiazol-5-yl]-1-methyl-6-(trifluoromethyl) uracil and 3-[3-[(1R,2R)-1,2-Epoxypropyl]-1,2-benzisothiazol-5-yl]-1-methyl-6-(trifluoromethyl) uracil

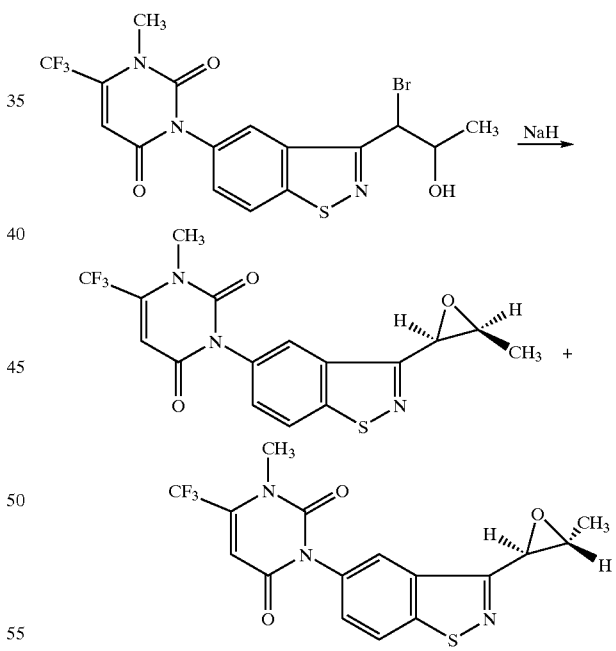

To a solution of 3-{3-[2(and 1)-bromo-1(and 2)hydroxypropyl]-1,2-benzisothiazol-5-yl}-1-methyl-6-(trifluoromethyl)-2,4(1H,3H)pyrimidinedione (0.760 g, 1.60 mmol) in tetrahydrofuran at 5° C. is added sodium hydride (60% in mineral oil, 0.0640 g, 1.60 mmol). The resultant mixture is stirred 30 min at ambient temperature, diluted with diethyl ether, washed with water and brine and dried over magnesium sulfate. Concentration in vacuo affords a white foam, which is chromatographed on silica gel with methylene chloride-diethyl ether. The 1R,2S diastereoisomer of the title product is obtained as a white foam (0.210 g, 34.5%, mp 172–176° C.). The 1R,2R diastereoisomer of the title product is obtained as a white solid (0.16 g, 26.2%, mp 156–160° C.). Both products are identified by IR and NMR spectral analyses.

EMAMPLE 86

Preparation of 5-[3,6-Dihydro-3-methyl-2,6-dioxo-4-(trifluoromethyl)-1(2H)-pyrimidinyl]-1,2-benzisothiazole-3-malononitrile

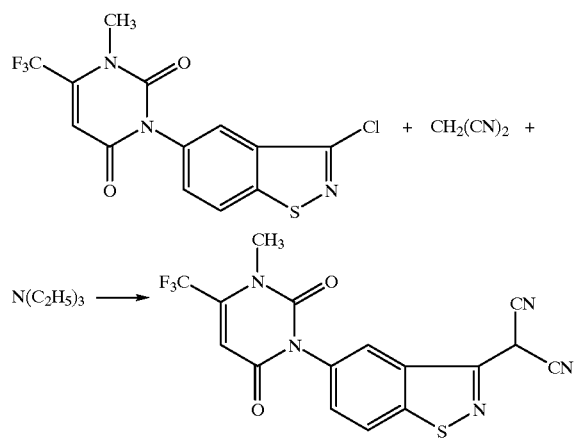

A mixture of 3-(3-chloro-1,2-benzisothiazol-5-yl)-1-methyl-6-(trifluoromethyl)-2,4(1H,3H)-pyrimidinedione (0.500 g), malononitrile (0.270 g) and triethylamine (1.50 g) in methyl sulfoxide is stirred at 60° C. for 15 minutes, cooled to room temperature, and diluted with water. The resultant aqueous mixture is extracted with ethyl acetate. The organic extract is washed with water, dried over anhydrous magnesium sulfate, and concentrated in vacuo to obtain a brown oil. The extracted aqueous phase is diluted with brine, acidified with concentrated hydrochloric acid, and extracted with ethyl acetate. The organic extract is dried over anhydrous magnesium sulfate and concentrated in vacuo to obtain a brown oil. Flash column chromatography of the combined oils using silica gel and an ethyl acetate/hexanes/methanol/acetic acid solution (10:10:4:1) gives the title product as an oil which is identified by NMR spectral analyses.

EXAMPLE 87

Postemergence Herbicidal Evaluation of Test Compounds

The postemergence herbicidal activity of the compounds of the present invention is demonstrated by the following tests wherein a variety of dicotyledonous and monocotyledonous plants are treated with test compounds. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.0040 kg to 1.000 kg per hectare of active compound when applied to the plants through a spray nozzle operating at 40 psi for a predetermined time. After spraying, the plants are placed on greenhouse benches and are cared for in accordance with conventional greenhouse procedures. From four to five weeks after treatment, the seedling plants are examined and rated according to the rating system set forth below. Data obtained are reported in Table I below. Where more than one test is involved for a given compound, the data are averaged.

| PLANT SPECIES EMPLOYED IN HERBICIDAL EVALUATIONS | | |
|---|---|---|
| Header Abbr. | Common Name | Scientific Name |
| ABUTH | Velvetleaf | *Abutilon theophrasti*, Medic. |
| AMBEL | Ragweed, Common | *Ambrosia artemisifolia*, L. |
| CASOB | Sicklepod | *Cassia obtusifolia*, L. |
| CHEAL | Lambsquarters, Common | *Chenopodium album*, L. |
| GALAP | Galium | *Galium aparine* |
| IPOHE | Morningglory, Ivyleaf | *Ipomoea hederacea*, (L.) Jacq. |
| IPOSS | Morningglory Spp. | Ipomoea Spp. |
| ECHCG | Barnyardgrass | *Echinochloa crus-galli*, (L.) Beau |
| SETVI | Foxtail, Green | *Setaria viridis*, (L.) Beau |
| GLXMAW | Soybean, Williams | *Glycine max*, (L.) Merr. cv Williams |
| GLXMA | Soybean | *Glycine max*, (L.) Merr. |
| ORYSAT | Rice, Tebonnet | *Oryza sativa*, (L.) Tebonnet |
| TRZAWR | Wheat, Winter, cv Riband | *Triticum aestivum*, cv Riband |
| ZEAMX | Corn, Field | *Zea mays*, L. |

Herbicide Rating Scale

Results of herbicide evaluation are expressed on a rating scale (0–9). The scale is based upon a visual observation of plant stand, vigor, malformation, size, chlorosis and overall plant appearance as compared with a control.

| RATING | % CONTROL AS COMPARED TO CHECK |
|---|---|
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | 0 |

Test Compounds

Compound Number
1. 1-methyl-3-[3-(3-thienyl)-1,2-benzisothiazol-5-yl]-6-(trifluoromethyl)uracil
2. ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate
3. 1-methyl-3-[3-(2-thienyl)-1,2-benzisothiazol-5-yl]-6-(trifluoromethyl)uracil
4. 1-methyl-3-[3-(3-methyl-2-thienyl)-1,2-benzisothiazol-5-yl]-6-(trifluoromethyl)uracil
5. 1-methyl-3-[3-(1-methylimidazol-2-yl)-1,2-benzisothiazol-5-yl]-6-(trifluoromethyl)uracil
6. 1-methyl-3-[3-(1-methylpyrrol-2-yl)-1,2-benzisothiazol-5-yl]-6-(trifluoromethyl)uracil
7. 1-methyl-3-[3-(4-methyl-2-thiazolyl)-1,2-benzisothiazol-5-yl]-6-(trifluoromethyl)uracil 8  3-[3-(2,5-diethyl-3-thienyl)-1,2-benzisothiazol-5-yl]-1-methyl-6-(trifluoromethyl)uracil
9  1-methyl-3-[3-(2-pyridyl)-1,2-benzisothiazol-5-yl]-6-(trifluoromethyl)uracil
10  3-[3-(3-methoxy-2-thienyl)-1,2-benzisothiazol-5-yl]-1-methyl-6-(trifluoromethyl)uracil Compound Number 11  1-methyl-3-[3-(3-pyridyl)-1,2-benzisothiazol-5-yl]-6-(trifluoromethyl)uracil
12  1-methyl-3-[3-(2-pyrimidinyl)-1,2-benzisothiazol-5-yl]-6-(trifluoromethyl)uracil
13  3-[3-[(1R,2S)-1,2-epoxypropyl]-1,2-benzisothiazol-5-yl]-1-methyl-6-(trifluoromethyl)uracil
14  3-[3-[(1R,2R)-1,2-epoxypropyl]-1,2-benzisothiazol-5-yl]-1-methyl-6-(trifluoromethyl)uracil
16  1-methyl-3-[3-(2-pyridyl)-1,2-benzisothiazol-5-yl]-6-(trifluoromethyl)uracil N',S,S-trioxide
16  1-methyl-3-[3-(5-methyl-1,3,4-oxadiazol-2-yl)-1,2-benzisothiazol-5-yl]-6-(trifluoromethyl)uracil
17  1-methyl-3-[3-(5-methyl-1,3,4-thiadiazol-2-yl)-1,2-benzisothiazol-5-yl]-6-(trifluoromethyl)uracil
18  1,2-benzisothiazole-3-carboxanilide, 4'-chloro-5-[3,6-dihydro-3-methyl-2,6-dioxo-4-(trifluoromethyl)-1(2H)-pyrimidinyl]-N-methyl-
19  1-methyl-3-[3-(3-methyl-2-pyridyl)-1,2-benzisothiazol-5-yl]-6-(trifluoromethyl)uracil
20  N-[3-(5-methyl-2-thienyl)-1,2-benzisothiazol-5-yl]-1-cyclohexene-1,2-dicarboximide Compound Number 21  1-methyl-3-[3-(5-methyl-2-thienyl)-1,2-benzisothiazol-5-yl]-6-(trifluoromethyl)uracil
22  Methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate
23  methyl 2-[(2-[5-[3,6-dihydro-3-methyl-2,6-dioxo-4-(trifluoromethyl)-1(2H)-pyrimidinyl]-1,2-benzisothiazol-3-yl]-3-thienyl]oxy]propionate
24  3-[3-(1,3-dithiolan-2-yl)-1,2-benzisothiazol-5-yl]-1-methyl-6-(trifluoromethyl)uracil
25  3-[6-fluoro-3-(2-pyridyl)-1,2-benzisothiazol-5-yl]-1-methyl-6-(trifluoromethyl)uracil
26  1-methyl-3-[3-(4-methyl-3-thienyl)-1,2-benzisothiazol-5-yl]-6-(trifluoromethyl)uracil
27  3-[3-(3,5-dimethyl-2-thienyl)-1,2-benzisothiazol-5-yl]-1-methyl-6-(trifluoromethyl)uracil
28  3-(3-m-dioxan-2-yl-1,2-benzisothiazol-5-yl)-1-methyl-6-(trifluoromethyl)uracil
29  3-acetyl-2-[5-[3,6-dihydro-3-methyl-2,6-dioxo-4-(trifluoromethyl)-1(2H)-pyrimidinyl]-1,2-benzisothiazol-3-yl]thiazolidine
30  3-benzoyl-2-[5-[3,6-dihydro-3-methyl-2,6-dioxo-4-(trifluoromethyl)-1(2H)-pyrimidinyl]-1,2-benzisothiazol-3-yl]thiazolidine
31  1-methyl-3-[3-(1,3-oxathiolan-2-yl)-1,2-benzisothiazol-5-yl]-6-(trifluoromethyl)uracil
32  1-methyl-3-[3-(1,3-oxathiolan-2-yl)-1,2-benzisothiazol-5-yl]-6-(trifluoromethyl)uracil S',S'-dioxide Compound Number 33  1,2-benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl) dithioacetal]
34  1-methyl-3-[3-(1,3-oxathian-2-yl)-1,2-benzisothiazol-5-yl]-6-(trifluoromethyl)uracil
35  1-methyl-3-[3-(1,3-oxathian-2-yl)-1,2-benzisothiazol-5-yl]-6-(trifluoromethyl)uracil S',S'-dioxide
36  3-[3(5,5-dimethyl-m-dioxan-2-yl)-1,2-benzisothiazol-5-yl]-1-methyl-6-(trifluoromethyl)uracil
37  1-methyl-3-[3-(4-methyl-m-dioxan-2-yl)-1,2-benzisothiazol-5-yl]-6-(trifluoromethyl)uracil
38  1-methyl-3-[3-(3-methylpyrazol-1-yl)-1,2-benzisothiazol-5-yl]-6-(trifluoromethl)uracil
39  2-propynyl [[2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate
40  3-[3-(4,6-dimethyl-2-pyrimidinyl)-1,2-benzisothiazol-5-yl]-1-methyl-6-(trifluoromethyl)uracil
41  3-[3-(3-methoxy-2-pyridyl)-1,2-benzisothiazol-5-yl]-1-methyl-6-(trifluoromethyl)uracil
42  1-methyl-3-[3-(5-methyl-2-pyridyl)-1,2-benzisothiazol-5-yl]-6-(trifluoromethyl)uracil
43  3-[3-(4,6-diethoxy-2-pyrimidinyl)-1,2-benzisothiazol-5-yl]-1-methyl-6-(trifluoromethyl)uracil Compound Number 44  3-[6-fluoro-3-(3-methyl-2-pyridyl)-1,2-benzisothiazol-5-yl]-1-methyl-6-(trifluoromethyl)uracil
45  3-[3-(1,3-dioxolan-2-yl)-1,2-benzisothiazol-5-yl]-1-methyl-6-(trifluoromethyl)uracil
46  N-[6-fluoro-3-(3-methyl-2-pyridyl)-1,2-benzisothiazol-5-yl]-1-cyclohexene-1,2-dicarboximide
47  3-[3-[(4R,5S)-4,5-dimethyl-1,3-dioxolan-2-yl]-1,2-benzisothiazol-5-yl]-1-methyl-6-(trifluoromethyl)uracil
48  3-[3-[(4R,5R)-4,5-dimethyl-1,3-dioxolan-2-yl]-1,2-benzisothiazol-5-yl]-1-methyl-6-(trifluoromethyl)uracil
49  1-methyl-6-(trifluoromethyl)-3-[3-(3,4,5-trimethylpyrazol-1-yl)-1,2-benzisothiazol-5-yl]uracil
50  3-[3-[(4R,6S)-4,6-dimethyl-m-dioxan-2-yl]-1,2-benzisothiazol-5-yl]-1-methyl-6-(trifluoromethyl)uracil
51  3-[3-[(4R,6S)-4,6-dimethyl-m-dioxan-2-yl]-1,2-benzisothiazol-5-yl]-1-methyl-6-(trifluoromethyl)uracil
52  3-[3-(3-chloro-2-thienyl)-1,2-benzisothiazol-5-yl]-1-methyl-6-(trifluoromethyl)uracil
53  1-methyl-3-[3-(2-thiazolyl)-1,2-benzisothiazol-5-yl]-6-(trifluoromethyl)uracil
54  1-methyl-3-[3-(2-methyl-1,3-dioxolan-2-yl)-1,2-benzisothiazol-5-yl]-6-(trifluoromethyl)uracil
55  1-methyl-6-(trifluoromethyl)-3-[3-(4,4,6-trimethyl-m-dioxan-2-yl)-1,2-benzisothiazol-5-yl]uracil
56  1-methyl-3-[3-(4,4,5,5-tetramethyl-1,3-dioxolan-2-yl)-1,2-benzisothiazol-5-yl]-6-(trifluoromethyl)uracil Compound Number 57  1-methyl-3-[3-(4-methyl-1,3-dioxolan-2-yl)-1,2-benzisothiazol-5-yl]-6-(trifluoromethyl)uracil
58  2,4(1H,3H)-pyrimidinedione, 1-methyl-3-[3-(5-methylene-m-dioxan-2-yl)-1,2-benzisothiazol-5-yl]-6-(trifluoromethyl)-
59  1-methyl-3-[3-(4-methylpyrazol-1-yl)-1,2-benzisothiazol-5-yl]-6-(trifluoromethyl)uracil
60  3-[3-(2-furyl)-1,2-benzisothiazol-5-yl]-1-methyl-6-(trifluoromethyl)uracil
61  3-[3-(1,3-dioxolan-2-yl)-6-fluoro-1,2-benzisothiazol-5-yl]-1-methyl-6-(trifluoromethyl)uracil
62  3-(3-m-dioxan-2-yl-6-fluoro-1,2-benzisothiazol-5-yl)-1-methyl-6-(trifluoromethyl)uracil
63  3-[3-[(4R,5S)-4,5-dimethyl-1,3-dioxolan-2-yl]-6-fluoro-1,2-benzisothiazol-5-yl]-1-methyl-6-(trifluoromethyl)uracil
64  3-[3-[4-(methoxymethyl)-1,3-dioxolan-2-yl]-1,2-benzisothiazol-5-yl]-1-methyl-6-(trifluoromethyl)uracil
65  3-[3-(3,6-dihydro-4,6,6-trimethyl-2H-pyran-2-yl)-1,2-benzisothiazol-5-yl]-1-methyl-6-(trifluoromethyl)uracil
66  3-[3-[(4R,5S-)-4,5-dimethyl-1,3-dioxolan-2-yl]-6-fluoro-1,2-benzisothiazol-5-yl]-1-methyl-6-(trifluoromethyl)uracil
67  3-[3-[(4R,6S)-4,6-dimethyl-m-dioxan-2-yl]-6-fluoro-1,2-benzisothiazol-5-yl]-1-methyl-6-(trifluoromethyl)uracil 68 2,4(1H,3H)-pyrimidinedione, 1-methyl-3-[3-(2-methyl-3-thienyl)-1,2-benzisothiazol-5-yl]-6-(trifluoromethyl)-

69 3-[3-[5-(bromomethyl)-5-hydroxy-m-diaxan-2-yl]-1,2-benzisothiazol-5-yl]-1-methyl-6-(trifluoromethyl)uracil Compound Number 70 1-methyl-3-(3-spiro[m-dioxane-5,2'-oxiran]-2-yl-1,2-benzisothiazol-5-yl)-6-(trifluoromethyl)uracil 71 3-[3-(4,4-dimethyl-5-oxo-1,3-dioxolan-2-yl)-1,2-benzisothiazol-5-yl]-1-methyl-6-(trifluoromethyl)uracil 72 3-[3-[4-(chloromethyl)-1,3-dioxolan-2-yl]-1,2-benzisothiazol-5-yl]-1-methyl-6-(trifluoromethyl)uracil 73 3-[3-[4-(hydroxymethyl)-1,3-dioxolan-2-yl]-1,2-benzisothiazol-5-yl]-1-methyl-6-(trifluoromethyl)uracil 74 3-[3-(4-isopropyl-2-oxazolin-2-yl)-1,2-benzisothiazol-5-yl]-1-methyl-6-(trifluoromethyl)uracil 74 1-methyl-3-[3(2-oxazolin-2-yl)-1,2-benzisothiazol-5-yl]-6-(trifluoromethyl)uracil 76 1-methyl-6-(trifluoromethyl)-3-[3-(4-vinyl-1,3-dioxolan-2-yl)-1,2-benzisothiazol-5-yl]uracil 77 1-methyl-3-[3-(4-propyl-1,3-dioxolan-2-yl)-1,2-benzisothiazol-5-yl]-6-(trifluoromethyl)uracil 78 1-methyl-3-[3-(4-phenyl-1,3-dioxolan-2-yl)-1,2-benzisothiazol-5-yl]-6-(trifluoromethyl)uracil 79 3-[3-[4-(bromomethyl)-1,3-dioxolan-2-yl]-1,2-benzisothiazol-5-yl]-1-methyl-6-(trifluoromethyl)uracil 80 3-[3-[3-(bromomethyl)-2-thienyl]-1,2-benzisothiazol-5-yl]-1-methyl-6-(trifluoromethyl)uracil 83 3-[3-(3-furyl)-1,2-benzisothiazol-5-yl]-1-methyl-6-(trifluoromethyl)uracil Compound Number 84 1-methyl-3-[3-[4-[(methylthio)methyl]-1,3-dioxolan-2-yl]-1,2-benzisothiazol-5-yl]-6-(trifluoromethyl)uracil 85 3-[3-[3-(hydroxymethyl)-2-thienyl]-1,2-benzisothiazol-5-yl]-1-methyl-6-(trifluoromethyl)uracil 86 1-methyl-3-[3-[4-[(methylsulfonyl)methyl]-1,3-dioxolan-2-yl]-1,2-benzisothiazol-5-yl]-6-(trifluoromethyl)uracil 87 1-methyl-3-[3-[4-[(methylsulfonyl)methyl]-1,3-dioxolan-2-yl]-1,2-benzisothiazol-5-yl]-6-(trifluoromethyl)uracil 88 1-methyl-3-[3-[4-[(methylsulfinyl)methyl]-1,3-dioxolan-2-yl]-1,2-benzisothiazol-5-yl]-6-(trifluoromethyl)uracil 89 [2-[5-[3,6-dihydro-3-methyl-2,6-dioxo-4-(trifluoromethyl)-1(2H)-pyrimidinyl]-1,2-benzisothiazol-3-1]-1,3-dioxolan-4-yl]methyl thiocyanate 90 3-[3-(3,4-dihydro-3-oxo-2-quinoxalinyl)-1,2-benzisothiazol-5-yl]-1-methyl-6-(trifluoromethyl)uracil 91 5-[5-[3,6-dihydro-3-methyl-2,6-dioxo-4-(trifluoromethyl)-1(2H)-pyrimidinyl]-1,2-benzisothiazol-3-yl]-1,6-hydro-6-oxo-2,3-pyrazinedicarbonitrile 92 1-methyl-3-[3-(4-oxo-delta-2-1,2,5-thiadiazolin-3-yl)-1,2-benzisothiazol-5-yl]-6-(trifluoromethyl)uracil S',S'-dioxide 93 3-[3-[2-(dimethylamino)-4-methoxy-5-oxo-2-imidazolin-4-yl]-1,2-benzisothiazol-5-yl]-1-methyl-6-(trifluoromethyl)uracil 94 3-[3-(4-hydroxy-5-oxo-2-phenyl-2-imidazolin-4-yl)-1,2-benzisothiazol-5-yl]-1-methyl-6-(trifluoromethyl)uracil Compound Number 95 3-[3-(2-tert-butyl-4-hydroxy-5-oxo-2-imidazolin-4-yl)-1,2-benzisothiazol-5-yl]-1-methyl-6-(trifluoromethyl)uracil 96 3-[3-(-hydroxy-5-imino-4,4-dimethyl-2-oxo-3-pyrrolidinyl)-1,2-benzisothiazol-5-yl]-1-methyl-6-(trifluoromethyl)uracil 97 3-[3[4-methoxy-2-(methylimino)-5-oxo-4-imidazolidinyl]-1,2-benzisothiazol-5-yl]-1-methyl-6-(trifluoromethyl)uracil 98 3-[3[4-methoxy-2-(ethylimino)-5-oxo-4-imidazolidinyl]-1,2-benzisothiazol-5-yl]-1-methyl-6-(trifluoromethyl)uracil

TABLE I

Postemergence Herbicidal Evaluation of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.1250 | 9.0 | 9.0 | 9.0 | 9.0 | 7.5 | 9.0 | | 4.0 | 8.0 | 7.8 | | 5.0 | 4.3 | 6.0 |
|   | 0.0620 | 9.0 | 9.0 | 7.5 | 9.0 | 6.5 | 9.0 | | 2.5 | 6.5 | 7.0 | | 3.5 | 3.5 | 5.8 |
|   | 0.0320 | 9.0 | 9.0 | 5.5 | 9.0 | 5.0 | 9.0 | | 2.0 | 7.0 | 6.8 | | 3.5 | 3.5 | 5.5 |
| 2 | 0.0620 | 9.0 | 9.0 | 4.0 | 9.0 | 6.0 | 9.0 | | 4.0 | 7.0 | 7.5 | | 6.5 | 6.5 | 7.0 |
|   | 0.0320 | 9.0 | 7.0 | 4.0 | 9.0 | 5.0 | 9.0 | | 3.0 | 6.0 | 7.0 | | 5.0 | 5.0 | 7.0 |
| 3 | 0.1250 | 9.0 | 9.0 | 9.0 | 9.0 | 6.0 | 9.0 | | 4.0 | 9.0 | 8.5 | | 4.5 | 5.0 | 6.5 |
|   | 0.0620 | 9.0 | 9.0 | 5.0 | 9.0 | 4.0 | 9.0 | | 3.0 | 9.0 | 6.5 | | 4.0 | 4.5 | 5.5 |
|   | 0.0320 | 9.0 | 9.0 | 4.0 | 9.0 | 5.0 | 9.0 | | 2.0 | 3.0 | 6.0 | | 3.0 | 2.5 | 5.0 |
| 4 | 0.1250 | 9.0 | 9.0 | 9.0 | 9.0 | 8.3 | 9.0 | | 1.7 | 7.3 | 7.3 | | 4.5 | 5.2 | 5.0 |
|   | 0.0620 | 9.0 | 8.3 | 6.2 | 9.0 | 6.0 | 9.0 | | 2.8 | 6.3 | 6.8 | 9.0 | 3.8 | 4.2 | 4.5 |
|   | 0.0320 | 9.0 | 8.1 | 5.2 | 9.0 | 3.3 | 8.6 | | 2.0 | 5.0 | 6.2 | | 2.8 | 3.7 | 4.4 |
| 5 | 0.0620 | 9.0 | 9.0 | 2.0 | 2.0 | 4.0 | 9.0 | | 0.0 | 1.0 | 6.0 | | 3.0 | 3.5 | 5.5 |
|   | 0.0320 | 9.0 | 2.0 | 0.0 | 0.0 | 0.0 | 9.0 | | 0.0 | 0.0 | 5.5 | | 2.0 | 2.5 | 4.5 |
| 6 | 0.1250 | 9.0 | 3.0 | 0.0 | 4.0 | 4.0 | 9.0 | | 0.0 | 0.0 | 5.5 | | 3.0 | 4.5 | 5.0 |
|   | 0.0620 | 9.0 | 3.0 | 0.0 | 0.0 | 4.0 | 7.0 | | 0.0 | 0.0 | 7.5 | | 2.5 | 4.0 | 5.0 |
|   | 0.0320 | 9.0 | 0.0 | 0.0 | 0.0 | 7.0 | 2.0 | | 0.0 | 2.0 | 3.0 | | 1.5 | 3.0 | 3.5 |
| 7 | 0.1250 | 9.0 | 9.0 | 3.0 | 9.0 | 9.0 | 9.0 | | 0.0 | 0.0 | 5.5 | | 7.0 | 6.0 | 7.5 |
|   | 0.0620 | 9.0 | 4.0 | 0.0 | 4.0 | 2.0 | 2.0 | | 0.0 | 0.5 | 5.0 | | 5.0 | 5.5 | 6.0 |
|   | 0.0320 | 9.0 | 2.0 | 0.0 | 4.0 | 6.0 | 2.0 | | 0.0 | 0.0 | 5.0 | | 4.5 | 4.5 | 5.0 |
| 8 | 0.0620 | 9.0 | 6.0 | 1.0 | 7.0 | 3.0 | 7.0 | | 0.0 | 4.0 | 5.5 | | 3.0 | 5.0 | 5.0 |
|   | 0.0320 | 9.0 | 3.0 | 1.0 | 4.0 | 5.0 | 9.0 | | 2.0 | 3.0 | 5.0 | | 3.0 | 4.0 | 5.0 |
| 9 | 0.1250 | 9.0 | 9.0 | 9.0 | 9.0 | 5.0 | 9.0 | | 8.0 | 9.0 | 9.0 | | 3.0 | 6.0 | 5.5 |
|   | 0.0620 | 9.0 | 9.0 | 8.0 | 9.0 | 7.0 | 9.0 | | 2.0 | 9.0 | 8.3 | | 4.3 | 4.5 | 5.8 |
|   | 0.0320 | 9.0 | 9.0 | 6.5 | 9.0 | 7.0 | 9.0 | | 1.0 | 8.0 | 8.3 | | 3.8 | 4.0 | 5.3 |
| 10 | 0.1250 | 9.0 | 9.0 | 1.0 | 4.0 | 9.0 | 9.0 | | 0.0 | 0.0 | 6.0 | | 3.0 | 4.0 | 5.0 |
|    | 0.0620 | 8.0 | 3.0 | 0.0 | 1.0 | 1.0 | 2.0 | | 0.0 | 0.5 | 5.0 | | 1.8 | 2.8 | 5.0 |
|    | 0.0320 | 8.0 | 2.0 | 0.0 | 1.0 | 1.0 | 2.0 | | 0.0 | 0.0 | 4.8 | | 1.3 | 2.5 | 3.8 |
| 11 | 0.0620 | 9.0 | 9.0 | 1.0 | 8.0 | 6.0 | 9.0 | | 0.0 | 7.0 | 6.5 | | 3.5 | 3.5 | 5.5 |
|    | 0.0320 | 9.0 | 2.0 | 0.0 | 2.0 | 4.0 | 3.0 | | 0.0 | 5.0 | 6.5 | | 3.0 | 3.0 | 5.0 |
| 12 | 0.0620 | 9.0 | 9.0 | 9.0 | 9.0 | 9.0 | 9.0 | | 4.0 | 9.0 | 8.5 | | 6.0 | 6.0 | 5.5 |
|    | 0.0320 | 9.0 | 9.0 | 6.0 | 9.0 | 6.0 | 7.0 | | 3.0 | 5.0 | 7.5 | | 7.0 | 5.0 | 5.0 |
| 13 | 0.0620 | 9.0 | 9.0 | 5.0 | 6.0 | 9.0 | 9.0 | | 3.0 | 7.0 | 7.0 | | 3.0 | 3.0 | 5.0 |
|    | 0.0320 | 9.0 | 9.0 | 1.0 | 2.0 | 4.0 | 2.0 | | 1.0 | 1.0 | 5.5 | | 2.5 | 2.5 | 4.0 |
| 14 | 0.0620 | 9.0 | 9.0 | 2.0 | 8.0 | 9.0 | 9.0 | | 2.0 | 3.0 | 7.5 | | 6.0 | 6.5 | 6.0 |
|    | 0.0320 | 9.0 | 7.0 | 2.0 | 7.0 | 9.0 | 7.0 | | 2.0 | 7.0 | 6.5 | | 4.5 | 4.0 | 5.0 |
| 15 | 0.0620 | 6.0 | 9.0 | 1.0 | | 1.0 | 9.0 | | 1.0 | 1.0 | 5.0 | | 3.5 | 3.5 | 5.0 |
|    | 0.0320 | 5.0 | 4.0 | 1.0 | 4.0 | 1.0 | 4.0 | | 1.0 | 1.0 | 4.0 | | 2.5 | 2.5 | 4.0 |
| 16 | 0.1250 | 4.5 | 4.5 | 3.5 | 3.5 | 3.0 | 4.5 | | 1.5 | 4.5 | 5.8 | | 3.0 | 3.0 | 4.3 |
|    | 0.0620 | 4.5 | 4.5 | 2.0 | 3.5 | 3.5 | 4.5 | | 1.0 | 1.5 | 5.5 | | 2.5 | 2.3 | 3.8 |
|    | 0.0320 | 3.5 | 1.5 | 0.5 | 1.0 | 2.0 | 3.5 | | 0.5 | 1.0 | 3.8 | | 1.8 | 1.5 | 3.3 |
|    | 0.0040 | 9.0 | 9.0 | 0.0 | 9.0 | 0.0 | 9.0 | | 0.5 | 0.0 | 2.8 | | 1.3 | 1.3 | 2.5 |
| 17 | 0.2500 | 9.0 | 9.0 | 2.0 | 4.0 | 6.0 | 9.0 | | 0.0 | 7.0 | 8.5 | | 7.5 | 3.5 | 5.0 |
|    | 0.1250 | 9.0 | 9.0 | 2.0 | 3.0 | 6.0 | 9.0 | | 0.0 | 3.0 | 8.0 | | 2.0 | 3.0 | 4.0 |
|    | 0.0620 | 9.0 | 9.0 | 0.0 | 3.0 | 1.0 | 9.0 | | 0.0 | 0.0 | 6.5 | | 1.5 | 3.0 | 4.0 |
|    | 0.0320 | 9.0 | 4.0 | 0.0 | 3.0 | 1.0 | 9.0 | | 0.0 | 0.0 | 5.0 | | 1.0 | 3.0 | 4.0 |

TABLE I-continued

Postemergence Herbicidal Evaluation of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 18 | 0.2500 | 9.0 | 9.0 | 6.0 | 9.0 | 9.0 | 9.0 | | 5.0 | 9.0 | 8.5 | | 5.5 | 6.0 | 7.0 |
|    | 0.1250 | 9.0 | 9.0 | 2.0 | 7.0 | 6.0 | 9.0 | | 0.0 | 5.0 | 8.0 | | 5.0 | 5.0 | 5.5 |
|    | 0.0620 | 9.0 | 9.0 | 1.0 | 7.0 | 4.0 | 9.0 | | 0.0 | 0.0 | 8.0 | | 3.0 | 4.0 | 5.0 |
|    | 0.0320 | 9.0 | 2.0 | 0.0 | 7.0 | 2.0 | 9.0 | | 0.0 | 0.0 | 6.0 | | 2.0 | 3.0 | 5.0 |
| 19 | 0.0620 | 9.0 | 9.0 | 5.0 | 9.0 | 6.0 | 9.0 | | 3.0 | 6.5 | 8.0 | | 3.5 | 4.3 | 5.3 |
|    | 0.0320 | 9.0 | 9.0 | 1.5 | 8.0 | 3.5 | 8.0 | | 2.0 | 4.0 | 8.3 | | 3.3 | 4.0 | 5.3 |
| 20 | 0.1250 | 9.0 | 6.0 | 1.0 | 5.0 | 1.0 | 9.0 | | 1.0 | 2.0 | 5.5 | | 4.5 | 4.5 | 5.5 |
|    | 0.0620 | 9.0 | 6.0 | 1.0 | 5.0 | 1.0 | 9.0 | | 1.0 | 2.0 | 5.5 | | 3.0 | 4.0 | 5.0 |
|    | 0.0320 | 7.0 | 6.0 | 1.0 | 3.0 | 1.0 | 6.0 | | 1.0 | 2.0 | 5.5 | | 2.5 | 3.5 | 5.0 |
| 21 | 0.1250 | 9.0 | 9.0 | 7.0 | 9.0 | 9.0 | 9.0 | | 4.0 | 9.0 | 6.0 | | 4.5 | 4.5 | 5.5 |
|    | 0.0620 | 9.0 | 9.0 | 4.0 | 9.0 | 4.0 | 9.0 | | 4.0 | 7.0 | 6.0 | | 3.5 | 4.5 | 5.5 |
|    | 0.0320 | 9.0 | 9.0 | 2.0 | 7.0 | 1.0 | 9.0 | | 6.0 | 2.0 | 5.5 | | 4.0 | 4.0 | 5.0 |
| 22 | 0.1250 | 9.0 | 9.0 | 1.0 | 4.0 | 1.0 | 6.0 | | 6.0 | 9.0 | 6.5 | | 4.5 | 4.5 | 5.5 |
|    | 0.0620 | 6.0 | 6.0 | 0.0 | 4.0 | 1.0 | 6.0 | | 6.0 | 9.0 | 5.5 | | 4.5 | 4.5 | 7.0 |
|    | 0.0320 | 4.0 | 4.0 | 0.0 | 1.0 | 0.0 | 4.0 | | 2.0 | 2.0 | 5.5 | | 3.5 | 3.5 | 6.0 |
| 23 | 0.1250 | 5.0 | 2.0 | 2.0 | 6.0 | 2.0 | 4.0 | | 0.0 | 3.0 | 5.0 | | 3.0 | 2.5 | 4.5 |
|    | 0.0620 | 9.0 | 9.0 | 0.0 | 4.0 | 2.0 | 9.0 | | 5.0 | 7.0 | 5.0 | | 5.0 | 5.0 | 7.0 |
|    | 0.0320 | 9.0 | 6.0 | 0.0 | 2.0 | 1.0 | 5.0 | | 1.0 | 1.0 | 5.0 | | 3.5 | 3.5 | 6.5 |
| 24 | 0.0620 | 9.0 | 2.0 | 9.0 | 9.0 | 4.0 | 6.0 | | 0.0 | 3.0 | 4.0 | | 2.5 | 2.5 | 5.0 |
|    | 0.0320 | 9.0 | 9.0 | 3.0 | 9.0 | 3.0 | 9.0 | | 2.0 | 0.0 | 8.5 | | 2.5 | 4.0 | 6.0 |
| 25 | 0.0620 | 9.0 | 9.0 | 0.0 | 9.0 | 4.0 | 9.0 | | 0.0 | 9.0 | 8.0 | | 2.0 | 4.0 | 5.5 |
|    | 0.0320 | 9.0 | 9.0 | 7.0 | 9.0 | 4.0 | 9.0 | | 3.0 | 9.0 | 9.0 | | 3.0 | 4.5 | 7.0 |
| 26 | 0.0620 | 9.0 | 9.0 | 9.0 | 9.0 | 6.0 | 9.0 | | 2.0 | 7.0 | 9.0 | | 2.5 | 4.0 | 5.5 |
|    | 0.0320 | 9.0 | 9.0 | 4.0 | 7.0 | 5.0 | 9.0 | | 3.0 | 9.0 | 6.5 | | 4.5 | 3.5 | 7.0 |
| 27 | 0.0620 | 9.0 | 9.0 | 3.0 | 9.0 | 4.0 | 9.0 | | 5.0 | 7.0 | 6.0 | | 3.5 | 5.5 | 5.0 |
|    | 0.0320 | 9.0 | 9.0 | 3.0 | 9.0 | 2.0 | 9.0 | | 4.0 | 9.0 | 6.0 | | 4.5 | 5.0 | 5.0 |
| 28 | 0.0620 | 9.0 | 9.0 | 9.0 | 9.0 | 9.0 | 9.0 | | 8.5 | 9.0 | 6.5 | | 6.5 | 6.5 | 6.3 |
|    | 0.0320 | 9.0 | 9.0 | 8.0 | 9.0 | 8.3 | 8.3 | | 4.3 | 8.5 | 9.0 | | 5.3 | 5.0 | 5.8 |
| 29 | 0.0620 | 9.0 | 9.0 | 5.0 | 9.0 | 6.0 | 9.0 | | 2.0 | 8.3 | 9.0 | | 3.0 | 4.5 | 6.0 |
|    | 0.0320 | 9.0 | 9.0 | 7.0 | 9.0 | 4.0 | 9.0 | | 0.0 | 5.0 | 9.0 | | 3.0 | 4.5 | 6.0 |
| 30 | 0.0620 | 9.0 | 9.0 | 1.0 | 9.0 | 3.0 | 9.0 | | 0.0 | 0.0 | 8.0 | | 3.0 | 4.5 | 6.0 |
|    | 0.0320 | 9.0 | 4.0 | 0.0 | 4.0 | 1.0 | 7.0 | | 2.0 | 4.0 | 7.5 | | 2.0 | 4.5 | 4.5 |
| 31 | 0.0620 | 9.0 | 9.0 | 8.0 | 9.0 | 9.0 | 9.0 | | 0.0 | 0.0 | 6.5 | | 5.5 | 4.5 | 5.5 |
|    | 0.0320 | 9.0 | 9.0 | 5.0 | 9.0 | 6.0 | 9.0 | | 2.0 | 7.0 | 6.0 | | 3.5 | 5.5 | 5.5 |
| 32 | 0.0620 | 9.0 | 9.0 | 9.0 | 9.0 | 6.0 | 9.0 | | 2.0 | 3.0 | 9.0 | | 5.5 | 5.0 | 5.5 |
|    | 0.0320 | 9.0 | 9.0 | 9.0 | 9.0 | 2.0 | 9.0 | | 5.0 | 6.0 | 8.5 | | 5.0 | 5.0 | 5.5 |
| 33 | 0.0620 | 9.0 | 9.0 | 7.0 | 9.0 | 3.0 | 9.0 | | 3.0 | 3.0 | 9.0 | | 5.0 | 5.0 | 5.5 |
|    | 0.0320 | 9.0 | 9.0 | 1.0 | 7.0 | 2.0 | 9.0 | | 3.0 | 4.0 | 8.0 | | 5.0 | 5.0 | 5.5 |
| 34 | 0.0620 | 9.0 | 9.0 | 0.0 | 3.0 | 0.0 | 7.0 | | 1.0 | 1.0 | 5.5 | | 4.0 | 4.0 | 5.0 |
|    | 0.0320 | 9.0 | 4.0 | 1.0 | 3.0 | 7.0 | 9.0 | | 6.0 | 8.0 | 5.0 | | 5.5 | 5.5 | 7.0 |
| 35 | 0.0620 | 9.0 | 9.0 | 9.0 | 9.0 | 6.0 | 9.0 | | 4.0 | 6.0 | 9.0 | | 7.0 | 5.5 | 6.0 |
|    | 0.0320 | 9.0 | 9.0 | 9.0 | 7.0 | 4.0 | 9.0 | | 4.0 | 9.0 | 9.0 | | 7.0 | 7.5 | 7.5 |
| 36 | 0.0620 | 9.0 | 9.0 | 9.0 | 9.0 | 3.0 | 9.0 | | 3.0 | 9.0 | 9.0 | | 6.5 | 7.0 | 7.5 |
|    | 0.0320 | 9.0 | 9.0 | 9.0 | 9.0 | 5.0 | 9.0 | | 3.0 | 9.0 | 7.5 | | 6.5 | 4.5 | 6.0 |
| 37 | 0.0620 | 9.0 | 9.0 | 9.0 | 7.0 | 4.0 | 9.0 | | 1.0 | 4.0 | 9.0 | | 7.0 | 4.0 | 5.0 |
|    | 0.0320 | 9.0 | 9.0 | 5.0 | 9.0 | 4.0 | 9.0 | | 4.0 | 9.0 | 9.0 | | 4.5 | 7.0 | 6.0 |
|    |        | 9.0 | 9.0 | 4.0 | 5.0 | 4.0 | 9.0 | | 4.0 | 9.0 | 9.0 | | 4.5 | 5.0 | 6.0 |

TABLE I-continued

Postemergence Herbicidal Evaluation of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 38 | 0.0620 | 9.0 | 0.0 | 1.0 | 3.0 | 4.0 | 9.0 | | 3.0 | 3.0 | 7.0 | | 3.5 | 4.0 | 5.5 |
|  | 0.0320 | 9.0 | 0.0 | 0.0 | 0.0 | 0.0 | 7.0 | | 0.0 | 0.0 | 5.5 | | 2.5 | 3.5 | 5.0 |
| 39 | 0.0620 | 9.0 | 3.0 | 0.0 | 4.0 | 1.0 | 4.0 | | 1.0 | 3.0 | 5.0 | | 2.0 | 2.0 | 4.5 |
|  | 0.0320 | 2.0 | 3.0 | 0.0 | 0.0 | 0.0 | 4.0 | | 0.0 | 0.0 | 5.0 | | 1.5 | 1.5 | 4.5 |
| 40 | 0.0620 | 9.0 | 9.0 | 6.0 | 6.0 | 2.0 | 9.0 | | 1.0 | 9.0 | 8.0 | | 2.0 | 4.0 | 5.0 |
|  | 0.0320 | 9.0 | 9.0 | 1.0 | 4.0 | 2.0 | 9.0 | | 0.0 | 3.0 | 7.0 | | 2.0 | 3.5 | 4.5 |
| 41 |  |  |  |  |  |  |  |  |  |  |  |  |  |  |  |
| 42 | 0.1250 | 9.0 | 9.0 | 4.0 | 9.0 | 3.0 | 9.0 | | 3.0 | 9.0 | 8.0 | | 1.5 | 5.0 | 5.5 |
|  | 0.0620 | 9.0 | 9.0 | 1.0 | 9.0 | 3.0 | 9.0 | | 1.0 | 5.0 | 8.0 | | 1.5 | 5.0 | 5.5 |
|  | 0.0320 | 9.0 | 9.0 | 1.0 | 9.0 | 1.0 | 9.0 | | 1.0 | 5.0 | 6.0 | | 1.0 | 4.0 | 5.5 |
| 43 | 0.0620 | 9.0 | 9.0 | 3.0 | 6.0 | 4.0 | 9.0 | | 2.0 | 4.0 | 6.0 | | 2.0 | 3.5 | 4.5 |
|  | 0.0320 | 9.0 | 9.0 | 2.0 | 6.0 | 4.0 | 9.0 | | 2.0 | 5.0 | 6.0 | | 2.0 | 2.5 | 4.5 |
| 44 | 0.0620 | 9.0 | 9.0 | 4.0 | 9.0 | 7.0 | 9.0 | | 3.0 | 9.0 | 8.5 | | 3.5 | 5.0 | 5.5 |
|  | 0.0320 | 9.0 | 9.0 | 2.0 | 9.0 | 4.0 | 9.0 | | 1.0 | 9.0 | 8.5 | | 2.0 | 4.0 | 5.0 |
| 45 | 0.0620 | 9.0 | 9.0 | 9.0 | 9.0 | 9.0 | 9.0 | | 4.0 | 9.0 | 8.8 | | 5.2 | 5.0 | 6.0 |
|  | 0.0320 | 9.0 | 9.0 | 5.0 | 8.5 | 8.5 | 9.0 | | 2.8 | 6.3 | 8.8 | | 4.3 | 4.4 | 5.5 |
| 46 | 0.1250 | 9.0 | 9.0 | 9.0 | 9.0 | 5.0 | 9.0 | | 4.0 | 9.0 | 7.5 | | 4.5 | 5.0 | 5.5 |
|  | 0.0620 | 9.0 | 9.0 | 9.0 | 9.0 | 6.0 | 9.0 | | 2.0 | 4.0 | 7.5 | | 3.5 | 4.5 | 4.5 |
|  | 0.0320 | 9.0 | 7.0 | 7.0 | 6.0 | 4.0 | 9.0 | | 2.0 | 3.0 | 6.0 | | 4.0 | 4.0 | 4.5 |
| 47 | 0.0620 | 9.0 | 9.0 | 9.0 | 9.0 | 9.0 | 9.0 | | 3.0 | 9.0 | 8.5 | | 6.5 | 6.0 | 4.0 |
|  | 0.0320 | 9.0 | 9.0 | 6.0 | 9.0 | 9.0 | 9.0 | | 0.0 | 9.0 | 7.5 | | 4.0 | 5.0 | 3.5 |
| 48 | 0.0620 | 9.0 | 9.0 | 7.0 | 9.0 | 9.0 | 9.0 | | 3.0 | 9.0 | 8.7 | | 6.0 | 5.7 | 5.7 |
|  | 0.0320 | 9.0 | 9.0 | 1.0 | 9.0 | 9.0 | 9.0 | | 5.0 | 9.0 | 8.0 | | 5.5 | 5.0 | 4.5 |
| 49 | 0.0620 | 0.0 | 0.0 | 0.0 | 0.0 | 0.0 | 8.0 | | 0.0 | 0.0 | 2.5 | | 1.5 | 1.5 | 2.5 |
|  | 0.0320 | 0.0 | 0.0 | 0.0 | 0.0 | 0.0 | 5.0 | | 0.0 | 0.0 | 1.5 | | 0.5 | 0.5 | 0.5 |
| 50 | 0.0620 | 9.0 | 9.0 | 5.0 | 9.0 | 8.0 | 9.0 | | 3.0 | 9.0 | 7.5 | | 4.5 | 4.5 | 5.0 |
|  | 0.0320 | 9.0 | 9.0 | 5.0 | 8.0 | 3.0 | 9.0 | | 3.0 | 9.0 | 7.5 | | 5.5 | 4.5 | 4.0 |
| 51 | 0.0620 | 9.0 | 9.0 | 6.0 | 8.0 | 5.0 | 9.0 | | 3.0 | 3.0 | 7.5 | | 4.0 | 4.0 | 5.5 |
|  | 0.0320 | 9.0 | 9.0 | 2.0 | 7.0 | 2.0 | 9.0 | | 3.0 | 3.0 | 5.0 | | 3.0 | 3.5 | 5.0 |
| 52 | 0.1250 | 9.0 | 9.0 | 8.0 | 9.0 | 7.0 | 8.0 | | 5.0 | 9.0 | 8.5 | | 4.0 | 5.0 | 5.0 |
|  | 0.0620 | 9.0 | 9.0 | 7.0 | 5.0 | 3.0 | 9.0 | | 1.0 | 3.0 | 7.0 | | 3.0 | 4.0 | 3.5 |
|  | 0.0320 | 9.0 | 9.0 | 1.0 | 5.0 | 5.0 | 9.0 | | 0.0 | 9.0 | 7.5 | | 3.0 | 4.0 | 3.5 |
| 53 | 0.1250 | 9.0 | 9.0 | 3.0 | 9.0 | 7.0 | 9.0 | | 1.0 | 9.0 | 8.0 | | 3.0 | 4.0 | 5.5 |
|  | 0.0620 | 9.0 | 9.0 | 4.0 | 7.0 | 3.0 | 9.0 | | 2.0 | 5.5 | 8.3 | | 3.5 | 4.0 | 5.0 |
|  | 0.0320 | 9.0 | 6.5 | 2.0 | 4.5 | 2.5 | 8.0 | | 1.0 | 2.5 | 6.8 | | 3.0 | 3.3 | 4.5 |
| 54 | 0.1250 | 9.0 | 9.0 | 9.0 | 9.0 | 9.0 | 9.0 | | 3.0 | 8.0 | 9.0 | | 7.0 | 7.5 | 5.5 |
|  | 0.0620 | 9.0 | 9.0 | 2.0 | 5.0 | 5.0 | 9.0 | | 1.0 | 9.0 | 8.5 | | 6.5 | 6.5 | 4.0 |
|  | 0.0320 | 9.0 | 9.0 | 2.0 | 5.0 | 5.0 | 9.0 | | 1.0 | 3.0 | 8.0 | | 5.0 | 5.0 | 5.0 |
| 55 | 0.0620 | 9.0 | 9.0 | 1.0 | 4.0 | 2.0 | 9.0 | | 1.0 | 1.0 | 5.0 | | 4.5 | 5.0 | 4.5 |
|  | 0.0320 | 9.0 | 9.0 | 2.0 | 5.0 | 2.0 | 9.0 | | 1.0 | 1.0 | 4.5 | | 3.0 | 3.0 | 4.5 |
| 56 | 0.0620 | 9.0 | 9.0 | 4.0 | 7.0 | 3.0 | 9.0 | | 4.0 | 4.0 | 6.5 | | 4.5 | 4.5 | 5.5 |
|  | 0.0320 | 9.0 | 9.0 | 2.0 | 9.0 | 3.0 | 9.0 | | 2.0 | 2.0 | 6.0 | | 3.5 | 3.5 | 5.0 |
| 57 | 0.0620 | 9.0 | 9.0 | 7.0 | 7.0 | 9.0 | 9.0 | | 3.0 | 9.0 | 8.5 | | 4.5 | 5.0 | 5.5 |
|  | 0.0320 | 9.0 | 9.0 | 8.0 | 5.0 | 6.0 | 9.0 | | 3.0 | 4.0 | 7.5 | | 4.0 | 4.5 | 5.5 |
| 58 | 0.0620 | 9.0 | 9.0 | 1.0 | 3.0 | 7.0 | 9.0 | | 1.0 | 1.0 | 7.0 | | 3.5 | 4.0 | 5.5 |

TABLE I-continued

Postemergence Herbicidal Evaluation of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 59 | 0.1250 | 9.0 | 9.0 | 3.0 | 9.0 | 3.0 | 9.0 | | 3.0 | 3.0 | 8.0 | | 2.5 | 4.0 | 7.0 |
| | 0.0620 | 9.0 | 9.0 | 3.0 | 9.0 | 3.0 | 8.0 | | 0.0 | 0.0 | 7.5 | | 2.5 | 3.5 | 6.5 |
| | 0.0320 | 9.0 | 9.0 | 0.0 | 8.0 | 0.0 | 8.0 | | 0.0 | 2.0 | 7.5 | | 2.0 | 3.0 | 5.5 |
| 60 | 0.0620 | 9.0 | 9.0 | 4.0 | 5.0 | 9.0 | 9.0 | | 2.0 | 3.0 | 7.0 | | 4.0 | 4.5 | 6.0 |
| | 0.0320 | 9.0 | 9.0 | 1.0 | 6.0 | 7.0 | 9.0 | | 2.0 | 8.0 | 5.0 | | 3.5 | 4.0 | 5.5 |
| 61 | 0.0620 | 9.0 | 9.0 | 9.0 | 9.0 | 9.0 | 9.0 | | 3.0 | 7.5 | 9.0 | 8.5 | 5.5 | 5.5 | 5.5 |
| | 0.0320 | 9.0 | 9.0 | 9.0 | 9.0 | 9.0 | 9.0 | | 5.0 | 9.0 | 9.0 | 8.5 | 6.0 | 6.5 | 7.0 |
| 62 | 0.0620 | 9.0 | 9.0 | 9.0 | 9.0 | 9.0 | 9.0 | | 6.0 | 9.0 | 9.0 | | 6.0 | 6.5 | 6.0 |
| | 0.0320 | 9.0 | 9.0 | 9.0 | 9.0 | 9.0 | 9.0 | | 7.0 | 7.0 | 6.5 | | 5.0 | 6.0 | 5.5 |
| 63 | 0.0620 | 9.0 | 9.0 | 5.0 | 9.0 | 6.0 | 9.0 | | 6.0 | 7.0 | 8.5 | | 5.5 | 5.0 | 5.5 |
| | 0.0320 | 9.0 | 9.0 | 4.0 | 9.0 | 9.0 | 9.0 | | 5.0 | 6.0 | 7.0 | | 5.0 | 4.0 | 5.5 |
| 64 | 0.0620 | 9.0 | 9.0 | 5.0 | 9.0 | 9.0 | 9.0 | | 3.0 | 7.0 | 5.5 | | 4.5 | 5.0 | 5.5 |
| | 0.0320 | 9.0 | 9.0 | 4.0 | 7.0 | 5.0 | 9.0 | | 4.0 | 3.0 | 9.0 | | 4.0 | 4.0 | 5.0 |
| 65 | 0.0620 | 9.0 | 9.0 | 9.0 | 9.0 | 9.0 | 9.0 | | 5.0 | 9.0 | 9.0 | | 4.5 | 4.0 | 5.5 |
| | 0.0320 | 9.0 | 9.0 | 8.0 | 9.0 | 9.0 | 9.0 | | 2.0 | 8.0 | 9.0 | | 4.5 | 4.0 | 5.5 |
| 66 | 0.0620 | 9.0 | 9.0 | 9.0 | 9.0 | 5.0 | 9.0 | | 4.0 | 7.0 | 9.0 | | 5.5 | 4.0 | 5.0 |
| | 0.0320 | 9.0 | 9.0 | 9.0 | 9.0 | 6.0 | 9.0 | | 3.0 | 9.0 | 9.0 | | 4.5 | 4.5 | 6.0 |
| 67 | 0.0620 | 9.0 | 9.0 | 6.0 | 9.0 | 9.0 | 9.0 | | 5.0 | 8.0 | 9.0 | | 5.0 | 4.0 | 5.5 |
| 68 | 0.0320 | 9.0 | 9.0 | 5.0 | 9.0 | 9.0 | 9.0 | | 4.0 | 4.0 | 7.0 | | 4.0 | 4.5 | 6.0 |
| | 0.0620 | 9.0 | 9.0 | 2.0 | 7.0 | 6.0 | 9.0 | | 3.0 | 2.0 | 7.0 | | 4.0 | 4.0 | 5.5 |
| 69 | 0.0320 | 9.0 | 9.0 | 0.0 | 9.0 | 4.0 | 9.0 | | 2.0 | 9.0 | 7.5 | | 4.0 | 4.5 | 5.5 |
| | 0.0620 | 9.0 | 9.0 | 5.0 | 9.0 | 9.0 | 9.0 | | 4.0 | 7.0 | 8.5 | | 6.0 | 5.5 | 6.5 |
| 70 | 0.0320 | 9.0 | 9.0 | 5.0 | 9.0 | 8.0 | 9.0 | | 3.0 | 9.0 | 7.0 | | 5.0 | 5.0 | 5.0 |
| | 0.0620 | 9.0 | 6.0 | 2.0 | 9.0 | 7.0 | 9.0 | | 3.0 | 7.0 | 4.5 | | 4.5 | 3.5 | 5.0 |
| 71 | 0.0320 | 9.0 | 7.0 | 0.0 | 6.0 | 2.0 | 9.0 | | 1.0 | 2.0 | 4.5 | | 3.0 | 3.0 | 4.5 |
| 72 | 0.0620 | 9.0 | 9.0 | 5.0 | 9.0 | 9.0 | 9.0 | | 3.0 | 8.0 | 8.5 | | 4.5 | 4.5 | 5.0 |
| | 0.0320 | 9.0 | 9.0 | 5.0 | 9.0 | 9.0 | 9.0 | | 3.0 | 8.0 | 6.5 | | 4.0 | 3.5 | 5.0 |
| 73 | 0.0620 | 9.0 | 9.0 | 4.0 | 9.0 | 9.0 | 9.0 | | 3.0 | 8.0 | 7.5 | | 4.0 | 4.0 | 5.0 |
| | 0.0320 | 9.0 | 9.0 | 3.0 | 9.0 | 5.0 | 9.0 | | 2.0 | 4.0 | 5.5 | | 3.0 | 3.5 | 4.5 |
| 74 | 0.0620 | 9.0 | 9.0 | 1.0 | 9.0 | 8.0 | 9.0 | | 2.0 | 2.0 | 7.0 | | 4.0 | 4.0 | 5.0 |
| | 0.0320 | 9.0 | 9.0 | 2.0 | 9.0 | 6.0 | 7.0 | | 2.0 | 9.0 | 5.5 | | 3.5 | 3.5 | 5.0 |
| 75 | 0.0620 | 9.0 | 9.0 | 2.0 | 7.0 | 7.0 | 9.0 | | 3.0 | 2.0 | 5.5 | | 3.5 | 3.5 | 5.0 |
| | 0.0320 | 9.0 | 9.0 | 2.0 | 7.0 | 5.0 | 9.0 | | 3.0 | 4.0 | 7.0 | | 2.5 | 2.0 | 4.5 |
| 76 | 0.0620 | 9.0 | 9.0 | 5.0 | 9.0 | 7.0 | 9.0 | | 3.0 | 2.0 | 5.5 | | 4.0 | 3.5 | 4.5 |
| | 0.0320 | 9.0 | 9.0 | 4.0 | 9.0 | 5.0 | 7.0 | | 3.0 | 9.0 | 8.0 | | 3.5 | 3.0 | 3.5 |
| 77 | 0.0620 | 9.0 | 9.0 | 4.0 | 9.0 | 7.0 | 9.0 | | 0.0 | 7.0 | 7.0 | | 3.5 | 3.5 | 3.5 |
| | 0.0320 | 9.0 | 9.0 | 6.0 | 9.0 | 5.0 | 9.0 | | 4.0 | 5.0 | 8.5 | | 4.0 | 3.5 | 3.0 |
| 78 | 0.0620 | 9.0 | 9.0 | 4.0 | 9.0 | 4.0 | 8.0 | | 4.0 | 9.0 | 7.5 | | 2.0 | 2.0 | 3.5 |
| | 0.0320 | 9.0 | 9.0 | 6.0 | 9.0 | 7.0 | 7.0 | | 3.0 | 7.0 | 5.5 | | 4.0 | 5.0 | 3.5 |
| 79 | 0.0620 | 9.0 | 9.0 | 6.0 | 9.0 | 4.0 | 9.0 | | 2.0 | 6.0 | 5.0 | | 2.0 | 3.5 | 3.0 |
| | 0.0320 | 9.0 | 9.0 | 5.0 | 8.0 | 4.0 | 9.0 | | 4.0 | 4.0 | 6.0 | | 3.5 | 2.5 | 3.5 |
| 80 | 0.0620 | 9.0 | 9.0 | 5.0 | 9.0 | 2.0 | 7.0 | | 0.0 | 3.0 | 5.0 | | 3.5 | 2.0 | 5.5 |
| | 0.0320 | 6.0 | 7.0 | 6.0 | 9.0 | 4.0 | 9.0 | | 0.0 | 2.0 | 7.0 | | 3.5 | 3.5 | 3.5 |
| 81 | 0.0620 | 9.0 | 9.0 | 5.0 | 9.0 | 3.0 | 9.0 | | 4.0 | 9.0 | 5.0 | | 6.5 | 6.5 | 7.0 |
| | 0.0320 | 9.0 | 7.0 | 6.0 | 7.0 | 2.0 | 9.0 | | 3.0 | 9.0 | 6.5 | | 5.5 | 4.0 | 5.0 |

TABLE I-continued

Postemergence Herbicidal Evaluation of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 82 | 0.0620 | 9.0 | 9.0 | 4.0 | 9.0 | 4.0 | 9.0 | | 3.0 | 4.0 | 5.5 | | 2.5 | 1.5 | 3.0 |
|  | 0.0320 | 9.0 | 4.0 | 4.0 | 7.0 | 2.0 | 7.0 | | 2.0 | 3.0 | 4.0 | | 1.5 | 1.5 | 3.0 |
| 83 | 0.0620 | 9.0 | 6.0 | 6.0 | 6.0 | 3.0 | 4.0 | | 3.0 | 4.0 | 6.0 | | 3.0 | 3.0 | 3.0 |
|  | 0.0320 | 6.0 | 2.0 | 4.0 | 3.0 | 2.0 | 2.0 | | 2.0 | 3.0 | 4.0 | | 1.5 | 2.0 | 2.5 |
| 84 | 0.1250 | 9.0 | 9.0 | 9.0 | 9.0 | 9.0 | 9.0 | | 9.0 | | 9.0 | | 9.0 | 9.0 | 8.5 |
|  | 0.0620 | 9.0 | 9.0 | 7.0 | 9.0 | 7.5 | 9.0 | | 6.5 | 9.0 | 9.0 | | 6.5 | 6.3 | 6.0 |
|  | 0.0320 | 9.0 | 7.5 | 7.0 | 9.0 | 6.5 | 9.0 | | 4.5 | 6.0 | 8.5 | | 5.3 | 4.8 | 4.8 |
| 85 | 0.0620 | 9.0 | 9.0 | 4.0 | 9.0 | 6.0 | 9.0 | | 2.0 | 9.0 | 4.0 | | 4.5 | 3.5 | 5.0 |
|  | 0.0320 | 9.0 | 5.0 | 4.0 | 9.0 | 4.0 | 9.0 | | 0.0 | 5.0 | 3.5 | | 3.5 | 2.0 | 4.5 |
| 86 | 0.0620 | 9.0 | 9.0 | 7.0 | 9.0 | 9.0 | 9.0 | | 5.0 | 9.0 | 9.0 | | 5.5 | 3.0 | 4.0 |
|  | 0.0320 | 9.0 | 9.0 | 9.0 | 9.0 | 9.0 | 9.0 | | 4.0 | 8.0 | 9.0 | | 4.0 | 2.5 | 4.0 |
| 87 | 0.0620 | 9.0 | 9.0 | 9.0 | 9.0 | 9.0 | 9.0 | | 4.0 | 9.0 | 8.5 | | 3.5 | 4.0 | 3.5 |
|  | 0.0320 | 9.0 | 9.0 | 9.0 | 9.0 | 9.0 | 9.0 | | 3.0 | 6.0 | 9.0 | | 3.0 | 3.0 | 3.5 |
| 88 | 0.0620 | 9.0 | 9.0 | 5.0 | 9.0 | 9.0 | 9.0 | | 5.0 | 9.0 | 9.0 | | 4.0 | 3.5 | 5.0 |
|  | 0.0320 | 9.0 | 9.0 | 9.0 | 9.0 | 9.0 | 9.0 | | 5.0 | 9.0 | 9.0 | | 4.0 | 3.0 | 4.0 |
| 89 | 0.1250 | 9.0 | 9.0 | 9.0 | 9.0 | 9.0 | 9.0 | | 4.0 | | 9.0 | | 4.0 | 4.0 | 3.5 |
|  | 0.0620 | 9.0 | 9.0 | 9.0 | 9.0 | 9.0 | 9.0 | | 3.0 | | 8.0 | | 3.0 | 3.0 | 3.5 |
|  | 0.0320 | 9.0 | 9.0 | 9.0 | 9.0 | 7.0 | 9.0 | | 0.0 | | 7.5 | | 3.0 | 3.0 | 3.5 |
|  | 0.0080 | 8.0 | 7.0 | 9.0 | 8.0 | 3.0 | 7.0 | | 0.0 | | 7.0 | | 1.5 | 1.5 | 3.0 |
| 90 | 0.1250 | 9.0 | 9.0 | 9.0 | 9.0 | 2.0 | 9.0 | | 0.0 | | 6.5 | | 2.0 | 2.0 | 2.5 |
|  | 0.0620 | 7.5 | 6.5 | 5.0 | 9.0 | 5.0 | 8.0 | | 4.0 | | 6.3 | | 2.5 | 2.8 | 3.3 |
|  | 0.0320 | 7.5 | 6.5 | 5.0 | 9.0 | 4.0 | 6.5 | | 3.0 | | 6.0 | | 2.0 | 2.8 | 3.0 |
| 91 | 0.1250 | 9.0 | 5.0 | 5.0 | 9.0 | 3.0 | 8.0 | | 2.0 | | 6.0 | | 1.0 | 0.0 | 3.0 |
|  | 0.0620 | 7.0 | 4.0 | 4.0 | 9.0 | 3.0 | 7.0 | | 0.0 | | 6.0 | | 0.5 | 0.0 | 2.5 |
|  | 0.0320 | 5.0 | 3.0 | 0.0 | 9.0 | 3.0 | 7.0 | | 0.0 | | 6.0 | | 0.0 | 0.0 | 1.5 |
| 92 | 0.1250 | 9.0 | 6.0 | 5.0 | 6.0 | 4.0 | 8.0 | | 4.0 | | 5.5 | | 1.0 | 1.5 | 3.0 |
|  | 0.0620 | 7.0 | 5.0 | 5.0 | 6.0 | 3.0 | 8.0 | | 3.0 | | 5.0 | | 1.0 | 1.5 | 2.5 |
|  | 0.0320 | 6.0 | 3.0 | 4.0 | 3.0 | 2.0 | 6.0 | | 2.0 | | 5.0 | | 1.0 | 1.0 | 2.0 |
| 93 | 0.0620 | 9.0 | 9.0 | 9.0 | 9.0 | 9.0 | 9.0 | | 9.0 | | 9.0 | | 8.0 | 7.5 | 5.5 |
|  | 0.0320 | 9.0 | 9.0 | 7.0 | 9.0 | 9.0 | 9.0 | | 9.0 | | 9.0 | | 4.0 | 5.5 | 5.5 |
| 97 | 1.0000 | 9.0 | 9.0 | | 9.0 | 9.0 | 9.0 | 9.0 | 4.0 | 7.0 | 9.0 | | 4.0 | 3.0 | 4.0 |
|  | 0.0620 | 9.0 | 8.0 | | 8.0 | | 8.0 | | 3.0 | 3.0 | | 8.0 | | | 3.5 |
|  | 0.0320 | 9.0 | 7.0 | | 8.0 | | 8.0 | | 2.0 | 3.0 | | 6.5 | | | 3.5 |
| 95 | 0.0620 | 9.0 | 8.0 | | 9.0 | | 9.0 | | 3.0 | 7.0 | | 8.0 | | | 3.5 |
|  | 0.0320 | 9.0 | 4.0 | | 8.0 | | 8.0 | | 2.0 | 4.0 | | 8.0 | | | 3.5 |
| 96 | 0.3000 | 9.0 | 6.0 | | 9.0 | 0.0 | | 3.0 | 0.0 | 4.0 | 5.0 | | 0.0 | 0.0 | 2.0 |
|  | 0.0620 | 4.0 | 5.0 | | 4.0 | | 6.0 | | 2.0 | 2.0 | | 6.0 | | | 3.0 |
|  | 0.0320 | 3.0 | 4.0 | | 3.0 | | 3.0 | | 1.0 | 2.0 | | 5.5 | | | 3.0 |
| 97 | 0.0620 | 9.0 | 8.0 | | 8.0 | | 7.0 | | 3.0 | 5.0 | | 7.5 | | | 4.0 |
|  | 0.0320 | 9.0 | 8.0 | | 7.0 | | 6.0 | | 2.0 | 5.0 | | 7.0 | | | 4.0 |
| 98 | 0.0620 | 9.0 | 8.0 | | 8.0 | | 8.0 | | 2.0 | 3.0 | | 8.0 | | | 3.5 |
|  | 0.0320 | 9.0 | 8.0 | | 6.0 | | 9.0 | | 2.0 | 3.0 | | 8.0 | | | 3.5 |

EXAMPLE 88

Preemergence Herbicidal Evaluation of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.0620 to 0.000 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 87. The plant species used and the compounds evaluated are the same as those shown in Example 87.

The data obtained are reported in Table II below.

TABLE II

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.2500 | 9.0 | 9.0 | 8.3 | 9.0 | 6.5 | 9.0 | | 9.0 | 9.0 | 9.0 | | 6.5 | 5.0 | 7.0 |
|   | 0.1250 | 9.0 | 9.0 | 8.3 | 9.0 | 7.0 | 9.0 | | 8.0 | 9.0 | 9.0 | | 5.0 | 4.0 | 6.7 |
|   | 0.0620 | 9.0 | 7.3 | 7.3 | 9.0 | 9.0 | 8.0 | | 7.3 | 9.0 | 7.0 | | 5.0 | 3.5 | 6.0 |
| 2 | 0.2500 | 9.0 | 9.0 | 7.0 | 9.0 | 9.0 | 9.0 | | 8.0 | 8.0 | 8.0 | | 7.0 | 7.0 | 7.5 |
|   | 0.1250 | 9.0 | 8.0 | 7.5 | 9.0 | 9.0 | 9.0 | | 6.0 | 8.0 | 8.0 | | 6.0 | 5.0 | 6.5 |
|   | 0.0620 | 9.0 | 7.0 | 5.0 | 9.0 | 5.0 | 9.0 | | 2.5 | 8.0 | 5.5 | | 3.0 | 2.0 | 3.5 |
| 3 | 0.2500 | 9.0 | 9.0 | 5.5 | 9.0 | 9.0 | 9.0 | | 9.0 | 9.0 | 9.0 | | 5.0 | 6.0 | 7.0 |
|   | 0.1250 | 9.0 | 9.0 | 4.5 | 9.0 | 9.0 | 9.0 | | 7.0 | 8.5 | 9.0 | | 5.0 | 5.0 | 6.5 |
|   | 0.0620 | 8.5 | 8.0 | 4.0 | 9.0 | 9.0 | 9.0 | | 7.5 | 9.0 | 5.5 | | 6.0 | 4.0 | 6.5 |
| 4 | 0.2500 | 9.0 | 8.9 | 5.0 | 8.0 | 9.0 | 7.6 | | 9.0 | 9.0 | 6.0 | | 2.8 | 4.3 | 5.4 |
|   | 0.1250 | 8.9 | 7.3 | 3.4 | 9.0 | 8.0 | 6.3 | | 8.3 | 9.0 | 4.4 | | 1.9 | 2.5 | 4.2 |
|   | 0.0620 | 7.8 | 5.9 | 1.3 | 9.0 | 5.0 | 4.7 | | 7.0 | 8.8 | 2.7 | | 1.4 | 1.2 | 3.2 |
| 5 | 0.2500 | 9.0 | 9.0 | 5.5 | 9.0 | 7.0 | 9.0 | | 9.0 | 9.0 | 6.5 | | 7.5 | 8.0 | 7.0 |
|   | 0.1250 | 9.0 | 9.0 | 1.0 | 9.0 | 5.0 | 9.0 | | 8.0 | 9.0 | 3.5 | | 5.0 | 7.0 | 6.5 |
|   | 0.0620 | 7.0 | 8.5 | 0.0 | 9.0 | 4.0 | 4.0 | | 2.5 | 8.0 | 2.0 | | 3.0 | 5.0 | 4.0 |
| 6 | 0.2500 | 9.0 | 9.0 | 0.0 | 9.0 | | 9.0 | | 9.0 | 9.0 | 4.0 | | 2.0 | 2.0 | 5.0 |
|   | 0.1250 | 9.0 | 3.0 | 0.0 | 9.0 | | 2.0 | | 0.0 | 9.0 | 0.0 | | 0.0 | 2.0 | 3.0 |
|   | 0.0620 | 0.0 | 0.0 | 0.0 | 9.0 | | 0.0 | | 0.0 | 9.0 | 0.0 | | 0.0 | 0.0 | 0.0 |
| 7 | 0.2500 | 9.0 | 0.0 | 9.0 | 9.0 | | 9.0 | | 3.0 | 9.0 | 2.0 | | 0.0 | 2.0 | 8.0 |
|   | 0.1250 | 9.0 | 0.0 | 3.0 | 9.0 | | 0.0 | | 3.0 | 9.0 | 0.0 | | 0.0 | 2.0 | 4.0 |
|   | 0.0620 | 9.0 | 0.0 | 0.0 | 9.0 | | 0.0 | | 0.0 | 9.0 | 0.0 | | 0.0 | 0.0 | 0.0 |
| 8 | 0.2500 | 9.0 | 2.0 | 0.0 | 9.0 | 9.0 | 1.0 | | 9.0 | 9.0 | 0.0 | | 0.0 | 0.0 | 3.0 |
|   | 0.1250 | 0.0 | 0.0 | 0.0 | 9.0 | 0.0 | 0.0 | | 0.0 | 9.0 | 0.0 | | 0.0 | 0.0 | 0.0 |
|   | 0.0620 | 0.0 | 0.0 | 0.0 | 9.0 | 0.0 | 0.0 | | 0.0 | 8.0 | 0.0 | | 0.0 | 0.0 | 0.0 |
| 9 | 0.2500 | 9.0 | 9.0 | 6.3 | 9.0 | 7.0 | 9.0 | | 9.0 | 9.0 | 8.7 | | 8.0 | 8.5 | 7.7 |
|   | 0.1250 | 9.0 | 9.0 | 2.7 | 9.0 | 3.0 | 8.3 | | 8.3 | 9.0 | 8.3 | | 6.7 | 7.5 | 6.7 |
|   | 0.0620 | 9.0 | 6.3 | 1.0 | 9.0 | 1.5 | 6.3 | | 5.0 | 9.0 | 4.0 | | 4.3 | 5.5 | 6.3 |
| 10 | 0.2500 | 9.0 | 7.0 | 1.0 | 9.0 | 8.0 | 2.0 | | 9.0 | 9.0 | 2.5 | | 7.0 | 7.0 | 7.0 |
|    | 0.1250 | 9.0 | 6.0 | 1.0 | 9.0 | 8.5 | 0.5 | | 5.0 | 9.0 | 1.0 | | 3.0 | 4.5 | 6.5 |
|    | 0.0620 | 7.0 | 4.0 | 0.5 | 8.0 | 5.0 | 0.5 | | 0.5 | 7.5 | 0.5 | | 1.0 | 1.5 | 4.0 |
| 11 | 0.2500 | 9.0 | 9.0 | 9.0 | 9.0 | 9.0 | 7.0 | | 8.0 | 9.0 | 7.5 | | 5.0 | 4.0 | 5.5 |
|    | 0.1250 | 8.0 | 8.5 | 7.5 | 9.0 | 9.0 | 3.5 | | 6.0 | 6.5 | 4.0 | | 3.0 | 2.0 | 3.5 |
|    | 0.0620 | 5.0 | 2.0 | 2.5 | 9.0 | 0.0 | 0.0 | | 3.0 | 9.0 | 2.0 | | 1.5 | 1.0 | 1.5 |
| 12 | 0.2500 | 9.0 | 9.0 | 8.5 | 9.0 | 9.0 | 9.0 | | 9.0 | 9.0 | 9.0 | | 8.5 | 9.0 | 8.5 |
|    | 0.1250 | 9.0 | 9.0 | 7.0 | 9.0 | 9.0 | 7.5 | | 8.0 | 9.0 | 6.5 | | 7.5 | 7.0 | 8.5 |
|    | 0.0620 | 9.0 | 9.0 | 6.5 | 9.0 | 9.0 | 9.0 | | 9.0 | 9.0 | 4.5 | | 7.0 | 3.0 | 6.0 |
| 13 | 0.2500 | 9.0 | 9.0 | 6.0 | 9.0 | 9.0 | 3.5 | | 7.5 | 9.0 | 7.5 | | 7.5 | 5.0 | 7.0 |
|    | 0.1250 | 9.0 | 8.5 | 4.5 | 9.0 | 9.0 | 2.5 | | 6.0 | 7.5 | 5.5 | | 6.5 | 4.0 | 5.5 |
|    | 0.0620 | 9.0 | 9.0 | 9.0 | 9.0 | 9.0 | 9.0 | | 9.0 | 9.0 | 4.0 | | 4.0 | 1.0 | 3.5 |
| 14 | 0.2500 | 9.0 | 9.0 | 9.0 | 9.0 | 9.0 | 9.0 | | 9.0 | 9.0 | 8.0 | | 9.0 | 9.0 | 8.5 |
|    | 0.1250 | 9.0 | 9.0 | 9.0 | 9.0 | 9.0 | 8.0 | | 8.0 | 9.0 | 9.0 | | 8.5 | 8.0 | 8.0 |
|    | 0.0620 | 7.0 | 7.0 | 0.0 | 9.0 | 0.0 | 6.0 | | 5.0 | 5.0 | 2.0 | | 7.0 | 3.0 | 7.0 |
| 15 | 0.2500 | 7.0 | 5.0 | 0.0 | 9.0 | 0.0 | 0.0 | | 0.0 | 1.0 | 1.0 | | 3.0 | 0.0 | 1.0 |
|    | 0.1250 | 4.0 | 0.0 | 0.0 | 9.0 | 0.0 | 0.0 | | 0.0 | 0.0 | 0.0 | | 0.0 | 0.0 | 0.0 |
|    | 0.0620 | 0.0 | 0.0 | 0.0 | 9.0 | 0.0 | 0.0 | | 0.0 | 0.0 | 0.0 | | 0.0 | 0.0 | 0.0 |

TABLE II-continued

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 16 | 0.2500 | 9.0 | 9.0 | 9.0 | 9.0 | 7.0 | 9.0 |  | 9.0 | 9.0 | 7.5 |  | 7.0 | 7.0 | 7.5 |
|  | 0.1250 | 9.0 | 9.0 | 6.5 | 9.0 | 9.0 | 8.0 |  | 6.5 | 9.0 | 6.0 |  | 6.0 | 5.0 | 6.5 |
|  | 0.0620 | 9.0 | 8.0 | 2.0 | 9.0 | 9.0 | 3.0 |  | 3.5 | 8.0 | 3.0 |  | 4.0 | 4.0 | 5.0 |
| 17 | 0.2500 | 9.0 | 9.0 | 3.0 | 9.0 | 9.0 | 9.0 |  | 5.0 | 9.0 | 5.0 |  | 1.0 | 5.0 | 8.0 |
|  | 0.1250 | 9.0 | 5.0 | 0.0 | 9.0 | 9.0 | 2.0 |  | 1.0 | 9.0 | 3.0 |  | 0.0 | 0.0 | 7.0 |
|  | 0.0620 | 9.0 | 4.0 | 0.0 | 9.0 | 7.0 | 0.0 |  | 0.0 | 0.0 | 0.0 |  | 0.0 | 0.0 | 6.0 |
| 18 | 0.2500 | 9.0 | 9.0 | 1.0 | 9.0 | 0.0 | 9.0 |  | 9.0 | 9.0 | 5.0 |  | 8.0 | 8.0 | 8.0 |
|  | 0.1250 | 9.0 | 9.0 | 1.0 | 9.0 | 0.0 | 9.0 |  | 2.0 | 9.0 | 4.0 |  | 5.0 | 4.0 | 8.0 |
|  | 0.0620 | 9.0 | 7.0 | 0.0 | 9.0 | 0.0 | 3.0 |  | 0.0 | 8.0 | 0.0 |  | 0.0 | 0.0 | 7.0 |
| 19 | 0.2500 | 9.0 | 9.0 | 8.3 | 9.0 | 9.0 | 9.0 |  | 9.0 | 9.0 | 7.7 |  | 8.0 | 8.5 | 7.7 |
|  | 0.1250 | 9.0 | 6.7 | 5.7 | 9.0 | 6.0 | 8.7 |  | 9.0 | 9.0 | 6.7 |  | 7.0 | 8.0 | 7.0 |
|  | 0.0620 | 7.7 | 2.0 | 4.7 | 3.0 | 0.5 | 9.0 |  | 9.0 | 8.0 | 6.3 |  | 5.3 | 5.5 | 7.0 |
| 20 | 0.2500 | 4.0 | 1.0 | 2.0 | 2.0 | 3.0 | 0.0 |  | 0.0 | 0.0 | 0.0 |  | 0.0 | 0.0 | 0.0 |
|  | 0.1250 | 2.0 | 0.0 | 0.0 | 0.0 | 0.0 | 0.0 |  | 0.0 | 0.0 | 0.0 |  | 0.0 | 0.0 | 0.0 |
|  | 0.0620 | 1.0 | 0.0 | 0.0 | 0.0 | 0.0 | 0.0 |  | 0.0 | 0.0 | 0.0 |  | 0.0 | 0.0 | 0.0 |
| 21 | 0.2500 | 9.0 | 7.5 | 2.0 | 9.0 | 9.0 | 5.0 |  | 6.5 | 9.0 | 2.0 |  | 3.5 | 2.0 | 4.5 |
|  | 0.1250 | 7.5 | 5.5 | 0.5 | 9.0 | 2.0 | 2.0 |  | 5.0 | 9.0 | 0.0 |  | 0.5 | 1.0 | 3.5 |
|  | 0.0620 | 4.0 | 2.0 | 0.0 | 9.0 | 3.0 | 0.0 |  | 0.0 | 6.5 | 0.0 |  | 0.0 | 0.0 | 1.0 |
| 22 | 0.2500 | 5.0 | 2.0 | 1.0 | 3.0 | 1.0 | 5.0 |  | 1.0 | 3.0 | 0.0 |  | 0.0 | 0.0 | 1.0 |
|  | 0.1250 | 4.0 | 0.0 | 0.0 | 0.0 | 0.0 | 2.0 |  | 0.0 | 1.0 | 0.0 |  | 0.0 | 0.0 | 0.0 |
|  | 0.0620 | 1.0 | 0.0 | 0.0 | 0.0 | 0.0 | 0.0 |  | 0.0 | 0.0 | 0.0 |  | 0.0 | 0.0 | 0.0 |
| 23 | 0.2500 | 0.0 | 9.0 | 6.0 | 4.0 | 0.0 | 0.0 |  | 1.0 | 1.0 | 0.0 |  | 0.0 | 0.0 | 0.0 |
|  | 0.1250 | 0.0 | 0.0 | 1.0 | 0.0 | 1.0 | 0.0 |  | 0.0 | 1.0 | 0.0 |  | 0.0 | 0.0 | 0.0 |
|  | 0.0620 | 0.0 | 0.0 | 0.0 | 0.0 | 0.0 | 0.0 |  | 0.0 | 0.0 | 0.0 |  | 0.0 | 0.0 | 0.0 |
| 24 | 0.2500 | 9.0 | 9.0 | 3.0 | 9.0 | 0.0 | 7.0 |  | 5.0 | 9.0 | 4.0 |  | 6.0 |  | 3.0 |
|  | 0.1250 | 7.0 | 8.0 | 0.0 | 9.0 | 5.0 | 6.5 |  | 1.5 | 8.0 | 2.5 |  | 3.0 | 2.0 | 1.0 |
|  | 0.0620 | 3.5 | 4.5 | 0.0 | 7.5 | 5.0 | 2.0 |  | 0.0 | 3.5 | 2.0 |  | 0.0 | 0.0 | 0.0 |
| 25 | 0.2500 | 9.0 | 9.0 | 9.0 | 9.0 | 9.0 | 9.0 |  | 9.0 | 9.0 | 7.0 |  | 9.0 | 9.0 | 8.0 |
|  | 0.1250 | 9.0 | 9.0 | 9.0 | 9.0 | 9.0 | 9.0 |  | 9.0 | 9.0 | 6.0 |  | 8.0 | 9.0 | 8.0 |
|  | 0.0620 | 9.0 | 8.5 | 6.0 | 9.0 | 9.0 | 8.0 |  | 9.0 | 9.0 | 4.5 |  | 5.5 | 7.0 | 6.5 |
| 26 | 0.2500 | 9.0 | 6.0 | 3.5 | 9.0 | 7.0 | 6.0 |  | 6.5 | 9.0 | 3.0 |  | 3.0 | 3.0 | 3.5 |
|  | 0.1250 | 4.0 | 3.0 | 1.0 | 9.0 | 8.0 | 4.0 |  | 7.0 | 7.5 | 1.0 |  | 2.0 | 2.0 | 2.5 |
|  | 0.0620 | 1.0 | 3.0 | 4.0 | 4.0 | 7.0 | 1.5 |  | 5.0 | 9.0 | 2.0 |  | 1.0 | 2.0 | 3.0 |
| 27 | 0.2500 | 0.0 | 9.0 | 5.0 | 0.0 | 8.0 | 3.0 |  | 7.0 | 8.0 | 2.5 |  | 2.0 | 2.0 | 3.0 |
|  | 0.1250 | 0.0 | 5.0 | 1.0 | 9.0 | 7.0 | 4.0 |  | 0.0 | 3.5 | 2.0 |  | 1.0 | 2.0 | 3.0 |
|  | 0.0620 | 9.0 | 5.0 | 0.0 | 9.0 | 9.0 |  |  | 6.0 | 6.0 | 4.0 |  | 2.0 | 2.0 | 3.0 |
| 28 | 0.2500 | 7.0 | 8.0 | 0.0 | 9.0 | 9.0 | 9.0 |  | 9.0 | 9.0 | 2.5 |  | 9.0 | 9.0 | 9.0 |
|  | 0.1250 | 3.5 | 4.5 | 0.0 | 7.5 | 9.0 | 9.0 |  | 9.0 | 8.0 | 2.0 |  | 0.0 | 9.0 | 0.0 |
|  | 0.0620 | 9.0 | 9.0 | 9.0 | 9.0 | 9.0 | 9.0 |  | 9.0 | 9.0 | 7.0 |  | 9.0 | 9.0 | 8.0 |
| 29 | 0.2500 | 9.0 | 9.0 | 9.0 | 9.0 | 9.0 | 9.0 |  | 9.0 | 9.0 | 6.0 |  | 9.0 | 9.0 | 8.0 |
|  | 0.1250 | 9.0 | 8.0 | 8.0 | 9.0 | 7.0 | 7.5 |  | 8.0 | 7.5 | 7.0 |  | 6.5 | 8.0 | 7.0 |
|  | 0.0620 | 8.0 | 7.0 | 6.5 | 9.0 | 3.0 | 5.0 |  | 6.5 | 6.5 | 6.5 |  | 5.0 | 2.0 | 7.0 |
| 30 | 0.2500 | 9.0 | 9.0 | 3.0 | 9.0 | 9.0 | 6.5 |  | 5.5 | 9.0 | 5.0 |  | 4.0 | 6.0 | 5.5 |
|  | 0.1250 | 9.0 | 7.5 | 1.5 | 9.0 | 7.0 | 1.5 |  | 4.0 | 8.0 | 0.0 |  | 1.0 | 2.0 | 3.5 |
|  | 0.0620 | 9.0 | 4.5 | 0.0 | 9.0 | 0.0 | 1.5 |  | 0.0 | 1.0 | 1.0 |  | 0.0 | 0.0 | 0.5 |
| 31 | 0.2500 | 9.0 | 9.0 | 9.0 | 9.0 | 9.0 | 9.0 |  | 9.0 | 9.0 | 9.0 |  | 8.5 | 9.0 | 8.5 |
|  | 0.1250 | 9.0 | 9.0 | 8.0 | 9.0 | 9.0 | 9.0 |  | 8.7 | 9.0 | 7.3 |  | 7.7 | 8.0 | 6.3 |
|  | 0.0620 | 8.3 | 9.0 | 5.0 | 9.0 | 5.0 | 5.0 |  | 4.7 | 7.7 | 8.5 |  | 4.0 | 7.0 | 4.7 |

TABLE II-continued

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 32 | 0.2500 | 9.0 | 9.0 | 9.0 | 9.0 | 9.0 | 9.0 | | 9.0 | 9.0 | 9.0 | | 8.5 | 9.0 | 9.0 |
|  | 0.1250 | 9.0 | 9.0 | 8.0 | 9.0 | 9.0 | 9.0 | | 9.0 | 9.0 | 9.0 | | 7.5 | 8.0 | 9.0 |
|  | 0.0620 | 9.0 | 9.0 | 6.5 | 9.0 | 9.0 | 9.0 | | 6.5 | 6.0 | 6.5 | | 5.0 | 7.0 | 6.0 |
| 33 | 0.2500 | 9.0 | 8.0 | 0.0 | 7.0 | 7.0 | 5.0 | | 5.0 | 0.0 | 3.0 | | 6.0 | 4.0 | 2.0 |
|  | 0.1250 | 9.0 | 4.0 | 0.0 | 7.0 | 2.0 | 5.0 | | 0.0 | 0.0 | 1.0 | | 3.0 | 1.0 | 2.0 |
|  | 0.0620 | 2.0 | 2.0 | 0.0 | 4.0 | 3.0 | 0.0 | | 0.0 | 0.0 | 0.0 | | 0.0 | 0.0 | 0.0 |
| 34 | 0.2500 | 9.0 | 9.0 | 9.0 | 9.0 | 9.0 | 9.0 | | 9.0 | 9.0 | 9.0 | | 9.0 | 8.0 | 9.0 |
|  | 0.1250 | 9.0 | 9.0 | 5.0 | 9.0 | 5.0 | 9.0 | | 8.0 | 9.0 | 9.0 | | 8.0 | 7.0 | 7.0 |
|  | 0.0620 | 9.0 | 9.0 | 9.0 | 9.0 | 9.0 | 9.0 | | 7.0 | 9.0 | 7.5 | | 5.5 | 5.0 | 5.0 |
| 35 | 0.2500 | 9.0 | 9.0 | 7.0 | 9.0 | 5.0 | 9.0 | | 9.0 | 9.0 | 9.0 | | 9.0 | 9.0 | 9.0 |
|  | 0.1250 | 9.0 | 9.0 | 7.0 | 9.0 | 9.0 | 9.0 | | 9.0 | 9.0 | 9.0 | | 9.0 | 9.0 | 9.0 |
|  | 0.0620 | 9.0 | 9.0 | 9.0 | 9.0 | 9.0 | 9.0 | | 9.0 | 9.0 | 8.0 | | 5.5 | 7.0 | 5.5 |
| 36 | 0.2500 | 9.0 | 9.0 | 9.0 | 9.0 | 9.0 | 9.0 | | 8.0 | 9.0 | 9.0 | | 9.0 | 9.0 | 8.0 |
|  | 0.1250 | 9.0 | 9.0 | 5.0 | 9.0 | 5.0 | 6.5 | | 9.0 | 9.0 | 8.0 | | 9.0 | 9.0 | 8.0 |
|  | 0.0620 | 9.0 | 9.0 | 9.0 | 9.0 | 9.0 | 3.5 | | 9.0 | 9.0 | 9.0 | | 7.5 | 9.0 | 9.0 |
| 37 | 0.2500 | 9.0 | 9.0 | 5.0 | 9.0 | 9.0 | 7.0 | | 9.0 | 9.0 | 9.0 | | 9.0 | 9.0 | 9.0 |
|  | 0.1250 | 9.0 | 9.0 | 8.0 | 9.0 | 9.0 | 8.0 | | 9.0 | 9.0 | 9.0 | | 9.0 | 9.0 | 9.0 |
|  | 0.0620 | 9.0 | 9.0 | 7.0 | 9.0 | 5.0 | 7.0 | | 9.0 | 9.0 | 9.0 | | 9.0 | 9.0 | 9.0 |
| 38 | 0.2500 | 6.0 | 7.0 | 0.0 | 9.0 | 5.0 | 6.0 | | 9.0 | 9.0 | 4.0 | | 7.0 | 5.0 | 8.0 |
|  | 0.1250 | 4.0 | 3.0 | 0.0 | 9.0 | 3.0 | 0.0 | | 9.0 | 9.0 | 4.0 | | 5.0 | 4.0 | 5.0 |
|  | 0.0620 | 4.0 | 0.0 | 0.0 | 9.0 | 5.0 | 0.0 | | 7.0 | 5.0 | 0.0 | | 4.0 | 3.0 | 5.0 |
| 39 | 0.2500 | 9.0 | 0.0 | 0.0 | 9.0 | 0.0 | 1.0 | | 0.0 | 6.0 | 1.0 | | 1.0 | 1.0 | 1.0 |
|  | 0.1250 | 1.0 | 0.0 | 0.0 | 5.0 | 0.0 | 0.0 | | 0.0 | 1.0 | 0.0 | | 0.0 | 0.0 | 0.0 |
|  | 0.0620 | 1.0 | 0.0 | 0.0 | 9.0 | 0.0 | 0.0 | | 0.0 | 0.0 | 0.0 | | 0.0 | 0.0 | 0.0 |
| 40 | 0.2500 | 9.0 | 9.0 | 5.0 | 9.0 | 8.0 | 9.0 | | 8.0 | 9.0 | 5.0 | | 4.0 | 9.0 | 9.0 |
|  | 0.1250 | 9.0 | 5.0 | 2.0 | 9.0 | 0.0 | 7.0 | | 7.0 | 9.0 | 3.0 | | 2.0 | 5.0 | 8.0 |
|  | 0.0620 | 9.0 | 3.0 | 1.0 | 9.0 | 0.0 | 2.0 | | 3.0 | 3.0 | 2.0 | | 1.0 | 1.0 | 4.0 |
| 42 | 0.2500 | 9.0 | 9.0 | 0.0 | 9.0 | 0.0 | 4.5 | | 8.5 | 9.0 | 2.5 | | 5.0 | 5.0 | 6.5 |
|  | 0.1250 | 6.5 | 4.5 | 0.5 | 9.0 | 3.0 | 2.0 | | 5.5 | 7.5 | 1.0 | | 3.5 | 2.0 | 6.0 |
|  | 0.0620 | 2.0 | 1.0 | 0.5 | 9.0 | 0.0 | 0.0 | | 1.0 | 5.0 | 0.0 | | 0.0 | 0.0 | 3.5 |
| 43 | 0.2500 | 9.0 | 7.0 | 1.0 | 9.0 | 5.0 | 2.0 | | 3.0 | 9.0 | 5.0 | | 2.0 | 2.0 | 6.0 |
|  | 0.1250 | 9.0 | 1.0 | 0.0 | 9.0 | 4.0 | 0.0 | | 0.0 | 9.0 | 3.0 | | 2.0 | 1.0 | 2.0 |
|  | 0.0620 | 4.0 | 0.0 | 0.0 | 9.0 | 1.0 | 2.0 | | 0.0 | 9.0 | 1.0 | | 1.0 | 1.0 | 2.0 |
| 44 | 0.2500 | 9.0 | 9.0 | 9.0 | 9.0 | 9.0 | 9.0 | | 9.0 | 9.0 | 9.0 | | 8.0 | 9.0 | 9.0 |
|  | 0.1250 | 9.0 | 8.0 | 5.5 | 9.0 | 9.0 | 7.5 | | 9.0 | 9.0 | 6.5 | | 8.0 | 7.0 | 7.5 |
|  | 0.0620 | 9.0 | 9.0 | 1.0 | 9.0 | 0.0 | 3.0 | | 9.0 | 9.0 | 5.0 | | 6.5 | 6.0 | 7.5 |
| 45 | 0.2500 | 9.0 | 9.0 | 9.0 | 9.0 | 9.0 | 9.0 | | 9.0 | 9.0 | 9.0 | 9.0 | 9.0 | 9.0 | 8.7 |
|  | 0.1250 | 9.0 | 9.0 | 8.7 | 9.0 | 7.0 | 7.0 | | 8.0 | 9.0 | 9.0 | 9.0 | 8.7 | 9.0 | 8.8 |
|  | 0.0620 | 2.0 | 9.0 | 3.0 | 9.0 | 0.0 | 2.0 | | 8.0 | 9.0 | 2.0 | 9.0 | 4.0 | 2.0 | 0.0 |
| 46 | 0.2500 | 9.0 | 9.0 | 1.0 | 9.0 | 0.0 | 0.0 | | 5.0 | 9.0 | 1.0 | | 0.0 | 0.0 | 0.0 |
|  | 0.1250 | 4.0 | 6.0 | 1.0 | 7.0 | 0.0 | 2.0 | | 1.0 | 9.0 | 0.0 | | 1.0 | 1.0 | 0.0 |
|  | 0.0620 | 5.0 | 1.0 | 1.0 | 9.0 | 0.0 | 0.0 | | 1.0 | 9.0 | 0.0 | | 1.0 | 0.0 | 0.0 |
| 47 | 0.2500 | 9.0 | 9.0 | 9.0 | 9.0 | | 9.0 | | 9.0 | 9.0 | 9.0 | | 9.0 | 8.0 | 9.0 |
|  | 0.1250 | 9.0 | 9.0 | 7.5 | 9.0 | | 8.0 | | 9.0 | 8.5 | 8.0 | | 7.5 | 8.0 | 8.0 |
|  | 0.0620 | 9.0 | 9.0 | 4.5 | 9.0 | | 7.5 | | 9.0 | 9.0 | 7.0 | | 7.5 | 6.0 | 7.5 |

TABLE II-continued

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 48 | 0.2500 | 9.0 | 9.0 | 9.0 | 9.0 | | 9.0 | | 9.0 | 9.0 | 9.0 | | 9.0 | 8.0 | 9.0 |
|    | 0.1250 | 9.0 | 9.0 | 7.5 | 9.0 | | 8.5 | | 9.0 | 9.0 | 9.0 | | 8.0 | 8.0 | 8.0 |
|    | 0.0620 | 9.0 | 9.0 | 5.0 | 0.0 | | 8.0 | | 9.0 | 9.0 | 9.0 | | 7.5 | 6.0 | 7.5 |
| 49 | 0.2500 | 0.0 | 0.0 | 0.0 | 0.0 | | 0.0 | | 0.0 | 0.0 | 0.0 | | 0.0 | 0.0 | 0.0 |
|    | 0.1250 | 0.0 | 0.0 | 0.0 | 0.0 | | 0.0 | | 0.0 | 0.0 | 0.0 | | 0.0 | 0.0 | 0.0 |
|    | 0.0620 | 0.0 | 0.0 | 0.0 | 0.0 | | 0.0 | | 0.0 | 0.0 | 0.0 | | 0.0 | 0.0 | 0.0 |
| 50 | 0.2500 | 9.0 | 9.0 | 9.0 | 9.0 | | 9.0 | | 9.0 | 9.0 | 8.0 | | 9.0 | 9.0 | 9.0 |
|    | 0.1250 | 9.0 | 9.0 | 6.5 | 9.0 | | 7.5 | | 9.0 | 9.0 | 9.0 | | 8.5 | 8.0 | 9.0 |
|    | 0.0620 | 9.0 | 9.0 | 5.5 | 9.0 | | 8.0 | | 9.0 | 9.0 | 7.5 | | 6.5 | 7.0 | 9.0 |
| 51 | 0.2500 | 9.0 | 9.0 | 9.0 | 9.0 | | 9.0 | | 9.0 | 9.0 | 9.0 | | 9.0 | 9.0 | 9.0 |
|    | 0.1250 | 9.0 | 9.0 | 9.0 | 9.0 | | 9.0 | | 9.0 | 9.0 | 9.0 | | 9.0 | 9.0 | 8.5 |
|    | 0.0620 | 9.0 | 9.0 | 9.0 | 9.0 | | 6.5 | | 9.0 | 9.0 | 9.0 | | 8.5 | 9.0 | 8.0 |
| 52 | 0.2500 | 9.0 | 9.0 | 4.0 | 9.0 | | 6.0 | | 9.0 | 9.0 | 9.0 | | 3.5 | 3.0 | 7.0 |
|    | 0.1250 | 8.5 | 8.5 | 1.0 | 9.0 | | 3.0 | | 8.5 | 9.0 | 4.0 | | 1.5 | 1.0 | 3.5 |
|    | 0.0620 | 9.0 | 3.5 | 1.0 | 9.0 | | 2.0 | | 7.5 | 9.0 | 1.5 | | 1.0 | 1.0 | 1.5 |
| 53 | 0.2500 | 9.0 | 8.5 | 3.0 | 9.0 | 9.0 | 8.0 | | 8.5 | 9.0 | 6.5 | | 5.0 | 5.0 | 7.0 |
|    | 0.1250 | 7.5 | 8.0 | 1.0 | 9.0 | 8.0 | 3.0 | | 4.5 | 9.0 | 2.5 | | 3.0 | 3.5 | 5.0 |
|    | 0.0620 | 5.0 | 4.0 | 0.0 | 9.0 | 8.0 | 1.0 | | 2.0 | 9.0 | 1.0 | | 1.0 | 1.0 | 4.0 |
| 54 | 0.2500 | 9.0 | 9.0 | 9.0 | 9.0 | | 9.0 | | 9.0 | 9.0 | 9.0 | | 9.0 | 9.0 | 9.0 |
|    | 0.1250 | 9.0 | 9.0 | 9.0 | 9.0 | | 9.0 | | 9.0 | 9.0 | 9.0 | | 9.0 | 9.0 | 8.5 |
|    | 0.0620 | 9.0 | 9.0 | 9.0 | 9.0 | | 8.0 | | 9.0 | 9.0 | 8.0 | | 9.0 | 9.0 | 8.0 |
| 55 | 0.2500 | 9.0 | 9.0 | 7.0 | 9.0 | | 7.5 | | 9.0 | 9.0 | 8.0 | | 9.0 | 9.0 | 9.0 |
|    | 0.1250 | 9.0 | 9.0 | 7.5 | 9.0 | | 7.5 | | 9.0 | 9.0 | 6.5 | | 7.5 | 9.0 | 8.0 |
|    | 0.0620 | 9.0 | 9.0 | 3.5 | 9.0 | | 9.0 | | 9.0 | 9.0 | 9.0 | | 6.0 | 8.0 | 8.0 |
| 56 | 0.2500 | 9.0 | 9.0 | 5.5 | 9.0 | | 7.5 | | 9.0 | 8.5 | 7.5 | | 6.0 | 6.0 | 7.0 |
|    | 0.1250 | 9.0 | 9.0 | 4.5 | 9.0 | | 7.5 | | 9.0 | 9.0 | 9.0 | | 5.0 | 6.0 | 7.0 |
|    | 0.0620 | 9.0 | 9.0 | 9.0 | 9.0 | | 9.0 | | 9.0 | 9.0 | 9.0 | | 9.0 | 9.0 | 9.0 |
| 57 | 0.2500 | 9.0 | 9.0 | 7.5 | 9.0 | | 9.0 | | 9.0 | 9.0 | 9.0 | | 8.0 | 8.0 | 8.5 |
|    | 0.1250 | 9.0 | 9.0 | 5.5 | 9.0 | | 9.0 | | 9.0 | 9.0 | 9.0 | | 8.0 | 8.0 | 9.0 |
|    | 0.0620 | 9.0 | 9.0 | 9.0 | 9.0 | 9.0 | 9.0 | | 9.0 | 8.0 | 8.0 | | 9.0 | 8.0 | 8.0 |
| 58 | 0.2500 | 9.0 | 9.0 | 6.5 | 9.0 | 9.0 | 7.5 | | 9.0 | 9.0 | 8.0 | | 9.0 | 8.0 | 8.0 |
|    | 0.1250 | 9.0 | 9.0 | 5.5 | 9.0 | 4.0 | 6.5 | | 7.0 | 8.0 | 3.0 | | 8.5 | 7.0 | 5.0 |
|    | 0.0620 | 7.0 | 6.0 | 0.0 | 9.0 | 5.0 | 3.0 | | 3.0 | 9.0 | 2.0 | | 2.0 | 2.0 | 5.0 |
| 59 | 0.2500 | 9.0 | 5.0 | 0.0 | 9.0 | 5.0 | 1.0 | | 2.0 | 6.0 | 0.0 | | 2.0 | 2.0 | 1.0 |
|    | 0.1250 | 0.0 | 0.0 | 0.0 | 9.0 | 7.0 | 0.0 | | 7.0 | 6.0 | 4.0 | | 1.0 | 1.0 | 6.0 |
|    | 0.0620 | 5.0 | 5.0 | 0.0 | 9.0 | 7.0 | 0.0 | | 6.0 | 7.0 | 3.0 | | 6.0 | 6.0 | 5.0 |
| 60 | 0.2500 | 5.0 | 0.0 | 0.0 | 7.0 | 6.0 | 0.0 | | 1.0 | 3.0 | 1.0 | | 4.0 | 4.0 | 3.0 |
|    | 0.1250 | 9.0 | 9.0 | 7.0 | 9.0 | 8.5 | 9.0 | | 9.0 | 9.0 | 9.0 | | 9.0 | 1.0 | 9.0 |
|    | 0.0620 | 9.0 | 0.0 | 7.3 | 2.0 | 0.0 | 0.0 | | 1.0 | 3.0 | 0.0 | | 8.7 | 8.5 | 8.3 |
| 61 | 0.0320 | 0.0 | 0.0 | 0.0 | 9.0 | 9.0 | 0.0 | | 0.0 | 0.0 | 0.0 | | 0.0 | 0.0 | 0.0 |
|    | 0.0160 | 9.0 | 9.0 | 9.0 | 9.0 | 9.0 | 9.0 | | 9.0 | 9.0 | 9.0 | | 9.0 | 9.0 | 9.0 |
|    | 0.0002 | 9.0 | 9.0 | 9.0 | 9.0 | 9.0 | 9.0 | | 9.0 | 9.0 | 9.0 | | 9.0 | 9.0 | 9.0 |
| 62 | 0.1250 | 9.0 | 9.0 | 9.0 | 9.0 | 9.0 | 9.0 | | 9.0 | 9.0 | 9.0 | | 9.0 | 9.0 | 9.0 |
|    | 0.0620 | 9.0 | 9.0 | 9.0 | 9.0 | 9.0 | 9.0 | | 9.0 | 9.0 | 9.0 | | 9.0 | 9.0 | 9.0 |

TABLE II-continued

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 63 | 0.0620 | 9.0 | 9.0 | 9.0 | 9.0 | 9.0 | 9.0 | | 9.0 | 9.0 | 9.0 | | 8.0 | 7.0 | 8.0 |
| 64 | 0.2500 | 9.0 | 9.0 | 9.0 | 9.0 | 9.0 | 9.0 | | 9.0 | 9.0 | 9.0 | | 9.0 | 9.0 | 9.0 |
|    | 0.1250 | 9.0 | 9.0 | 9.0 | 9.0 | 9.0 | 9.0 | | 9.0 | 9.0 | 9.0 | | 9.0 | 9.0 | 9.0 |
|    | 0.0620 | 9.0 | 9.0 | 7.5 | 9.0 | 9.0 | 7.0 | | 9.0 | 9.0 | 6.0 | | 8.5 | 9.0 | 8.5 |
| 65 | 0.2500 | 9.0 | 9.0 | 0.0 | 9.0 | 7.0 | 9.0 | | 9.0 | 9.0 | 6.0 | | 9.0 | 9.0 | 9.0 |
|    | 0.1250 | 9.0 | 9.0 | 0.0 | 9.0 | 7.0 | 3.0 | | 9.0 | 9.0 | 3.0 | | 7.0 | 7.0 | 8.0 |
|    | 0.0620 | 9.0 | 8.0 | 0.0 | 9.0 | 5.0 | 0.0 | | 9.0 | 9.0 | 2.0 | | 7.0 | 5.0 | 7.0 |
| 66 | 0.0620 | 9.0 | 9.0 | 6.0 | 9.0 | 7.0 | 7.5 | | 9.0 | 9.0 | 9.0 | | 8.5 | 8.0 | 8.0 |
| 67 | 0.1250 | 9.0 | 9.0 | 5.0 | 9.0 | 7.0 | 9.0 | | 9.0 | 9.0 | 9.0 | | 9.0 | 9.0 | 9.0 |
|    | 0.0620 | 9.0 | 9.0 | 5.5 | 9.0 | 8.0 | 7.0 | | 9.0 | 9.0 | 9.0 | | 9.0 | 9.0 | 9.0 |
| 68 | 0.2500 | 9.0 | 9.0 | 5.5 | 9.0 | 9.0 | 4.5 | | 9.0 | 9.0 | 7.5 | | 5.0 | 7.0 | 6.0 |
|    | 0.1250 | 9.0 | 5.0 | 3.0 | 9.0 | 6.0 | 3.0 | | 9.0 | 9.0 | 3.0 | | 3.5 | 5.0 | 4.0 |
|    | 0.0620 | 8.5 | 3.5 | 0.5 | 9.0 | 7.0 | 1.5 | | 8.5 | 9.0 | 1.5 | | 2.0 | 2.0 | 2.5 |
| 69 | 0.2500 | 9.0 | 8.0 | 6.0 | 9.0 | 9.0 | 9.0 | | 8.0 | 9.0 | 9.0 | | 5.0 | 5.0 | 7.0 |
|    | 0.1250 | 9.0 | 9.0 | 1.0 | 9.0 | 7.0 | 1.0 | | 8.0 | 9.0 | 9.0 | | 2.0 | 2.0 | 3.0 |
| 70 | 0.1250 | 9.0 | 7.0 | 0.0 | 9.0 | 9.0 | 1.0 | | 4.0 | 7.0 | 2.0 | | 1.0 | 1.0 | 1.0 |
|    | 0.0620 | 9.0 | 9.0 | 2.0 | 9.0 | 9.0 | 7.0 | | 7.0 | 9.0 | 9.0 | | 6.0 | 7.0 | 9.0 |
| 71 | 0.2500 | 9.0 | 7.0 | 2.0 | 9.0 | 7.0 | 4.0 | | 3.0 | 6.0 | 3.0 | | 3.0 | 3.0 | 2.0 |
|    | 0.1250 | 9.0 | 9.0 | 7.5 | 9.0 | 9.0 | 9.0 | | 8.0 | 9.0 | 6.0 | | 8.5 | 8.0 | 8.5 |
| 72 | 0.2500 | 9.0 | 9.0 | 6.5 | 9.0 | 9.0 | 9.0 | | 5.5 | 8.0 | 4.5 | | 8.0 | 7.0 | 8.0 |
|    | 0.1250 | 8.0 | 8.0 | 3.5 | 9.0 | 6.0 | 7.0 | | 5.5 | 8.0 | 2.5 | | 5.5 | 4.0 | 5.5 |
|    | 0.0620 | 9.0 | 9.0 | 8.0 | 9.0 | 9.0 | 8.0 | | 9.0 | 9.0 | 9.0 | | 9.0 | 9.0 | 9.0 |
| 73 | 0.1250 | 9.0 | 9.0 | 6.5 | 9.0 | 8.0 | 6.5 | | 9.0 | 9.0 | 6.5 | | 8.5 | 9.0 | 8.5 |
|    | 0.0620 | 9.0 | 9.0 | 3.0 | 9.0 | 9.0 | 3.5 | | 9.0 | 9.0 | 8.0 | | 8.5 | 7.0 | 8.0 |
| 74 | 0.2500 | 9.0 | 9.0 | 8.0 | 9.0 | 8.0 | 9.0 | | 9.0 | 9.0 | 7.0 | | 8.0 | 8.0 | 9.0 |
|    | 0.1250 | 9.0 | 9.0 | 6.0 | 9.0 | 8.0 | 9.0 | | 9.0 | 9.0 | 4.0 | | 7.0 | 6.0 | 9.0 |
|    | 0.0620 | 9.0 | 8.5 | 2.5 | 9.0 | 8.0 | 7.0 | | 7.5 | 9.0 | 9.0 | | 6.0 | 4.0 | 6.5 |
| 75 | 0.2500 | 9.0 | 9.0 | 3.0 | 9.0 | 9.0 | 8.0 | | 6.0 | 8.0 | 1.0 | | 5.0 | 5.0 | 4.0 |
|    | 0.1250 | 7.0 | 6.0 | 0.0 | 9.0 | 7.0 | 0.0 | | 2.0 | 2.0 | 1.0 | | 1.0 | 2.0 | 2.0 |
|    | 0.0620 | 3.0 | 0.0 | 0.0 | 9.0 | 6.0 | 0.0 | | 0.0 | 0.0 | 4.0 | | 1.0 | 1.0 | 2.0 |
| 76 | 0.2500 | 9.0 | 7.0 | 1.0 | 9.0 | 9.0 | 7.0 | | 6.0 | 6.0 | 1.0 | | 7.0 | 7.0 | 3.0 |
|    | 0.1250 | 1.0 | 3.0 | 1.0 | 6.0 | 7.0 | 4.0 | | 1.0 | 1.0 | 0.0 | | 2.0 | 2.0 | 2.0 |
|    | 0.0620 | 1.0 | 1.0 | 0.0 | 9.0 | 5.0 | 0.0 | | 0.0 | 0.0 | 0.0 | | 0.0 | 0.0 | 1.0 |
| 77 | 0.2500 | 9.0 | 9.0 | 9.0 | 9.0 | 9.0 | 9.0 | | 9.0 | 9.0 | 9.0 | | 9.0 | 8.0 | 8.5 |
|    | 0.1250 | 9.0 | 9.0 | 8.5 | 9.0 | 9.0 | 9.0 | | 9.0 | 9.0 | 9.0 | | 8.5 | 8.0 | 8.5 |
|    | 0.0620 | 9.0 | 9.0 | 5.0 | 9.0 | 7.0 | 7.5 | | 9.0 | 9.0 | 7.5 | | 7.0 | 7.0 | 8.5 |
| 78 | 0.2500 | 9.0 | 9.0 | 7.5 | 9.0 | 9.0 | 7.5 | | 9.0 | 9.0 | 9.0 | | 5.5 | 6.0 | 7.5 |
|    | 0.1250 | 9.0 | 9.0 | 4.5 | 9.0 | 7.0 | 4.0 | | 8.5 | 8.5 | 6.0 | | 5.0 | 6.0 | 7.0 |
|    | 0.0620 | 9.0 | 8.5 | 2.5 | 9.0 | | 3.0 | | 8.0 | 9.0 | 4.0 | | 5.0 | 6.0 | 6.0 |
| 79 | 0.2500 | 9.0 | 9.0 | 6.0 | 9.0 | 7.0 | 6.0 | | 8.5 | 9.0 | 5.0 | | 3.0 | 5.0 | 3.5 |
|    | 0.1250 | 9.0 | 9.0 | 4.0 | 9.0 | 7.0 | 5.0 | | 8.0 | 9.0 | 6.0 | | 2.5 | 5.0 | 3.0 |
|    | 0.0620 | 9.0 | 9.0 | 2.0 | 9.0 | 7.0 | 2.0 | | 8.5 | 9.0 | 2.5 | | 2.0 | 3.0 | 3.0 |
|    | 0.2500 | 9.0 | 9.0 | 9.0 | 9.0 | 9.0 | 7.0 | | 9.0 | 9.0 | 9.0 | | 8.0 | 8.0 | 7.0 |
|    | 0.1250 | 9.0 | 9.0 | 6.5 | 9.0 | 9.0 | 4.5 | | 9.0 | 9.0 | 8.0 | | 8.0 | 7.0 | 8.5 |
|    | 0.0620 | 9.0 | 8.5 | 2.0 | 9.0 | 7.0 | 2.5 | | 9.0 | 9.0 | 6.5 | | 7.0 | 6.0 | 7.0 |

TABLE II-continued

Preemergence Herbicidal Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|
| 80 | 0.2500 | 9.0 | 9.0 | 1.5 | 9.0 | 7.0 | 4.0 | | 6.5 | 7.5 | 6.0 | | 6.0 | 2.0 | 2.5 |
|  | 0.1250 | 9.0 | 9.0 | 0.0 | 7.5 | 5.0 | 2.0 | | 2.0 | 4.5 | 0.5 | | 2.5 | 0.0 | 1.5 |
|  | 0.0620 | 4.0 | 5.0 | 0.0 | 5.5 | 4.0 | 0.5 | | 0.5 | 1.5 | 0.5 | | 0.5 | 0.0 | 0.5 |
| 81 | 0.2500 | 9.0 | 9.0 | 4.5 | 9.0 | 9.0 | 9.0 | | 9.0 | 9.0 | 7.0 | | 5.5 | 7.0 | 6.5 |
|  | 0.1250 | 9.0 | 9.0 | 3.0 | 9.0 | 9.0 | 6.0 | | 9.0 | 9.0 | 7.0 | | 4.5 | 5.0 | 6.0 |
|  | 0.0620 | 9.0 | 9.0 | 2.5 | 9.0 | 9.0 | 6.0 | | 9.0 | 9.0 | 6.5 | | 3.0 | 5.0 | 4.5 |
| 82 | 0.2500 | 9.0 | 6.5 | 2.0 | 9.0 | 9.0 | 7.0 | | 7.5 | 9.0 | 2.0 | | 0.0 | 0.0 | 2.5 |
|  | 0.1250 | 9.0 | 5.5 | 1.5 | 9.0 | 9.0 | 3.0 | | 6.0 | 9.0 | 0.5 | | 0.0 | 0.0 | 1.0 |
|  | 0.0620 | 4.5 | 3.5 | 0.0 | 9.0 | 9.0 | 0.5 | | 3.0 | 8.0 | 0.0 | | 0.0 | 0.0 | 0.0 |
| 83 | 0.2500 | 9.0 | 9.0 | 1.0 | 9.0 | 7.0 | 5.5 | | 9.0 | 9.0 | 6.0 | | 5.5 | 5.0 | 6.0 |
|  | 0.1250 | 7.5 | 7.5 | 0.0 | 9.0 | | 5.0 | | 6.5 | 9.0 | 2.5 | | 3.5 | 4.0 | 5.0 |
|  | 0.0620 | 2.0 | 6.0 | 0.0 | 4.0 | 4.0 | 3.0 | | 2.0 | 6.0 | 0.0 | | 0.0 | 3.0 | 3.0 |
| 84 | 0.2500 | 9.0 | 9.0 | 9.0 | 9.0 | 9.0 | 9.0 | | 9.0 | 9.0 | 9.0 | 9.0 | 6.0 | | 8.0 |
|  | 0.1250 | 9.0 | 9.0 | 8.0 | 9.0 | 8.0 | 8.3 | | 6.7 | 7.5 | 9.0 | 9.0 | 3.5 | | 6.3 |
|  | 0.0620 | 9.0 | 9.0 | 4.0 | 9.0 | 7.0 | 6.3 | | 4.0 | 3.5 | 7.0 | 9.0 | 2.5 | | 3.7 |
| 85 | 0.2500 | 9.0 | 9.0 | 5.0 | 9.0 | 9.0 | 7.0 | | 4.0 | 7.0 | 9.0 | | 7.0 | | 3.0 |
|  | 0.1250 | 9.0 | 9.0 | 3.0 | 9.0 | 6.0 | 4.0 | | 3.0 | 9.0 | 3.0 | | 6.0 | | 3.0 |
|  | 0.0620 | 9.0 | 8.0 | 0.0 | 9.0 | 4.0 | 0.0 | | 0.0 | 4.0 | 0.0 | | 2.0 | | 0.0 |
| 86 | 0.2500 | 9.0 | 9.0 | 9.0 | 9.0 | 9.0 | 9.0 | | 9.0 | 9.0 | 9.0 | 9.0 | 9.0 | 5.0 | 9.0 |
|  | 0.1250 | 9.0 | 9.0 | 9.0 | 9.0 | 4.0 | 9.0 | | 9.0 | 9.0 | 9.0 | 9.0 | 7.0 | 2.0 | 8.0 |
|  | 0.0620 | 9.0 | 9.0 | 4.0 | 9.0 | 3.0 | 4.0 | | 7.5 | 7.5 | 7.0 | 5.0 | 5.0 | 3.0 | 5.0 |
| 87 | 0.2500 | 9.0 | 9.0 | 7.0 | 9.0 | 9.0 | 9.0 | | 9.0 | 9.0 | 9.0 | 9.0 | 5.0 | 0.0 | 8.5 |
|  | 0.1250 | 9.0 | 9.0 | 9.0 | 9.0 | 9.0 | 9.0 | | 6.5 | 8.0 | 9.0 | 9.0 | 3.0 | | 8.0 |
|  | 0.0620 | 9.0 | 9.0 | 6.0 | 9.0 | 6.0 | 5.0 | | 5.5 | 6.0 | 9.0 | 9.0 | 2.0 | | 5.5 |
| 88 | 0.2500 | 9.0 | 9.0 | 9.0 | 9.0 | 9.0 | 9.0 | | 9.0 | 9.0 | 9.0 | 9.0 | 8.0 | | 7.0 |
|  | 0.1250 | 9.0 | 9.0 | 9.0 | 9.0 | 9.0 | 7.5 | | 6.5 | 9.0 | 9.0 | 9.0 | 5.0 | | 6.0 |
|  | 0.0620 | 9.0 | 9.0 | 5.0 | 9.0 | 7.0 | 6.0 | | 5.5 | 5.5 | 9.0 | 9.0 | 4.0 | | 3.5 |
| 89 | 0.2500 | 9.0 | 9.0 | | | 9.0 | 9.0 | | 7.0 | | | 9.0 | | | 4.0 |
|  | 0.1250 | 9.0 | 9.0 | | | 6.0 | 8.0 | | 3.0 | | | 6.0 | | | 3.0 |
|  | 0.0620 | 9.0 | 4.0 | | | 3.0 | 7.0 | | 1.0 | | | 3.0 | | | 0.0 |
| 90 | 0.2500 | 9.0 | 3.5 | | | 3.0 | 1.5 | | 0.0 | | | 0.0 | | | 0.0 |
|  | 0.1250 | 3.5 | 1.5 | | | 0.0 | 0.0 | | 0.0 | | | 0.0 | | | 0.0 |
|  | 0.0620 | 0.0 | 0.0 | | | 0.0 | 0.0 | | 0.0 | | | 0.0 | | | 0.0 |
| 91 | 0.2500 | 0.0 | 0.0 | | | 0.0 | 0.0 | | 0.0 | | | 0.0 | | | 0.0 |
|  | 0.1250 | 0.0 | 0.0 | | | 0.0 | 0.0 | | 0.0 | | | 0.0 | | | 0.0 |
|  | 0.0620 | 0.0 | 0.0 | | | 0.0 | 0.0 | | 0.0 | | | 0.0 | | | 0.0 |
| 92 | 0.2500 | 3.0 | 0.0 | | | 2.0 | 4.0 | | 0.0 | | | 0.0 | | | 0.0 |
|  | 0.1250 | 0.0 | 0.0 | | | 0.0 | 0.0 | | 0.0 | | | 0.0 | | | 0.0 |
|  | 0.0620 | 0.0 | 0.0 | | | 0.0 | 0.0 | | 0.0 | | | 0.0 | | | 0.0 |
| 93 | 0.2500 | 9.0 | 9.0 | | | | 9.0 | | 4.0 | | | 7.0 | | | 0.0 |
|  | 0.1250 | 9.0 | 7.0 | | | | 9.0 | | 0.0 | | | 6.0 | | | 0.0 |
|  | 0.0620 | 9.0 | 4.0 | | | | 3.0 | | 0.0 | | | 4.0 | | | 0.0 |
| 94 | 1.0000 | 7.0 | 5.0 | | 8.0 | 8.0 | | 7.0 | 2.0 | 5.0 | 5.0 | | 6.0 | 5.0 | 3.0 |
| 96 | 0.3000 | 6.0 | 0.0 | | 7.0 | 6.0 | | 4.0 | 0.0 | 0.0 | 0.0 | | 0.0 | 0.0 | 0.0 |

EXAMPLE 89

Post-transplant Evaluation of Rice Tolerance And Preemergence Weed Control of Test Compounds Under Flooded Paddy Conditions The tolerance of transplanted rice to post-transplanted herbicide application is determined as follows: two ten-day-old rice seedlings (cv. Tebonnet) are transplanted into silt loam soil in 32 oz. plastic containers with a diameter of 10.5 cm and no drainage holes. After transplanting, the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of about 0.0080 to 0.1250 kg/ha of active ingredient. The treated containers are placed on greenhouse benches, watered such that the water level is maintained as stated above, and cared for in accordance with conventional greenhouse procedures. Three to four weeks after treatment, the test is terminated and each container is examined and herbicidal effect rated according to the rating system provided in Example 87. The data obtained are reported in Table III. The compounds used in this evaluation are the same as those identified in Example 87.

Preemergence herbicidal activity under flooded paddy conditions is determined as follows: plant seeds or propagating organs are planted in the top 0.5 cm of silt loam soil in 32 oz. plastic containers with a diameter of 10.5 cm and no drainage holes. Water is added to these containers and maintained at 1.5 to 3 cm above the soil surface for the duration of the experiment. The test compounds are applied as aqueous/acetone mixtures 50/50 v/v pipetted directly into the flood water to give the equivalent of about 0.0080 to 0.1250 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 87. The data obtained are reported in Table III.

PLANT SPECIES EMPLOYED IN RICE TOLERANCE/PREEMERGENCE WEED CONTROL EVALUATIONS

| Header Abbr. | Common Name | Scientific Name |
|---|---|---|
| ECHORC | Watergrass (Calif) | *Echinochloa oryzoides* (Ard.) Fritsch. |
| CYPIR | Rice Flatsedge | *Cyperus iria* |
| CYPSE | Flatsedge | *Cyperus serotinus*, Rottb. |
| MOOVA | Monochoria | *Monochoria vaginalis*, Presl. |
| SAGPY | Arrowhead (Pygmaea) | *Sagittaria pygmaea*, L. |
| ORYSAT | Rice, Tebonnet | *Oryza sativa*, (L.) Tebonnet |

TABLE III

Flooded Paddy, Post-Transplant Rice, Preemergence Weed Evaluation Of Test Compounds

| Compound Number | Rate (kg/ha) | ECHORC | CYPIR | CYPSE | MOOVA | SAGPY | ORYSAT |
|---|---|---|---|---|---|---|---|
| 1 | 0.1250 | 9.0 | 9.0 | 9.0 | 9.0 | 5.5 | 7.0 |
|   | 0.0320 | 9.0 | 9.0 | 3.5 | 9.0 | 4.0 | 5.5 |
|   | 0.0080 | 6.0 | 9.0 |     | 9.0 | 4.0 | 4.0 |
| 2 | 0.1250 | 2.0 | 2.0 | 0.0 | 9.0 | 0.0 | 4.0 |
|   | 0.0320 | 0.0 | 0.0 | 0.0 | 6.0 | 0.0 | 1.0 |
| 3 | 0.1250 | 9.0 | 9.0 | 6.5 | 9.0 | 5.5 | 5.5 |
|   | 0.0320 | 8.0 | 8.5 | 6.5 | 9.0 | 1.0 | 3.5 |
|   | 0.0080 | 2.0 | 0.0 | 0.0 | 9.0 | 0.0 | 3.0 |
| 4 | 0.1250 | 9.0 | 9.0 | 9.0 | 9.0 | 5.5 | 4.0 |
|   | 0.0320 | 9.0 | 9.0 | 6.5 | 9.0 | 2.0 | 3.5 |
|   | 0.0080 | 4.0 | 2.0 | 0.0 | 9.0 | 0.0 | 2.0 |
| 5 | 0.1250 | 2.0 | 7.0 | 0.0 | 9.0 | 0.0 | 3.0 |
|   | 0.0320 | 0.0 | 0.0 | 0.0 | 2.0 | 0.0 | 2.0 |
| 6 | 0.1250 | 2.0 | 9.0 | 9.0 | 9.0 | 4.0 | 3.0 |
|   | 0.0320 | 0.0 | 9.0 | 9.0 | 6.0 | 0.0 | 0.0 |
| 7 | 0.1250 | 9.0 | 9.0 | 0.0 | 9.0 | 1.0 | 5.0 |
|   | 0.0320 | 5.0 | 8.5 | 0.0 | 9.0 | 0.0 | 2.0 |
|   | 0.0080 | 0.0 | 7.0 | 0.0 | 9.0 | 0.0 | 3.0 |
| 8 | 0.1250 | 9.0 | 9.0 | 4.5 | 9.0 | 0.0 | 2.7 |
|   | 0.0320 | 9.0 | 9.0 |     | 9.0 | 0.0 | 1.5 |
|   | 0.0080 | 2.0 | 8.5 |     | 9.0 | 0.0 | 1.0 |
| 9 | 0.1250 | 9.0 | 9.0 |     | 9.0 | 9.0 | 6.0 |
|   | 0.0320 | 7.0 | 7.0 |     | 9.0 | 3.0 | 3.0 |
|   | 0.0080 | 4.0 | 8.0 |     | 8.0 | 0.0 | 4.0 |
| 10 | 0.1250 | 5.0 | 9.0 | 0.0 | 9.0 | 0.0 | 4.0 |
|    | 0.0320 | 0.0 | 4.0 | 0.0 | 9.0 | 0.0 | 0.0 |
| 11 | 0.1250 | 5.0 | 9.0 | 0.0 | 9.0 | 0.0 | 3.0 |
|    | 0.0320 | 0.0 | 9.0 | 0.0 | 9.0 | 0.0 | 0.0 |
| 12 | 0.1250 | 8.7 | 9.0 | 7.0 | 9.0 | 3.7 | 7.0 |
|    | 0.0320 | 3.3 | 5.7 | 4.0 | 9.0 | 3.0 | 6.3 |
|    | 0.0080 | 0.0 | 3.5 | 0.0 | 6.0 | 0.0 | 3.5 |
| 13 | 0.1250 | 6.0 | 8.0 | 6.5 | 9.0 | 4.0 | 7.5 |
|    | 0.0320 | 3.5 | 4.5 | 4.0 | 9.0 | 4.0 | 7.5 |
|    | 0.0080 | 0.0 | 4.0 | 4.0 | 9.0 | 0.0 | 4.0 |
| 14 | 0.1250 | 8.0 | 9.0 | 8.0 | 9.0 | 9.0 | 9.0 |
|    | 0.0320 | 4.5 | 6.5 | 2.0 | 9.0 | 6.5 | 6.5 |
|    | 0.0080 | 2.0 | 0.0 | 2.0 | 8.0 | 2.0 | 7.0 |

TABLE III-continued

Flooded Paddy, Post-Transplant Rice,
Preemergence Weed Evaluation Of Test Compounds

| Compound Number | Rate (kg/ha) | ECHORC | CYPIR | CYPSE | MOOVA | SAGPY | ORYSAT |
|---|---|---|---|---|---|---|---|
| 15 | 0.1250 | 0.0 | 0.0 | 0.0 |  | 0.0 | 0.0 |
|  | 0.0320 | 0.0 | 0.0 | 0.0 |  | 0.0 | 0.0 |
| 16 | 0.1250 | 8.0 | 8.5 | 6.0 | 9.0 | 4.5 | 5.5 |
|  | 0.0320 | 5.0 | 7.0 | 0.0 | 9.0 | 4.0 | 2.5 |
|  | 0.0080 | 0.0 | 0.0 |  | 0.0 | 0.0 | 0.0 |
| 17 | 0.1250 | 6.0 | 7.0 | 4.5 | 9.0 | 5.5 | 4.5 |
|  | 0.0320 | 3.0 | 3.5 | 3.0 | 9.0 | 2.5 | 2.5 |
|  | 0.0080 | 0.0 | 0.0 | 0.0 | 6.0 | 0.0 | 0.0 |
| 18 | 0.1250 | 9.0 | 7.5 | 4.0 | 9.0 | 5.0 | 5.0 |
|  | 0.0320 | 6.0 | 6.5 | 4.0 | 9.0 | 1.5 | 1.5 |
|  | 0.0080 | 0.0 | 0.0 |  | 0.0 | 0.0 | 0.0 |
| 19 | 0.1250 | 9.0 | 9.0 | 6.5 | 9.0 | 7.0 | 8.0 |
|  | 0.0320 | 8.0 | 5.0 | 0.0 | 9.0 | 2.5 | 6.5 |
|  | 0.0080 | 2.0 | 0.0 | 0.0 | 4.0 | 0.0 | 2.0 |
| 20 | 0.1250 | 7.0 | 3.0 | 7.0 | 9.0 |  | 2.0 |
|  | 0.0320 | 5.0 | 2.0 | 4.0 | 9.0 |  | 2.0 |
| 21 | 0.1250 | 9.0 | 9.0 | 4.5 | 9.0 | 6.0 | 3.0 |
|  | 0.0320 | 8.5 | 9.0 | 4.5 | 9.0 | 0.0 | 2.0 |
|  | 0.0080 | 4.0 | 4.0 | 0.0 | 7.0 | 0.0 | 0.0 |
| 22 | 0.1250 | 5.0 | 3.0 | 0.0 | 4.5 | 0.0 | 2.5 |
|  | 0.0320 | 0.0 | 2.5 | 0.0 | 4.5 | 0.0 | 2.0 |
|  | 0.0080 | 0.0 | 0.0 |  | 0.0 | 0.0 | 0.0 |
| 23 | 0.1250 | 3.0 | 9.0 | 9.0 | 9.0 |  | 3.0 |
|  | 0.0320 | 0.0 | 9.0 | 0.0 | 9.0 |  | 0.0 |
| 24 | 0.1250 | 7.0 | 5.0 | 2.0 | 8.0 | 5.0 |  |
|  | 0.0320 | 5.0 | 0.0 | 0.0 | 5.0 | 0.0 | 0.0 |
| 25 | 0.1250 | 9.0 | 9.0 | 9.0 | 9.0 | 9.0 | 9.0 |
|  | 0.0320 | 9.0 | 8.0 |  | 9.0 | 5.0 | 3.0 |
|  | 0.0080 | 7.0 | 0.0 |  | 3.0 | 0.0 | 0.0 |
| 26 | 0.1250 | 9.0 | 9.0 | 3.0 | 9.0 | 8.0 | 4.3 |
|  | 0.0320 | 9.0 | 8.3 | 0.0 | 9.0 | 5.3 | 2.0 |
|  | 0.0080 | 8.0 | 8.5 |  | 9.0 | 1.5 | 0.0 |
| 27 | 0.1250 | 9.0 | 9.0 | 6.0 | 9.0 | 8.3 | 3.7 |
|  | 0.0320 | 9.0 | 9.0 | 4.5 | 9.0 | 1.7 | 2.0 |
|  | 0.0080 | 6.5 | 4.5 | 0.0 | 6.0 | 0.0 | 1.0 |
| 28 | 0.1250 | 9.0 | 9.0 | 9.0 | 9.0 | 9.0 | 9.0 |
|  | 0.0320 | 8.5 | 9.0 | 9.0 | 9.0 | 8.0 | 9.0 |
|  | 0.0080 | 5.0 | 8.0 |  | 9.0 | 0.0 | 7.0 |
| 29 | 0.1250 | 9.0 | 9.0 | 6.0 | 9.0 | 9.0 | 7.0 |
|  | 0.0320 | 7.0 | 7.0 | 0.0 | 9.0 | 3.5 | 3.5 |
|  | 0.0080 | 0.0 | 0.0 |  | 0.0 | 0.0 | 0.0 |
| 30 | 0.1250 | 9.0 | 9.0 | 3.0 | 9.0 | 6.0 | 5.0 |
|  | 0.0320 | 4.0 | 7.0 | 0.0 | 8.5 | 1.0 | 3.0 |
|  | 0.0080 | 3.0 | 0.0 |  | 0.0 | 0.0 | 0.0 |
| 31 | 0.1250 | 9.0 | 9.0 | 5.0 | 9.0 | 9.0 | 9.0 |
|  | 0.0320 | 8.0 | 9.0 | 4.0 | 9.0 | 9.0 | 7.5 |
|  | 0.0080 | 3.0 | 0.0 |  | 5.0 | 0.0 | 0.0 |
| 32 | 0.1250 | 0.0 | 7.0 |  | 9.0 |  | 3.0 |
|  | 0.0320 | 0.0 | 4.0 | 0.0 | 6.0 |  | 0.0 |
| 33 | 0.1250 | 2.0 | 3.0 | 0.0 | 4.0 |  | 1.0 |
|  | 0.0320 | 0.0 | 0.0 | 0.0 | 0.0 |  | 0.0 |
| 34 | 0.1250 | 9.0 | 7.5 | 9.0 | 9.0 | 6.0 | 9.0 |
|  | 0.0620 | 8.0 | 7.0 | 9.0 | 9.0 | 3.5 | 8.5 |
|  | 0.0080 | 5.0 | 0.0 |  | 0.0 | 0.0 | 3.0 |
| 35 | 0.1250 | 7.5 | 9.0 | 5.0 | 9.0 | 8.0 | 7.5 |
|  | 0.0320 | 5.5 | 6.0 | 2.0 | 5.0 | 4.5 | 4.0 |
|  | 0.0080 | 0.0 | 0.0 |  | 0.0 | 0.0 | 0.0 |
| 36 | 0.1250 | 9.0 | 9.0 | 9.0 |  | 9.0 | 9.0 |
|  | 0.0320 | 8.5 | 9.0 | 9.0 | 9.0 | 3.5 | 7.5 |
|  | 0.0080 | 5.0 | 0.0 |  | 9.0 | 0.0 | 5.0 |
| 37 | 0.1250 | 9.0 | 9.0 | 9.0 |  | 9.0 | 9.0 |
|  | 0.0320 | 9.0 | 9.0 | 9.0 | 9.0 | 7.0 | 8.5 |
|  | 0.0080 | 3.0 | 0.0 |  | 3.0 | 0.0 | 5.0 |
| 38 | 0.1250 | 9.0 | 9.0 | 9.0 |  | 9.0 | 9.0 |
|  | 0.0320 | 7.0 | 9.0 | 9.0 | 9.0 | 4.5 | 3.5 |
|  | 0.0080 | 0.0 | 3.0 |  | 3.0 | 0.0 | 0.0 |
| 39 | 0.1250 | 0.0 | 5.0 | 0.0 | 9.0 | 3.0 | 4.0 |
|  | 0.0320 | 0.0 | 5.0 | 0.0 | 9.0 | 0.0 | 0.0 |
| 40 | 0.1250 | 6.0 | 6.0 | 0.0 | 9.0 | 5.0 | 7.0 |
|  | 0.0320 | 2.0 | 5.0 | 0.0 | 7.0 | 0.0 | 5.0 |
| 41 |  |  |  |  |  |  |  |
| 42 | 0.1250 | 6.0 | 6.0 | 0.0 | 9.0 | 3.0 | 4.0 |
|  | 0.0320 | 2.0 | 3.0 | 0.0 | 8.0 | 0.0 | 3.0 |

TABLE III-continued

Flooded Paddy, Post-Transplant Rice,
Preemergence Weed Evaluation Of Test Compounds

| Compound Number | Rate (kg/ha) | ECHORC | CYPIR | CYPSE | MOOVA | SAGPY | ORYSAT |
|---|---|---|---|---|---|---|---|
| 43 | 0.1250 | 9.0 | 5.0 | 0.0 | 6.0 | 2.0 | 2.0 |
|  | 0.0320 | 5.0 | 0.0 | 0.0 | 4.0 | 0.0 | 0.0 |
| 44 | 0.1250 | 9.0 | 9.0 | 9.0 | 9.0 | 9.0 | 7.5 |
|  | 0.0320 | 8.5 | 8.0 | 9.0 | 8.5 | 4.5 | 7.5 |
|  | 0.0080 | 3.0 | 0.0 | 0.0 | 0.0 | 0.0 | 0.0 |
| 45 | 0.1250 | 9.0 | 9.0 | 9.0 | 9.0 | 9.0 | 9.0 |
|  | 0.0320 | 7.3 | 9.0 | 9.0 | 9.0 | 8.0 | 9.0 |
|  | 0.0080 | 3.5 | 9.0 | 9.0 | 4.5 | 7.0 | 8.5 |
| 46 | 0.1250 | 7.0 | 3.0 | 0.0 | 7.0 | 2.0 | 3.0 |
|  | 0.0320 | 5.0 | 1.0 |  | 7.0 | 0.0 | 2.0 |
| 47 | 0.1250 | 9.0 | 9.0 | 9.0 | 9.0 | 9.0 | 9.0 |
|  | 0.0320 | 8.5 | 8.5 | 9.0 | 9.0 | 7.5 | 7.5 |
|  | 0.0080 | 5.0 | 0.0 |  |  | 0.0 | 3.0 |
| 48 | 0.1250 | 9.0 | 9.0 | 9.0 | 9.0 | 9.0 | 9.0 |
|  | 0.0320 | 9.0 | 8.0 | 9.0 | 9.0 | 7.5 | 8.0 |
|  | 0.0080 | 8.0 | 0.0 |  |  | 0.0 | 5.0 |
| 49 | 0.1250 | 0.0 | 0.0 | 0.0 |  | 0.0 | 0.0 |
|  | 0.0320 | 0.0 | 0.0 | 0.0 | 0.0 | 0.0 | 0.0 |
| 50 | 0.1250 | 9.0 | 8.0 | 7.0 | 9.0 | 4.5 | 8.5 |
|  | 0.0320 | 7.5 | 7.5 | 5.0 | 9.0 | 0.0 | 6.5 |
|  | 0.0080 | 7.0 | 0.0 |  |  | 0.0 | 3.0 |
| 51 | 0.1250 | 9.0 | 9.0 | 9.0 | 9.0 | 9.0 | 9.0 |
|  | 0.0320 | 9.0 | 8.0 | 9.0 | 9.0 | 7.0 | 9.0 |
|  | 0.0080 | 8.0 | 3.0 |  |  | 0.0 | 7.0 |
| 52 | 0.1250 | 9.0 | 9.0 | 9.0 | 9.0 | 7.7 | 5.7 |
|  | 0.0320 | 9.0 | 9.0 | 9.0 | 9.0 | 3.7 | 3.7 |
|  | 0.0080 | 8.5 | 9.0 |  | 9.0 | 0.0 | 1.0 |
| 53 | 0.1250 | 9.0 | 9.0 | 9.0 | 9.0 | 9.0 | 5.0 |
|  | 0.0320 | 9.0 | 8.3 | 3.0 | 9.0 | 4.3 | 2.7 |
|  | 0.0080 | 3.0 | 9.0 |  | 9.0 | 0.0 | 0.5 |
| 54 | 0.1250 | 9.0 | 9.0 | 9.0 | 9.0 | 9.0 | 9.0 |
|  | 0.0320 | 8.0 | 7.5 | 9.0 | 9.0 | 7.0 | 8.5 |
|  | 0.0080 | 8.0 | 0.0 |  |  | 0.0 | 7.0 |
| 55 | 0.1250 | 9.0 | 9.0 | 9.0 | 9.0 | 7.0 | 9.0 |
|  | 0.0320 | 7.5 | 6.0 | 9.0 | 9.0 | 0.0 | 4.5 |
|  | 0.0080 | 5.0 | 0.0 |  |  | 0.0 | 3.0 |
| 56 | 0.1250 | 9.0 | 9.0 | 9.0 | 9.0 | 6.3 | 8.0 |
|  | 0.0320 | 9.0 | 8.0 | 5.5 | 9.0 | 0.0 | 4.3 |
|  | 0.0080 | 9.0 | 6.0 | 0.0 | 9.0 | 0.0 | 1.0 |
| 57 | 0.1250 | 9.0 | 9.0 | 9.0 | 9.0 | 7.5 | 9.0 |
|  | 0.0320 | 8.0 | 7.5 | 9.0 | 9.0 | 4.5 | 8.0 |
|  | 0.0080 | 5.0 | 0.0 |  |  | 0.0 | 3.0 |
| 58 | 0.1250 | 9.0 | 9.0 |  | 9.0 | 5.0 | 7.0 |
|  | 0.0320 | 6.0 | 6.0 |  | 9.0 | 2.0 | 4.0 |
| 59 | 0.1250 | 3.0 | 9.0 |  | 9.0 | 0.0 | 0.0 |
|  | 0.0320 | 0.0 | 3.0 |  | 3.0 | 0.0 | 0.0 |
|  | 0.0080 | 0.0 | 0.0 |  | 0.0 | 0.0 | 0.0 |
| 60 | 0.1250 | 7.0 | 7.0 |  | 9.0 | 2.5 | 2.5 |
|  | 0.0320 | 4.0 | 6.0 |  | 9.0 | 0.0 | 1.5 |
|  | 0.0080 | 1.5 | 0.0 |  | 0.0 | 0.0 | 0.0 |
| 61 | 0.1250 | 9.0 | 9.0 | 9.0 | 9.0 | 9.0 | 9.0 |
|  | 0.0320 | 9.0 | 9.0 | 9.0 | 9.0 | 8.3 | 9.0 |
|  | 0.0080 | 8.7 | 8.7 |  | 8.5 | 3.0 | 8.0 |
| 62 | 0.1250 | 9.0 | 9.0 |  | 9.0 | 9.0 | 9.0 |
|  | 0.0320 | 9.0 | 9.0 |  | 9.0 | 6.0 | 9.0 |
|  | 0.0080 | 8.5 | 4.5 |  | 8.0 | 9.0 | 9.0 |
| 63 | 0.1250 | 9.0 | 9.0 |  | 9.0 | 9.0 | 9.0 |
|  | 0.0320 | 9.0 | 9.0 |  | 9.0 | 7.0 | 9.0 |
|  | 0.0080 | 9.0 | 4.0 |  | 3.0 | 3.0 | 7.0 |
| 64 | 0.1250 | 9.0 | 9.0 |  | 9.0 | 9.0 | 9.0 |
|  | 0.0320 | 9.0 | 6.0 |  | 9.0 | 3.0 | 8.0 |
|  | 0.0080 | 1.5 | 1.5 |  | 0.0 | 0.0 | 5.5 |
| 65 | 0.1250 | 7.0 | 9.0 |  | 3.0 | 0.0 | 0.0 |
|  | 0.0320 | 0.0 | 0.0 |  | 0.0 | 0.0 | 0.0 |
|  | 0.0080 | 0.0 | 0.0 |  | 0.0 | 0.0 | 0.0 |
| 66 | 0.1250 | 9.0 | 9.0 |  | 9.0 | 9.0 | 9.0 |
|  | 0.0320 | 9.0 | 6.0 |  | 9.0 | 9.0 | 9.0 |
|  | 0.0080 | 4.5 | 2.5 |  | 0.0 | 2.5 | 1.5 |
| 67 | 0.1250 | 9.0 | 9.0 |  | 9.0 | 7.0 | 9.0 |
|  | 0.0320 | 9.0 | 7.0 |  | 9.0 | 7.0 | 9.0 |
|  | 0.0080 | 4.5 | 4.5 |  | 0.0 | 1.5 | 5.5 |

TABLE III-continued

Flooded Paddy, Post-Transplant Rice,
Preemergence Weed Evaluation Of Test Compounds

| Compound Number | Rate (kg/ha) | ECHORC | CYPIR | CYPSE | MOOVA | SAGPY | ORYSAT |
|---|---|---|---|---|---|---|---|
| 68 | 0.1250 | 9.0 | 9.0 | | 9.0 | 9.0 | 3.5 |
| | 0.0320 | 8.5 | 9.0 | | 9.0 | 0.0 | 2.5 |
| | 0.0080 | 7.0 | 0.0 | | 7.0 | 0.0 | 1.5 |
| 69 | 0.1250 | 3.0 | 3.0 | | 3.0 | 3.0 | 3.0 |
| | 0.0320 | 0.0 | 0.0 | | 0.0 | 0.0 | 0.0 |
| | 0.0080 | 0.0 | 0.0 | | 0.0 | 0.0 | 0.0 |
| 70 | 0.1250 | 0.0 | 0.0 | | 0.0 | 0.0 | 0.0 |
| | 0.0320 | 0.0 | 0.0 | | 0.0 | 0.0 | 0.0 |
| | 0.0080 | 0.0 | 0.0 | | 0.0 | 0.0 | 0.0 |
| 71 | 0.1250 | 0.0 | 0.0 | | 0.0 | 0.0 | 0.0 |
| | 0.0320 | 0.0 | 0.0 | | 0.0 | 0.0 | 0.0 |
| | 0.0080 | 0.0 | 0.0 | | 0.0 | 0.0 | 0.0 |
| 72 | 0.1250 | 9.0 | 9.0 | | 9.0 | 8.0 | 8.0 |
| | 0.0320 | 9.0 | 3.0 | | 9.0 | 0.0 | 7.0 |
| | 0.0080 | 5.0 | 0.0 | | 0.0 | 0.0 | 0.0 |
| 73 | 0.1250 | 7.0 | 9.0 | | 9.0 | 3.0 | 5.0 |
| | 0.0320 | 0.0 | 0.0 | | 0.0 | 0.0 | 0.0 |
| | 0.0080 | 0.0 | 0.0 | | 0.0 | 0.0 | 0.0 |
| 74 | 0.1250 | 9.0 | 9.0 | | 9.0 | 7.0 | 6.0 |
| | 0.0320 | 8.0 | 6.0 | | 9.0 | 1.5 | 4.0 |
| | 0.0080 | 5.5 | 0.0 | | 4.5 | 0.0 | 1.5 |
| 75 | 0.1250 | 8.5 | 9.0 | | 9.0 | 9.0 | 6.0 |
| | 0.0320 | 4.0 | 7.0 | | 7.0 | 4.5 | 4.5 |
| | 0.0080 | 1.5 | 0.0 | | 0.0 | 0.0 | 2.5 |
| 76 | 0.1250 | 9.0 | 9.0 | | 9.0 | 9.0 | 9.0 |
| | 0.0320 | 7.0 | 8.0 | | 9.0 | 0.0 | 3.0 |
| | 0.0080 | 5.0 | 7.0 | | 9.0 | 0.0 | 2.0 |
| 77 | 0.1250 | 9.0 | 9.0 | | 9.0 | 5.0 | 7.0 |
| | 0.0320 | 5.0 | 7.0 | | 9.0 | 0.0 | 3.0 |
| | 0.0080 | 0.0 | 0.0 | | 0.0 | 0.0 | 0.0 |
| 78 | 0.1250 | 9.0 | 9.0 | | 9.0 | 9.0 | 8.5 |
| | 0.0320 | 9.0 | 9.0 | | 9.0 | 1.0 | 5.7 |
| | 0.0080 | 8.0 | 0.0 | | 7.7 | 0.0 | 4.0 |
| 79 | 0.1250 | 9.0 | 9.0 | | 9.0 | 3.0 | 7.0 |
| | 0.0320 | 8.0 | 3.0 | | 9.0 | 0.0 | 5.0 |
| | 0.0080 | 0.0 | 0.0 | | 0.0 | 0.0 | 0.0 |
| 80 | 0.1250 | 8.0 | 9.0 | | 9.0 | 7.0 | 8.0 |
| | 0.0320 | 4.0 | 4.5 | | 9.0 | 4.5 | 5.5 |
| | 0.0080 | 1.0 | 0.0 | | 0.0 | 0.0 | 2.5 |
| 81 | 0.1250 | 9.0 | 9.0 | | 9.0 | 9.0 | 8.0 |
| | 0.0320 | 9.0 | 9.0 | | 9.0 | 4.7 | 6.7 |
| | 0.0080 | 8.0 | 7.0 | | 7.7 | 0.0 | 5.0 |
| 82 | 0.1250 | 9.0 | 9.0 | 9.0 | 9.0 | 3.5 | 3.5 |
| | 0.0320 | 9.0 | 9.0 | 9.0 | 9.0 | 0.0 | 2.0 |
| | 0.0080 | 7.0 | 6.5 | | 8.5 | 0.0 | 0.5 |
| 83 | 0.1250 | 7.0 | 3.0 | | 9.0 | 0.0 | 2.0 |
| | 0.0320 | 6.0 | 0.0 | | 9.0 | 0.0 | 2.0 |
| | 0.0080 | 0.0 | 0.0 | | 0.0 | 0.0 | 0.0 |
| 84 | 0.1250 | 8.0 | 6.0 | | 9.0 | 4.0 | 5.5 |
| | 0.0320 | 7.5 | 1.5 | | 9.0 | 0.0 | 1.5 |
| | 0.0080 | 0.0 | 0.0 | | 9.0 | 0.0 | 0.0 |
| 85 | 0.1250 | 8.0 | 6.0 | | 9.0 | 7.0 | 5.5 |
| | 0.0320 | 5.0 | 0.0 | | 7.0 | 1.5 | 1.5 |
| | 0.0080 | 0.0 | 0.0 | | 9.0 | 0.0 | 0.0 |
| 86 | 0.1250 | 3.0 | 0.0 | | 9.0 | 0.0 | 5.0 |
| | 0.0320 | 0.0 | 0.0 | | 5.0 | 0.0 | 0.0 |
| 87 | 0.1250 | 0.0 | 5.0 | | 8.0 | 0.0 | 3.0 |
| | 0.0320 | 0.0 | 0.0 | | 0.0 | 0.0 | 0.0 |
| 88 | 0.1250 | 0.0 | 9.0 | | 9.0 | 0.0 | 5.0 |
| | 0.0320 | 0.0 | 0.0 | | 0.0 | 0.0 | 0.0 |
| 89 | 0.1250 | 5.0 | 8.0 | | 8.0 | 9.0 | 6.0 |
| | 0.0320 | 3.0 | 0.0 | | 0.0 | 0.0 | 0.0 |
| 90 | 0.1250 | 0.0 | 0.0 | | 0.0 | 0.0 | 0.0 |
| | 0.0320 | 0.0 | 0.0 | | 0.0 | 0.0 | 0.0 |

TABLE III-continued

Flooded Paddy, Post-Transplant Rice,
Preemergence Weed Evaluation Of Test Compounds

| Compound Number | Rate (kg/ha) | ECHORC | CYPIR | CYPSE | MOOVA | SAGPY | ORYSAT |
|---|---|---|---|---|---|---|---|
| 91 | 0.1250 | 0.0 | 0.0 | | 0.0 | 0.0 | 0.0 |
|  | 0.0320 | 0.0 | 0.0 | | 0.0 | 0.0 | 0.0 |
| 92 | 0.1250 | 0.0 | 8.0 | | 8.0 | 0.0 | 0.0 |
|  | 0.0320 | 0.0 | 0.0 | | 0.0 | 0.0 | 0.0 |
| 93 | 0.1250 | 6.0 | 9.0 | | 9.0 | 9.0 | 8.0 |
|  | 0.0320 | 0.0 | 0.0 | | 0.0 | 0.0 | |

EXAMPLE 90

Post-transplant And Postemergence Evaluation of Rice Tolerance And Postemergence Weed Control of Test Compounds Under Flooded Paddy Conditions Plastic containers containing weeds which are 3 to 5 cm tall and rice seedlings at the 1.5 to 2.5 leaf stage are flooded with water. The water is maintained at 1.5 to 3 cm above the soil surface for the duration of the experiment. Test compounds are applied as aqueous/acetone mixtures 50/50 v/v directly into the flood water to provide the equivalent of about 0.0320 to 0.2500 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 87. The compounds evaluated are identified in Example 87 and plant species used are identified in Example 89. The results are summarized in Table IV

TABLE IV

PADDY CONDITIONS - POST-TRANSPLANT RICE POSTEMERGENCE WEEDS

| Compound Number | Rate (kg/ha) | ECHORC | CYPIR | CYPSE | MOOVA | SAGPY | ORYSAT |
|---|---|---|---|---|---|---|---|
| 1 | 0.1250 | 9.0 | 9.0 | 7.0 | 9.0 | 9.0 | 7.0 |
|  | 0.0620 | 9.0 | 9.0 | 4.0 | 9.0 | 7.0 | 7.0 |
|  | 0.0320 | 9.0 | 9.0 | 2.0 | 9.0 | 4.0 | 7.0 |
| 8 | 0.1250 | 5.0 | 9.0 | 0.0 | 5.5 | 1.0 | 2.0 |
|  | 0.0620 | 4.0 | 9.0 | 0.0 | 4.5 | 0.0 | 2.0 |
|  | 0.0320 | 3.5 | 9.0 | 0.0 | 4.5 | 0.0 | 1.0 |
| 12 | 0.1250 | 1.0 | 9.0 | 0.0 | 2.0 | 0.0 | 2.0 |
|  | 0.0620 | 0.0 | 7.0 | 0.0 | 1.0 | 0.0 | 2.0 |
|  | 0.0320 | 0.0 | 2.0 | 0.0 | 0.0 | 0.0 | 2.0 |
| 21 | 0.1250 | 9.0 | 9.0 | 0.0 | 9.0 | 0.0 | 7.0 |
|  | 0.0620 | 9.0 | 9.0 | 0.0 | 9.0 | 0.0 | 7.0 |
|  | 0.0320 | 6.0 | 9.0 | 0.0 | 9.0 | 0.0 | 4.0 |
| 22 | 0.1250 | 0.0 | 0.0 | 0.0 | 0.0 | 0.0 | 0.0 |
|  | 0.0620 | 0.0 | 0.0 | 0.0 | 0.0 | 0.0 | 0.0 |
|  | 0.0320 | 0.0 | 0.0 | 0.0 | 0.0 | 0.0 | 0.0 |
| 26 | 0.1250 | 9.0 | 9.0 | 7.0 | 6.0 | 0.0 | 6.0 |
|  | 0.0620 | 9.0 | 9.0 | 7.0 | 4.0 | 0.0 | 5.0 |
|  | 0.0320 | 7.0 | 9.0 | 7.0 | 4.0 | 0.0 | 4.0 |
| 27 | 0.1250 | 9.0 | 9.0 | 4.0 | 9.0 | 0.0 | 6.0 |
|  | 0.0620 | 7.0 | 9.0 | 0.0 | 9.0 | 0.0 | 4.0 |
|  | 0.0320 | 0.0 | 9.0 | 0.0 | 6.0 | 0.0 | 2.0 |
| 52 | 0.1250 | 8.0 | 9.0 | 8.0 | 9.0 | 4.0 | 7.0 |
|  | 0.0620 | 9.0 |  | 7.0 | 2.0 | 0.0 | 6.0 |
|  | 0.0320 | 6.0 |  |  | 2.0 | 0.0 | 4.0 |
| 53 | 0.1250 | 8.0 | 7.0 | 8.0 | 2.0 | 0.0 | 6.0 |
|  | 0.0620 | 7.0 |  | 8.0 | 0.0 | 0.0 | 4.0 |
|  | 0.0320 | 2.0 | 0.0 | 0.0 | 0.0 | 0.0 | 2.0 |
| 56 | 0.1250 | 9.0 |  | 9.0 | 7.0 | 2.0 | 9.0 |
|  | 0.0620 | 9.0 |  | 0.0 | 4.0 | 0.0 | 7.0 |
|  | 0.0320 | 9.0 |  |  | 2.0 | 0.0 | 7.0 |
| 61 | 0.1250 | 9.0 | 9.0 | 9.0 | 9.0 | 9.0 | 9.0 |
|  | 0.0620 | 9.0 | 9.0 | 9.0 | 9.0 | 8.0 | 9.0 |
|  | 0.0320 | 9.0 | 9.0 | 9.0 | 9.0 | 6.0 | 9.0 |
| 82 | 0.2500 | 9.0 | 9.0 | 9.0 | 9.0 | 0.0 | 5.0 |
|  | 0.1250 | 4.0 | 9.0 | 0.0 | 9.0 | 0.0 | 4.0 |
|  | 0.0620 | 4.0 | 9.0 | 0.0 | 9.0 | 0.0 | 3.0 |

What is claimed is:
1. A compound of formula I
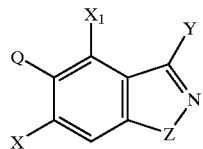
wherein
Q is a radical of formula
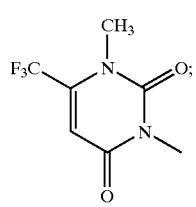
X is hydrogen, halogen or $C_1$–$C_4$ alkyl;
$X_1$ is hydrogen, halogen, $C_1$–$C_4$ alkyl, $C_1$–$C_4$ haloalkyl, $C_1$–$C_4$ alkoxy or, $C_1$–$C_4$ haloalkoxy;
Y is a heterocyclic radical $Y_1$, $Y_2$, $Y_3$, $Y_4$, $Y_5$, $Y_{10}$, $Y_{11}$, $Y_{24}$, $Y_{25}$, $Y_{26}$, $Y_{27}$, $Y_{28}$ or $Y_{29}$, wherein
$Y_1$ is 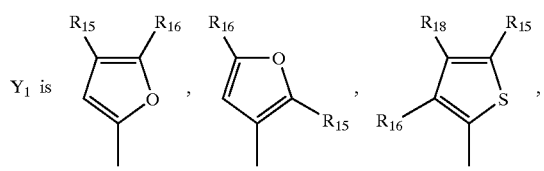
$Y_2$ is 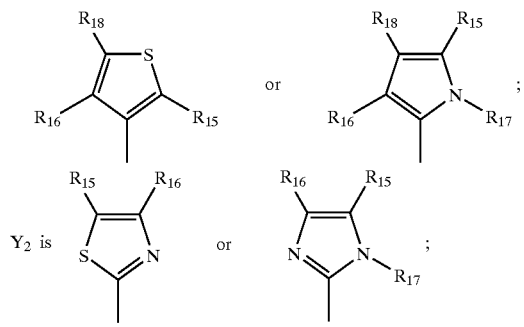
$Y_3$ is 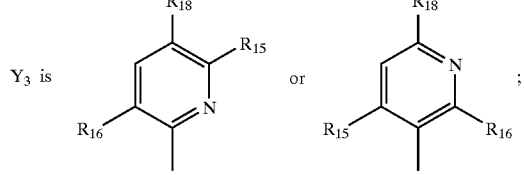
$Y_5$ is 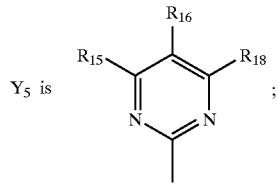
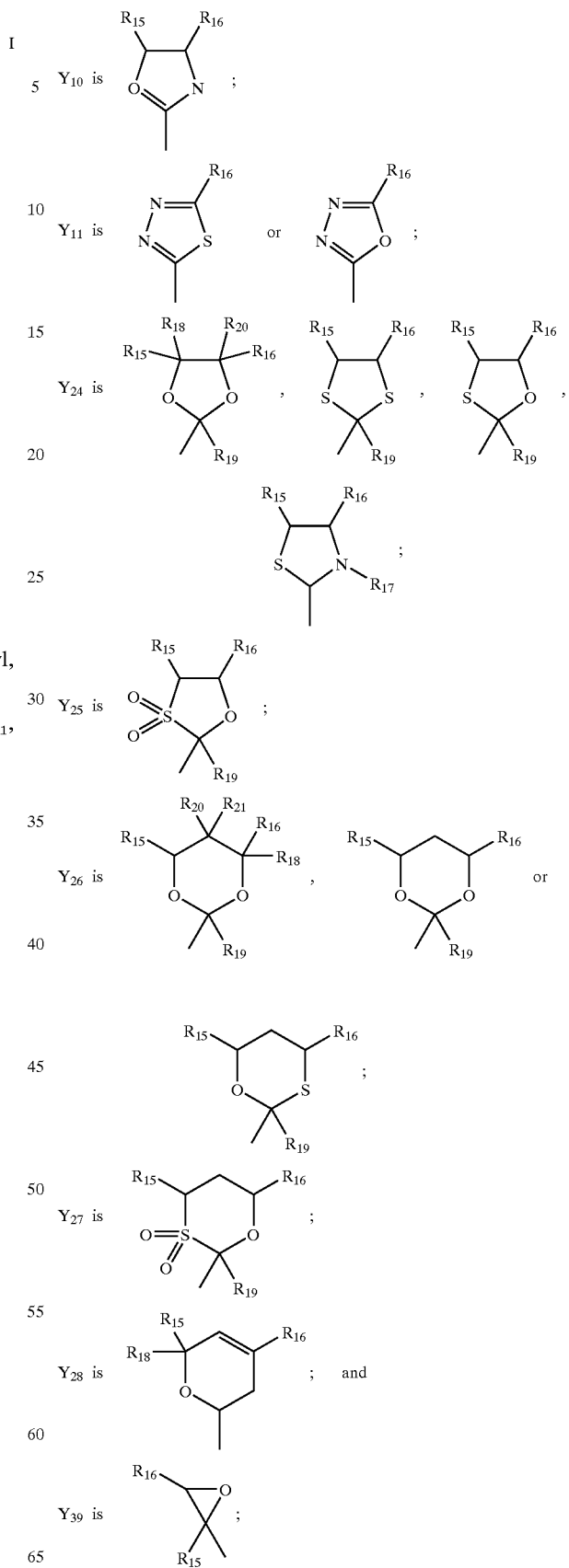

R$_{15}$, R$_{18}$, R$_{20}$, and R$_{21}$ are each independently hydrogen, C$_1$–C$_3$ alkyl, C$_1$–C$_3$ haloalkyl, C$_1$–C$_3$ alkoxy;

R$_{16}$ is hydrogen, halogen, C$_1$–C$_8$ alkyl optionally substituted with X$_2$R$_{24}$; C$_1$–C$_3$ haloalkyl, phenyl or C$_2$–C$_4$ alkenyl;

R$_{17}$ is hydrogen, methyl or C(O)R$_{25}$;

R$_{19}$ is hydrogen or C$_1$–C$_3$ alkyl;

R$_{24}$ is hydrogen or C$_1$–C$_3$ alkyl;

R$_{25}$ is C$_1$–C$_3$ alkyl or phenyl; and

X$_2$ is oxygen;

Z is S(O)$_m$; and m is zero, 1 or 2; or an optical isomer or diastereomer thereof.

2. The compound of formula I defined in claim 1, which is selected from the group consisting of:

1-methyl-3-[3-(3-thienyl)-1,2-benzisothiazol-5-yl]-6-(trifluoromethyl)uracil;

ethyl (R)-2-[5-[3,6-dihydro-3-methyl-2,6-dioxo-4-(trifluoromethyl)-1-(2H)-pyrimidinyl]-1,2-benzisothiazol-3-yl]-4-thiazolidinecarboxylate;

1-methyl-3-[3-(2-thienyl)-1,2-benzisothiazol-5-yl]-6-(trifluoromethyl)uracil;

1-methyl-3-[3-(3-methyl-2-thienyl)-1,2-benzisothiazol-5-yl]-6-(trifluoromethyl)uracil;

1-methyl-3-[3-(1-methylimidazol-2-yl)-1,2-benzisothiazol-5-yl]-6-(trifluoromethyl)uracil;

1-methyl-3-[3-(1-methylpyrrol-2-yl)-1,2-benzisothiazol-5-yl]-6-(trifluoromethyl)uracil;

1-methyl-3-[3-(4-methyl-2-thiazolyl)-1,2-benzisothiazol-5-yl]-6-(trifluoromethyl)uracil;

3-[3-(2,5-diethyl-3-thienyl)-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil;

3-[3-(3-methoxy-2-thienyl)-1,2-benzisothiazol-5-yl]-1-methyl-6-(trifluoromethyl)uracil;

1-methyl-3-[3-(3-pyridyl)-1,2-benzisothiazol-5-yl]-6-(trifluoromethyl)uracil;

1-methyl-3-[3-(2-pyrimidinyl)-1,2-benzisothiazol-5-yl]-6-(trifluoromethyl)uracil;

3-[3-[(1R,2S)-1,2-epoxypropyl]-1,2-benzisothiazol-5-yl]-1-methyl-6-(trifluoromethyl)uracil;

1-methyl-6-(trifluoromethyl)uracil;

3-[3-[(1R,2R)-1,2-epoxypropyl]-1,2-benzisothiazol-5-yl]-1-methyl-3-[3-(2-pyridyl)-1,2-benzisothiazol-5-yl]-6-(trifluoromethyl)-uracil N",S,S-trioxide;

1-methyl-3-[3-(5-methyl-1,3,4-oxadiazol-2-yl)-1,2-benzisothiazol-5-yl]-6-(trifluoromethyl)uracil;

1-methyl-3-[3-(5-methyl-1,3,4-thiadiazol-2-yl)-1,2-benzisothiazol-5-yl]-6-(trifluoromethyl)uracil;

1,2-benzisothiazole-3-carboxanilide, 4'-chloro-5-[3,6-dihydro-3-methyl-2,6-dioxo-4-(trifluoromethyl)-1(2H)-pyrimdinyl]-N-methyl-;

1-methyl-3-[3-(3-methyl-2-pyridyl)-1,2-benzisothiazol-5-yl]-6-(trifluoromethyl)uracil;

N-[3-(5-methyl-2-thienyl)-1,2-benzisothiazol-5-yl]-1-cyclohexene-1,2-dicarboximide;

1-methyl-3-[3-(5-methyl-2-thienyl)-1,2-benzisothiazol-5-yl]-6-(trifluoromethyl)uracil;

methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-acetate;

methyl 2-[(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-propionate;

3-[3-(1,3-dithiolan-2-yl)-1,2-benzisothiazol-5-yl]-1-methyl-6-(trifluoromethyl)uracil;

3-[6-fluoro-3-(2-pyridyl)-1,2-benzisothiazol-5-yl]-1-methyl-6-(trifluoromethyl)uracil;

1-methyl-3-[3-(4-methyl-3-thienyl)-1,2-benzisothiazol-5-yl]-6-(trifluoromethyl)uracil;

3-[3-(3,5-dimethyl-2-thienyl)-1,2-benzisothiazol-5-yl]-1-methyl-6-(trifluoromethyl)uracil;

3-(3-m-dioxan-2-yl-1,2-benzisothiazol-5-yl)-1-methyl-6-(trifluoromethyl)uracil;

3-acetyl-2-[5-[3,6-dihydro-3-methyl-2,6-dioxo-4-trifluoromethyl)-1(2H)-pyrimidinyl]-1,2-benzisothiazol-3-yl]thiazolidine;

3-benzoyl-2-[5-[3,6-dihydro-3-methyl-2,6-dioxo-4-(trifluoromethyl)-1(2H)-pyrimidinyl]-1,2-benzisothiazol-3-yl]thiazolidine;

1-methyl-3-[3-(1,3-oxathiolan-2-yl)-1,2-benzisothiazol-5-yl]-6-(trifluoromethyl)uracil;

1-methyl-3-[3-(1,3-oxathiolan-2-yl)-1,2-benzisothiazol-5-yl]-6-(trifluoromethyl)uracil S',S'-dioxide;

1,2-benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl) dithioacetal];

1-methyl-3-[3-(1,3-oxathian-2-yl)-1,2-benzisothiazol-5-yl]-6-(trifluoromethyl)uracil;

1-methyl-3-[3-(1,3-oxathian-2-yl)-1,2-benzisothiazol-5-yl]-6-(trifluoromethyl)uracil S',S'-dioxide;

3-[3(5,5-dimethyl-m-dioxan-2-yl)-1,2-benzisothiazol-5-yl]-1-methyl-6-(trifluoromethyl)uracil;

1-methyl-3-[3-(4-methyl-m-dioxan-2-yl)-1,2-benzisothiazol-5-yl]-6-(trifluoromethyl)uracil;

1-methyl-3-[3-(3-methylpyrazol-1-yl)-1,2-benzisothiazol-5-yl]-6-(trifluorometyhl)uracil;

2-propynyl[[2-[5-[3,6-dihydro-3-methyl-2,6-dioxo-4-(trifluoromethyl)-1(2H)-pyrimidinyl]-1,2-benzisothiazol-3-yl]-3-thienyl]oxy]acetate;

3-[3-(4,6-dimethyl-2-pyrimidinyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[3-(4,6-diethoxy-2-pyrimidinyl)-1,2-benzisothiazol-5-yl]-1-methyl-6-(trifluoromethyl)uracil;

3-[6-fluoro-3-(3-methyl-2-pyridyl)-1,2-benzisothiazol-5-yl]-1-methyl-6-(trifluoromethyl)uracil;

3-[3-(1,3-dioxolan-2-yl)-1,2-benzisothiazol-5-yl]-1-methyl-6-(trifluoromethyl)uracil;

N-[6-fluoro-3-(3-methyl-2-pyridyl)-1,2-benzisothiazol-5-yl]-1-cyclohexene-1,2-dicarboximide;

3-[3-[(4R,5S)-4,5-dimethyl-1,3-dioxolan-2-yl]-1,2-benzisothiazol-5-yl]-1-methyl-6-(trifluoromethyl) uracil 3-[3-[(4R,5R)-4,5-dimethyl-1,3-dioxolan-2-yl]-1,2-benzisothiazol-5-yl]-1-methyl-6-(trifluoromethyl) uracil;

1-methyl-6-(trifluoromethyl)-3-[3-(3,4,5-trimethylpyrazol-1-yl)-1,2-benzisothiazol-5-yl]uracil;

3-[3-[(4R,6S)-4,6-dimethyl-m-dioxan-2-yl]-1,2-benzisothiazol-5-yl]-1-methyl-6-(trifluoromethyl) uracil 3-[3-[(4R,6S)-4,6-dimethyl-m-dioxan-2-yl]-1,2-benzisothiazol-5-yl]-1-methyl-6-(trifluoromethyl)uracil;

3-[3-(3-chloro-2-thienyl)-1,2-benzisothiazol-5-yl]-1-methyl-6-(trifluoromethyl)uracil;

1-methyl-3-[3-(2-thiazolyl)-1,2-benzisothiazol-5-yl]-6-(trifluoromethyl)uracil;

1-methyl-3-[3-(2-methyl-1,3-dioxolan-2-yl)-1,2-benzisothiazol-5-yl]-6-(trifluoromethyl)uracil;

1-methyl-6-(trifluoromethyl)-3-[3-(4,4,6-trimethyl-m-dioxan-2-yl)-1,2-benzisothiazol-5-yl]uracil;

1-methyl-3-[3-(4,4,5,5-tetramethyl-1,3-dioxolan-2-yl)-1,2-benzisothiazol-5-yl]-6-(trifluoromethyl)uracil;

1-methyl-3-[3-(4-methyl-1,3-dioxolan-2-yl)-1,2-benzisothiazol-5-yl]-6-(trifluoromethyl)uracil;

2,4(1H,3H)-pyrimidinedione, 1-methyl-3-[3-(5-methylene-m-dioxan-2-yl)-1,2-benzisothiazol-5-yl]-6-(trifluoromethyl)-;

1-methyl-3-[3-(4-methylpyrazol-1-yl)-1,2-benzisothiazol-5-yl]-6-(trifluoromethyl)uracil;

3-[3-(2-furyl)-1,2-benzisothiazol-5-yl]-1-methyl-6-(trifluoromethyl)uracil;

3-[3-(1,3-dioxolan-2-yl)-6-fluoro-1,2-benzisothiazol-5-yl]-1-methyl-6-(trifluoromethyl)uracil;

3-(3-m-dioxan-2-yl-6-fluoro-1,2-benzisothiazol-5-yl)-1-methyl-6-(trifluoromethyl)uracil;

3-[3-[(4R,5S)-4,5-dimethyl-1,3-dioxolan-2-yl]-6-fluoro-1,2-benzisothiazol-5-yl]-1-methyl-6-(trifluoromethyl)uracil;

3-[3-[4-(methoxymethyl)-1,3-dioxolan-2-yl]-1,2-benzisothiazol-5-yl]-1-methyl-6-(trifluoromethyl)uracil;

3-[3-(3,6-dihydro-4,6,6-trimethyl-2H-pyran-2-yl)-1,2-benzisothiazol-5-yl]-1-methyl-6-(trifluoromethyl)uracil;

3-[3-[(4R,5S-)-4,5-dimethyl-1,3-dioxolan-2-yl]-6-fluoro-1,2-benzisothiazol-5-yl]-1-methyl-6-(trifluoromethyl)uracil;

3-[3-[(4R,6S)-4,6-dimethyl-m-dioxan-2-yl]-6-fluoro-1,2-benzisothiazol-5-yl]-1-methyl-6-(trifluoromethyl)uracil;

2,4(1H,3H)-pyrimidinedione, 1-methyl-3-[3-(2-methyl-3-thienyl)-1,2-benzisothiazol-5-yl]-6-(trifluoromethyl)-;

3-[3-[5-(bromomethyl)-5-hydroxy-m-dioxan-2-yl]-1,2-benzisothiazol-5-yl]-1-methyl-6-(trifluoromethyl)uracil;

1-methyl-3-(3-spiro[m-dioxane-5,2'-oxiran]-2-yl-1,2-benzisothiazol-5-yl)-6-(trifluoromethyl)uracil;

3-[3-(4,4-dimethyl-5-oxo-1,3-dioxolan-2-yl)-1,2-benzisothiazol-5-yl]-1-methyl-6-(trifluoromethyl)uracil;

3-[3-[4-(chloromethyl)-1,3-dioxolan-2-yl]-1,2-benzisothiazol-5-yl]-1-methyl-6-(trifluoromethyl)uracil;

3-[3-[4-(hydroxymethyl)-1,3-dioxolan-2-yl]-1,2-benzisothiazol-5-yl]-1-methyl-6-(trifluoromethyl)uracil;

3-[3-(4-isopropyl-2-oxazolin-2-yl)-1,2-benzisothiazol-5-yl]-1-methyl-6-(trifluoromethyl)uracil;

1-methyl-3-[3(2-oxazolin-2-yl)-1,2-benzisothiazol-5-yl]-6-(trifluoromethyl)uracil;

1-methyl-6-(trifluoromethyl)-3-[3-(4-vinyl-1,3-dioxolan-2-yl)-1,2-benzisothiazol-5-yl]uracil;

1-methyl-3-[3-(4-propyl-1,3-dioxolan-2-yl)-1,2-benzisothiazol-5-yl]-6-(trifluoromethyl)uracil;

1-methyl-3-[3-(4-phenyl-1,3-dioxolan-2-yl)-1,2-benzisothiazol-5-yl]-6-(trifluoromethyl)uracil;

3-[3-[4-(bromomethyl)-1,3-dioxolan-2-yl]-1,2-benzisothiazol-5-yl]-1-methyl-6-(trifluoromethyl)uracil;

3-[3-[3-(bromomethyl)-2-thienyl]-1,2-benzisothiazol-5-yl]-1-methyl-6-(trifluoromethyl)uracil;

3-[3-[3-(methoxymethyl)-2-thienyl]-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-(3-furyl)-1,2-benzisothiazol-5-yl]-1-methyl-6-(trifluoromethyl)uracil;

1-methyl-3-[3-[4-[(methylthio)methyl]-1,3-dioxolan-2-yl]-1,2-benzisothiazol-5-yl]-6-(trifluoromethyl)uracil;

3-[3-[3-(hydroxymethyl)-2-thienyl]-1,2-benzisothiazol-5-yl]-1-methyl-6-(trifluoromethyl)uracil;

1-methyl-3-[3-[4-[(methylsulfonyl)methyl]-1,3-dioxolan-2-yl]-1,2-benzisothiazol-5-yl]-6-(trifluoromethyl)uracil;

1-methyl-3-[3-[4-[(methylsulfonyl)methyl]-1,3-dioxolan-2-yl]-1,2-benzisothiazol-5-yl]-6-(trifluoromethyl)uracil;

1-methyl-3-[3-[4-[(methylsulfinyl)methyl]-1,3-dioxolan-2-yl]-1,2-benzisothiazol-5-yl]-6-(trifluoromethyl)uracil;

[2-[5-[3,6-dihydro-3-methyl-2,6-dioxo-4-(trifluoromethyl)-1(2H)-pyrimidinyl]-1,2-benzisothiazol-3-yl]-1,3-dioxolan-4-yl]methyl thiocyanate;

3-[3-(3,4-dihydro-3-oxo-2-quinoxalinyl)-1,2-benzisothiazol-5-yl]-1-methyl-6-(trifluoromethyl)uracil;

5-[5-[3,6-dihydro-3-methyl-2,6-dioxo-4-(trifluoromethyl)-1(2H)-pyrimidinyl]-1,2-benzisothiazol-3-yl]-1,6-hydro-6-oxo-2,3-pyrazinedicarbonitrile;

1-methyl-3-[3-(4-oxo-delta-2-1,2,5-thiadiazolin-3-yl)-1,2-benzisothiazol-5-yl]-6-(trifluoromethyl)uracil S',S'-dioxide;

3-[3-[2-(dimethylamino)-4-methoxy-5-oxo-2-imidazolin-4-yl]-1,2-benzisothiazol-5-yl]-1-methyl-6-(trifluoromethyl)uracil;

3-[3-(4-hydroxy-5-oxo-2-phenyl-2-imidazolin-4-yl)-1,2-benzisothiazol-5-yl]-1-methyl-6-(trifluoromethyl)uracil;

3-[3-(2-tert-butyl-4-hydroxy-5-oxo-2-imidazolin-4-yl)-1,2-benzisothiazol-5-yl]-1-methyl-6-(trifluoromethyl)uracil;

3-[3-(-hydroxy-5-imino-4,4-dimethyl-2-oxo-3-pyrrolidinyl)-1,2-benzisothiazol-5-yl]-1-methyl-6-(trifluoromethyl)uracil;

3-[3-[4-methoxy-2-(methylimino)-5-oxo-4-imidazolidinyl]-1,2-benzisothiazol-5-yl]-1-methyl-6-(trifluoromethyl)uracil; and 3-[3-[4-methoxy-2-(ethylimino)-5-oxo-4-imidazolidinyl]-1,2-benzisothiazol-5-yl]-1-methyl-6-(trifluoromethyl)uracil.

3. A method for the control of undesirable plants which comprises applying to the foliage of said plant, or to soil or water which contains seeds or other propagating organs of said plants, a herbicidally effective amount of the compound of formula I defined in claim 1.

4. The method of claim 3 wherein the formula I compound is selected from the group consisting of:

1-methyl-3-[3-(3-thienyl)-1,2-benzisothiazol-5-yl]-6-(trifluoromethyl)uracil;

ethyl (R)-2-[5-[3,6-dihydro-3-methyl-2,6-dioxo-4-(trifluoromethyl)-1(2H)-pyrimidinyl]-1,2benzisothiazol-3-yl]-4-thiazolidinecarboxylate;

1-methyl-3-[3-(2-thienyl)-1,2-benzisothiazol-5-yl]-6-(trifluoromethyl)uracil;

1-methyl-3-[3-(3-methyl-2-thienyl)-1,2-benzisothiazol-5-yl]-6-(trifluoromethyl)uracil;

1-methyl-3-[3-(1-methylimidazol-2-yl)-1,2-benzisothiazol-5-yl]-6-(trifluoromethyl)uracil;

1-methyl-3-[3-(1-methylpyrrol-2-yl)-1,2-benzisothiazol-5-yl]-6-(trifluoromethyl)uracil;

1-methyl-3-[3-(4-methyl-2-thiazolyl)-1,2-benzisothiazol-5-yl]-6-(trifluoromethyl)uracil;

3-[3-(2,5-diethyl-3-thienyl)-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil;

3-[3-(3-methoxy-2-thienyl)-1,2-benzisothiazol-5-yl]-1-methyl-6-(trifluoromethyl)uracil;

1-methyl-3-[3-(3-pyridyl)-1,2-benzisothiazol-5-yl]-6-(trifluoromethyl)uracil;

1-methyl-3-[3-(2-pyrimidinyl)-1,2-benzisothiazol-5-yl]-6-(trifluoromethyl)uracil;

3-[3-[(1R,2S)-1,2-epoxypropyl]-1,2-benzisothiazol-5-yl]-1-methyl-6-(trifluoromethyl)uracil;

3-[3-[(1R,2R)-1,2-epoxypropyl]-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil N",S,S-trioxide;

1-methyl-3-[3-(5-methyl-1,3,4-oxadiazol-2-yl)-1,2-benzisothiazol-5-yl]-6-(trifluoromethyl)uracil;

1-methyl-3-[3-(5-methyl-1,3,4-thiadiazol-2-yl)-1,2-benzisothiazol-5-yl]-6-(trifluoromethyl)uracil;

1,2-benzisothiazole-3-carboxanilide, 4'-chloro-5-[3,6-dihydro-3-methyl-2,6-dioxo-4-(trifluoromethyl)-1(2H)-pyrimidinyl]-N-methyl-;

1-methyl-3-[3-(3-methyl-2-pyridyl)-1,2-benzisothiazol-5-yl]-6-(trifluoromethyl)uracil;

N-[3-(5-methyl-2-thienyl)-1,2-benzisothiazol-5-yl]-1-cyclohexene-1,2-dicarboximide;

1-methyl-3-[3-(5-methyl-2-thienyl)-1,2-benzisothiazol-5-yl]-6-(trifluoromethyl)uracil;

methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-acetate;

methyl 2-[(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-propionate;

3-[3-(1,3-dithiolan-2-yl)-1,2-benzisothiazol-5-yl]-1-methyl-6-(trifluoromethyl)uracil;

3-[6-fluoro-3-(2-pyridyl)-1,2-benzisothiazol-5-yl]-1-methyl-6-(trifluoromethyl)uracil;

1-methyl-3-[3-(4-methyl-3-thienyl)-1,2-benzisothiazol-5-yl]-6-(trifluoromethyl)uracil;

3-[3-(3,5-dimethyl-2-thienyl)-1,2-benzisothiazol-5-yl]-1-methyl-6-(trifluoromethyl)uracil;

3-(3-m-dioxan-2-yl-1,2-benzisothiazol-5-yl)-1-methyl-6-(trifluoromethyl)uracil;

3-acetyl-2-[5-[3,6-dihydro-3-methyl-2,6-dioxo-4-(trifluoromethyl)-1(2H)-pyrimidinyl]-1,2-benzisothiazol-3-yl]thiazolidine;

3-benzoyl-2-[5-[3,6-dihydro-3-methyl-2,6-dioxo-4-(trifluoromethyl)-1(2H)-pyrimidinyl]-1,2-benzisothiazol-3-yl]thiazolidine;

1-methyl-3-[3-(1,3-oxathiolan-2-yl)-1,2-benzisothiazol-5-yl]-6-(trifluoromethyl)uracil;

1-methyl-3-[3-(1,3-oxathiolan-2-yl)-1,2-benzisothiazol-5-yl]-6-(trifluoromethyl)uracil S',S'-dioxide;

1,2-benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl)dithioacetal];

1-methyl-3-[3-(1,3-oxathian-2-yl)-1,2-benzisothiazol-5-yl]-6-(trifluoromethyl)uracil;

1-methyl-3-[3-(1,3-oxathian-2-yl)-1,2-benzisothiazol-5-yl]-6-(trifluoromethyl)uracil S',S'-dioxide;

3-[3(5,5-dimethyl-m-dioxan-2-yl)-1,2-benzisothiazol-5-yl]-1-methyl-6-(trifluoromethyl)uracil;

1-methyl-3-[3-(4-methyl-m-dioxan-2-yl)-1,2-benzisothiazol-5-yl]-6-(trifluoromethyl)uracil;

1-methyl-3-[3-(3-methylpyrazol-1-yl)-1,2-benzisothiazol-5-yl]-6-(trifluoromethyl)uracil;

2-propynyl [[2-[5-[3,6-dihydro-3-methyl-2,6-dioxo-4-(trifluoromethyl)-1(2H)-pyrimidinyl]-1,2-benzisothiazol-3-yl]-3-thienyl]oxy]-acetate;

3-[3-(4,6-dimethyl-2-pyrimidinyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[3-(4,6-diethoxy-2-pyrimidinyl)-1,2-benzisothiazol-5-yl]-1-methyl-6-(trifluoromethyl)uracil;

3-[6-fluoro-3-(3-methyl-2-pyridyl)-1,2-benzisothiazol-5-yl]-1-methyl-6-(trifluoromethyl)uracil;

3-[3-(1,3-dioxolan-2-yl)-1,2-benzisothiazol-5-yl]-1-methyl-6-(trifluoromethyl)uracil;

N-[6-fluoro-3-(3-methyl-2-pyridyl)-1,2-benzisothiazol-5-yl]-1-cyclohexene-1,2-dicarboximide;

3-[3-[(4R,5S)-4,5-dimethyl-1,3-dioxolan-2-yl]-1,2-benzisothiazol-5-yl]-1-methyl-6-(trifluoromethyl)uracil 3-[3-[(4R,5R)-4,5-dimethyl-1,3-dioxolan-2-yl]-1,2-benzisothiazol-5-yl]-1-methyl-6-(trifluoromethyl)uracil;

1-methyl-6-(trifluoromethyl)-3-[3-(3,4,5trimethylpyrazol-1-yl)-1,2-benzisothiazol-5-yl]uracil;

3-[3-[(4R,6S)-4,6-dimethyl-m-dioxan-2-yl]-1,2-benzisothiazol-5-yl]-1-methyl-6-(trifluoromethyl)uracil 3-[3-[(4R,6S)-4,6-dimethyl-m-dioxan-2-yl]-1,2-benzisothiazol-5-yl]-1-methyl-6-(trifluoromethyl)uracil;

3-[3-(3-chloro-2-thienyl)-1,2-benzisothiazol-5-yl]-1-methyl-6-(trifluoromethyl)uracil;

1-methyl-3-[3-(2-thiazolyl)-1,2-benzisothiazol-5-yl]-6-(trifluoromethyl)uracil;

1-methyl-3-[3-(2-methyl-1,3-dioxolan-2-yl)-1,2-benzisothiazol-5-yl]-6-(trifluoromethyl)uracil;

1-methyl-6-(trifluoromethyl)-3-[3-(4,4,6-trimethyl-m-dioxan-2-yl)-1,2-benzisothiazol-5-yl]uracil;

1-methyl-3-[3-(4,4,5,5-tetramethyl-1,3-dioxolan-2-yl)-1,2-benzisothiazol-5-yl]-6-(trifluoromethyl)uracil;

1-methyl-3-[3-(4-methyl-1,3-dioxolan-2-yl)-1,2-benzisothiazol-5-yl]-6-(trifluoromethyl)uracil;

2,4(1H,3H)-pyrimidinedione, 1-methyl-3-[3-(5-methylene-m-dioxan-2-yl)-1,2-benzisothiazol-5-yl]-6-(trifluoromethyl)-;

1-methyl-3-[3-(4-methylpyrazol-1-yl)-1,2-benzisothiazol-5-yl]-6-(trifluoromethyl)uracil;

3-[3-(2-furyl)-1,2-benzisothiazol-5-yl]-1-methyl-6-(trifluoromethyl)uracil;

3-[3-(1,3-dioxolan-2-yl)-6-fluoro-1,2-benzisothiazol-5-yl]-1-methyl-6-(trifluoromethyl)uracil;

3-(3-m-dioxan-2-yl-6-fluoro-1,2-benzisothiazol-5-yl)-1-methyl-6-(trifluoromethyl)uracil;

3-[3-[(4R,5S)-4,5-dimethyl-1,3-dioxolan-2-yl]-6-fluoro-1,2-benzisothiazol-5-yl]-1-methyl-6-(trifluoromethyl)uracil;

3-[3-[4-(methoxymethyl)-1,3-dioxolan-2-yl]-1,2-benzisothiazol-5-yl]-1-methyl-6-(trifluoromethyl)uracil;

3-[3-(3,6-dihydro-4,6,6-trimethyl-2H-pyran-2-yl)-1,2-benzisothiazol-5-yl]-1-methyl-6-(trifluoromethyl)uracil;

3-[3-[(4R,5S-)-4,5-dimethyl-1,3-dioxolan-2-yl]-6-fluoro-1,2-benzisothiazol-5-yl]-1-methyl-6-(trifluoromethyl)uracil;

3-[3-[(4R,6S)-4,6-dimethyl-m-dioxan-2-yl]-6-fluoro-1,2-benzisothiazol-5-yl]-1-methyl-6-(trifluoromethyl)uracil;

1-methyl-3-[3-(2-methyl-3-thienyl)-1,2-benzisothiazol-5yl]-6-(trifluoromethyl)-2,4(1H,3H)-pyrimidinedione;

3-[3-[5-(bromomethyl)-5-hydroxy-m-dioxan-2-yl]-1,2-benzisothiazol-5-yl]-1-methyl-6-(trifluoromethyl)uracil;

1-methyl-3-(3-spiro[m-dioxane-5,2'-oxiran]-2-yl-1,2-benzisothiazol-5-yl)-6-(trifluoromethyl)uracil;

3-[3-(4,4-dimethyl-5-oxo-1,3-dioxolan-2-yl)-1,2-benzisothiazol-5-yl]-1-methyl-6-(trifluoromethyl)uracil;

3-[3-[4-(chloromethyl)-1,3-dioxolan-2-yl]-1,2-benzisothiazol-5-yl]-1-methyl-6-(trifluoromethyl)uracil;

3-[3-[4-(hydroxymethyl)-1,3-dioxolan-2-yl]-1,2-benzisothiazol-5-yl]-1-methyl-6-(trifluoromethyl)uracil;

3-[3-(4-isopropyl-2-oxazolin-2-yl)-1,2-benzisothiazol-5yl]-1-methyl-6-(trifluoromethyl)uracil;

1-methyl-3-[3(2-oxazolin-2-yl)-1,2-benzisothiazol-5-yl]-6-(trifluoromethyl)uracil;

1-methyl-6-(trifluoromethyl)-3-[3-(4-vinyl-1,3-dioxolan-2-yl)-1,2-benzisothiazol-5-yl]uracil;

1-methyl-3-[3-(4-propyl-1,3-dioxolan-2-yl)-1,2-benzisothiazol-5-yl]-6-(trifluoromethyl)uracil;

1-methyl-3-[3-(4-phenyl-1,3-dioxolan-2-yl)-1,2-benzisothiazol-5-yl]-6-(trifluoromethyl)uracil;

3-[3-[4-(bromomethyl)-1,3-dioxolan-2-yl]-1,2-benzisothiazol-5-yl]-1-methyl-6-(trifluoromethyl)uracil;

3-[3-[3-(bromomethyl)-2-thienyl]-1,2-benzisothiazol-5-yl]-1-methyl-6-(trifluoromethyl)uracil;

3-[3-[3-(methoxymethyl)-2-thienyl]-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-(3-furyl)-1,2-benzisothiazol-5-yl]-1-methyl-6-(trifluoromethyl)uracil;

1-methyl-3-[3-[4-[(methylthio)methyl]-1,3-dioxolan-2-yl]-1,2-benzisothiazol-5-yl]-6-(trifluoromethyl)uracil;

3-[3-[3-(hydroxymethyl)-2-thienyl]-1,2-benzisothiazol-5yl]-1-methyl-6-(trifluoromethyl)uracil;

1-methyl-3-[3-[4-[(methylsulfonyl)methyl]-1,3-dioxolan-2-yl]-1,2-benzisothiazol-5-yl]-6-(trifluoromethyl)uracil;

1-methyl-3-[3-[4-[(methylsulfonyl)methyl]-1,3-dioxolan-2-yl]-1,2-benzisothiazol-5-yl]-6-(trifluoromethyl)uracil;

1-methyl-3-[3-[4-[(methylsulfinyl)methyl]-1,3-dioxolan-2-yl]-1,2-benzisothiazol-5-yl]-6-(trifluoromethyl)uracil;

[2-[5-[3,6-dihydro-3-methyl-2,6-dioxo-4-(trifluoromethyl)-1(2H)-pyrimidinyl]-1,2-benzisothiazol-3-1]-1,3-dioxolan-4-yl]methyl thiocyanate;

3-[3-(3,4-dihydro-3-oxo-2-quinoxalinyl)-1,2-benzisothiazol-5-yl]-1-methyl-6-(trifluoromethyl)uracil;

5-[5-[3,6-dihydro-3-methyl-2,6-dioxo-4-(trifluoromethyl)-1(2H)-pyrimidinyl]-1,2-benzisothiazol-3-yl]-1,6-hydro-6-oxo-2,3-pyrazinedicarbonitrile;

1-methyl-3-[3-(4-oxo-delta-2-1,2,5-thiadiazolin-3-yl)-1,2-benzisothiazol-5-yl]-6-(trifluoromethyl)uracil S',S'-dioxide;

3-[3-[2-(dimethylamino)-4-methoxy-5-oxo-2-imidazolin-4-yl]-1,2-benzisothiazol-5-yl]-1-methyl-6-(trifluoromethyl)uracil;

3-[3-(4-hydroxy-5-oxo-2-phenyl-2-imidazolin-4-yl)-1,2-benzisothiazol-5-yl]-1-methyl-6-(trifluoromethyl)uracil;

3-[3-(2-tert-butyl-4-hydroxy-5-oxo-2-imidazolin-4-yl)-1,2-benzisothiazol-5-yl]-1-methyl-6-(trifluoromethyl)uracil;

3-[3-(-hydroxy-5-imino-4,4-dimethyl-2-oxo-3-pyrrolidinyl)-1,2-benzisothiazol-5-yl]-1-methyl-6-(trifluoromethyl)uracil;

3-[3[4-methoxy-2-(methylimino)-5-oxo-4-imidazolidinyl]-1,2-benzisothiazol-5-yl]-1-methyl-6-(trifluoromethyl)uracil; and 3-[3[4-methoxy-2-(ethylimino)-5-oxo-4-imidazolidinyl]-1,2-benzisothiazol-5-yl]-1-methyl-6-(trifluoromethyl)uracil.

5. The method of claim 3 wherein the formula I compound is applied to the foliage of the undesirable plant, or to soil or water which contains seeds or other propagating organs of said plants, in the presence of a crop plant, crop seed or other crop propagating organ.

6. The method of claim 5 wherein said crop is a cereal crop.

7. The method of claim 6 wherein said cereal crop is corn, wheat or rice.

8. The method of claim 7 wherein said crop is corn and the formula I compound is selected from the group consisting of:

1-methyl-3-[3-(3-thienyl)-1,2-benzisothiazol-5-yl]-6-(trifluoromethyl)uracil;

3-[3-(3-chloro-2-thienyl)-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-[(4R,5S)-4,5-dimethyl-1,3-dioxolan-2-yl]-1,2-benzisothiazol-5-yl]-1-methyl-6-(trifluoromethyl)uracil;

3-[3-[(4R,5R)-4,5-dimethyl-1,3-dioxolan-2-yl]-1,2-benzisothiazol-5-yl]-1-methyl-6-(trifluoromethyl)uracil; and ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

9. The method of claim 7 said crop is wheat and the formula I compound is selected from the group consisting of:

1-methyl-3-[3-(3-thienyl)-1,2-benzisothiazol-5-yl]-6-(trifluoromethyl)uracil;

1-methyl-3-[3-(2-thienyl)-1,2-benzisothiazol-5-yl]-6-(trifluoromethyl)uracil;

1-methyl-3-[3-(3-methyl-2-thienyl)-1,2-benzisothiazol-5-yl]-6-(trifluoromethyl)uracil 1-methyl-3-[3-(5-methyl-2-thienyl)-1,2-benzisothiazol-5-yl]-6-(trifluoromethyl)uracil;

3-[3-(3-chloro-2-thienyl)-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-(2,5-diethyl-3-thienyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

3-[3-[(4R,5S)-4,5-dimethyl-1,3-dioxolan-2-yl]-1,2-benzisothiazol-5-yl]-1-methyl-6-(trifluoromethyl)uracil;

3-[3-[(4R,r %)-4,5-dimethyl-1,3-dioxolan-2-yl]-6-fluoro-1,2-benzisothiazol-5-yl]-1-methyl-6-(trifluoromethyl)uracil;

3-[3-[4-(hydroxymethyl)-1,3-dioxolan-2-yl]-1,2-benzisothiazol-5-yl]-1-methyl-6-(trifluoromethyl)uracil;

1-methyl-6-(trifluoromethyl)-3-[3-(4-vinyl-1,3-dioxolan-2-yl)-1,2-benzisothiazol-5-yl]uracil;

1-methyl-3-[3-(4-propyl-1,3-dioxolan-2-yl)-1,2-benzisothiazol-5-yl]-6-(trifluoromethyl)uracil;

3-[3-[4-(bromethyl)-1,3-dioxolan-2-yl]-1,2-benzisothiazol-5-yl]-1-methyl-6-(trifluoromethyl)uracil;

3-[3-(4-isopropyl-2-oxazolin-2-yl)-1,2-benzisothiazol-5-yl]-1-methyl-6-(trifluoromethyl)uracil; and ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

10. The method of claim 7 wherein said crop is rice and the formula I compound is selected from the group consisting of:

1-methyl-3-[3-(5-methyl-2-thienyl)-1,2-benzisothiazol-5-yl]-6-(trifluoromethyl)uracil;

3-[3-(3-chloro-2-thienyl)-1,2-benzisothiazol-5-yl]-1-methyl-6-(trifluoromethyl)uracil;

3-[3-[3-(methoxymethyl)-2-thienyl]-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-(2,5-diethyl-3-thienyl)-1,2-benzisothiazol-5-yl]-1-methyl-6-(trifluoromethyl)uracil;

3-[6-fluoro-3-(2-pyridyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[6-fluoro-3-(3-methyl-2-pyridyl)-1,2-benzisothiazol-5-yl]-1-methyl-6-(trifluoromethyl)uracil;

3-[3-(1,3-dioxolan-2-yl)-1,2-benzisothiazol-5-yl]-1-methyl-6-(trifluoromethyl)uracil;

3-[3-[(4R,5S)-4,5-dimethyl-1,3-dioxolan-2-yl]-1,2-benzisothiazol-5-yl]-1-methyl-6-(trifluoromethyl)uracil;

1-methyl-3-[3-(2-methyl-1,3-dioxolan-2-yl)-1,2-benzisothiazol-5-yl]-6-(trifluoromethyl)uracil;

3-[3-[(4R,r %)-4,5-dimethyl-1,3-dioxolan-2-yl]-6-fluoro-1,2-benzisothiazol-5-yl]-1-methyl-6-(trifluoromethyl)uracil;

1-methyl-6-(trifluoromethyl)-3-[3-(4-vinyl-1,3-dioxolan-2-yl)-1,2-benzisothiazol-5-yl]uracil;

1-methyl-3-[3-(4-propyl-1,3-dioxolan-2-yl)-1,2-benzisothiazol-5-yl]-6-(trifluoromethyl)uracil;

3-[3-(4-isopropyl-2-oxazolin-2-yl)-1,2-benzisothiazol-5-yl]-1-methyl-6-(trifluoromethyl)uracil;

1-methyl-3-[3-(2-thiazolyl)-1,2-benzisothiazol-5-yl]-6-(trifluoromethyl)uracil; and ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate.

11. The method of claim 5 wherein said crop is soybean.

12. The method of claim 11 wherein the formula I compound is selected from the group consisting of:

1-methyl-3-[3-(3-thienyl)-1,2-benzisothiazol-5-yl]-6-(trifluoromethyl)uracil;

3-[3-(3-methoxy-2-thienyl)-1,2-benzisothiazol-5-yl]-1-methyl-6-(trifluoromethyl)uracil;

1-methyl-3-[3-(5-methyl-2-thienyl)-1,2-benzisothiazol-5-yl]-6-(trifluoromethyl)uracil;

3-[3-(3-chloro-2-thienyl)-1,2-benzisothiazol-5-yl]-1-methyl-6-(trifluoromethyl)uracil;

3-[3-(3,4-dimethyl-2-thienyl)-1,2-benzisothiazol-5-yl]-1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[3-[4-(hydroxymethyl)-1,3-dioxolan-2-yl]-1,2-benzisothiazol-5-yl]-1-methyl-6-(trifluoromethyl)uracil;

1-methyl-3-[3-(2-pyrimidinyl)-1,2-benzisothiazol-5-yl]-6-(trifluoromethyl)uracil;

3-[3-[(4R,6S)-4,6-dimethyl-m-dioxan-2-yl]-6-fluoro-1,2-benzisothiazol-5-yl]-1-methyl-6-(trifluoromethyl)uracil; and 3-[3-(4-isopropyl-2-oxazolin-2-yl)-1,2-benzisothiazol-5-yl]-1-methyl-6-(trifluoromethyl)uracil.

13. The method of claim 3 wherein the formula I compound is applied at a rate of about 0.001 kg/ha to 1.0 kg/ha.

14. A herbicidal composition which comprises an inert solid or liquid carrier and an effective amount of the compound of formula I defined in claim 1.

15. The composition defined in claim 14 wherein the formula I compound is selected from the group consisting of:

1-methyl-3-[3-(3-thienyl)-1,2-benzisothiazol-5-yl]-6-(trifluoromethyl)uracil;

ethyl (R)-2-[5-[3,6-dihydro-3-methyl-2,6-dioxo-4-(trifluoromethyl)-1(2H)-pyrimidinyl]-1,2-benzisothiazol-3-yl]-4-thiazolidinecarboxylate;

1-methyl-3-[3-(2-thienyl)-1,2-benzisothiazol-5-yl]-6-(trifluoromethyl)uracil;

1-methyl-3-[3-(3-methyl-2-thienyl)-1,2-benzisothiazol-5-yl]-6-(trifluoromethyl)uracil;

1-methyl-3-[3-(1-methylimidazol-2-yl)-1,2-benzisothiazol-5-yl]-6-(trifluoromethyl)uracil;

1-methyl-3-[3-(1-methylpyrrol-2-yl)-1,2-benzisothiazol-5-yl]-6-(trifluoromethyl)uracil;

1-methyl-3-[3-(4-methyl-2-thiazolyl)-1,2-benzisothiazol-5-yl]-6-(trifluoromethyl)uracil;

3-[3-(2,5-diethyl-3-thienyl)-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil;

3-[3-(3-methoxy-2-thienyl)-1,2-benzisothiazol-5-yl]-1-methyl-6-(trifluoromethyl)uracil;

1-methyl-3-[3-(3-pyridyl)-1,2-benzisothiazol-5-yl]-6-(trifluoromethyl)uracil;

1-methyl-3-[3-(2-pyrimidinyl)-1,2-benzisothiazol-5-yl]-6-(trifluoromethyl)uracil;

3-[3-[(1R,2S)-1,2-epoxypropyl]-1,2-benzisothiazol-5-yl]-1-methyl-6-(trifluoromethyl)uracil;

3-[3-[(1R,2R)-1,2-epoxypropyl]-1,2-benzisothiazol-5-yl]-1-methyl-6-(trifluoromethyl)uracil;

1-methyl-3-[3-(2-pyridyl)-1,2-benzisothiazol-5-yl]-6-(trifluoromethyl)uracil N",S,S-trioxide;

1-methyl-3-[3-(5-methyl-1,3,4-oxadiazol-2-yl)-1,2-benzisothiazol-5-yl]-6-(trifluoromethyl)uracil;

1-methyl-3-[3-(5-methyl-1,3,4-thiadiazol-2-yl)-1,2-benzisothiazol-5-yl]-6-(trifluoromethyl)uracil;

1,2-benzisothiazole-3-carboxanilide, 4'-chloro-5-[3,6-dihydro-3-methyl-2,6-dioxo-4-(trifluoromethyl)-1(2H)-pyrimidinyl]-N-methyl-;

1-methyl-3-[3-(3-methyl-2-pyridyl)-1,2-benzisothiazol-5-yl]-6-(trifluoromethyl)uracil;

N-[3-(5-methyl-2-thienyl)-1,2-benzisothiazol-5-yl]-1-cyclohexene-1,2-dicarboximide;

1-methyl-3-[3-(5-methyl-2-thienyl)-1,2-benzisothiazol-5-yl]-6-(trifluoromethyl)uracil;

methyl [(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-acetate;

methyl 2-[(2-[5-[3,6-dihydro-3-methyl-2,6-dioxo-4-(trifluoromethyl)-1(2H)-pyrimidinyl]-1,2-benzisothiazol-3-yl]-3-thienyl]oxy]-propionate;

3-[3-(1,3-dithiolan-2-yl)-1,2-benzisothiazol-5-yl]-1-methyl-6-(trifluoromethyl)uracil;

3-[6-fluoro-3-(2-pyridyl)-1,2-benzisothiazol-5-yl]-1-methyl-6-(trifluoromethyl)uracil;

1-methyl-3-[3-(4-methyl-3-thienyl)-1,2-benzisothiazol-5-yl]-6-(trifluoromethyl)uracil;

3-[3-(3,5-dimethyl-2-thienyl)-1,2-benzisothiazol-5-yl]-1-methyl-6-(trifluoromethyl)uracil;

3-(3-m-dioxan-2-yl-1,2-benzisothiazol-5-yl)-1-methyl-6-(trifluoromethyl)uracil;

3-acetyl-2-[5-[3,6-dihydro-3-methyl-2,6-dioxo-4-(trifluoromethyl)-1(2H)-pyrimidinyl]-1,2-benzisothiazol-3-yl]thiazolidine;

3-benzoyl-2-[5-[3,6-dihydro-3-methyl-2,6-dioxo-4-(trifluoromethyl)-1(2H)-pyrimidinyl]-1,2-benzisothiazol-3-yl]thiazolidine;

1-methyl-3-[3-(1,3-oxathiolan-2-yl)-1,2-benzisothiazol-5-yl]-6-(trifluoromethyl)uracil;

1-methyl-3-[3-(1,3-oxathiolan-2-yl)-1,2-benzisothiazol-5-yl]-6-(trifluoromethyl)uracil S',S'-dioxide;

1,2-benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl) dithioacetal];

1-methyl-3-[3-(1,3-oxathian-2-yl)-1,2-benzisothiazol-5-yl]-6-(trifluoromethyl)uracil;

1-methyl-3-[3-(1,3-oxathian-2-yl)-1,2-benzisothiazol-5-yl]-6-(trifluoromethyl)uracil S',S'-dioxide;

3-[3(5,5-dimethyl-m-dioxan-2-yl)-1,2-benzisothiazol-5-yl]-1-methyl-6-(trifluoromethyl)uracil;

1-methyl-3-[3-(4-methyl-m-dioxan-2-yl)-1,2-benzisothiazol-5-yl]-6-(trifluoromethyl)uracil;

1-methyl-3-[3-(3-methylpyrazol-1-yl)-1,2-benzisothiazol-5-yl]-6-(trifluoromethyl)uracil;

2-propynyl [[2-[5-[3,6-dihydro-3-methyl-2,6-dioxo-4-(trifluoromethyl)-1(2H)-pyrimidinyl]-1,2-benzisothiazol-3-yl]-3-thienyl]oxy]-acetate;

3-[3-(4,6-dimethyl-2-pyrimidinyl)-1,2-benzisothiazol-5-yl]1-methyl-6-(trifluoromethyl)uracil;

3-[3-(3-methoxy-2-pyridyl)-1,2-benzisothiazol-5-yl]-1-methyl-6-(trifluoromethyl)uracil;

1-methyl-3-[3-(5-methyl-2-pyridyl)-1,2-benzisothiazol-5-yl]-6-(trifluoromethyl)uracil;

3-[3-(4,6-diethoxy-2-pyrimidinyl)-1,2-benzisothiazol-5-yl]-1-methyl-6-(trifluoromethyl)uracil;

3-[6-fluoro-3-(3-methyl-2-pyridyl)-1,2-benzisothiazol-5-yl]-1-methyl-6-(trifluoromethyl)uracil;

3-[3-(1,3-dioxolan-2-yl)-1,2-benzisothiazol-5-yl]-1-methyl-6-(trifluoromethyl)uracil;

N-[6-fluoro-3-(3-methyl-2-pyridyl)-1,2-benzisothiazol-5-yl]-1-cyclohexene-1,2-dicarboximide;

3-[3-[(4R,5S)-4,5-dimethyl-1,3-dioxolan-2-yl]-1,2-benzisothiazol-5-yl]-1-methyl-6-(trifluoromethyl)uracil 3-[3-[(4R,5R)-4,5-dimethyl-1,3-dioxolan-2-yl]-1,2-benzisothiazol-5-yl]-1-methyl-6-(trifluoromethyl)uracil;

1-methyl-6-(trifluoromethyl)-3-[3-(3,4,5-trimethylpyrazol-1-yl)-1,2-benzisothiazol-5-yl]uracil;

3-[3-[(4R,6S)-4,6-dimethyl-m-dioxan-2-yl]-1,2-benzisothiazol-5-yl]-1-methyl-6-(trifluoromethyl)uracil 3-[3-[(4R,6S)-4,6-dimethyl-m-dioxan-2-yl]-1,2-benzisothiazol-5-yl]-1-methyl-6-(trifluoromethyl)uracil;

3-[3-(3-chloro-2-thienyl)-1,2-benzisothiazol-5-yl]-1-methyl-6-(trifluoromethyl)uracil;

1-methyl-3-[3-(2-thiazolyl)-1,2-benzisothiazol-5-yl]-6-(trifluoromethyl)uracil;

1-methyl-3-[3-(2-methyl-1,3-dioxolan-2-yl)-1,2-benzisothiazol-5-yl]-6-(trifluoromethyl)uracil;

1-methyl-6-(trifluoromethyl)-3-[3-(4,4,6-trimethyl-m-dioxan-2-yl)-1,2-benzisothiazol-5-yl]uracil;

1-methyl-3-[3-(4,4,5,5-tetramethyl-1,3-dioxolan-2-yl)-1,2-benzisothiazol-5-yl]-6-(trifluoromethyl)uracil;
1-methyl-3-[3-(4-methyl-1,3-dioxolan-2-yl)-1,2-benzisothiazol-5-yl]-6-(trifluoromethyl)uracil;
2,4(1H,3H)-pyrimidinedione, 1-methyl-3-[3-(5-methylene-m-dioxan-2-yl)-1,2-benzisothiazol-5-yl]-6-(trifluoromethyl)-;
1-methyl-3-[3-(4-methylpyrazol-1-yl)-1,2-benzisothiazol-5-yl]-6-(trifluoromethyl)uracil;
3-[3-(2-furyl)-1,2-benzisothiazol-5-yl]-1-methyl-6-(trifluoromethyl)uracil;
3-[3-(1,3-dioxolan-2-yl)-6-fluoro-1,2-benzisothiazol-5-yl]-1-methyl-6-(trifluoromethyl)uracil;
3-(3-m-dioxan-2-yl-6-fluoro-1,2-benzisothiazol-5-yl)-1-methyl-6-(trifluoromethyl)uracil;
3-[3-[(4R,r %)-4,5-dimethyl-1,3-dioxolan-2-yl]-6-fluoro-1,2-benzisothiazol-5-yl]-1-methyl-6-(trifluoromethyl)uracil;
3-[3-[4-(methoxymethyl)-1,3-dioxolan-2-yl]-1,2-benzisothiazol-5-yl]-1-methyl-6-(trifluoromethyl)uracil;
3-[3-(3,6-dihydro-4,6,6-trimethyl-2H-pyran-2-yl)-1,2-benzisothiazol-5-yl]-1-methyl-6-(trifluoromethyl)uracil;
3-[3-[(4R,5S-)-4,5-dimethyl-1,3-dioxolan-2-yl]-6-fluoro-1,2-benzisothiazol-5-yl]-1-methyl-6-(trifluoromethyl)uracil;
3-[3-[(4R,6S)-4,6-dimethyl-m-dioxan-2-yl]-6-fluoro-1,2-benzisothiazol-5-yl]-1-methyl-6-(trifluoromethyl)uracil;
2,4(1H,3H)-pyrimidinedione, 1-methyl-3-[3-(2-methyl-3-thienyl)-1,2-benzisothiazol-5-yl]-6-(trifluoromethyl)-;
3-[3-[5-(bromomethyl)-5-hydroxy-m-dioxan-2-yl]-1,2-benzisothiazol-5-yl]-1-methyl-6-(trifluoromethyl)uracil;
1-methyl-3-(3-spiro[m-dioxane-5,2'-oxiran]-2-yl-1,2-benzisothiazol-5-yl)-6-(trifluoromethyl)uracil;
3-[3-(4,4-dimethyl-5-oxo-1,3-dioxolan-2-yl)-1,2-benzisothiazol-5-yl]-1-methyl-6-(trifluoromethyl)uracil;
3-[3-[4-(chloromethyl)-1,3-dioxolan-2-yl]-1,2-benzisothiazol-5-yl]-1-methyl-6-(trifluoromethyl)uracil;
3-[3-[4-(hydroxymethyl)-1,3-dioxolan-2-yl]-1,2-benzisothiazol-5-yl]-1-methyl-6-(trifluoromethyl)uracil;
3-[3-(4-isopropyl-2-oxazolin-2-yl)-1,2-benzisothiazol-5-yl]-1-methyl-6-(trifluoromethyl)uracil;
1-methyl-3-[3(2-oxazolin-2-yl)-1,2-benzisothiazol-5-yl]-6-(trifluoromethyl)uracil;
1-methyl-6-(trifluoromethyl)-3-[3-(4-vinyl-1,3-dioxolan-2-yl)-1,2-benzisothiazol-5-yl]uracil;
1-methyl-3-[3-(4-propyl-1,3-dioxolan-2-yl)-1,2-benzisothiazol-5-yl]-6-(trifluoromethyl)uracil;
1-methyl-3-[3-(4-phenyl-1,3-dioxolan-2-yl)-1,2-benzisothiazol-5-yl]-6-(trifluoromethyl)uracil;
3-[3-[4-(bromomethyl)-1,3-dioxolan-2-yl]-1,2-benzisothiazol-5-yl]-1-methyl-6-(trifluoromethyl)uracil;
3-[3-[3-(bromomethyl)-2-thienyl]-1,2-benzisothiazol-5-yl]-1-methyl-6-(trifluoromethyl)uracil;
3-[3-[3-(methoxymethyl)-2-thienyl]-1,2-benzisothiazol-5-yl]-1-methyl-6-(trifluoromethyl)uracil;
3-[3-(3,4-dimethyl-2-thienyl)-1,2-benzisothiazol-5-yl]-1-methyl-6-(trifluoromethyl)uracil;
3-[3-(3-furyl)-1,2-benzisothiazol-5-yl]-1-methyl-6-(trifluoromethyl)uracil;
1-methyl-3-[3-[4-[(methylthio)methyl]-1,3-dioxolan-2-yl]-1,2-benzisothiazol-5-yl]-6-(trifluoromethyl)uracil;
3-[3-[3-(hydroxymethyl)-2-thienyl]-1,2-benzisothiazol-5-yl]-1-methyl-6-(trifluoromethyl)uracil;
1-methyl-3-[3-[4-[(methylsulfonyl)methyl]-1,3-dioxolan-2-yl]-1,2-benzisothiazol-5-yl]-6-(trifluoromethyl)uracil;
1-methyl-3-[3-[4-[(methylsulfonyl)methyl]-1,3-dioxolan-2-yl]-1,2-benzisothiazol-5-yl]-6-(trifluoromethyl)uracil;
1-methyl-3-[3-[4-[(methylsulfinyl)methyl]-1,3-dioxolan-2-yl]-1,2-benzisothiazol-5-yl]-6-(trifluoromethyl)uracil;
[2-[5-[3,6-dihydro-3-methyl-2,6-dioxo-4-(trifluoromethyl)-1(2H)-pyrimidinyl]-1,2-benzisothiazol-3-yl]-1,3-dioxolan-4-yl]methyl thiocyanate;
3-[3-(3,4-dihydro-3-oxo-2-quinoxalinyl)-1,2-benzisothiazol-5-yl]-1-methyl-6-(trifluoromethyl)uracil;
5-[5-[3,6-dihydro-3-methyl-2,6-dioxo-4-(trifluoromethyl)-1(2H)-pyrimidinyl]-1,2-benzisothiazol-3-yl]-1,6-hydro-6-oxo-2,3-pyrazinedicarbonitrile;
1-methyl-3-[3-(4-oxo-delta-2-1,2,5-thiadiazolin-3-yl)-1,2-benzisothiazol-5-yl]-6-(trifluoromethyl)uracil S',S'-dioxide;
3-[3-[2-(dimethylamino)-4-methoxy-5-oxo-2-imidazolin-4-yl]-1,2-benzisothiazol-5-yl]-1-methyl-6-(trifluoromethyl)uracil;
3-[3-(4-hydroxy-5-oxo-2-phenyl-2-imidazolin-4-yl)-1,2-benzisothiazol-5-yl]-1-methyl-6-(trifluoromethyl)uracil;
3-[3-(2-tert-butyl-4-hydroxy-5-oxo-2-imidazolin-4-yl)-1,2-benzisothiazol-5-yl]-1-methyl-6-(trifluoromethyl)uracil;
3-[3-(-hydroxy-5-imino-4,4-dimethyl-2-oxo-3-pyrrolidinyl)-1,2-benzisothiazol-5-yl]-1-methyl-6-(trifluoromethyl)uracil;
3-[3[4-methoxy-2-(methylimino)-5-oxo-4-imidazolidinyl]-1,2-benzisothiazol-5-yl]-1-methyl-6-(trifluoromethyl)uracil; and
3-[3[4-methoxy-2-(ethylimino)-5-oxo-4-imidazolidinyl]-1,2-benzisothiazol-5-yl]-1-methyl-6-(trifluoromethyl)uracil.

16. A compound of formula II, XLIV or XL

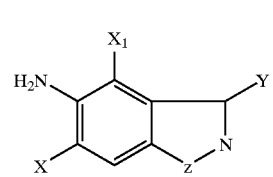

(II)

-continued (XLIV)

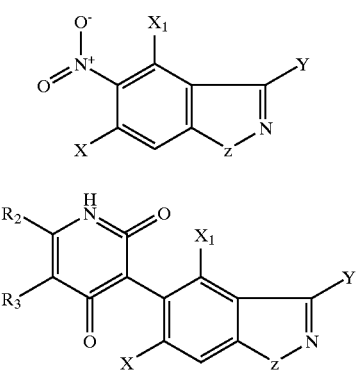

(XL)

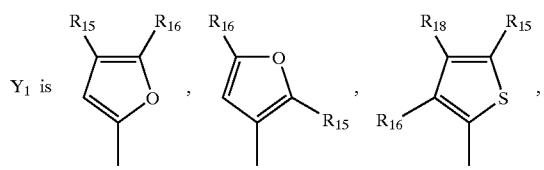

wherein

X is hydrogen, halogen or $C_1$–$C_4$ alkyl;

$X_1$ is hydrogen, halogen, $C_1$–$C_4$ alkyl, $C_1$–$C_4$ haloalkyl, $C_1$–$C_4$ alkoxy or, $C_1$–$C_4$ haloalkoxy;

Y is a heterocyclic radical $Y_1$, $Y_2$, $Y_3$, $Y_4$, $Y_5$, $Y_{10}$, $Y_{11}$, $Y_{24}$, $Y_{25}$, $Y_{26}$, $Y_{27}$, $Y_{28}$ or $Y_{29}$, wherein $Y_1$ is 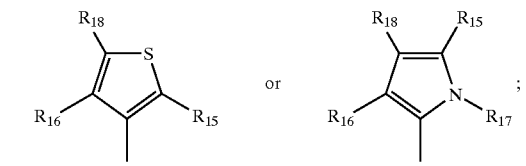

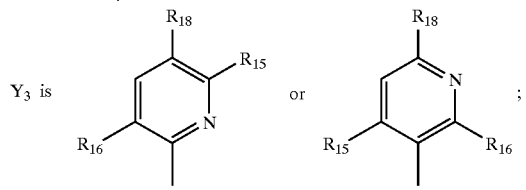

$Y_2$ is 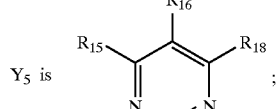

$Y_3$ is 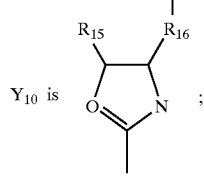

$Y_5$ is $Y_{10}$ is $Y_{11}$ is 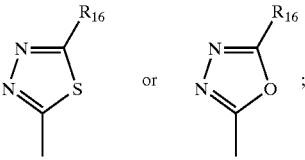

$Y_{24}$ is 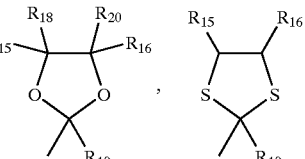

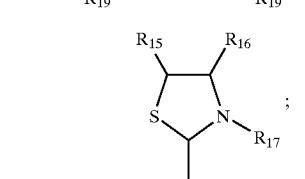

$Y_{25}$ is 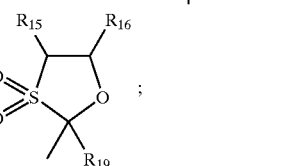

$Y_{26}$ is 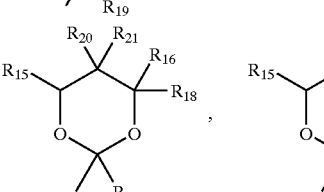

$Y_{27}$ is 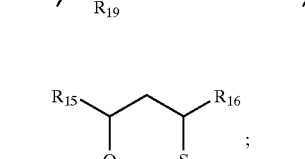

$Y_{28}$ is 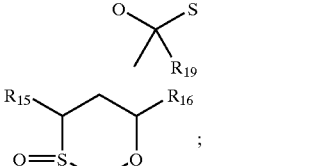 ; and $Y_{39}$ is $R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy;

$R_{16}$ is hydrogen, halogen, $C_1$–$C_8$ alkyl optionally substituted with $X_2R_{24}$; $C_1$–$C_3$ haloalkyl, phenyl or $C_2$–$C_4$ alkenyl;

$R_{17}$ is hydrogen, methyl or $C(O)R_{25}$;

$R_{19}$ is hydrogen or $C_1$–$C_3$ alkyl;

$R_{24}$ is hydrogen or $C_1$–$C_3$ alkyl;

$R_{25}$ is $C_1$–$C_3$ alkyl or phenyl; and
$X_2$ is oxygen;
Z is $S(O)_m$;
m is zero, 1 or 2;
$R_2$ is trifluoromethyl; and
$R_3$ is hydrogen; or
an optical isomer or diastereomer thereof.

17. A compound of formula CXIII

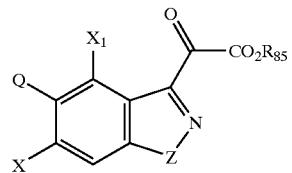

(CXIII)

wherein

Q is a radical of formula

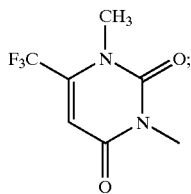

$R_{85}$ is $C_1$–$C_6$ alkyl, $C_2$–$C_6$ alkenyl, $C_2$–$C_6$ alkynyl, $C_3$–$C_7$ cycloalkyl or benzyl;

X is hydrogen, halogen or $C_1$–$C_4$ alkyl;

$X_1$ is hydrogen, halogen, $C_1$–$C_4$ alkyl, $C_1$–$C_4$ haloalkyl, $C_1$–$C_4$ alkoxy or, $C_1$–$C_4$ haloalkoxy;

Z is $S(O)_m$; and m is zero, 1 or 2; or an optical isomer or diastereomer thereof.

18. A process for the preparation of the compound of formula I defined in claim 1, which process comprises:

(a) reacting an amine of formula II

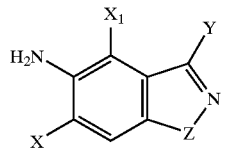

(II)

with a 2-dialkylamino-6H-1,3-oxazin-6-one of formula XXXIX

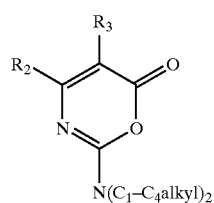

(XXXIX)

in the presence of an organic acid to form an intermediate compound of formula XL

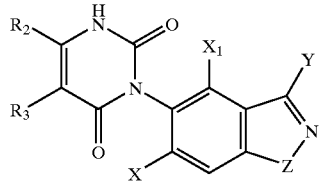

(XL)

(b) reacting said intermediate compound with an electrophile, $Z_1R$, wherein $Z_1$ is chlorine, bromine or iodine, in the presence of a base.

19. A process for the preparation of a compound of formula XL

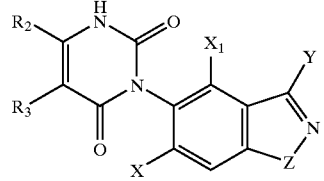

(XL)

wherein

X is hydrogen, halogen or $C_1$–$C_4$ alkyl;

$X_1$ is hydrogen, halogen, $C_1$–$C_4$ alkyl, $C_1$–$C_4$ haloalkyl, $C_1$–$C_4$ alkoxy or, $C_1$–$C_4$ haloalkoxy;

Y is a heterocyclic radical $Y_1$, $Y_2$, $Y_3$, $Y_4$, $Y_5$, $Y_{10}$, $Y_{11}$, $Y_{24}$, $Y_{25}$, $Y_{26}$, $Y_{27}$, $Y_{28}$ or $Y_{29}$, wherein $Y_1$ is 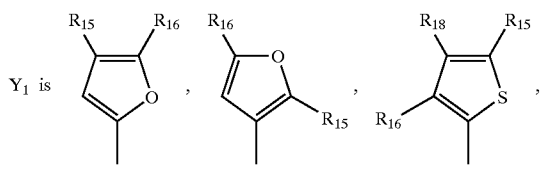

$Y_2$ is 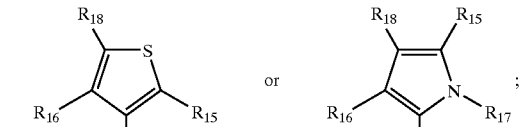

$Y_3$ is 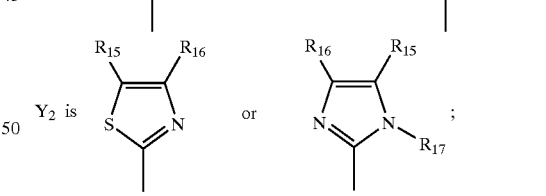

$Y_5$ is 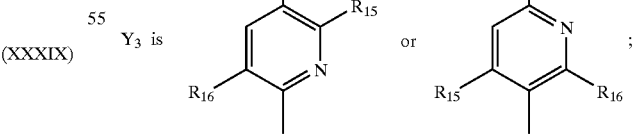

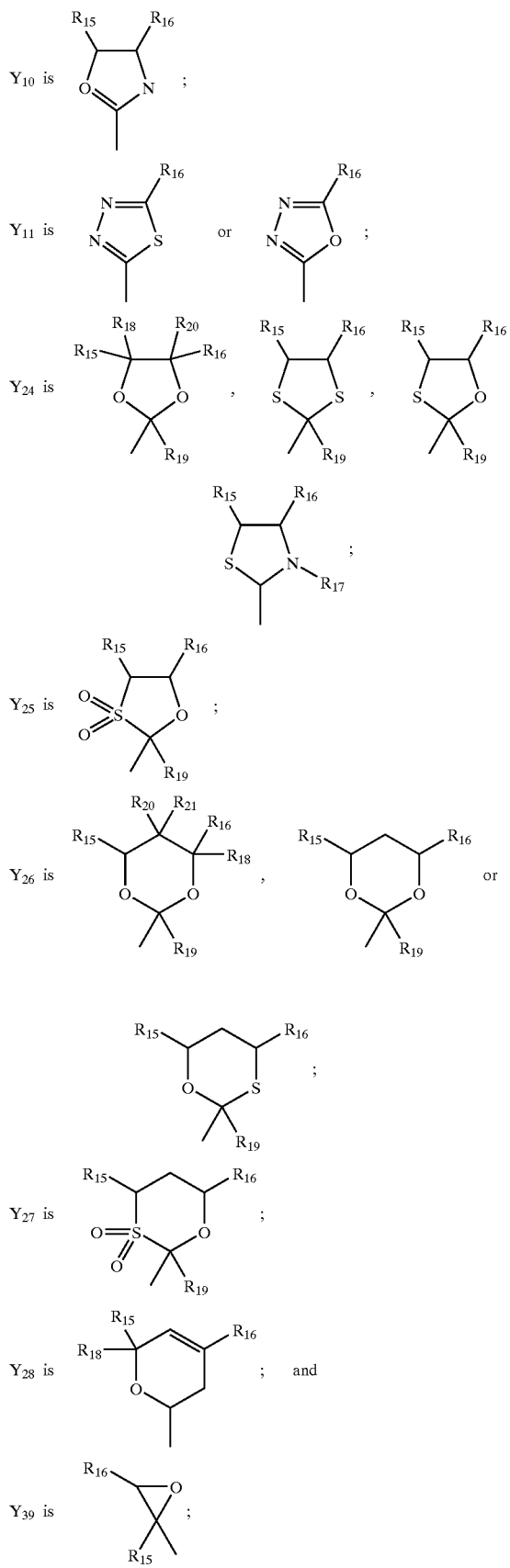

$R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy;

$R_{16}$ is hydrogen, halogen, $C_1$–$C_9$ alkyl optionally substituted with $X_2R_{24}$; $C_1$–$C_3$ haloalkyl, phenyl or $C_2$–$C_4$ alkenyl;

$R_{17}$ is hydrogen, methyl or $C(O)R_{25}$;

$R_{19}$ is hydrogen or $C_1$–$C_3$ alkyl;

$R_{24}$ is hydrogen or $C_1$–$C_3$ alkyl;

$R_{25}$ is $C_1$–$C_3$ alkyl or phenyl; and $X_2$ is oxygen;

Z is $S(O)_m$;

m is zero, 1 or 2;

$R_2$ is trifluoromethyl; and $R_3$ is hydrogen;

which process comprises reacting an amine of formula II

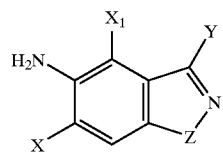
(II)

with a urea of formula XLI

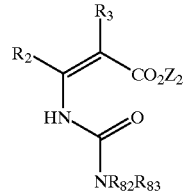
XLI wherein $Z_2$ is $C_1$–$C_6$ alkyl; and $R_{82}$ and $R_{83}$ are each independently $C_1$–$C_6$ alkyl or $R_{82}$ and $R_{83}$ may be taken together with the atom to which they are attached to form a 5- or 6-membered ring optionally containing one oxygen atom in the presence of a base.

20. A process for the preparation of the compound of formula I defined in claim 1, which process comprises reacting an amine of formula II

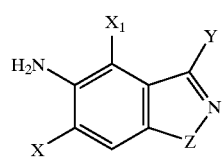
(II)

with a carbamate of formula LXII

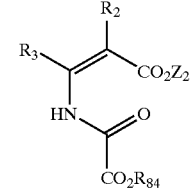
(LXII)

wherein $Z_2$ is $C_1$–$C_6$ alkyl; $R_{84}$ is $C_1$–$C_6$ alkyl, benzyl, $C_2$–$C_6$ alkenyl, $C_2$–$C_6$ alkynyl or $C_3$–$C_7$ cyclopropyl; in the presence of a base.

21. A process for the preparation of a compound of formula II

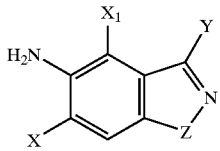

(II)

wherein
X is hydrogen, halogen or $C_1$–$C_4$ alkyl;
$X_1$ is hydrogen, halogen, $C_1$–$C_4$ alkyl, $C_1$–$C_4$ haloalkyl, $C_1$–$C_4$ alkoxy or, $C_1$–$C_4$ haloalkoxy;
Z is $S(O)_m$;
m is an integer of 0, 1 or 2; and
Y is a heterocyclic radical $Y_1$, $Y_2$, $Y_3$, $Y_4$, $Y_5$, $Y_{10}$, $Y_{11}$, $Y_{24}$, $Y_{25}$, $Y_{26}$, $Y_{27}$, $Y_{28}$ or $Y_{29}$, wherein $Y_1$ is 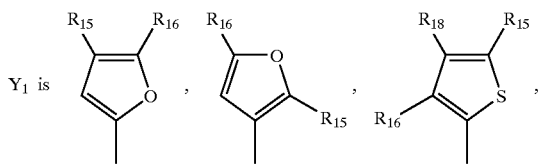

$Y_2$ is 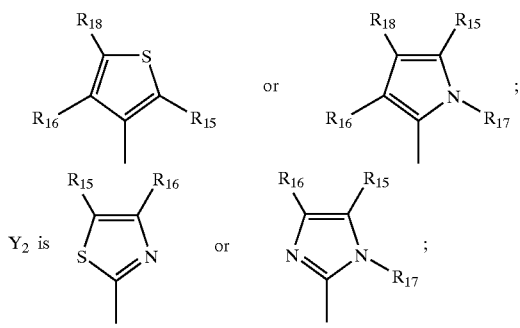

$Y_3$ is 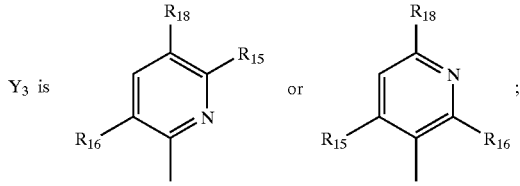

$Y_5$ is 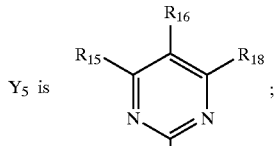

$Y_{10}$ is 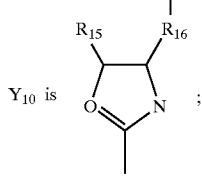

$Y_{11}$ is 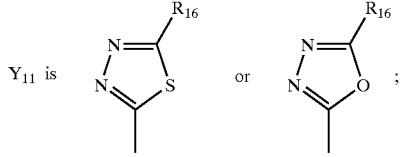

$Y_{24}$ is 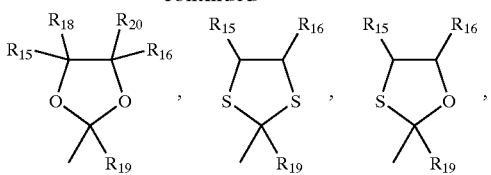

$Y_{25}$ is 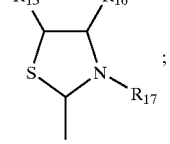

$Y_{26}$ is 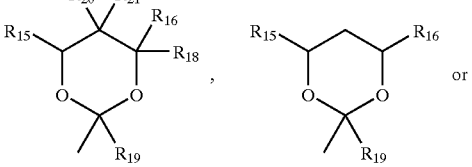

$Y_{27}$ is 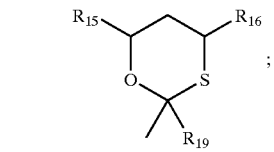

$Y_{28}$ is 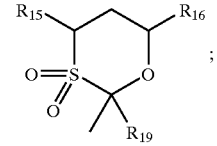; and $Y_{39}$ is 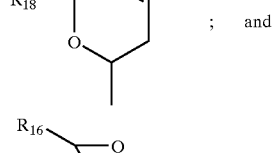

$R_{15}$, $R_{18}$, $R_{20}$, and $R_{21}$ are each independently hydrogen, $C_1$–$C_3$ alkyl, $C_1$–$C_3$ haloalkyl, $C_1$–$C_3$ alkoxy;
$R_{16}$ is hydrogen, halogen, $C_1$–$C_8$ alkyl optionally substituted with $X_2R_{24}$; $C_1$–$C_3$ haloalkyl, phenyl or $C_2$–$C_4$ alkenyl;
$R_{17}$ is hydrogen, methyl or $C(O)R_{25}$;
$R_{19}$ is hydrogen or $C_1$–$C_3$ alkyl;
$R_{24}$ is hydrogen or $C_1$–$C_3$ alkyl;
$R_{25}$ is $C_1$–$C_3$ alkyl or phenyl; and
$X_2$ is oxygen;

which process comprises reacting an amine of formula XLVII
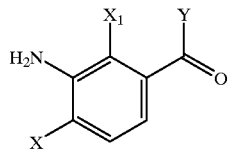
(XLVII)
with sodium or potassium thiocyanate and bromine to form an isothiocyanate of formula XLVIII
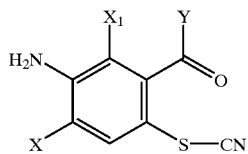
(XLVIII)
and reacting said isothiocyanate with an ammonium salt to form the desired formula II compound.
22. The compound of formula I defined in claim 1, wherein Z is sulfur.
* * * * *

UNITED STATES PATENT AND TRADEMARK OFFICE
CERTIFICATE OF CORRECTION

PATENT NO. : 6,706,663 B2 Page 1 of 1
DATED : March 16, 2004
INVENTOR(S) : Wepplo et al.

It is certified that error appears in the above-identified patent and that said Letters Patent is hereby corrected as shown below:

Title page,
Item [*] Notice, delete the phrase "by 131 days" and insert -- by 0 days --

Signed and Sealed this

Nineteenth Day of October, 2004

JON W. DUDAS
*Director of the United States Patent and Trademark Office*